United States Patent [19]

Hartwell et al.

[11] Patent Number: 5,866,338
[45] Date of Patent: Feb. 2, 1999

[54] CELL CYCLE CHECKPOINT GENES

[75] Inventors: Leland H. Hartwell, Seattle, Wash.; Ted A. Weinert, Tucson, Ark.; Sharon E. Plon, Houston, Tex.; Mark T. Groudine, Seattle, Wash.

[73] Assignees: University of Washington, Seattle, Wash.; Arizona Board of Regents on Behalf of the University of Arizona, Tucson, Ariz.; Fred Hutchinson Cancer Research Center, Seattle, Wash.

[21] Appl. No.: 870,693

[22] Filed: Jun. 6, 1997

Related U.S. Application Data

[63] Continuation of Ser. No. 198,446, Feb. 18, 1994, Pat. No. 5,674,996, which is a continuation-in-part of PCT/US93/04458 May 12, 1997, which is a continuation-in-part of Ser. No. 884,426, May 14, 1992, abandoned, and a continuation-in-part of Ser. No. 882,051, May 12, 1992, abandoned.

[51] Int. Cl.$^6$ ..................................................... C12Q 1/68
[52] U.S. Cl. ......................... 435/6; 536/24.32; 530/387.9
[58] Field of Search ............................. 435/6; 536/24.32; 530/387.9

[56] References Cited

PUBLICATIONS

Weinert, T.A. and L.H. Hartwell, "Cell Cycle Arrest of cdc Mutants and Specificity of the RAD9 Checkpoint," *Genetics* 134:63–80 (1993).
Millar, J.B.A. and Russell, P., "The cdc25 M–Phase Inducer: An Unconventional Protein Phosphatase," *Cell* 68:407–410 (1992).
Hunter, T. and Pines, J., "Cyclins and Cancer," *Cell* 66:1071–1074 (1991).
Koff, A. et al., "Human Cyclin E, a New Cyclin That Interacts with Two Members of the CDC2 Gene Family," *Cell* 66:1–12 (1991).
Haas, A.L. et al., "Ubiquitin Conjugation by the Yeast RAD6 and CDC34 Gene Products: Comparison to Their Putative Rabbit Homologs, $E2_{20k}$ and $E2_{32K}$," *The Journal of Biological Chemistry* 266(8):5104–5112 (1991).
Hunt, T., "Destruction's Our Delight," *Nature* 349:100–101 (1991).
Glotzer, M. et al., "Cyclin is Degraded by the Ubiquitin Pathway," *Nature* 349:132–138 (1991).
Lew, et al., *Cell* 66:1197–1206 (1991).
Igarashi, et al., *Nature* 353:80–83 (1991).
Weinert, T.A. and Hartwell, L.H., "Characterization of RAD9 of *Saccharomyces cerevisiae* and Evidence that its Function Acts Posttranslationally in Cell Cycle Arrest after DNA Damage," *Molecular and Cellular Biology* 10(12):6554–6564 (1990).
Lock, R.B. and Ross, W.E., "Inhibition of p34$^{cdc2}$ Kinase Activity by Etoposide or Irradiation as a Mechanism of $G_2$ Arrest in Chinese Hamster Ovary Cells$^1$," *ExpH. and Cell Res.* 50:3761–3766 (1990).

Seufert, W. and Jentsch, S., "Ubiquitin–conjugating enzymes UBC4 and UBC5 mediate selective degradation of short–lived and abnormal proteins," *The EMBO Journal* 9(2):543–550 (1990).
Lock, et al., *Canc. Res.* 50:3767–3771 (1990).
Hartwell, L.H. and Weinert, T.A., "Checkpoints: Controls That Ensure the Order of Cell Cycle Events," *Science* 246:629–633 (1989).
Schiestl, R.H. et al., "Cloning and Sequence Analysis of the *Saccharomyces cerevisiae* RAD9 Gene and Further Evidence that Its Product Is Required for Cell Cycle Arrest Induced by DNA Damage," *Molecular and Cellular Biology* 9:1882–1896 (1989).
Goebl, M.G. et al., "The Yeast Cell Cycle Gene CDC34 Encodes a Ubiquitin–Conjugating Enzyme," *Science* 241:1331–1335 (1988).
Weinert, T.A. and Hartwell, L.H., "The RAD9 Gene Controls the Cell Cycle Response to DNA Damage in *Saccharomyces cerevisiae*," *Science* 241:317–322 (1988).
Lee, M.G. and Nurse, P., "Complementation used to clone a human homologue of the fission yeast cell cycle gene cdc2," *Nature* 327:31–35 (1987).
Pringle, J.R. and Hartwell, L.H., "The *Saccharomyces cerevisiae* cell cycle," In: *The Molecular Biology of the Yeast Saccharomyces: Life cycle and Inheritance* (ed. J.N. Strathen et al.), Cold Spring Harbor Laboratory, Cold Spring Harbor, New York, p. 97 (1981).

(List continued on next page.)

*Primary Examiner*—Scott W. Houtteman
*Attorney, Agent, or Firm*—Christensen, O'Connor, Johnson & Kindness PLLC

[57] ABSTRACT

Human checkpoint huCDC34, huRAD9$_{compA}$, and huRAD9$_{compB}$ cDNAs shown in FIGS. 1, 2, and 3. A method for isolating a human checkpoint cDNA that is capable of restoring growth at a restrictive temperature in a yeast test cell, wherein the yeast test cell comprises a genome having a first gene that forms a DNA strand break at a restrictive temperature and a second gene that fails to induce a cell cycle arrest in response to the DNA strand break, whereby the growth of the yeast test cell is inhibited at the restrictive temperature, the method comprising the steps of: obtaining a human cDNA library comprising a plurality of human cDNA clones; inserting the human cDNA clones individually into plasmid vectors comprising a selectable marker gene; transforming a culture of the yeast test cells with the plasmid vectors from the preceding step; selecting for yeast test cells transformed with the selectable marker gene; growing the selected transformants at the restrictive temperature and isolating a candidate transformant capable of growing at the restrictive temperature; and identifying the human cDNA carried by the candidate transformant as a human checkpoint cDNA by sequencing the human cDNA carried by the candidate transformant and determining that the human cDNA is less than 50% homologous with both the first gene and the second gene. Also yeast checkpoint RAD17, RAD24, MEC1, MEC2, and MEC3 cDNAs shown in FIGS. 4–8.

7 Claims, 17 Drawing Sheets

OTHER PUBLICATIONS

Hartwell, L.H., "Three Additional Genes Required for Deoxyribonucleic Acid Synthesis in *Saccharomyces cerevisiae,*" *Journal of Bacteriology* 115(3):966–974 (1973).

Zheng, P. et al., "SPK1 Is an Essential S–Phase–Specific Gene of *Saccharomyces cerevisiae* That Encodes a Nuclear Serine/Threonine/Tyrosine Kinase," *Molecular and Cellular Biology* 13(9):5829–5842 (1993).

Weinert, T.A. et al., "Mitotic checkpoint genes in budding yeast and the dependence of mitosis on DNA replication and repair," In: *Genes & Development,* Cold Spring Harbor Laboratory, Cold Sprin Harbor, New York, pp. 1–14 (1994).

Stern, D.F. et al., "Spkl, a New Kinase from *Saccharomyces cerevisiae,* Phosphorylates Proteins on Serine, Threonine, and Tyrosine," *Molecular and Cellular Biology* 11(2):987–1001 (1991).

Hennessy, K.M. et al., "Subcellular Localization of yeast CDC46 varies with the cell cycle," *Genes & Development,* Cold Spring Harbor Laboratory, Cold Spring Harbor, New York, pp. 2252–2263 (1990).

Plon, S.E. and Groudine, M., "Defining the human cell checkpoint system," 42nd Annual Meeting of The American Society of Human Genetics, San Francisco, California, Nov. 9–13, 1992. *The American J. of Human Genetics* 51(4) Abstract No. 259 (1992).

Plon, S.E. et al., "Complementation of yeast cell–cycle checkpoint mutations by human cDNAS," Abstracts of papers presented at the 1992 Meeting on *The Cell Cycle,* May 13–17, 1992, Cold Spring Harbor Laboratory, Cold Spring Harbor, New York, p. 153 (1992).

Plon, S.E. et al., "Cloning of the human CDC34 cell cycle gene and a putative human G2 checkpoint gene by complementation in yeast," 43rd Annual Meeting of The American Society of Human Genetics, New Orleans, Louisiana, Oct. 5–9, 1993. *The American J. of Human Genetics* 53(3) Abstract No. 30 (1993).

Plon, S.E. et al., "Isolation of human cell cycle genes: CDC34 and a potential G2 checkpoint gene, CCCI," Abstracts of papers presented at the 1994 Meeting on *The Cell Cycle,* May 18–22, 1994, Cold Spring Harbor Laboratory, Cold Spring Harbor, New York, p. 221 (1994).

Human CDC34 cDNA sequence

ATTGGTGAATCCGTCCACTCAGTGCTGGACGTGGCTCCAGGACCTGGAGCTGACA
GGCAGGACCGGCCCCTCCGGACCGCTACACCTGGGCCTCCCAGGCTGGTAGTGTC
AGGAAACGGCCCCCCGNNCACGTTCCCAGCAGCGCCCCCGTGGCTCCTCCGGGT
GCGGCCAGTCCGGAAGCTGGGGGACCCCGGTAGAAGTCGGGCTCAGCTCCCCTC
CCGAGGGGACAGTGGGCCGGCGGCCGCTCCCACCCTGGCCCCGTCCACCGAGCCC
GAGTGACGTGAGTGGCGGTGGGGCAGCCCCTCTTCTGAAGCACGTGAAAACCC
AGAACAGACATGGGAGGGAGGAGAAAAAGCCAAAACGAAACAACCAGAGGAGACG
GGGACCAGCACAAAACCTCCGTGAGGTAGTCTGTCGTCTAAGGAGCCACGGGTCC
GGCCCTAGTGAGGTAAACTCGGCAAGTTTATTCTGGTGGTGTCAGGACTCCTCCG
TGCCAGAGTCATCCTCATCGTCCCCGAAGCAGCTGTCGGCCTCCTCCTCCACCTCG
CCGTCTCGTAGTAGTCGTCGTAGAAGAGTTCGAGCCTGGGCCCTCGTCGGGCCGCGC
CTTGGTCTTCACGCAGTACTCGGCCAGCGTGGTGGGCACCTTCACGCCGTCACGC
TCCGCGTCCACCTTGGTCTCCCCAGGACCTGCTTCCGGATGATGTCTGTGTACTCCCG
ATCCTTCCCCTTGCTCTCTCTTTCCACTTCCTGTACATCACGGAGGCGTCCACGTTTG
CGGGCGAGAAGGTGTTGGGCTCGTCGTTCAGGAGGAGATCACACTCAGGAGAATGG
TCCTGACGTTCTGCGTGGGGGTTCCACCTCTCTGAGGGCAGCTCCCCGCTCTGGGG
GTCGTCCACCGGCGGGTGGAGGATGGAGATACACACGTCCCCCGTCTCGTAGATG
TTAGGGTGCCACATCTTGGTCAGGAACCGAAAGGCTGGTGGAGAGTATGGGTAG
TCGATGGGAACTTGAGGCGCGCCTTGAAGTAGCCGCCCTTCGTAGTAGGTGTTGG
GGGGCCCGAAAATGCCCACCTCCCAGTTGTATAGATCGCCCTCGTCGTCCACCAGTGT
CACGCGGAATCCCTCGCAGCTCGACCGGCTCTTCCTGCCGAGCCCCTTGAGCTCCAGCAGC
GCCTTCTGCGAGCAGCAGCGCGGCACTAGCGGCGCCGAGCCATGGCGCGGGGAGGGGCCC
GGGGTCGAGAGCAGCGCGNGGCCGCGACCACCGCGAGTTCGCGAGACGGCCG
GGCCGCCACCGTCCGGGGGGAGCCACCCGGGCCGCCCGCCTCGCGCCTCCTCCTC

*Fig. 1.*

RAD9compA cDNA sequence

```
ATTGTTCTATTGATGCAGGTAATCATCACTCTTCACTAGCTGAGCATTCGGTCCACTAACCTGAGTCATATCCGGCACTGGTTT
CTCTAGAAAGGGNTCCGACGGGAATGCTGATGCACAGGCACTTCTGCGGGTGTTCTGGGGTGATGGGTGGAGCTGTGCCCAA
GGCTGGTGATGAGGGTGTGAGGTGAAGACTGTGGTGCAAGCCCGGTGAGGCTGAGGACAGGTTGGAACTGCTGAAA
AGATGGCTGTTGACCAGGATGTGTTGCCAGGTATCAGTCGTTCCAGGACTGCTGTGGGTCTCCAAGGCCAACACCAGACAA
CCATTGGCCTCATGTGCCCAGTCAGTCAATTCCCTTGGTGCCGAGGACATGCCTATAAATGGACGAGACTGCTGCATGTTTCTGGGC
CCATATTCCTCTGTCCAGCACTTCCCGGCCATGCACCAGGGCTGTTGAGGATGCTGAGGATGGCATATATTGCTTTCATGGGTGACATGGGA
CATTGGTATCCCAGACACTTCCCGGCCTGAGGCTGTGAAGATGCATAGTTTGTTGTTCATTGGGTACTGTTGAGCCACTGGGTGGATGG
GTGGAGAGGCATAAGTTCCTGACCACTGTCCTTGACCACTGTCTTGATGGGAATCCTACACAGCATTGGGTATCTGGTACTGTTGATTCATTGGAGT
GCTGCTGGTGCATTAGTCCTAAATTTGATTCATCCTGTATTGTTAACTAATCCCTGATTGTTACTGTAAGGATATCGAGAATAC
ATTATTGTAAGGCCTAAATTTGATTCATCCTGTATTGTTAACTAATCCCTGATTGTTACTGTAAGGATATCGAGAATAC
TGCCCTGAGTGTGTTTATAGTAGGAGAGGACTGTCTGGCTCCGAGAACTAAAGTTAAGGGTTTGCGGCCTAACAGCCCCTTGTT
GGGGAGGATTCGGGAGAATCTGGACTGTGGGCAACGGATTCTCCATGGAGAGCAGTAGAGGGGTGGTGATGGAACTGCTGCAC
CGAGTGACGCAAGGAAGGAGTGCCATGCTGGACTGCTGGGCCTTGGGAAAACTGGCTGGGATCAGTTGGGCTGGACCATGGACCATGGCAGGGGCAATAAAAGGA
TTTCCCTGATTGAGGCCTGCCCATAGCTGCCTCTGCCATGCTGCCTGGGACTGCTGCCCTTCAGCTCTGGAGGGTCAGGGGCACCATGGAAAAATCCC
CACGTGACGCAAGGAAGGAGTGCCATGCTGGACTGCTGGGCCTTGGGAAAACTGGCTGTGGGAGGGTGCTGCATGGAAGAGCCGGCTGGCTG
CGGTGCTGCTGCTGCTGCTGCTAGGGGCTCGTATCGTCGGTCTGGTACCTGGTATCTGGTCTCGTATCGTCGGTCTGGTACTGGTTCTGTCC
ACAAAGGATTGCCCATGCCTCTCATTCTGCATGCGGAGACGCGAGTCCGTTCCCAGGGGTGTTGCTCATCATTCTGTTCGGCTGATCCAT
GAACGGGAGGGTGTGATACTGCGAGTGCGGAGAGTCCGAGTCCGTTCCCAGGGGTGTTGCTCATCATTCTGTTCGGCTGATCCAT
CAGATGCATCATCTTTTGTTGTTCATACTGATTATAGTGATCAAAATGTGCTGACCGTCAGCTTTGTTGTTTGATTAGTTGAAGGATGATGA
AGGGATGGCTGTAAAGAGGCAAAGCCTTCACTGAAATATTCCCATCCGCCAAAAGACTCATTCCTGATCTGCCATCTTATTCCA
CTCCGAGGCCTTCAAGACCTTCACTGAAATATTCCCATCCGCCAAAAGACTCATTCCTGATCTGCCATCTTATTCCA
ACACACGGCTCCTCCAAACCACCACAGCTCAGGAGCTTGCCTTGCTCTTCACTGAGGTGTTTGCCCTCAAAGCCTATATGACCA
ATCCCTAATTGCTGTCCTGATGATGA
```

Fig. 2.

Human RAD9compB sequence

ATTGCAGGTTCCGTAGCTTTCTAGTTTTTTTTTTTTCACTTGGATCAAATAGTTTGATAGACAGAAAAAGATCTGTACCAT
TATTTCCTTTCCTTAACAGCTATTGTAATTCCTGGACTTGGTTGCTTTTCACTTGGCAGTTAAGAAGACACAGCTTGTTTCC
CCATCAGTTTTCTCTCTCTCCTTCGTGTGTGTGTGTGTGTGTGTGTGTGCGTGCCGTGCCGTGCCACAGGCCA
ATCTTCAGGCTTATGGCTTTTGGAACATTTCTTAATTAATAGAGAACAGAATTCAATGATTAGCAACATCACTAAAATTAC
CCCATTTCTTCCATGAGTCACTGACACCCGATGCGCATGAACAGTCCAACGTCCACCTCGTAAGATGTCATCGGGGTTCAGGG
TTCAGAAGCATCGAGGACTGTGGTGCCGCGGTCCCTAGGGGACGAGGGGTTCCTCCTCCTCAATTGCTTTATGTGCTTCACTCAGTGAAC
GGTGCCACAAGCTTGGGTCTGCTCGTCGACAACCTGACTTTTAAACCTAAGGGTTGGGCCTGGGATTCCCGCGGATTCAGCCACAGAGTTCTGACAT
CCCAATGGGATGACAACCTGACTTTTAAACCTAAGGGTTGGGCCTGGGATTCCCGCGGATTCAGCCACAGAGTTCTGACAT
GAATGTGTGTTCCTGTGATATTGACGTTGACATCCCGCGATTCAGCCACATCCCTGCGGATTCAGCAAGCTGGAGGAAGCAATGGTAAT
TTTGGCTTTTCGGTTGTTTCTTCAGATAATGAAACAGCTGAGTGTCAATATGAGTTCTATGGCTTCAATCT
CCTTTAAAATAAAATTCTTAAGGTCCAAAAAGAAAAAAATTGCTGATATTGCCACAACATTAGAAATCCTGACATGCTGAAACCAAAT
ACCAAACCCAAACAAGAAAAAGAAAAATCAGTGACTTGTTTTAATTTGTTTTCTTTTCTGCCCTTTGCCGTCCGATT
GGTGATGTTATTCAAACAGGACCCGGATCCGTAAGTGCAGGAGGAACCCTGCAGGAGGAGGGACCTTGCTGCCGCTTCATCTCCTTCATCGCTCG
GGGGCTTTTCGGTGCGTCTCTTTTGAGGGGCAGTGTGTCGCTGGACTTCCTGCCGAAGTGCTGGGCGCTTCTTGT
GCTGGGATGCGTACCCGCTGTCCCCAGAGAATCCTTGGGCCTCCTCCTTCGTGTCGTCGTCAAACTCATAGTGGTCGTCGGCT
GCTTCGTCGTGGAAGCCTCCGAAGCTGGGCTGCCCCTCGCTGGCGCAGGTGCTGCCCCTTGGTGGGCAAACTCATAGTGGTCGTCGGCT
GAGGAGGAGGAGGAGAGATGAGTCTCCGCTGACCACTGGGAGCCACAAGATGGCTTGGCACTGCCTGCTGTAGTTGTGATCCT
CCTTGGGGTCTCCGCTGACCACTGGGAGCCACAAGATGGCTTGGCACTGCCTGCTGTAGTTGTGATCCT
GGCCGCTGTCACCCCAATGGGAGTGATTGGCA

Fig. 3.

Yeast RAD17 cDNA Sequence

```
LOCUS        RAD17MARCH      2150 BP DS-
BASE COUNT   748 A    372 C    425 G    605 T    0 OTHER
ORIGIN       POSITION 1 OF RAD17MARCH
    1 AGCAGGAATT GGTAACGCCA GGTTTTCCCG ATCAGACGTT GTAAAACAGG CCAGTGAATT
   61 GTAATACGAC TCACTATAGG GCGAATTGGG TACCGGGCCC CCCCTCGAGG TCGACGGTAT
  121 CGATAAGCTT GATATCGAAT TCCTGCAGCC CCTAAAATGC CATTGTTCA  AATGGATCAA
  181 ATTTCCCAAT TTTTATCATT TCGAGAAAA  TATGGTGTGC CTGAAGATGA ACTGTTTCAG
  241 ACAATTGATC TTTTTGAGAA AAAGGATCCT GCCATTGTTT TCCAAACGTT GAAGTCACTA
  301 TCTCGTTACG CCAACAAAAA ACATACAGAT AGATTTCCAG TTCTAGGACC ACAACTGTCA
  361 ACAAAGAAGC CAAGACCCCC GGTTAAGTCT AAACCAAAAC ATCTACAAGA TGGTACTGGA
  421 TGGAGCACTT TTGAATACGG TTATATGAAA GGTGCATCTC AGGCTACTGA AGGAGTGGTG
  481 TTAGGACAAC GGAGAGATAT AGTTTAGAGA ATTATTATTA ACACTTTCTC TGCCAGAAAT
  541 TGATAAATAA ACATTTAAGA ACCCTATATA CGCAACCAAA GTTCCTTTGA TATATTTAG
  601 TTTTCCATCA AAGTTTTCCT ACATAAACAC TAAGGTGGCT AGAGACGCGT AACAAAAGTT
  661 AACGTTACCG GTAAAAATGT GATTATACAA ATCAATCTCA CAGAACGGTG TGAAACAAA
  721 GTAGTTGAAG GATTTCAACT ATG CGAATCA ACAGTGAGCT AGCGAACAAG TTTTCTGCCT
  781 CAACGGTGCA CTTAGAACAT ATCACAACTG CTTTAAGTTG TTTAACACCT TTTGGTTCTA
  841 AAGACGATGT GCTTATATTC ATTGATGCTG ATGGGCTGTC ATGGCTGTGT ATTTGTCAGG GAGAATAATC
  901 ATGTGATAAA AATCCAACTA CTGTTATCTC GGGAGCTATT TAIGTCTTAT TCGTATAGAA
  961 ATGAAACTGA GGATCACATG AAACTTTGTG TAAAAATAAA TCATATCTTA GATAGCGTTA
 1021 GCGTGATGAA CAGGAATTCG GATGACATTG TTGAGTGTAC TTTATCTTAT GATGGACATG
 1081 GATCACCATT TGTACTAATA TTTGAAGACT CGTTCATTTC TGAGAGAGTG GAGTACTCTA
 1141 CCTACTTAAT TAAGGATTTT GATACTAATG GACTAGAACT CGATAGAGAA AGGATAAGCT
 1201 TTGAGGCAAT TATTAAGGGC GAAGCCCTTC ATTCAGCCTT AAAGGATCTA AAGAAATCGG
 1261 GATGCAAAGA GTGCTATGTA TATGCAAAGA CCGAGGCGAA TGATGAGAAT GTATTGCCC
 1321 TGATATCTAA ATCTCAGCTA GGATTTTCTA AATAAAATT  ACCCAGTAAC AGATCCATAC
 1381 TAGAGAAGTT ACAAGTATTT GACGGAGATT CCACAACAGT AATAGATGGT TTTGCTGTAA
 1441 TTGGGTTCTT CGATTTCACC TCGTTTGATA AAATCAGAAA GAGTACTAAA ATTGCAAGCA
 1501 AAGTCCTTTT CAGGATGGAT GTTCATGGCG TATTGAGTGT AAATATTCTA AGTCAAACAG
```

Fig. 4A.

```
1561 ACGATGTCAT TATCACTGAT ACTACAAGAC CTTCAAATAA TCGACCAGGT AGTATTCGCC
1621 AACTGCAGCT ACCCAAGGAT TATCCCGGTA TAGTAATTGA GGTTTGCATG CTAGAAAAAG
1681 AATCCATAGA TGAGGCAGCA CAGACAGAAA TAGAACTCCT GATGGAGACT AATGAACTTG
1741 GCAATCGTAA TAGTTTTAAA AAATCAACTA TAAGAAAAAG ATATGGTACA GATAAAGGCA
1801 ATGAAACTTC AAATGACAAC TTGCTGCAAT TGAATGGGAA AAAAATTAAA CTACCATCTG
1861 AAGAAGAAAA CAATAAAAAC AGGGAAAGTG AGGATGAAGA GAATCACTGC AAGTATCCAA
1921 CAAAGGATAT TCCTATATTT TTTTAAGTCA ATATCCAGCA TCGCAGAAAA CGCAGAACTT
1981 CATTCAGCAT TTGGTAATTT TATAACATAT AACTTACAAT TAAATAAAAG TTTAACTATA
2041 TATTATTATG TGATCTAACT CTAGAAAAAG TACTAATGAA CATCACACCG TTTATTGTTG
2101 GGAGAAGTGT TCCATGGGGG ATCCACTAGT TCTAGAGCGG CGCCACCGCG
```

*Fig. 4B.*

Yeast RAD24 cDNA Sequence

```
BASE COUNT    927 A    518 C    526 G    791 T    0 OTHER
ORIGIN    POSITION 1 OF ORF60.MV COPY
   1 ATATGGATAG TACGAATTTG AACAAACGGCC CTTATTACA ATATAGTCTC AGTTCATTGG
  61 GCTCGCAAAT AACAAAATGG AGCTCATCTA GACCGACTTC GCCAGTTCGT AAGGCGAGAA
 121 GCACTGAAAA TGACTTTCTT TCCAAGCAAG ATACGTCTAG TATCCTCCCA AGTATCAACG
 181 ACGACGGCGG TGAACAGTGG TACGAAAAGT TCAAGCCCAA TTGTTTGGAG CAAGTGCCCA
 241 TACATAAAAG AAAACTTAAA GATGTACAAG AAGCTTTAGA TGCCATGTTT TTACCTAACG
 301 CCAAGCATAG GATCCTACTA CTGTCTGGCC CCAGTGGATG CTCTAAAAGT ACGGTCATAA
 361 AAGAACTCTC AAAAATCTTA GTTCCTAAAT ACAGACAAAA CAGCAACGGA ACGTCCTTTC
 421 GAAGCACCCC GAACGAGCAT AAAGTGACCG AGTTTAGAGG TGATTGTATA GTCAACGATC
 481 TTCCTCAGAT GGAAAGCTTT AGTGAGTTCT TAAAAGGCGC ACGGTATCTT GTGATGTCCA
 541 ACCTGTCATT AATACTTATC GAGGACCCTC CCAACGTCTT CCATATAGAT ACCAGACGTC
 601 GATTTCAACA ACTTATATTA CAGTGGCTAT ATAGTTCGGA GCCTCTATTA CCTCCCCTTG
 661 TTATATGTAT AACTGAATGT GAAATTCCAG GAAACGATAA TAATTATCGC AAATTTGGTA
 721 TTGATTATAC ATTTAGTGCA GAAACCATAA TGAACAAAGA AATATTGATG CATCCAAGGT
 781 TGAAAAGAAT TAAGTTTAAT CCAATTAACA GCACTTTATT AAAAAAGCAC TTGAAATTTA
 841 TTTGTGTACA GAATATGAAA ATGTTGAAGG AGAAAAATAA ATGGAATAAA AGACAGGAAG
 901 TCATAGATTA TATTGCGCAA GAGACTGGTG ATATTAGGTC GGCCATTACG ACCCTTCAAT
 961 TTTGGGCGAC ATCAAGTGGA AGTTTGCCGA TTTCAACCCG AGAATCCACC ATATCATACT
1021 TTCATGCCAT TGGGAAGGTG ATACATGGTT CCCATAGCAC GAATAACGAT AACGAAATGA
1081 TTAATAACCT CTTCGAAAAT TCGAACAATT TGTTATCGAA AGAGGATTTC CATTTCTGAT AGAGGATTTC AAATTAGGAA
1141 TATTAGAGAA CTATAACACA TTTAATAAAG GCGAATTCAG CATTTCTGAT GCATCATCAA
1201 TTGTGGATTG CCTGAGCGAG TGTGATAATA TGAATGGTCT ACATCAGTAA AATGAGTATG
1261 GTTACGAGA AGTGCGCAAA ACCTTTCGTA ACATCAGTAA GAAAATTACA AAATTCATTT AAAGTTCAAG
1321 CGGTTTATTT TCCAAGAGAA TGGAAAGTAA AGAAAATTACA GGTACATTCT TTCAGGAATA
1381 CTGAAGATTG GTTAAATGTT AGTCTTTATA TACGCACCTC GTGTCAGAGT TATAAAAAAA
1441 TAACTCTAGA ATTTGGCTAC TACGCACCTC TAATTAGAAA GTGTCAGAGT TATAAAAAAA
1501 AATACATTCT CTATTATTTG AAGAATCTTC CGAGTGGCTC CTCGGGCCCC AAACAAACCA
1561 TGGACAAATT TAGTGATATA ATGAAAGTTG AGAACGGAAT CGACGTTGTG GATCGGATAG
```

Fig. 5A.

```
1621  GCGGGCCTAT CGAAGCACTA TCTGTGGAGG ATGGACTAGC ACCATTGATG GATAATGATA
1681  GCAATAATTG TGACCATTTA GAGGATCAAA AAAAGGAAAG GGACAGAAGG CTTCGCATGT
1741  TGATTGACCA ATATGAAAGA AATGTGATGA TGGCTAACGA CGATCTTGAA GACGAAGAAA
1801  CTTCTTTTAA TGATGACCCT ATTGTCGATA GCGAAGACGA TAACAGCAAT AATATTGGCA
1861  ATGAAACATT TGGTAGAAGC GACGAAGACG AGTCTCTATG TGAAATTCTG TCCCAGAGAC
1921  AGCCGCGTAA AGCGCCAGTT ATCAGTGAGT CCCTTTCAGA TTCAGATCTG GAAATACTCT
1981  AACTTTTTAC TCTTTAAATT TGACGAGAAA ACCCCAGGAA ATATTCCACA CAAATCTATG
2041  CACATTACAT TCTAGAATAA ATTAATAAAT AAAAATATAT TAAGGCTTAC TAATATGTAT
2101  ATATGTATGA ATATAGTTTT CATTACAAAA AATATCCAAA TGTAGAGCAT GTTGGAAATA
2161  TTCAGGATCT TCTTCTATAG ATTCCTTGAT AGAAAACTTC CCTCCCTGGA ACTCCCCATT
2221  GATATATAAC TGAGGAAAAG TAGGCCAATC CCTTATTTGG TTCAAGCTTT GTCTAACGTT
2281  TTCGTCTCTT AATATATCAA AAAATCCGAA TGATGGGCTT TGTTCTCTGA GGATACCAAC
2341  TAACTGTCTA GAAAATCCGC ATTTAGGTTC AGCATTTATT CCTTTCATGA ATAGCATCAC
2401  AGGTGCAGCT TGTACTAGCT TCACCAGCCT TCTTCTTCAG TTTCGTCCTC
2461  TTCATCATCG GAAGACCCGC TGCTTTCCTC ATCAGACGTA GATTAGGAC CCTTGGCATT
2521  GTTCGCTAGT GAGGCAGAAG CATTCGAAAG AATTTCTAAG CTTTTCACAA ACTCCTTAGG
2581  ATCTGCGGCT GATATTTCTT TTACAATAGT ACCATTTTGA ATGAAGACGA AGTATGGTAC
2641  GGCTGCAATC TCAAAAAGGT CTGATATTTC TGGATGTTCG TCTGCATCTA TTGATAAAAA
2701  CCGGACATCC TCTTGCCTAA CTTTTTCACT AACAGCTTCT AGCACCTGGC TCATAGTTTT
2761  GC
```

*Fig. 5B.*

Yeast MEC1 cDNA Sequence

```
LOCUS       MEC1.MV           8351 BP DS-
BASE COUNT     2835 A     1522 C     1557 G     2437 T     0 OTHER
ORIGIN      POSITION 1 OF MEC1.MV
    1 ATAAGCTTAC TGACCAAGAA AGAGCACGCG TGTTGGAGTT TCAAGATTCC ATTCACTATT
   61 CTCCGCGGTA CTCAGACGAT AACTATGAGT ACAGGCATGT GATGTTACCT AAGGCCATGC
  121 TAAAAGTTAT CCCATCTGAT TACTTCAATT CGGAAGTGGG GACCCTGCGT ATATTAACAG
  181 AAGACGAATG GAGAGGCCTC GGCATCACAC AGTCTTTGGG GTGGAACAT TATGAATGCC
  241 ATGCCCCAGA ACTACACATT TTGCTATTCA AAAGGCCGCT GAACTACGAG GCCGAGCTGA
  301 GGGCAGCGAC CGCTGCTGCT CAACAGCAAC AGCAACAGCA GCAACAGCAG CAACAACAAC
  361 AACAGCAACA TCAAACACAA TCGATTTCGA ACGATATGCA AGTTCCACCC CAAATCTCCT
  421 AGCTTTGATA TACTCTAATT ACTGAAATTG AATTCCTTTT CAAGGCTCCA TAACTATATG
  481 GAGCATACTA TGTACTTATC ATAATAAAGA ATAACAAAC AAGCAAACAA AAAAAAAAA
  541 AACTATGGAT CATAGTTTTC ACCAACAAGC ATTAGAATAC AAATAAAATT TATATAGTGA
  601 ATATCCTTCA AATAAAATTC TTCTTTCCCT TATAAATCAA ATAGATGGAA CGCACGCTCC
  661 AAAACTAGTC AACTAGAAAA AAATACCCGC CGACGGACAA TTTTGAAGAG AGATGATTAA
  721 TGAAGACAAA GTGAGGCTGG ACAACAAGAA CGACATACAC CGCGTAAAGG CCCACAAGAC
  781 TGCATGGAAT CACACGTCAA ATATCTTGAC GAATTGATAT TGGCAATAAA AGACCTGAAC
  841 TCGGGGGTGG ATTCAAAGGT GCAGATTAAA AAAGTGCCCA CGGATCCATC TTCTTCTCAG
  901 GAGTACGCCA AGAGTTTAAA GATCCTGAAC ACCCTCATAA GAAACCTAAA AGATCAAAGA
  961 AGGAACAATA TCATGAAAAA TGATACTATA TTTTCGAAAA CAGTTTCCGC CCTTGCCTTA
 1021 TTGTTGGAGT ACAACCCCTT CTTGCTTGTT ATGAAGGATT CCAACGGGAA CTTTGAGATA
 1081 CAAAGGCTGA TAGATGATTT CCTCAACATA TCCGTTCTGA ACTATGATAA TTACCACAGA
 1141 ATATGGTTTA TGAGGCGAAA ATTAGGCAGC TGGTGCAAAG CATGTGTCGA ATTTACGGA
 1201 AAACCTGCTA AGTTTCAGCT TACTGCACAT TTTGAGAACA CCATGAATCT TTACGAACAG
 1261 GCCTTGACTG AAGTCTTGTT GGGCAAGACT GAGCTTCTCA AATTTATGA CACCTTGAAG
 1321 GGTCTATACA TTCTTTTATA CTGGTTCACT TCGGAGTATA GTACTTTTGG GAACTCTATA
 1381 GCATTCTTAG ATTCTTCTTT GGGGTTCACG AAATTTGACT TTAACTTCCA ACGATTAATC
 1441 AGGATTGTTC TTTACGTCTT TGATTCCTGC GAACTAGCAG CACTAGAATA TGCCGAAATC
 1501 CAACTCAAAT ATATTTCTCT AGTTGTGGAC TATGTTTGCA ATAGAACAAT TTCCACAGCC
```

Fig. 6A.

```
1561  CTGGATGCCC  CAGCGTTAGT  TTGTTGTGAA  CAATTAAAGT  TTGTATTGAC  TACTATGCAT
1621  CATTTTTTGG  ATAACAAGTA  TGGGCTCTTG  GATAATGACC  CCACTATGGC  CAAAGGAATT
1681  CTTCGACTAT  ATTCTCTTTG  CATTTCTAAC  GATTTCTCAA  AATGCTTTGT  AGACCACTTC
1741  CCAATTGACC  AGTGGGCAGA  TTTTTCACAA  AGTGAACATT  TTCCGTTCAC  GCAGTTGACT
1801  AATAAAGCTC  TCTCGATTGT  ATATTTTGAT  TTGAAAAGAA  GGTCCCTACC  TGTTGAAGCT
1861  TTAAAGTACG  ATAATAAGTT  CAACATCTGG  GTATACCAAT  CGGAGCCGGA  CTCGAGCTTG
1921  AAAAATGTCA  CTTCTCCCTT  TGATGATCGA  TATAAGCAGC  TGGAAAAGCT  AAGGTTGCTA
1981  GTACTAAAGA  AGTTTAACAA  GACAGAAAGA  GGAACTTTGC  TCAAATACCG  CGTGAACCAG
2041  CTAAGTCCTG  GATTTTTTCA  AAGAGCTGGA  AACGATTTCA  AGCTAATTTT  AAATGAAGCA
2101  TCTGTATCCA  TTCAAACTTG  TTTCAAGACA  AACAATATAA  CAAGGCTAAC  ATCATGGACT
2161  GTAATTCTCG  GACGTCTAGC  CTGTCTAGAA  TCAGAGAAGT  TTTCCGGCAC  TCTGCCAAAT
2221  TCCACAAAGG  ATATGGATAA  TTGGTATGTT  TGTCATTTAT  GCGATATTGA  GAAAACTGGC
2281  AACCCTTTCG  TGCGAATAAA  TCCAAATAGA  CCAGAGGCTG  CGGGTAAATC  AGAAATCTTC
2341  AGGATACTTC  ATTCAAACTT  TCTATCTCAC  ATATTTTCAC  ATGAATTTAG  CGAATCTTTG
2401  TTAAGTGGCA  TCTTATTTTC  TCTACATAGG  TTTAAACTGG  ACTTTCAACC  TCCAAAACTT
2461  ACAGATGGAA  ACGGTCAAAT  CAATAAGAGC  TTTAAACTGG  TACAAAGTG   CTTTATGAAT
2521  TCTAACAGAT  ACCTACGTTT  ATTAAGTACT  AGAATTATAC  CTTTATTCAA  TATATCAGAC
2581  TCTCATAATT  CCGAAGATGA  ACACACTGCC  ACGCTGATAA  AGTTTCTACA  ATCTCAAAAA
2641  TTGCCAGTGG  TGAAAGAAAA  TTTAGTCATT  GCTTGGACAC  AATTAACATT  GACGACTTCT
2701  AATGATGTAT  TTGATACACT  ACTTTTGAAA  CTGATTGATA  TTTTCAATTC  TGATGATTAT
2761  AGTTTACGAA  TAATGATGAC  TTTGCAAATT  AAAAATATGG  CCAAAATTTT  AAAGAAAACA
2821  CCATATCAAT  TACTATCGCC  TATTTTACCT  GTATTACTAA  GACAGTTGGG  AAAAACCTC
2881  GTGGAAAGAA  AAGTTGGCTT  TCAAAATTTA  ATAGAATTAT  TGGGATATCC  TTCAAAAACA
2941  ATTCTCGATA  TTTTCCAGAG  ATATATCATC  CCTTATGCAA  TTATTCAATA  TAAGAGCGAT
3001  GTGCTAAGTG  AAATTGCTAA  GATTATGTGT  GATGGCGATA  CAAGTTTAAT  TAACCAAATG
3061  AAGGTTAATT  TACTGAAAAA  AAACAGTAGG  CAAATATTTG  CCGTAGCTTT  GGTAAAACAC
3121  GGATTATTTT  CTTTGGATAT  CTTGGAAACC  CTTTTTTAA   ATAGGGCTCC  AACTTTTGAC
3181  AAAGGATATA  TAACTGCATA  CCTTCCCGAT  TATAAAACTT  TAGCTGAAAT  AACGAAGCTC
3241  TACAAAAACA  GCGTTACTAA  AGATGCAAGT  GACAGCGAGA  ATGCTAATAT  GATTTATGC
3301  TCTTTGCGAT  TTTAATCAC   CAATTTGAA   AAAGACAAAA  GGCATGGTTC  GAAGTACAAA
3361  AATATCAATA  ACTGGACGGA  TGATCAGGAA  CAAGCGTTCC  AAAAGAAACT  ACAGGATAAT
```

*Fig. 6B.*

```
3421  ATCTTAGTTA  TTTTCCAAGT  TTTTTCGAGT  GACATACATG  ATGTTGAAGG  CCGCACCACT
3481  TACTACGAAA  AGTTAAGGGT  TATCAATGGC  ATTTCTTTTC  TTATCATATA  TGCCCCCAAA
3541  AAATCAATAA  TTTCCGCATT  AGCCCAGATT  AGTATTTGTT  TGCAAACAGG  ACTTGGGCTT
3601  AAGGAAGTTC  GATACGAGGC  CTTTAGATGT  TGCCATCTGT  TAGTTCGCCA  TCTAAATGAT
3661  GAAGAACTCT  CTACTGTTAT  AGATAGCTTA  ATTGCATTCA  TACTTCAAAA  GTGGTCTGAG
3721  TTCAACGAAA  AACTTCGAAA  TATAGTGTAC  AGTATACTGG  ATACCTTAAT  CAAAGAGAAA
3781  TCGGACCTGA  TTTTGAAATT  AAAACCTTAC  ACTACTTTGG  CTTTAGTAGG  CAAGCCTGAA
3841  TTAGTTATTT  TAGCTCGTGA  TGGCCAATTT  GCAAGAATGG  TGAATAAAAT  AAGAAGTACC
3901  ACGGACCTTA  TACCCATATT  TGCTAATAAC  TTGAAAAGTA  GTAACAAGTA  TGTCATAAAC
3961  CAAAATTTAG  ACGATATAGA  GGTATATCTT  CGGAGAAAGC  AGACAGAAAG  ATCGATTGAT
4021  TTTACACCAA  AGAAGGTTGG  GCAAACTTCT  GATATAACAT  TAGTTTTGGG  TGCTTTATTA
4081  GACACTTCTC  ATAAGTTTAG  AAATTTAGAC  AAGGACCTAT  GCGAGAAGTG  CGCCAAATGT
4141  ATCAGTATGA  TTGGTGTTTT  AGACGTTACA  AAGCATGAGT  TTAAAAGAAC  AACATATTCA
4201  GAAAACGAAG  TTTATGATTT  GAATGATAGT  GTTCAAACTA  TTAAGTTCTT  GATATGGGTC
4261  ATAAATGATA  TCCTCGTTCC  TGCGTTTTGG  CAAAGTGAGA  ATCCCAGCAA  GCAATTGTTT
4321  GTTGCCCTTG  TCATACAGGA  ATCATTAAAA  TATTGCGGGC  TAAGTTCAGA  GTCATGGGAT
4381  ATGAACCATA  AAGAATTATA  TCCAAATGAA  GCCAAACTAT  GGGAAAAGTT  TAACTCTGTC
4441  TCCAAGACAA  CCATCTATCC  GCTTTTATCT  TCCTTGTATC  TTGCGCAATC  ATGGAAAGAA
4501  TATGTCCCGC  TAAAATATCC  TTCTAATAAC  TTCAAGGAAG  GATACCAAAT  TTGGGTGAAA
4561  AGTTTACAT   TGGATTTATT  GAAAACAGGT  ACAACAGAAA  ATCATCCAGG  ACACGTGTTT
4621  TCCTCTTTGA  TTAGGGAAGA  TGATGGCTCA  CTATCAAATT  TTTTGCTACC  TTATATTTCT
4681  CTGGACATTA  TTATCAAGGC  AGAAAAAGGA  ACTCCATACG  CTGATATTTT  AAACGGATT
4741  ATTATTGAAT  TTGACAGCAT  TTTCACGTGC  AATCTGGAAG  GAATGAATAA  CTTGCAAGTG
4801  GATTCGTTAA  GAATGTGCTA  TGAATCCATC  TTCAGAGTTT  TCGAATATTG  CAAAAAATGG
4861  GCAACTGAGT  TTAAACAAAA  TTACAGTAAA  CTACACGGCA  CTTTATCAT   TAAAGATACG
4921  AAAACAACTA  ACATGCTTTT  GAGAATAGAT  GAGTTTTTGC  GAACAACCCC  TTCAGATTTG
4981  CTAGCTCAAC  GCTCCTTAGA  GACGATTCT   TTTGAAAGGT  CTGCTCTATA  CCTTGAACAG
5041  TGCTATCGAC  AGAATCCTCA  CGATAAGAAC  CAAAATGGAC  AACTACTGAA  AAATTACAA
5101  ATCACATACG  AAGAAATAGG  AGACATTGAC  TCACTCGATG  GTGTACTGAG  AACCTTTGCT
5161  ACAGGAAACT  TGGTTTCTAA  AATTGAAGAA  TTGCAATATT  CTGAAAACTG  GAAACTCGCA
5221  CAAGACTGCT  TTAATGTCCT  CGGCAAATTT  TCAGATGACC  CCAAAACTAC  AACCAGGATG
```

*Fig. 6C.*

```
5281 CTAAAGTCTA TGTATGACCA CCAATTGTAT TCTCAAATAA TATCGAACTC TTCGTTCCAT
5341 TCTTCAGACG GAAAAATTTC TTTGTCTCCA GATGTGAAGG AATGGTACAG CATAGGTCTT
5401 GAAGCTGCAA ATCTAGAAGG CAATGTTCAA ACTTTGAAAA ATTGGGTAGA ACAAATAGAG
5461 AGTTTAAGAA ATATTGACGA TAGAGAAGTA CTTTTGCAGT ACAATATTGC GAAAGCTTTA
5521 ATTGCCATCT CAAACGAGGA TCCATTAAGG ACTCAAAAAT ACATCCACAA TTCCTTTAGG
5581 CTTATCGGAA CAAATTTTAT AACGTCATCT AAAGAGACGA CGCTGCTAAA GAAACAGAAT
5641 TTATTGATGA AATTACACAG TTTATATGAC CTCAGTTTTT TATCTTCTGC GAAAGATAAG
5701 TTTGAATACA AAAGTAACAC TACCATACTC GATTATCGAA TGGAACGTAT TGGGGCTGAC
5761 TTCGTGCCAA ATCATTACAT ATTGTCAATG AGAAAGTCAT TTGACCAATT GAAAATGAAT
5821 GAACAAGCAG ACGCTGACTT AGGAAAAACA TTCTTCACTT TAGCCCAATT GGCGAGAAAC
5881 AACGCTAGGC TAGATATAGC CTCCGAATCA TTAATGCATT GTTTGGAAAG GCGGTTGCCT
5941 CAGGCAGAGT TGGAGTTTGC TGAAATACTA TGGAAGCAAG GTGAGAATGA TAGAGCCTTA
6001 AAGATAGTGC AAGAAATACA TGAAAAGTAT CAAGAAAATT CCTCGGTTAA TGCTCGCGAT
6061 CGTGCCGCCG TGCTATTAAA GTTTACTGAA TGGTTAGACC TTTCGAACAA TTCAGCGTCC
6121 GAACAAATTA TTAAACAATA TCAGGATATT TTTCAGATTG ATTCTAAATG GGATAAACCA
6181 TATTACTCTA TTGGCTTATA CTATAGTAGA CTACTTGAGC GCAAAAAAGC AGAGGGTTAT
6241 ATTACTAATG GTCGTTTTGA GTACAGGGCA ATATCTTACT TTTTATTGGC ATTTGAAAAG
6301 AACACTGCTA AAGTAAGAGA AAATTTGCCC AAAGTTATCA CGTTTTGGCT AGATATTGCG
6361 GCCGCATCAA TTTCTGAAGC TCCTGGAAAC AGGAAGGAAA TGCTGAGTAA GGCTACGGAA
6421 GATATATGTA GTCATGTTGA AGAAGCGCTG CAGCATTGTC CCACTTATAT TTGGTACTTT
6481 GTTTTGACTC AGTTGTTATC TAGGTTATTA CATTCTCATC AATCATCGGC CCAGATAATA
6541 ATGCACATAC TGCTAAGTTT GGCTGTTGAA TACCCCTCTC ATATTTTATG GTATATCACA
6601 GCCCTTGTAA ATTCCAATTC TTCAAAAAGA GTTCTTCGTG GTAAGCATAT TTTAGAAAAG
6661 TATAGACAAC ATTCGCAAAA TCCTCATGAT CTAGTTTCTA GTGCATTGGA TTTAACGAAA
6721 GCATTAACTC GTGTCTGTTT GCAAGATGTC AAAAGCATTA CAAGTAGATC AGGCAAATCT
6781 TTAGAAAAAG ACTTCAAATT TGACATGAAC GTGGCCCCAT CTGCAATGGT TGTTCCAGTA
6841 AGAAAAAATT TAGACATCAT TTCACCACTA GAGTCTAACT CAATGAGGGG CTATCAACCA
6901 TTTAGGCCGG TTGTTTCTAT AATTAGATTC GGATCATCTT ATAAAGTGTT TTCTTCATTA
6961 AAGAAGCCAA AACAATTGAA CATAATAGGT TCAGATGGCA ACATTATGG GATCATGTGT
7021 AAGAAGGAAG ATGTCCGACA AGATAACCAA TATATGCAGT TCGCCACAAC AATGGATTTT
7081 CTTCTGAGTA AGGACATAGC TTCAAGAAAA AGAAGCCTGG AGAAGCCTAC TTACTACCGT
```

Fig. 6D.

| | | | | |
|---|---|---|---|---|
|7141|ACTATCTCTT|CGAGAAGACT|GTGGGATATT|GGAAATGGTA|CCGAATGTTG|TAACTTTAAG|
|7201|ATCTATTCTT|TCTACAAGTA|CGAAAGTCTG|AAAATTAAGT|ATAGCCTGAA|AAGTCTACAT|
|7261|GATAGGTGGC|AGCACACCGC|AGTAGATGGA|AAACTCGAGT|TTTACATGGA|ACAGGTAGAT|
|7321|AAATTCCCTC|CAATCTTGTA|CCAATGGTTT|TTCCTGATCC|TTTACATGGA|AATCAATTGG|
|7381|TTCAACGCCA|GGAATACGTA|TGCCAGATCT|TACGCCGTCA|TGGCAATGGT|TGGCCATATA|
|7441|TTAGGTCTAG|GTGATAGGCA|CTGTGAAAAC|ATATTACTAG|ATATACAGAC|GGGTAAAGTT|
|7501|CTTCATGTAG|ACTTCGACTG|TTTATTTGAG|AAAGGCAAAA|GGTTACCTGT|CCCAGAAATT|
|7561|GTTCCCTTCA|GACTAACACC|AAATTTATTG|GATGCGTTGG|GCATAATTGG|GACAGAAGGA|
|7621|ACATTTAAGA|AGTCTAGTGA|AGTCACGTTG|GCTTTAATGA|GAAAAAATGA|AGTAGCGTTG|
|7681|ATGAATGTGA|TCGAAACAAT|TATGTACGAT|AGAAACATGG|ACCACTCAAT|TCAAAAAGCG|
|7741|CTAAAGGTCT|TAAGAAACAA|AATCCGCGGT|ATAGATCCGC|AGGATGGCCT|GGTATTGAGT|
|7801|GTTGCTGGCC|AAACAGAAAC|ATTGATCCAA|GAAGCAACAT|CAGAAGACAA|TCTAAGCAAG|
|7861|ATGTATATTG|GTTGGCTTCC|ATTTTGGTAA|CGACTTTCCA|CCATTTCGG|CAACAGACGA|
|7921|ACTTCCTCTT|GATCTAACCA|TCACTGCAGG|TGCTTTTCTC|CGGCGGAGTT|AATAGATACT|
|7981|TATCCCCGCT|TCATGTCATA|CTATCTCTCT|TAACAGGGAT|GTTGACACCA|TATAAGTTAA|
|8041|CATAACATAT|ACGTACGTAA|TAATATTAAG|GACTATCTCC|GATTTCAAAA|GAGAAACAAC|
|8101|CTAATCAAGC|CTTATTATAA|GAGCAAATTA|TTCAAAAAAA|GTCTACGGAG|AAAATTATTA|
|8161|TGGTGGTTTT|AGACAAGAAG|TTATTGGAAA|GATTGACTTC|TCGTAAGGTT|CCTTAGAAGA|
|8221|GCTCGAAGAT|ATGGAAAACG|ATGCTTGTTG|TCTACTTTAC|ATAACAAGAT|GCCTTGATTG|
|8281|GGACTTACAT|AAGAAATGCG|TTAAGAATTT|CCCGAACAGT|TGCATGTATA|TCTCTTCCAA|
|8341|ATGGCTCGTG|T| | | | |

*Fig. 6E.*

Yeast MEC2 cDNA Sequence

```
LOCUS        MEC2 SEQUE      2934 BP DS-
BASE COUNT    1025 A    501 C    637 G    771 T    0 OTHER
ORIGIN       POSITION 1 OF MEC2 SEQUENCE
   1 ATTAATAGCC TGCTTCCTTT TAATTAAGCC GGAAAGTGTT TGTCACAGAT GTCAATGAAA
  61 CGTGCATCTA TTAACATATT TATTTTCATT TCGAGGGTGA GGTGGTGTGG ACGCGTTGAT
 121 ACGGCAACGG GAGTGACGCG TAAAATTGGC AGAAAAATCA TCACCGTGGG TAGACTTGGA
 181 AATGAAAACA TTTATAGAAT AAAGGTACAG GTTGAGAAGA TAAAGGGTAC CAAAGTTACC
 241 ATTTTGAAAT CTCTGATCAA GAAAAGGTAA GAAAGCAGAA AAGGACGGTA GAGATTATTG
 301 GAAGACAAAC TAATTTTGTA TATGCATTCG ATTTTCTTAA GCTTTAAAAG AGAGAATAGT
 361 GAGAAAAGAT AGTGTTACAC AACATCAACT AAAAATGAA AATATTACAC AACCCACACA
 421 GCAATCCACG CAGGCTACTC AAAGGTTTTT GATTGAGAAG TTTTCTCAAG AACAGATCGG
 481 CGAAAACATT GTGTGCAGGG TCATTTGTAC CACGGGTCAA ATTCCCATCC GAGATTTGTC
 541 AGCTGATATT TCACAAGTGC TTAAGGAAAA ACGATCCATA AAGAAAGTTT GGACATTTGG
 601 TAGAAACCCA GCCTGTGACT ATCATTTAGG AAACATTTCA AGACTGTCAA ATAAGCATTT
 661 CCAAATACTA CTAGGAGAAG ACGGTAACCT TTTATTGAAT GACATTTCCA CTAATGGGAC
 721 CTGGTTAAAT GGGCAAAAAG TCGAGAAGAA CAGCAATCAG TTACTGTCTC AAGGTGATGA
 781 AATAACCGTT GGTGTAGGCG TGGAATCAGA TATTTTATCT CTGTCATTT TCATAAACGA
 841 CAAATTTAAG CAGTGCCTCG AGCAGAACAA AGTTGATCGC ATAAGATCTA ACCTGAAAAA
 901 TACCTCTAAA ATAGCTTCTC CTGGTCTTAC ATCATCTACT GCATCATCAA TGGTGCCAA
 961 CAAGACTGGT ATTTTTAAGG ATTTTTCGAT TATTGACGAA GTGGTGGGCC AGGGTGCATT
1021 TGCCACAGTA AAGAAAGCCA TTGAAAGAAC TACTGGGAAA ACATTCGCGG TGAAGATTAT
1081 AAGTAAACGC AAAGTAATAG GCAATATGGA TGGTGTGACA AGAGAGTTAG AAGTATTGCA
1141 AAAGCTCAAT CATCCAAGGA TAGTACGATT GAAAGGATTT TATGAAGATA CTGAGAGTTA
1201 TTATATGGTG ATGGAGTTCG TTTCTGGTGG TGACTTAATG GATTTTGTTG CTGCTCATGG
1261 TGCGGTTGGA GAAGATGCTG GGAGGGAGAT ATCCAGGCAG ATACTCACAG CAATAAAATA
1321 CATTCACTCT ATGGGCATCA GCCATCGTGA CCTAAAGCCC CTTTGGTCTG TTATTGAACA
1381 AGACGATCCT GTATTGGTAA AGATAACCGA CTTTGGTCTG GCAAAAGTAC AAGGAAATGG
1441 GTCTTTTATG AAAACCTTCT GTGGCACTTT GGCATATGTG GCACCTGAAG TCATCAGAGG
1501 TAAAGATACA TCCGTATCTC CTGATGAATA CGAAGAAAGG AATGAGTACT CTTCGTTAGT
```

Fig. 7A.

```
1561 GGATATGTGG TCAATGGGAT GTCTTGTGTA TGTTATCCTA ACGGGCCACT TACCTTTTAG
1621 TGGTAGCACA CAGGACCAAT TATATAAACA GATTGGAAGA GGCTCATATC ATGAAGGGCC
1681 CCTCAAAGAT TTCCGGATAT CTGAAGAAGC AAGAGATTTC ATAGATTCAT TGTTACAGGT
1741 GGATCCAAAT AATAGGTCGA CAGCTGCAAA AGCCCTTGAAT CATCCCTGGA TCAAGATGAG
1801 TCCATTGGGC TCACAATCAT ATGGTGATTT TTCACAAATA TCCTTATCAC AATCGTTGTC
1861 GCAGCAGAAA TTATTAGAAA ATATGGACGA TGCTCAATAC GAATTTGTCA AAGCGCAAAG
1921 GAAATTACAA ATGGAGCAAC AACTTCAAGA ACAGGATCAG GAAGACCAAG ATGGAAAAAT
1981 TCAAGGATTT AAAATACCCG CACACGCCCC TATTCGATAT ACACAGCCCA AAAGCATTGA
2041 AGCAGAAACT AGAGAACAAA AACTTTTACA TTCCAATAAT ACTGAGAATG TCAAGAGCTC
2101 AAAGAAAAAG GGTAATGGTA GGTTTTTAAC TTTAAAACCA TTGCCTGACA GCATTATTCA
2161 AGAAAGCCTG GAGATTCAGC AAGGTGTGAA TCCATTTTTC ATTGGTAGAT CCGAGGATTG
2221 CAATTGTAAA ATTGAAGACA ATAGGTTGTC TCGAGTTCAT TGCTTCATTT TCAAAAAGAG
2281 GCATGCTGTA GGCAAAAGCA TGTATGAAAT TCCGGCACAA GGTTTAGATG ATATTGGTTA
2341 TTGCCACACC GGAACTAACG TGAGCTATTT AATAATAAC CGCATGATAC AGGGTACGAA
2401 ATTCCTTTTA CAAGACGGAG ATGAAAATCAA GATCATTTGG GATAAAAACA ATAAATTGT
2461 CATTGGCTTT AAAGTGGAAA TTAACGATAC TACAGGTCTG TTTAACGAGG GATTAGGTAT
2521 GTTACAAGAA CAAAGAGTAG TACTTAAGCA AACAGCCGAA GAAAAAGATT TGGTGAAAAA
2581 GTTAACCCAG ATGATGGCAG CTCAACGTGC AAATCAACCC TCGGCTTCTT CTTCATCAAT
2641 GTCGGCTAAG AAGCCGCCAG TTAGCGATAC GGCAATAATT CGGTACTAAA
2701 CGACTTGGTA GAGTCACCGA TAATGCGAA TACGGGGAAC ATTTGAAGA GAATACATTC
2761 GGTAAGTTTA TCGCAATCAC AAATTGATCC TAGTAAGAAG GTTAAAAGGG CAAAATTGGA
2821 CCAAACCTCA AAAGGCCCCG AGAATTTGCA ATTTTCGTAA CCAAGGACAA ATACCCATAG
2881 AAAATGCTGC CCCTTTTTAA GAGAGAAGAT GGTAGATACC AATACTCAGA ATTC
```

*Fig. 7B.*

Yeast MEC3 cDNA Sequence

```
LOCUS       MEC3.MV              3551 BP DS-
BASE COUNT  1110 A    640 C    704 G    1097 T    0 OTHER
ORIGIN      POSITION 1 OF MEC3.MV
```

```
   1 AACTTCTTCA AATGCAGCGA TAGCTTGGAA CACACCTTCC AAGTCTTTGC AAGGGATGAC
  61 CACTTCATGT GTCGACGAAC TTTCCTGTTC AGCCTTTTCC ACCATAACGG ATATGTCATT
 121 AAATTCAGTA TCACCGCTAG TATCAGCTGT GTAAATGTTT CCCCGCGTAT CTGGCATCGA
 181 GCTATCCTCA ATTCTTAATA AATCTTCATC GTAGCGGATA TTCTCTTCCA TCTCTCGATC
 241 TCTAGTATTG GTATATAGTG AAGACATCGG TTTATCCGCT TCGATAATCG GAAGAGATCC
 301 TTCCTCCTGC CGGCCGTCTG TGTCGATGTG CTGGTTTTGG GAAGGATTGT CAGTGAGCCC
 361 TTCTTGGCGT TGTATCACAG AATCTAAGGG TCCATTCCAA CATATTTCCA AATGCCAATC
 421 TAATTCATTC ACAATTATCT TGAGTTCTAC ATCATCACCT TCATTTCCAT GCTCCTTTTT
 481 TTTGACTCCC ATTAAATGAA TGTGGTTGAC ATTGCTGTAC CGTTCAACAC GTCTAATGAA
 541 CCCGTGGAAG CGGAGCCAAA CTCACCCGAT ATTGGTGGTA GCTTGTACAT CATCAGTTGA
 601 ATATAGTTAA TCATTGGCTC TTGTATTCGC GTATGCTTGT GCTCGGAATA ATAGTTTGAC
 661 AGGTACTTTG AACGAATGAT ATAACCTTAT TGCTTGCTAG TAGATTTCCT GTGCCTACTG
 721 TGGTTGGTAA ACCATTGTGC TCATCCACTC CCCCATCCAT AACTATAGCG TCATTGGGC
 781 CGCTGGTATG TACAATTTCT TCGAATGTTA TACCTAAAGC ACAAATGGGG TTCGTTTTG
 841 AGGTTGTATC TACGCCTCCT GCTGTTCCTC CTGAAAGTGT TCCGTTATTT GTATTCCATT
 901 CTGGCATTGA CTGTAGTTTT ATAATCATAT TAGAGAAGAT CCTTGGTTCA TTACTCGATC
 961 ATATCTTTTA AACACACTCA ATAAACAATC ACAATTGACA CTCCATTGTT ATTGTATTAA
1021 GCTCGCGAGC TGATATAACT GTTATATAAT CTGAATACAT CATGAGGAAT GGTACACCAA
1081 AGCTGACCAG TATCCCCTCG TAATATTGTA CCGTTGTTAC TGCTGTTGAG TGATGATTTT
1141 GGAGTGGATA TTATTGTCAA TCTTTCACTA TTAAATCTTA AGATAGCCGT CTTTCGTAGC
1201 GAACGAACTG TATTGATAGT AGTTCTTAGC AATTTATAAT CATCAGGTGC TTCACAACCA
1261 TTTACTATCA ATTTTAATTT CATTTAACTG AATTAAGACA CACCTTTTGT CTTCTTTTTT
1321 CTCTCATCAT CTCCGTATGT TTATCTTGCT ATTTGATGT AAATAAAAAA GTTGAATAAT
1381 AGACGAGGGC AAGTATAACT CGCCTATATT GTAGCCGCAA CCATTGAAAA AAAGCCATGA
1441 ATATGAGAAA ATAGTTGCAC ATAAAATG TGAAATTTAG AATTAGGCCA AATAGACATA
1501 TACGGTGTTA TAAACGACAC GCATATTTCT TACGATATAA CCATACGACT ACCCCTGCAC
```

Fig. 8A.

```
1561  AGAAGTTACA  AGCACAGATC  GAGCAAATAC  CTCTCGAAAA  TTACAGAAAT  TTTTCTATAG
1621  TTGCCCATGT  TGACCATGGG  AAGTCAACCT  TAAGTGACAG  ACTGCTGGAA  ATAACGCATG
1681  TCATCGATCC  CAATGCGAGA  AATAAACAAG  TTTTGGATAA  ATTGGAAGTC  GAAAGAGAAA
1741  GAGGTATTAC  TATAAAGGCG  CAAACATGTT  CGATGTTTTA  TAAAGATAAG  AGGACCGGAA
1801  AAAACTATCT  TTTACATTTA  ATTGACACGC  CAGGACATGT  GGACTTCAGA  GGTGAAGTTT
1861  CACGGTCATA  TGCGTCTTGT  GGGGGAGCAA  TTCTTTTGGT  TGATGCATCA  CAAGCATAC
1921  AAGCACAGAC  GGTTGCTAAT  TTTTATTTAG  CCTTTCAGTTT  AGGATTGAAA  TTGATTCCAG
1981  TAATAAACAA  AATTGATCTC  AATTTTACAG  ATGTTAAACA  GGTAAAGGAT  CAGATAGTGA
2041  ATAACTTTGA  GCTCCCCGAG  GAAGATATAA  TCGGAGTAAG  TCGTAAAACA  GCATTAAATG
2101  TAGAGGAACT  GTTACTACCG  GCTATAATTG  ATCGTATACC  ACCACCAACT  GGGAGGCCTG
2161  ATAAACCCTT  CAGAGCATTA  TTAGTGGATT  CTTGGTACGA  CGCATACTTA  GGAGCGGTTC
2221  TTCTAGTGAA  TATTGTTGAT  GGTTTTGTAC  GTAAAAATGA  CAAAGTTATT  TGTGCTCAGA
2281  CAAAAGAAAA  ATACGAAGTC  AAAGATATTG  GAATCATGTA  TCCTGACAGA  ACTTCTACAG
2341  GTACGCTAAA  GACAGGACAA  GTTGGCTATC  TAGTGCTGGG  AATGAAGGAT  TCTAAAGAAG
2401  CAAAAATTGG  AGATACTATA  ATGCATTTAA  GTAAAGTAAA  TGAAACGGAA  GTACTTCCCG
2461  GATTTGAAGA  ACAAAAACCC  ATGGTATTTG  TGGGTGCTTT  CCCGGCTGAT  GGGATTGAAT
2521  TCAAACCCAT  GGATGATGAT  ATGAGTAGAC  TTGTTCTCAA  CGATAGGTCA  GTTACTTTGG
2581  AACGTCAGAC  CTCCAATGCT  TTGGGTCAAG  GTTGGAGATT  GGGCTTTTTA  GGATCTTTAC
2641  ATGCATCTGT  TTTTCGTGAA  CGACTAGAGA  AAGAGTATGG  TTCGAAATTG  ATCATTACTC
2701  AACCCACAGT  TCCTTATTTG  GTGGAGTTTA  CCGATGGTAA  GAAAAAACTT  ATAACAAATC
2761  CGGATGAGTT  TCCAGACGGA  GCAACAAAGA  GGGTGAACGT  TGCTGCTTTC  CATGAACCGT
2821  TTATAGAGGC  AGTTATGACA  TTGCCCCAGG  AATATTAGG   TAGTGTCATA  CGCTTATGCG
2881  ATAGTAATAG  AGGAGAACAA  ATTGATATAA  CATACCTAAA  CACCAATGGA  CAAGTGATGT
2941  TAAAATATTA  CCTTCCGCTA  TCGCATCTAG  TCGATGACTT  TTTTGGTAAA  TTAAAATCGG
3001  TGTCCAGAGG  ATTTGCCTCT  TTAGATTATG  AGGATGCTGG  CTATAGAATT  TCTGATGTTG
3061  TAAAACTGCA  ACTCTTGGTT  AATGGAAATG  CGATTGATGC  CTTGTCAAGA  GTACTTCATA
3121  AATCGGAAGT  AGAGAGAGTG  CGTAGAGAAT  GGGTAAAGAA  GTTAAAGAG   TATGTTAAAT
3181  CACAATTATA  TGAGGTCTTA  TACAGGCCCG  AGCTAATAAC  AAGA[TAA]TCG  CTAGAGAAAC
3241  AATTAAGGCA  AGAAGAAAAG  ATGTTCTCCA  AAAGCTGCAT  GCTTCTGATG  TCTCACGAAG
3301  GAAAAAACTT  TTGGCGAAAC  AGAAAGAGGG  AAAAAGCATA  TGAAAACTGT  AGGTAATATT
3361  CAAATCAACC  AAGAGGCATA  TCAGGCTTTT  TTGCGCCGTT  AGCATTGCAT  ATTATTGTTA
```

*Fig. 8B.*

```
3421 TTACCATTTT AAAATTATAC CAAGCTGTAC ATAGTTAAGT ACTTTTCATT TGTAAATAAA
3481 AGAGAAAAAT AGATTAATAA ATATTATAAT GACATAACAT TATGCTTTAA GTATTCTCA
3541 AGTGTAACTA C
```

Fig. 8C.

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 1023 base pairs
        ( B ) TYPE: nucleic acid
        ( C ) STRANDEDNESS: single
        ( D ) TOPOLOGY: linear ( i i ) MOLECULE TYPE: cDNA to mRNA
        ( A ) DESCRIPTION: yeast RAD17 cDNA ( i i i ) HYPOTHETICAL: NO ( i v ) ANTI-SENSE: NO ( v i ) ORIGINAL SOURCE:
        ( A ) ORGANISM: Saccharomyces cerevisiae ( x i ) SEQUENCE DESCRIPTION: SEQ ID NO:1:

```
AGCAGGAATT  GGTAACGCCA  GGTTTTCCCG  ATCAGACGTT  GTAAAACAGG  CCAGTGAATT        60
GTAATACGAC  TCACTATAGG  GCGAATTGGG  TACCGGGCCC  CCCCTCGAGG  TCGACGGTAT       120
CGATAAGCTT  GATATCGAAT  TCCTGCAGCC  CCTAAAATGC  CATTGTTCA   AATGGATCAA       180
ATTTCCCAAT  TTTTATCATT  TTCGAGAAAA  TATGGTGTGC  CTGAAGATGA  ACTGTTTCAG       240
ACAATTGATC  TTTTTGAGAA  AAAGGATCCT  GCCATTGTTT  TCCAAACGTT  GAAGTCACTA       300
TCTCGTTACG  CCAACAAAAA  ACATACAGAT  AGATTTCCAG  TTCTAGGACC  ACAACTGTCA       360
ACAAAGAAGC  CAAGACCCCC  GGTTAAGTCT  AAACCAAAAC  ATCTACAAGA  TGGTACTGGA       420
TGGAGCACTT  TTGAATACGG  TTATATGAAA  GGTGCATCTC  AGGCTACTGA  AGGAGTGGTG       480
TTAGGACAAC  GGAGAGATAT  AGTTTAGAGA  ATTATTATTA  ACACTTTCTC  TGGCAGAAAT       540
TGATAAATAA  ACATTTAAGA  ACCCTATATA  CGCAACCAAA  GTTCCTTTGA  TATATTTTAG       600
TTTTCCATCA  AAGTTTTCCT  ACATAAACAC  TAAGGTGGCT  AGAGACGCGT  AACAAAAGTT       660
AACGTTACCG  GTAAAAATGT  GATTATACAA  ATCAATCTCA  CAGAACGGTG  TGGAAACAAA       720
GTAGTTGAAG  GATTTCAACT  ATGCGAATCA  ACAGTGAGCT  AGCGAACAAG  TTTTCTGCCT       780
CAACGGTGCA  CTTAGAACAT  ATCACAACTG  CTTAAGTTG   TTTAACACCT  TTTGGTTCTA       840
AAGACGATGT  GCTTATATTC  ATTGATGCTG  ATGGGCTGTC  ATTTGTCAGG  GAGAATAATC       900
ATGTGATAAA  AATCCAACTA  CTGTTATCTC  GGGAGCTATT  TATGTCTTAT  TCGTATAGAA       960
ATGAAACTGA  GGATCACATG  AAACTTTGTG  TAAAAATAAA  TCATATCTTA  GATAGCGTTA      1020
GCG                                                                         1023
```

( 2 ) INFORMATION FOR SEQ ID NO:2:

( i ) SEQUENCE CHARACTERISTICS:
        ( A ) LENGTH: 1021 base pairs
        ( B ) TYPE: nucleic acid
        ( C ) STRANDEDNESS: single
        ( D ) TOPOLOGY: linear ( i i ) MOLECULE TYPE: cDNA to mRNA
        ( A ) DESCRIPTION: yeast RAD24 cDNA ( i i i ) HYPOTHETICAL: NO ( i v ) ANTI-SENSE: NO (vi) ORIGINAL SOURCE:
 (A) ORGANISM: Saccharomyces cerevisiae (xi) SEQUENCE DESCRIPTION: SEQ ID NO:2:

| | | | | | | |
|---|---|---|---|---|---|---|
| GATCTTTTCC | TTTCGCTCTT | CAATATTACC | ATCCTCATTT | TCCTCATTTT | CTTCAATTGT | 60 |
| CTGATGAATA | TATCAGCAGT | TCCAATAATA | AGATCATGGG | GTATATCATT | GCCTAAAACT | 120 |
| TCTGTAACCC | ACTGCAAAAT | CTGCTCGTAA | GTTCGACAT | TTGAGGGATC | CTTTGGATAA | 180 |
| TAATGTAACC | TGAAATCGGA | GGAAGAATTC | AAAATGGTGT | TATGCTGCTG | AATTTTTTC | 240 |
| AATGATGCGC | TCTTTCCAGT | TTTTCAACG | GCTACATCAT | TTTCTTTTAG | TCCTTTATTA | 300 |
| ATGTTATTGC | ACAGGCCCTG | TCCCATATCC | TTAGCACTAA | TTCTACCACT | CATGGATTTT | 360 |
| GGTTGTGATA | TTTCCGCATC | CCTTTGAGGA | TTTGGCTGGT | ATTCATAAAG | CGTTATCAA | 420 |
| CTTTCAACAC | CTTATTGGAC | ATCTCATCAT | AACGATAAAT | TTCTCTAATT | TTTTGGCCT | 480 |
| TATCCTTCGT | TTCATGCTCA | GTCATTTTA | ATAACGAAGG | CTCACGGTAA | ATCTTCCAAA | 540 |
| GCAATTACTT | ATATTTACCT | TCACCTTATT | TTACTCAAGA | TTATCTCTAT | TAGTGTATTA | 600 |
| TTCCTTTATA | GTAGACATAG | CTTTAGTAGC | ATAAATTTTT | AATATTCTCG | TAAAGAGCGA | 660 |
| CAATATTCAA | TATTAGATCG | TCAAAGAAGC | AAACACGCAT | TGATATCTGA | GAGATCATCA | 720 |
| CAATGCGTTA | ATAGTACTTG | ATTCAACACC | ACTAATTATC | AAGTTTGTTC | CTGTCTGAAT | 780 |
| GATATGGATA | GTACGAATTT | GAACAAACGG | CCCTTATTAC | AATATAGTCT | CAGTTCATTG | 840 |
| GGCTCGCAAA | TAACAAAATG | GAGCTCATCT | AGACCGACTT | CGCCAGTTCG | TAAGGCGAGA | 900 |
| AGCACTGAAA | ATGACTTTCT | TTCCAAGCAA | GATACGTCTA | GTATCCTCCC | AAGTATCAAC | 960 |
| GACGACGGCG | GTGAACAGTG | GTACGAAAAG | TTCAAGCCCA | ATTGTTTGGA | GCAAGTGGCC | 1020 |
| A | | | | | | 1021 |

(2) INFORMATION FOR SEQ ID NO:3:

(i) SEQUENCE CHARACTERISTICS:
   (A) LENGTH: 1022 base pairs
   (B) TYPE: nucleic acid
   (C) STRANDEDNESS: single
   (D) TOPOLOGY: linear (ii) MOLECULE TYPE: cDNA to mRNA
   (A) DESCRIPTION: yeast MEC1 cDNA (iii) HYPOTHETICAL: NO (iv) ANTI-SENSE: NO (vi) ORIGINAL SOURCE:
   (A) ORGANISM: Saccharomyces cerevisiae (xi) SEQUENCE DESCRIPTION: SEQ ID NO:3:

| | | | | | | |
|---|---|---|---|---|---|---|
| ATAAGCTTAC | TGACCAAGAA | AGAGCACGCG | TGTTGGAGTT | TCAAGATTCC | ATTCACTATT | 60 |
| CTCCGCGGTA | CTCAGACGAT | AACTATGAGT | ACAGGCATGT | GATGTTACCT | AAGGCCATGC | 120 |
| TAAAAGTTAT | CCCATCTGAT | TACTTCAATT | CGGAAGTGGG | GACCCTGCGT | ATATTAACAG | 180 |
| AAGACGAATG | GAGAGGCCTC | GGCATCACAC | AGTCTTTGGG | GTGGGAACAT | TATGAATGCC | 240 |
| ATGCGCCAGA | ACTACACATT | TTGCTATTCA | AAAGGCCGCT | GAACTACGAG | GCCGAGCTGA | 300 |
| GGGCAGCGAC | CGCTGCTGCT | CAACAGCAAC | AGCAACAGCA | GCAACAGCAG | CAACAACAAC | 360 |
| AACAGCAACA | TCAAACACAA | TCGATTTCGA | ACGATATGCA | AGTTCCACCC | CAAATCTCCT | 420 |
| AGCTTTGATA | TACTCTAATT | ACTGAAATTG | AATTCCTTTT | CAAGGCTCCA | TAACTATATG | 480 |
| GAGCATACTA | TGTACTTATC | ATAATAAAGA | ATAAACAAAC | AAGCAAACAA | AAAAAAAAA | 540 |

-continued

```
AACTATGGAT CATAGTTTTC ACCAACAAGC ATTAGAATAC AAATAAAATT TATATAGTGA      600

ATATCCTTCA AATAAATTTC TTCTTTCCCT TATAAATCAA ATAGATGGAA CGCACGCTCC      660

AAAACTAGTC AACTAGAAAA AAATACCCGC CGACGGACAA TTTTGAAGAG AGATGATTAA      720

TGAAGACAAA GTGAGGCTGG ACAACAAGAA CGACATACAC CGCGTAAAGG CCCACAAGAC      780

TGCATGGAAT CACACGTCAA ATATCTTGAC GAATTGATAT TGGCAATAAA AGACCTGAAC      840

TCGGGGGTGG ATTCAAAGGT GCAGATTAAA AAAGTGCCCA CGGATCCATC TTCTTCTCAG      900

GAGTACGCCA AGAGTTTAAG ATCCTGAACA CCCTCATAAG AAACCTAAAA GATCAAAGAA      960

GGAACAATAT CATGAAAAAT GATACTATAT TTTCGAAAAC AGTTTCCGCC CTTGCCTTAT     1020

TG                                                                   1022
```

( 2 ) INFORMATION FOR SEQ ID NO:4:

( i ) SEQUENCE CHARACTERISTICS:
        ( A ) LENGTH: 1023 amino acids
        ( B ) TYPE: amino acid
        ( C ) STRANDEDNESS: single
        ( D ) TOPOLOGY: linear ( i i ) MOLECULE TYPE: protein
        ( A ) DESCRIPTION: yeast MEC1 protein ( i i i ) HYPOTHETICAL: NO ( v i ) ORIGINAL SOURCE:
        ( A ) ORGANISM: Saccharomyces cerevisiae ( x i ) SEQUENCE DESCRIPTION: SEQ ID NO:4:

```
Met Glu Ser His Val Lys Tyr Leu Asp Glu Leu Ile Leu Ala Ile Lys
 1               5                  10                  15

Asp Leu Asn Ser Gly Val Asp Ser Lys Val Gln Ile Lys Lys Val Pro
             20                  25                  30

Thr Asp Pro Ser Ser Ser Gln Glu Tyr Ala Lys Ser Leu Lys Ile Leu
         35                  40                  45

Asn Thr Leu Ile Arg Asn Leu Lys Asp Gln Arg Arg Asn Asn Ile Met
     50                  55                  60

Lys Asn Asp Thr Ile Phe Ser Lys Thr Val Ser Ala Leu Ala Leu Leu
 65                  70                  75                  80

Leu Glu Tyr Asn Pro Phe Leu Leu Val Met Lys Asp Ser Asn Gly Asn
                 85                  90                  95

Phe Glu Ile Gln Arg Leu Ile Asp Asp Phe Leu Asn Ile Ser Val Leu
            100                 105                 110

Asn Tyr Asp Asn Tyr His Arg Ile Trp Phe Met Arg Arg Lys Leu Gly
        115                 120                 125

Ser Trp Cys Lys Ala Cys Val Glu Phe Tyr Gly Lys Pro Ala Lys Phe
    130                 135                 140

Gln Leu Thr Ala His Phe Glu Asn Thr Met Asn Leu Tyr Glu Gln Ala
145                 150                 155                 160

Leu Thr Glu Val Leu Leu Gly Lys Thr Glu Leu Leu Lys Phe Tyr Asp
                165                 170                 175

Thr Leu Lys Gly Leu Tyr Ile Leu Leu Tyr Trp Phe Thr Ser Glu Tyr
                180             185                 190

Ser Thr Phe Gly Asn Ser Ile Ala Phe Leu Asp Ser Ser Leu Gly Phe
            195                 200                 205

Thr Lys Phe Asp Phe Asn Phe Gln Arg Leu Ile Arg Ile Val Leu Tyr
        210                 215                 220

Val Phe Asp Ser Cys Glu Leu Ala Ala Leu Glu Tyr Ala Glu Ile Gln
```

-continued

|     |     |     |     | 225 |     |     |     | 230 |     |     |     | 235 |     |     |     | 240 |
| --- | --- | --- | --- | --- | --- | --- | --- | --- | --- | --- | --- | --- | --- | --- | --- | --- |
| Leu | Lys | Tyr | Ile | Ser | Leu | Val | Val | Asp | Tyr | Val | Cys | Asn | Arg | Thr | Ile |
|     |     |     |     | 245 |     |     |     | 250 |     |     |     | 255 |
| Ser | Thr | Ala | Leu | Asp | Ala | Pro | Ala | Leu | Val | Cys | Cys | Glu | Gln | Leu | Lys |
|     |     |     |     | 260 |     |     |     | 265 |     |     |     | 270 |
| Phe | Val | Leu | Thr | Thr | Met | His | His | Phe | Leu | Asp | Asn | Lys | Tyr | Gly | Leu |
|     |     |     | 275 |     |     |     | 280 |     |     |     | 285 |
| Leu | Asp | Asn | Asp | Pro | Thr | Met | Ala | Lys | Gly | Ile | Leu | Arg | Leu | Tyr | Ser |
|     | 290 |     |     |     |     | 295 |     |     |     | 300 |
| Leu | Cys | Ile | Ser | Asn | Asp | Phe | Ser | Lys | Cys | Phe | Val | Asp | His | Phe | Pro |
| 305 |     |     |     |     | 310 |     |     |     | 315 |     |     |     |     |     | 320 |
| Ile | Asp | Gln | Trp | Ala | Asp | Phe | Ser | Gln | Ser | Glu | His | Phe | Pro | Phe | Thr |
|     |     |     |     | 325 |     |     |     | 330 |     |     |     | 335 |
| Gln | Leu | Thr | Asn | Lys | Ala | Leu | Ser | Ile | Val | Tyr | Phe | Asp | Leu | Lys | Arg |
|     |     |     | 340 |     |     |     | 345 |     |     |     | 350 |
| Arg | Ser | Leu | Pro | Val | Glu | Ala | Leu | Lys | Tyr | Asp | Asn | Lys | Phe | Asn | Ile |
|     |     | 355 |     |     |     | 360 |     |     |     | 365 |
| Trp | Val | Tyr | Gln | Ser | Glu | Pro | Asp | Ser | Ser | Leu | Lys | Asn | Val | Thr | Ser |
|     | 370 |     |     |     |     | 375 |     |     |     | 380 |
| Pro | Phe | Asp | Asp | Arg | Tyr | Lys | Gln | Leu | Glu | Lys | Leu | Arg | Leu | Leu | Val |
| 385 |     |     |     |     | 390 |     |     |     | 395 |     |     |     |     |     | 400 |
| Leu | Lys | Lys | Phe | Asn | Lys | Thr | Glu | Arg | Gly | Thr | Leu | Leu | Lys | Tyr | Arg |
|     |     |     |     | 405 |     |     |     | 410 |     |     |     | 415 |
| Val | Asn | Gln | Leu | Ser | Pro | Gly | Phe | Phe | Gln | Arg | Ala | Gly | Asn | Asp | Phe |
|     |     |     | 420 |     |     |     | 425 |     |     |     | 430 |
| Lys | Leu | Ile | Leu | Asn | Glu | Ala | Ser | Val | Ser | Ile | Gln | Thr | Cys | Phe | Lys |
|     |     | 435 |     |     |     | 440 |     |     |     | 445 |
| Thr | Asn | Asn | Ile | Thr | Arg | Leu | Thr | Ser | Trp | Thr | Val | Ile | Leu | Gly | Arg |
|     | 450 |     |     |     |     | 455 |     |     |     | 460 |
| Leu | Ala | Cys | Leu | Glu | Ser | Glu | Lys | Phe | Ser | Gly | Thr | Leu | Pro | Asn | Ser |
| 465 |     |     |     |     | 470 |     |     |     | 475 |     |     |     |     |     | 480 |
| Thr | Lys | Asp | Met | Asp | Asn | Trp | Tyr | Val | Cys | His | Leu | Cys | Asp | Ile | Glu |
|     |     |     |     | 485 |     |     |     | 490 |     |     |     | 495 |
| Lys | Thr | Gly | Asn | Pro | Phe | Val | Arg | Ile | Asn | Pro | Asn | Arg | Pro | Glu | Ala |
|     |     |     | 500 |     |     |     | 505 |     |     |     | 510 |
| Ala | Gly | Lys | Ser | Glu | Ile | Phe | Arg | Ile | Leu | His | Ser | Asn | Phe | Leu | Ser |
|     |     | 515 |     |     |     | 520 |     |     |     | 525 |
| His | Pro | Asn | Ile | Asp | Glu | Phe | Ser | Glu | Ser | Leu | Leu | Ser | Gly | Ile | Leu |
|     | 530 |     |     |     |     | 535 |     |     |     | 540 |
| Phe | Ser | Leu | His | Arg | Ile | Phe | Ser | His | Phe | Gln | Pro | Pro | Lys | Leu | Thr |
| 545 |     |     |     |     | 550 |     |     |     | 555 |     |     |     |     |     | 560 |
| Asp | Gly | Asn | Gly | Gln | Ile | Asn | Lys | Ser | Phe | Lys | Leu | Val | Gln | Lys | Cys |
|     |     |     |     | 565 |     |     |     | 570 |     |     |     | 575 |
| Phe | Met | Asn | Ser | Asn | Arg | Tyr | Leu | Arg | Leu | Leu | Ser | Thr | Arg | Ile | Ile |
|     |     |     | 580 |     |     |     | 585 |     |     |     | 590 |
| Pro | Leu | Phe | Asn | Ile | Ser | Asp | Ser | His | Asn | Ser | Glu | Asp | Glu | His | Thr |
|     |     | 595 |     |     |     | 600 |     |     |     | 605 |
| Ala | Thr | Leu | Ile | Lys | Phe | Leu | Gln | Ser | Gln | Lys | Leu | Pro | Val | Val | Lys |
|     | 610 |     |     |     |     | 615 |     |     |     | 620 |
| Glu | Asn | Leu | Val | Ile | Ala | Trp | Thr | Gln | Leu | Thr | Leu | Thr | Thr | Ser | Asn |
| 625 |     |     |     |     | 630 |     |     |     | 635 |     |     |     |     |     | 640 |
| Asp | Val | Phe | Asp | Thr | Leu | Leu | Leu | Lys | Leu | Ile | Asp | Ile | Phe | Asn | Ser |
|     |     |     |     | 645 |     |     |     | 650 |     |     |     | 655 |

```
Asp  Asp  Tyr  Ser  Leu  Arg  Ile  Met  Met  Thr  Leu  Gln  Ile  Lys  Asn  Met
              660                      665                      670

Ala  Lys  Ile  Leu  Lys  Lys  Thr  Pro  Tyr  Gln  Leu  Leu  Ser  Pro  Ile  Leu
              675                      680                      685

Pro  Val  Leu  Leu  Arg  Gln  Leu  Gly  Lys  Asn  Leu  Val  Glu  Arg  Lys  Val
     690                           695                      700

Gly  Phe  Gln  Asn  Leu  Ile  Glu  Leu  Leu  Gly  Tyr  Pro  Ser  Lys  Thr  Ile
705                           710                      715                      720

Leu  Asp  Ile  Phe  Gln  Arg  Tyr  Ile  Ile  Pro  Tyr  Ala  Ile  Ile  Gln  Tyr
                    725                      730                      735

Lys  Ser  Asp  Val  Leu  Ser  Glu  Ile  Ala  Lys  Ile  Met  Cys  Asp  Gly  Asp
                740                      745                      750

Thr  Ser  Leu  Ile  Asn  Gln  Met  Lys  Val  Asn  Leu  Leu  Lys  Lys  Asn  Ser
              755                      760                      765

Arg  Gln  Ile  Phe  Ala  Val  Ala  Leu  Val  Lys  His  Gly  Leu  Phe  Ser  Leu
     770                           775                      780

Asp  Ile  Leu  Glu  Thr  Leu  Phe  Leu  Asn  Arg  Ala  Pro  Thr  Phe  Asp  Lys
785                           790                      795                      800

Gly  Tyr  Ile  Thr  Ala  Tyr  Leu  Pro  Asp  Tyr  Lys  Thr  Leu  Ala  Glu  Ile
                    805                      810                      815

Thr  Lys  Leu  Tyr  Lys  Asn  Ser  Val  Thr  Lys  Asp  Ala  Ser  Asp  Ser  Glu
                820                      825                      830

Asn  Ala  Asn  Met  Ile  Leu  Cys  Ser  Leu  Arg  Phe  Leu  Ile  Thr  Asn  Phe
              835                      840                      845

Glu  Lys  Asp  Lys  Arg  His  Gly  Ser  Lys  Tyr  Lys  Asn  Ile  Asn  Asn  Trp
     850                           855                      860

Thr  Asp  Asp  Gln  Glu  Gln  Ala  Phe  Gln  Lys  Lys  Leu  Gln  Asp  Asn  Ile
865                           870                      875                      880

Leu  Gly  Ile  Phe  Gln  Val  Phe  Ser  Ser  Asp  Ile  His  Asp  Val  Glu  Gly
                    885                      890                      895

Arg  Thr  Thr  Tyr  Tyr  Glu  Lys  Leu  Arg  Val  Ile  Asn  Gly  Ile  Ser  Phe
                900                      905                      910

Leu  Ile  Ile  Tyr  Ala  Pro  Lys  Lys  Ser  Ile  Ile  Ser  Ala  Leu  Ala  Gln
              915                      920                      925

Ile  Ser  Ile  Cys  Leu  Gln  Thr  Gly  Leu  Gly  Leu  Lys  Glu  Val  Arg  Tyr
              930                      935                      940

Glu  Ala  Phe  Arg  Cys  Trp  His  Leu  Leu  Val  Arg  His  Leu  Asn  Asp  Glu
945                           950                      955                      960

Glu  Leu  Ser  Thr  Val  Ile  Asp  Ser  Leu  Ile  Ala  Phe  Ile  Leu  Gln  Lys
                    965                      970                      975

Trp  Ser  Glu  Phe  Asn  Gly  Lys  Leu  Arg  Asn  Ile  Val  Tyr  Ser  Ile  Leu
                980                      985                      990

Asp  Thr  Leu  Ile  Lys  Glu  Lys  Ser  Asp  Leu  Ile  Leu  Lys  Leu  Lys  Pro
              995                      1000                     1005

Tyr  Thr  Thr  Leu  Ala  Leu  Val  Gly  Lys  Pro  Glu  Leu  Gly  Ile  Leu
              1010                     1015                     1020
```

( 2 ) INFORMATION FOR SEQ ID NO:5:

( i ) SEQUENCE CHARACTERISTICS:
        ( A ) LENGTH: 1019 base pairs
        ( B ) TYPE: nucleic acid
        ( C ) STRANDEDNESS: single
        ( D ) TOPOLOGY: linear ( i i ) MOLECULE TYPE: cDNA to mRNA
        ( A ) DESCRIPTION: yeast MEC2 cDNA ( i i i ) HYPOTHETICAL: NO ( i v ) ANTI-SENSE: NO ( v i ) ORIGINAL SOURCE:
    ( A ) ORGANISM: Saccharomyces cerevisiae ( x i ) SEQUENCE DESCRIPTION: SEQ ID NO:5:

| | | | | | | |
|---|---|---|---|---|---|---|
| AGAAAAGATA | GTGTTACACA | ACATCAACTA | AAAATGGAAA | ATATTACACA | ACCCACACAG | 60 |
| CAATCCACGC | AGGCTACTCA | AAGGTTTTTG | ATTGAGAAGT | TTTCTCAAGA | ACAGATCGGC | 120 |
| GAAAACATTG | TGTGCAGGGT | CATTTGTACC | ACGGGTCAAA | TTCCCATCCG | AGATTTGTCA | 180 |
| GCTGATATTT | CACAAGTGCT | TAAGGAAAAA | CGATCCATAA | AGAAAGTTTG | GACATTTGGT | 240 |
| AGAAACCCAG | CCTGTGACTA | TCATTTAGGA | AACATTTCAA | GACTGTCAAA | TAAGCATTTC | 300 |
| CAAATACTAC | TAGGAGAAGA | CGGTAACCTT | TTATTGAATG | ACATTTCCAC | TAATGGGACC | 360 |
| TGGTTAAATG | GGCAAAAAGT | CGAGAAGAAC | AGCAATCAGT | TACTGTCTCA | AGGTGATGAA | 420 |
| ATAACCGTTG | GTGTAGGCGT | GGAATCAGAT | ATTTTATCTC | TGGTCATTTT | CATAAACGAC | 480 |
| AAATTTAAGC | AGTGCCTCGA | GCAGAACAAA | GTTGATCGCA | TAAGATCTAA | CCTGAAAAAT | 540 |
| ACCTCTAAAA | TAGCTTCTCC | TGGTCTTACA | TCATCTACTG | CATCATCAAT | GGTGGCCAAC | 600 |
| AAGACTGGTA | TTTTTAAGGA | TTTTTCGATT | ATTGACGAAG | TGGTGGGCCA | GGGTGCATTT | 660 |
| GCCACAGTAA | AGAAAGCCAT | TGAAAGAACT | ACTGGGAAAA | CATTCGCGGT | GAAGATTATA | 720 |
| AGTAAACGCA | AAGTAATAGG | CAATATGGAT | GGTGTGACAA | GAGAGTTAGA | AGTATTGCAA | 780 |
| AAGCTCAATC | ATCCAAGGAT | AGTACGATTG | AAAGGATTTT | ATGAAGATAC | TGAGAGTTAT | 840 |
| TATATGGTGA | TGGAGTTCGT | TTCTGGTGGT | GACTTAATGG | ATTTTGTTGC | TGCTCATGGT | 900 |
| GCGGTTGGAG | AAGATGCTGG | GAGGGAGATA | TCCAGGCAGA | TACTCACAGC | AATAAAATAC | 960 |
| ATTCACTCTA | TGGGCATCAG | CCATCGTGAC | CTAAAGCCCG | ATAATATTCT | TATTGAACA | 1019 |

( 2 ) INFORMATION FOR SEQ ID NO:6:

( i ) SEQUENCE CHARACTERISTICS:
        ( A ) LENGTH: 821 amino acids
        ( B ) TYPE: amino acid
        ( C ) STRANDEDNESS: single
        ( D ) TOPOLOGY: linear ( i i ) MOLECULE TYPE: protein
        ( A ) DESCRIPTION: yeast MEC2 protein ( x i ) SEQUENCE DESCRIPTION: SEQ ID NO:6:

| | | | | | | | | | | | | | | |
|---|---|---|---|---|---|---|---|---|---|---|---|---|---|---|
| Met | Glu | Asn | Ile | Thr | Gln | Pro | Thr | Gln | Gln | Ser | Thr | Gln | Ala | Thr | Gln |
| 1 | | | | 5 | | | | | 10 | | | | | 15 | |
| Arg | Phe | Leu | Ile | Glu | Lys | Phe | Ser | Gln | Gln | Ile | Gly | Glu | Asn | Ile | |
| | | | 20 | | | | | 25 | | | | | 30 | | |
| Val | Cys | Arg | Val | Ile | Cys | Thr | Thr | Gly | Gln | Ile | Pro | Ile | Arg | Asp | Leu |
| | | 35 | | | | | 40 | | | | | 45 | | | |
| Ser | Ala | Asp | Ile | Ser | Gln | Val | Leu | Lys | Glu | Lys | Arg | Ser | Ile | Lys | Lys |
| | 50 | | | | | 55 | | | | | 60 | | | | |
| Val | Trp | Thr | Phe | Gly | Arg | Asn | Pro | Ala | Cys | Asp | Tyr | His | Leu | Gly | Asn |
| 65 | | | | | 70 | | | | | 75 | | | | | 80 |
| Ile | Ser | Arg | Leu | Ser | Asn | Lys | His | Phe | Gln | Ile | Leu | Leu | Gly | Glu | Asp |
| | | | | 85 | | | | | 90 | | | | | 95 | |
| Gly | Asn | Leu | Leu | Leu | Asn | Asp | Ile | Ser | Thr | Asn | Gly | Thr | Trp | Leu | Asn |
| | | | | 100 | | | | | 105 | | | | | 110 | |
| Gly | Gln | Lys | Val | Glu | Lys | Asn | Ser | Asn | Gln | Leu | Leu | Ser | Gln | Gly | Asp |

-continued

```
                 115                      120                         125
    Glu  Ile  Thr  Val  Gly  Val  Val  Glu  Ser  Asp  Ile  Leu  Ser  Leu  Val
         130                      135                      140

Ile  Phe  Ile  Asn  Asp  Lys  Phe  Lys  Gln  Cys  Leu  Glu  Gln  Asn  Lys  Val
    145                      150                      155                      160

Asp  Arg  Ile  Arg  Ser  Asn  Leu  Lys  Asn  Thr  Ser  Lys  Ile  Ala  Ser  Pro
                        165                      170                      175

Gly  Leu  Thr  Ser  Ser  Thr  Ala  Ser  Ser  Met  Val  Ala  Asn  Lys  Thr  Gly
                   180                      185                      190

Ile  Phe  Lys  Asp  Phe  Ser  Ile  Ile  Asp  Glu  Val  Val  Gly  Gln  Gly  Ala
              195                      200                      205

Phe  Ala  Thr  Val  Lys  Lys  Ala  Ile  Glu  Arg  Thr  Thr  Gly  Lys  Thr  Phe
         210                      215                      220

Ala  Val  Lys  Ile  Ile  Ser  Lys  Arg  Lys  Val  Ile  Gly  Asn  Met  Asp  Gly
    225                      230                      235                      240

Val  Thr  Arg  Glu  Leu  Glu  Val  Leu  Gln  Lys  Leu  Asn  His  Pro  Arg  Ile
                        245                      250                      255

Val  Arg  Leu  Lys  Gly  Phe  Tyr  Glu  Asp  Thr  Glu  Ser  Tyr  Tyr  Met  Val
                   260                      265                      270

Met  Glu  Phe  Val  Ser  Gly  Gly  Asp  Leu  Met  Asp  Phe  Val  Ala  Ala  His
              275                      280                      285

Gly  Ala  Val  Gly  Glu  Asp  Ala  Gly  Arg  Glu  Ile  Ser  Arg  Gln  Ile  Leu
         290                      295                      300

Thr  Ala  Ile  Lys  Tyr  Ile  His  Ser  Met  Gly  Ile  Ser  His  Arg  Asp  Leu
    305                      310                      315                      320

Lys  Pro  Asp  Asn  Ile  Leu  Ile  Glu  Gln  Asp  Pro  Val  Leu  Val  Lys
                        325                      330                      335

Ile  Thr  Asp  Phe  Gly  Leu  Ala  Lys  Val  Gln  Gly  Asn  Gly  Ser  Phe  Met
                   340                      345                      350

Lys  Thr  Phe  Cys  Gly  Thr  Leu  Ala  Tyr  Val  Ala  Pro  Glu  Val  Ile  Arg
              355                      360                      365

Gly  Lys  Asp  Thr  Ser  Val  Ser  Pro  Asp  Glu  Tyr  Glu  Glu  Arg  Asn  Glu
         370                      375                      380

Tyr  Ser  Ser  Leu  Val  Asp  Met  Trp  Ser  Met  Gly  Cys  Leu  Val  Tyr  Val
    385                      390                      395                      400

Ile  Leu  Thr  Gly  His  Leu  Pro  Phe  Ser  Gly  Ser  Thr  Gln  Asp  Gln  Leu
                        405                      410                      415

Tyr  Lys  Gln  Ile  Gly  Arg  Gly  Ser  Tyr  His  Glu  Gly  Pro  Leu  Lys  Asp
                   420                      425                      430

Phe  Arg  Ile  Ser  Glu  Glu  Ala  Arg  Asp  Phe  Ile  Asp  Ser  Leu  Leu  Gln
              435                      440                      445

Val  Asp  Pro  Asn  Asn  Arg  Ser  Thr  Ala  Ala  Lys  Ala  Leu  Asn  His  Pro
         450                      455                      460

Trp  Ile  Lys  Met  Ser  Pro  Leu  Gly  Ser  Gln  Ser  Tyr  Gly  Asp  Phe  Ser
    465                      470                      475                      480

Gln  Ile  Ser  Leu  Ser  Gln  Ser  Leu  Ser  Gln  Gln  Lys  Leu  Leu  Glu  Asn
                        485                      490                      495

Met  Asp  Asp  Ala  Gln  Tyr  Glu  Phe  Val  Lys  Ala  Gln  Arg  Lys  Leu  Gln
                   500                      505                      510

Met  Glu  Gln  Gln  Leu  Gln  Glu  Gln  Asp  Gln  Glu  Asp  Gln  Asp  Gly  Lys
              515                      520                      525

Ile  Gln  Gly  Phe  Lys  Ile  Pro  Ala  His  Ala  Pro  Ile  Arg  Tyr  Thr  Gln
         530                      535                      540
```

| | | | | | | | | | | | | | | |
|---|---|---|---|---|---|---|---|---|---|---|---|---|---|---|
| Pro 545 | Lys | Ser | Ile | Glu 550 | Ala | Glu | Thr | Arg | Gln 555 | Lys | Leu | Leu | His | Ser 560 |
| Asn | Asn | Thr | Glu | Asn 565 | Val | Lys | Ser | Ser | Lys 570 | Lys | Lys | Gly | Asn | Arg 575 |
| Phe | Leu | Thr | Leu 580 | Lys | Pro | Leu | Pro | Asp 585 | Ser | Ile | Ile | Gln | Ser 590 | Leu |
| Glu | Ile | Gln 595 | Gln | Gly | Val | Asn | Pro 600 | Phe | Phe | Ile | Gly | Arg 605 | Ser | Glu | Asp |
| Cys | Asn 610 | Cys | Lys | Ile | Glu | Asp 615 | Asn | Arg | Leu | Ser | Arg 620 | Val | His | Cys | Phe |
| Ile 625 | Phe | Lys | Lys | Arg | His 630 | Ala | Val | Gly | Lys | Ser 635 | Met | Tyr | Glu | Ser | Pro 640 |
| Ala | Gln | Gly | Leu | Asp 645 | Asp | Ile | Trp | Tyr | Cys 650 | His | Thr | Gly | Thr | Asn 655 | Val |
| Ser | Tyr | Leu | Asn 660 | Asn | Asn | Arg | Met | Ile 665 | Gln | Gly | Thr | Lys | Phe 670 | Leu | Leu |
| Gln | Asp | Gly 675 | Asp | Glu | Ile | Lys | Ile 680 | Ile | Trp | Asp | Lys | Asn 685 | Asn | Lys | Phe |
| Val | Ile | Gly 690 | Phe | Lys | Val | Glu 695 | Ile | Asn | Asp | Thr | Thr 700 | Gly | Leu | Phe | Asn |
| Glu 705 | Gly | Leu | Gly | Met | Leu 710 | Gln | Glu | Gln | Arg | Val 715 | Val | Leu | Lys | Gln | Thr 720 |
| Ala | Glu | Glu | Lys | Asp 725 | Leu | Val | Lys | Lys | Leu 730 | Thr | Gln | Met | Met | Ala 735 | Ala |
| Gln | Arg | Ala | Asn 740 | Gln | Pro | Ser | Ala | Ser 745 | Ser | Ser | Ser | Met | Ser 750 | Ala | Lys |
| Lys | Pro | Pro 755 | Val | Ser | Asp | Thr | Asn 760 | Asn | Asn | Gly | Asn 765 | Ser | Val | Leu |
| Asn | Asp 770 | Leu | Val | Glu | Ser | Pro 775 | Ile | Asn | Ala | Asn | Thr 780 | Gly | Asn | Ile | Leu |
| Lys 785 | Arg | Ile | His | Ser | Val 790 | Ser | Leu | Ser | Gln | Ser 795 | Gln | Ile | Asp | Pro | Ser 800 |
| Lys | Lys | Val | Lys | Arg 805 | Ala | Lys | Leu | Asp | Gln 810 | Thr | Ser | Lys | Gly | Pro 815 | Glu |
| Asn | Leu | Gln | Phe 820 | Ser | | | | | | | | | | | |

( 2 ) INFORMATION FOR SEQ ID NO:7:

( i ) SEQUENCE CHARACTERISTICS:
        ( A ) LENGTH: 1313 base pairs
        ( B ) TYPE: nucleic acid
        ( C ) STRANDEDNESS: single
        ( D ) TOPOLOGY: linear ( i i ) MOLECULE TYPE: cDNA to mRNA
        ( A ) DESCRIPTION: human CDC34 cDNA ( i i i ) HYPOTHETICAL: NO ( i v ) ANTI-SENSE: YES ( v ) ORIGINAL SOURCE:
        ( A ) ORGANISM: Homo sapiens ( x i ) SEQUENCE DESCRIPTION: SEQ ID NO:7:

```
ATTGGTGAAT  CCGTCCACTC  AGTGCTGGAC  GTGGCTCCAG  GACCTGGAGC  TGACAGGCAG      60
GACCGGGCCC  CTCGGACCGC  TACACCTGGG  CCTCCCAGGC  TGGTAGTGTC  AGGAAACGGC     120
CCCCCGNNCA  CGTTCCCAGC  AGCGCCCCCG  TGGCTCCTCC  GGGGTGCGGC  CAGTCCGGAA     180
```

-continued

```
GCTGGGGGAC CCCGGTAGAA GTCGGGCTCA GCTCCCCTCC CGAGGGGACA GGTGGGCCGG       240
CCGCTCCCAC CCTGGGCCCG TCCACCGAGC CCCGAGTGAC GTGAGTGGCG GTGGGGCAGC       300
CCCTCTTCTC TGAAGCACGT GAAAACCCAG AACAGACATG GGGAGGGAGA AAAAGCCAAA       360
ACGAAACAAC CAGAGGAGAC GGGGACCAGC ACAAACCTC CGTGAGGTAG TCTGTCGTCT        420
AAGGAGCCAC GGGTCCGGCC CTAGTGAGGT AAACTCGGCA AGTTTATTCT GGTGGTGTCA      480
GGACTCCTCC GTGCCAGAGT CATCCTCATC GTCCCCGAAG CAGCTGTCGG CCTCCTCCTC      540
CACCTCGCCG TCTCGTAGTA GTCGTCGTAG AAGAGGTCTG AGCCCTCGTC GGGCGCCGGC      600
GCCTTGGTCT TCACGCAGTA CTCGGCCAGC GTGGTGGGCA CCTTCACGCC GTCACGCTCC      660
GCGTCCACCT TGGTCCCCAG GACCTGCTTC CGGATGATGT CTGTGTACTC CCGATCCTTC      720
CCCTTGCTCT CTTTCCACTT CCTGTACATC ACGGAGGCGT CCACGTTTGC GGGCGAGAAG      780
GTGTTGGGCT CGTTCAGGAG GGAGATCACA CTCAGGAGAA TGGTCCTGAC GTTCTGCGTG      840
GGGTTCCACC TCTCTGAGGG CAGCTCCCCG CTCTGGGGGT CGTCCACCGG CGGGTGGAGG      900
ATGGAGATAC ACACGTCCCC CGTCTCGTAG ATGTTAGGGT GCCACATCTT GGTCAGGAAC      960
CGAAAGGCTG GTGGAGAGTA TGGGTAGTCG ATGGGGAACT TGAGGCGCGC CTTGAAGTAG      1020
CCGCCCTCGT AGTAGGTGTT GGGGGGCCCG AAAATGGCCA CCTCCCAGTT GTATAGATCG      1080
CCCTCGTCCA CCAGTGTCAC GCGGAATCCC TCGACCGGCT CTTCCTGCAG CCCCTTGAGC      1140
TCCAGCAGCA GCGCCTTCTG CGAGCTGGGC ACTAGCGGCC GAGCCATGGC GGCGGCGGAG      1200
GGGCCCGGGG TCGGAGCAGC GCGNGGCCGC GCGACCACCG CGAGTTCGCG AGACGGGCCG      1260
GGCCGCGCAC CGTCCGGGGG GGAGCCACCG GGGCCGCCGC CTGCCTCCTC CTC             1313
```

( 2 ) INFORMATION FOR SEQ ID NO:8:

( i ) SEQUENCE CHARACTERISTICS:
    ( A ) LENGTH: 1896 base pairs
    ( B ) TYPE: nucleic acid
    ( C ) STRANDEDNESS: single
    ( D ) TOPOLOGY: linear ( i i ) MOLECULE TYPE: cDNA to mRNA
    ( A ) DESCRIPTION: human RAD9compA cDNA ( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:8:

```
ATTGTTCTAT TGATGGCAGG TAATCATCAC TCTTCACTAG CTGAGCATTC GGTCCACTAA       60
CCTGAGTCAT ATCCGGCACT GGTTTCTCTA GAAAGGGNTC CGACGGGGAA TGCTGATGCA      120
CAGGCACTTT CTGCGGGGTG TTCTGGGGTG ATGGGTGGAG CTGTGCCCAA GGCTGGTGAT      180
GAGGGTGTGG AGGTGAAGAC TGGTGGTGCA AGCCCGGGTG AGGCTGCAGT GGAGGACAGG      240
TTGGAACTGC TGAAAAGATG GCTGTTGACC AGGATGTTGT TGGCCAGGTA TCAGTCGTTC      300
CTGGATTGCT TGTGGGTCTC CAAGGCCAAC ACCAGGACAA CCATTTGGCC TCATGTGCCC      360
AGTCAATTCC CTTGGTGCCG AGGACATGCC TATAAATGGA CGAGACTGCT GCATGTTTCT      420
GGGCCCATA TTCCTCTGTC CGATTCCCAT GGCACCAGGG GGCTGGTGAG ATGGCTGAGG       480
ATGGGGCATA TTTGGATAAC TGCCAACTTC CATTGGTATC CCAGCACTTC CCGGCCTGAC      540
TTGTGGAGGA GGAGTGCCTG CTGGATTACT CATTGCTTTC ATGGGTGACA TGGGAGGTGG      600
```

-continued

| | | | | | | |
|---|---|---|---|---|---|---|
| AGAGGCATAA | GTTCCCTGAG | GCTGTGAAGG | ATGCATAGTT | TGTGTGTTCA | TTTGGTTAAG | 660 |
| TGAGCCACTG | GGGTGGATGG | GCTGCTGGTG | CATTAGTCCT | TGACCACTGT | TTGATGGGAA | 720 |
| TCCTACAGCA | TTGGGGTATC | TTGGTACGGA | CTGATTCATT | GGAGTATTAT | TTGTAAGGCC | 780 |
| TAAATTTTGA | TTCATCCCTG | TATTGTTAAC | TAATCCCTGA | TTTAGGTTAC | TGTAAGGATA | 840 |
| TCGAGAATAC | TGCCCTGAGT | TGTTTATAGT | AGGAGAGGGG | ACTGTCTGGC | TCCGAGAACT | 900 |
| AAAGTTAAGG | GTTTGCGGCC | TAACAGCCCC | TTGTTGGGGA | GGATTCGGGG | AGAATCTGGG | 960 |
| ACTGTGGGCA | ACGGATTCTC | CATGGAGAGC | AGTAGAGGGG | TGGTGATGGA | ACTGCTGCAC | 1020 |
| CGAGTGACGC | AAGGAAGGTG | CCATGCTGGG | ACTCTGCTGG | GGCACGTGGG | ACAAGTGGCC | 1080 |
| AGGTCCTGAG | GTGGCAATAA | AAGGATTTCC | CTGATTGAGG | CCCTCTTGGC | CTTGGGAAAA | 1140 |
| CTGGCTCATC | CTCTGCTGTG | GCTGACCATG | CTGCTGCATG | GAAAAATCCC | CACGTGCCAT | 1200 |
| ATAGCTGCCC | ATCTGCTGCA | TGTGCTGAGG | GTGGCCCTGT | GCAGGGGCC | CCGACGGAGC | 1260 |
| CGGCTGCGGT | GGCTGCGGCT | GTGGCTGCTG | CTGCTGGTAG | GGGGCTCGTA | TCTGGTCTGG | 1320 |
| TACCTGAACA | GCCCTGGGGC | CCCACATGGA | GCTGCTGTCC | ACAAAGGATT | GCCCATGCCT | 1380 |
| CTCATTCTGC | ATGCCAGGGT | AGACACCCAT | CTGACCGCCA | CCACTGCCAC | CATGGGGCAC | 1440 |
| CTGAGGAACG | GGAGGGGTGT | GATACTGCGA | GTGCGGAGAC | GCGAGTCCGT | TCCCAGGGGT | 1500 |
| GTTGCTCATC | ATTCTGTTCG | GCTGATCCAT | CAGATGCATC | TTTTGTTGTT | CATACTGATT | 1560 |
| ATAGTGATCA | AAATGTGTCA | GCTTTGTTTG | ATTTTGATTA | GTTGAAGGAT | GATGAAGGGA | 1620 |
| TGGCTGTAAA | GAGGCAAAGC | CTTGGTCTAT | TGGCATTTGC | TGACCCATAG | GATTTACTGG | 1680 |
| ATTTTCCGGG | TAACCACATT | CTCCGAGGCC | TTCAAGACCT | TCACTGAAAA | TATTCCCATC | 1740 |
| CTCGCCAAAA | AGACTCATCA | TTCCTGGATC | TGCCATCTTA | TTCCAACACA | CGGCTCCTCC | 1800 |
| AAACCACAGC | TCAGGAGCTT | GCCTGTGCTT | CACTTCACTG | AGGTGTTTGC | CCTCAAAGCC | 1860 |
| TATATGACCA | ATCCCTAATT | GCTGTCCTGA | TGATGA | | | 1896 |

( 2 ) INFORMATION FOR SEQ ID NO:9:

( i ) SEQUENCE CHARACTERISTICS:
        ( A ) LENGTH: 1647 base pairs
        ( B ) TYPE: nucleic acid
        ( C ) STRANDEDNESS: single
        ( D ) TOPOLOGY: linear ( i i ) MOLECULE TYPE: cDNA to mRNA
        ( A ) DESCRIPTION: human RAD9compB cDNA ( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:9:

| | | | | | | |
|---|---|---|---|---|---|---|
| ATTGCAGGTT | CCGTAGCTTT | CTAGTTTTTT | TTTTTTTTC | ACTTGGATCA | AATAGTTTTG | 60 |
| ATAGACAGAA | AAAGATCTGT | ACCATTATTT | CCTTTCCTTA | ACAGCTATTG | TAATTTCCTG | 120 |
| GACTTGGTTG | CTTTTCACTT | GGGCAGTTAA | GAAGACACAG | CTTGTTTTCC | CCATCAGTTT | 180 |
| TCTCTCTCTC | TCCTTCGTGT | GTGTGTGTGT | GTGTGTGTGT | GTGTGTGTGT | GTGTGTGCGT | 240 |
| GCGTGCACAG | GGCCAATCTT | CAGGCTTATG | GCTTTTGGAA | CATTTCTTA | ATTTAATAGA | 300 |
| GAACAGAATT | CAATGATTAG | CAACATCACT | AAAAATTTAC | CCCATTTCTT | CTCCATAGT | 360 |
| CACTGACACC | CGATGCGCAT | GAACAGTCCA | ACGTCCACCT | CGTAAGATGT | CATCGGGGTT | 420 |
| CAGGGTTCAG | AAGCATCGAG | GACTGGTGGC | CGGCCCTCTG | TGCTCGCCGT | GTGACAATTC | 480 |

-continued

| | | | | | |
|---|---|---|---|---|---|
|CAGTGGCTTT|CCTGGCACCA|TCAGATGCCT|GGTGCCACAA|GCTTGGGTCT|GCTCCTAGGG|540|
|GGACGAGGGG|TTCCTCCTCC|TCCTCAATTG|CTTTATGTGC|CTTCACTCAG|TGAACCCCAA|600|
|TGGGATGGAC|AACCTGACTT|TTTAAACCTA|AGGGTTGGGC|CTGAACGATG|ATTACTTTGC|660|
|CCACGTGCCT|TCTAGGTGCC|GAATGTGTGT|TCCTGTGATA|TTGACGTTGA|CATCCCTGCG|720|
|GATTCAGCCA|CAGGTTTCTG|ACAAGCTGGA|GGAAGCAATG|GTAATTTTGG|CTTTTTCGGT|780|
|TTTGTCTTCA|GATAATGAAA|AGCTTTTGTA|AAACAGCTGA|GTGTCAATAT|GAGTTCTATG|840|
|GCTTCAATCT|CCTTTAAAAA|TAAAATTCTT|AAGGGTCCAA|AACAAAGAAG|AGGGGGCAAA|900|
|TTAAAACCCA|ATAAAAGGAA|AAGAAAAGAA|AGAAAACCAA|ACCCCAAACA|AGAAAAAAGA|960|
|AAAAAAATTG|CTGATATTGC|CACAAATCAT|TAGAAATCTC|CTGACATGCT|GAAACCAAAT|1020|
|GGTCGTAAGT|TCAAAACAAA|TCAGTGACTT|GTTTTAATT|TTTTGTGGTT|TCCTTTTGCT|1080|
|CTTTCTGCCC|CTTTGCCGTC|CGATTGGTGA|TGTTATTCAA|ACAGGACCGG|ATCCCTGCTA|1140|
|AGTGCAGGAG|GGACCCTGCC|GCTTCTTTCA|TCTCCTCATC|ATCGCTCTCG|GGGGCTTTT|1200|
|CGGTGCGTCT|CTTTTTGAGG|GGCAGTGTGT|CGCTGGGGAC|CTTCCTGGCC|TTGGCGAAGT|1260|
|GCTGGCGCTT|CTTGTGCTGG|GATGCGTACC|CGCTGTCCCC|CAGAGAATCC|TTGGGCTCCT|1320|
|TCTGGCTGTG|CTTCCTGTCG|TCCTCTTCCG|TGTCGCTGGG|GCTCTCGTGG|CTCCGGAAGC|1380|
|TCCCCTCGCT|GCCCTCGCTG|CCCTCCTGGC|TCCCCTTGGT|GGCAAACTCA|TAGTGGTCGT|1440|
|CGGCTGAGGA|GGAGGAGGAG|GAGATGGAGT|CGCTGGTGGG|CGAGGTGCTC|CGGGCGTTGG|1500|
|AGGACTTGGC|ACTGCTGTAG|TTGTGATCCT|CCTTGGGGTC|TCCGCTGACC|ACTGGGAGC|1560|
|CACAAGATGG|CTCACTCTCA|GTCCGCATCC|GGCAGCTGGT|GATGCCATTC|CTCATGGCCG|1620|
|CTGTCACCCC|AATGGGAGTG|ATTGGCA|||| 1647|

( 2 ) INFORMATION FOR SEQ ID NO:10:

( i ) SEQUENCE CHARACTERISTICS:
        ( A ) LENGTH: 2150 base pairs
        ( B ) TYPE: nucleic acid
        ( C ) STRANDEDNESS: single
        ( D ) TOPOLOGY: linear ( i i ) MOLECULE TYPE: cDNA to mRNA
        ( A ) DESCRIPTION: yeast RAD17 cDNA ( i i i ) HYPOTHETICAL: NO ( i v ) ANTI-SENSE: NO ( v i ) ORIGINAL SOURCE:
        ( A ) ORGANISM: Saccharomyces cerevisiae ( i x ) FEATURE:
        ( A ) NAME/KEY: CDS
        ( B ) LOCATION: 741..1947

( x i ) SEQUENCE DESCRIPTION: SEQ ID NO:10:

| | | | | | |
|---|---|---|---|---|---|
|AGCAGGAATT|GGTAACGCCA|GGTTTTCCCG|ATCAGACGTT|GTAAACAGG|CCAGTGAATT|60|
|GTAATACGAC|TCACTATAGG|GCGAATTGGG|TACCGGGCCC|CCCCTCGAGG|TCGACGGTAT|120|
|CGATAAGCTT|GATATCGAAT|TCCTGCAGCC|CCTAAAATGC|CATTTGTTCA|AATGGATCAA|180|
|ATTTCCCAAT|TTTTATCATT|TTCGAGAAAA|TATGGTGTGC|CTGAAGATGA|ACTGTTTCAG|240|
|ACAATTGATC|TTTTTGAGAA|AAAGGATCCT|GCCATTGTTT|TCCAAACGTT|GAAGTCACTA|300|
|TCTCGTTACG|CCAACAAAAA|ACATACAGAT|AGATTTCCAG|TTCTAGGACC|ACAACTGTCA|360|
|ACAAAGAAGC|CAAGACCCCC|GGTTAAGTCT|AAACCAAAAC|ATCTACAAGA|TGGTACTGGA|420|

| | | | | | |
|---|---|---|---|---|---|
| TGGAGCACTT | TTGAATACGG | TTATATGAAA | GGTGCATCTC | AGGCTACTGA | AGGAGTGGTG | 480 |
| TTAGGACAAC | GGAGAGATAT | AGTTTAGAGA | ATTATTATTA | ACACTTTCTC | TGGCAGAAAT | 540 |
| TGATAAATAA | ACATTTAAGA | ACCCTATATA | CGCAACCAAA | GTTCCTTTGA | TATATTTTAG | 600 |
| TTTTCCATCA | AAGTTTTCCT | ACATAAACAC | TAAGGTGGCT | AGAGACGCGT | AACAAAGTT | 660 |
| AACGTTACCG | GTAAAAATGT | GATTATACAA | ATCAATCTCA | CAGAACGGTG | TGGAAACAAA | 720 |

```
GTAGTTGAAG GATTTCAACT ATG CGA ATC AAC AGT GAG CTA GCG AAC AAG     770
                     Met Arg Ile Asn Ser Glu Leu Ala Asn Lys
                       1               5                  10

TTT TCT GCC TCA ACG GTG CAC TTA GAA CAT ATC ACA ACT GCT TTA AGT    818
Phe Ser Ala Ser Thr Val His Leu Glu His Ile Thr Thr Ala Leu Ser
             15                  20                  25

TGT TTA ACA CCT TTT GGT TCT AAA GAC GAT GTG CTT ATA TTC ATT GAT    866
Cys Leu Thr Pro Phe Gly Ser Lys Asp Asp Val Leu Ile Phe Ile Asp
         30                  35                  40

GCT GAT GGG CTG TCA TTT GTC AGG GAG AAT AAT CAT GTG ATA AAA ATC    914
Ala Asp Gly Leu Ser Phe Val Arg Glu Asn Asn His Val Ile Lys Ile
         45                  50                  55

CAA CTA CTG TTA TCT CGG GAG CTA TTT ATG TCT TAT TCG TAT AGA AAT    962
Gln Leu Leu Leu Ser Arg Glu Leu Phe Met Ser Tyr Ser Tyr Arg Asn
         60                  65                  70

GAA ACT GAG GAT CAC ATG AAA CTT TGT GTA AAA ATA AAT CAT ATC TTA   1010
Glu Thr Glu Asp His Met Lys Leu Cys Val Lys Ile Asn His Ile Leu
 75                  80                  85                  90

GAT AGC GTT AGC GTG ATG AAC AGG AAT TCG GAT GAC ATT GTT GAG TGT   1058
Asp Ser Val Ser Val Met Asn Arg Asn Ser Asp Asp Ile Val Glu Cys
                 95                 100                 105

ACT TTA TCT TAT GAT GGA CAT GGA TCA CCA TTT GTA CTA ATA TTT GAA   1106
Thr Leu Ser Tyr Asp Gly His Gly Ser Pro Phe Val Leu Ile Phe Glu
             110                 115                 120

GAC TCG TTC ATT TCT GAG AGA GTG GAG TAC TCT ACC TAC TTA ATT AAG   1154
Asp Ser Phe Ile Ser Glu Arg Val Glu Tyr Ser Thr Tyr Leu Ile Lys
         125                 130                 135

GAT TTT GAT ACT AAT GGA CTA GAA CTC GAT AGA GAA AGG ATA AGC TTT   1202
Asp Phe Asp Thr Asn Gly Leu Glu Leu Asp Arg Glu Arg Ile Ser Phe
         140                 145                 150

GAG GCA ATT ATT AAG GGC GAA GCC CTT CAT TCA GCC TTA AAG GAT CTA   1250
Glu Ala Ile Ile Lys Gly Glu Ala Leu His Ser Ala Leu Lys Asp Leu
155                 160                 165                 170

AAA GAA ATC GGA TGC AAA GAG TGC TAT GTA TAT GCA AAG ACC GAG GCG   1298
Lys Glu Ile Gly Cys Lys Glu Cys Tyr Val Tyr Ala Lys Thr Glu Ala
                 175                 180                 185

AAT GAT GAG AAT GTA TTT GCC CTG ATA TCT AAA TCT CAG CTA GGA TTT   1346
Asn Asp Glu Asn Val Phe Ala Leu Ile Ser Lys Ser Gln Leu Gly Phe
             190                 195                 200

TCT AAA ATA AAA TTA CCC AGT AAC AGA TCC ATA CTA GAG AAG TTA CAA   1394
Ser Lys Ile Lys Leu Pro Ser Asn Arg Ser Ile Leu Glu Lys Leu Gln
         205                 210                 215

GTA TTT GAC GGA GAT TCC ACA ACA GTA ATA GAT GGT TTT GCT GTA ATT   1442
Val Phe Asp Gly Asp Ser Thr Thr Val Ile Asp Gly Phe Ala Val Ile
         220                 225                 230

GGG TTC TTC GAT TTC ACC TCG TTT GAT AAA ATC AGA AAG AGT ACT AAA   1490
Gly Phe Phe Asp Phe Thr Ser Phe Asp Lys Ile Arg Lys Ser Thr Lys
235                 240                 245                 250

ATT GCA AGC AAA GTC CTT TTC AGG ATG GAT GTT CAT GGC GTA TTG AGT   1538
Ile Ala Ser Lys Val Leu Phe Arg Met Asp Val His Gly Val Leu Ser
                 255                 260                 265

GTA AAT ATT CTA AGT CAA ACA GAC GAT GTC ATT ATC ACT GAT ACT ACA   1586
Val Asn Ile Leu Ser Gln Thr Asp Asp Val Ile Ile Thr Asp Thr Thr
```

```
                              270                      275                        280
AGA  CCT  TCA  AAT  AAT  CGA  CCA  GGT  AGT  ATT  CGC  CAA  CTG  CAG  CTA  CCC              1634
Arg  Pro  Ser  Asn  Asn  Arg  Pro  Gly  Ser  Ile  Arg  Gln  Leu  Gln  Leu  Pro
          285                      290                      295

AAG  GAT  TAT  CCC  GGT  ATA  GTA  ATT  GAG  GTT  TGC  ATG  CTA  GAA  AAA  GAA              1682
Lys  Asp  Tyr  Pro  Gly  Ile  Val  Ile  Glu  Val  Cys  Met  Leu  Glu  Lys  Glu
     300                      305                      310

TCC  ATA  GAT  GAG  GCA  GCA  CAG  ACA  GAA  ATA  GAA  CTC  CTG  ATG  GAG  ACT              1730
Ser  Ile  Asp  Glu  Ala  Ala  Gln  Thr  Glu  Ile  Glu  Leu  Leu  Met  Glu  Thr
315                      320                      325                      330

AAT  GAA  CTT  GGC  AAT  CGT  AAT  AGT  TTT  AAA  AAA  TCA  ACT  ATA  AGA  AAA              1778
Asn  Glu  Leu  Gly  Asn  Arg  Asn  Ser  Phe  Lys  Lys  Ser  Thr  Ile  Arg  Lys
                    335                      340                      345

AGA  TAT  GGT  ACA  GAT  AAA  GGC  AAT  GAA  ACT  TCA  AAT  GAC  AAC  TTG  CTG              1826
Arg  Tyr  Gly  Thr  Asp  Lys  Gly  Asn  Glu  Thr  Ser  Asn  Asp  Asn  Leu  Leu
               350                      355                      360

CAA  TTG  AAT  GGG  AAA  AAA  ATT  AAA  CTA  CCA  TCT  GAA  GAA  GAA  AAC  AAT              1874
Gln  Leu  Asn  Gly  Lys  Lys  Ile  Lys  Leu  Pro  Ser  Glu  Glu  Glu  Asn  Asn
          365                      370                      375

AAA  AAC  AGG  GAA  AGT  GAG  GAT  GAA  GAG  AAT  CAC  TGC  AAG  TAT  CCA  ACA              1922
Lys  Asn  Arg  Glu  Ser  Glu  Asp  Glu  Glu  Asn  His  Cys  Lys  Tyr  Pro  Thr
     380                      385                      390

AAG  GAT  ATT  CCT  ATA  TTT  TTT  TAA  G TCAATATCCA  GCATCGCAGA                             1967
Lys  Asp  Ile  Pro  Ile  Phe  Phe
395                      400

AAACGCAGAA  CTTCATTCAG  CATTTGGTAA  TTTTATAACA  TATAACTTAC  AATTAAATAA                       2027

AAGTTTAACT  ATATATTATT  ATGTGATCTA  ACTCTAGAAA  AAGTACTAAT  GAACATCACA                       2087

CCGTTTATTG  TTGGGAGAAG  TGTTCCATGG  GGGATCCACT  AGTTCTAGAG  CGGCGCCACC                       2147

GCG                                                                                          2150
```

( 2 ) INFORMATION FOR SEQ ID NO:11:

( i ) SEQUENCE CHARACTERISTICS:
        ( A ) LENGTH: 401 amino acids
        ( B ) TYPE: amino acid
        ( D ) TOPOLOGY: linear ( i i ) MOLECULE TYPE: protein
        ( A ) DESCRIPTION: yeast RAD17 protein ( x i ) SEQUENCE DESCRIPTION: SEQ ID NO:11:

```
Met  Arg  Ile  Asn  Ser  Glu  Leu  Ala  Asn  Lys  Phe  Ser  Ala  Ser  Thr  Val
1                    5                        10                       15

His  Leu  Glu  His  Ile  Thr  Thr  Ala  Leu  Ser  Cys  Leu  Thr  Pro  Phe  Gly
               20                       25                       30

Ser  Lys  Asp  Asp  Val  Leu  Ile  Phe  Ile  Asp  Ala  Asp  Gly  Leu  Ser  Phe
          35                       40                       45

Val  Arg  Glu  Asn  Asn  His  Val  Ile  Lys  Ile  Gln  Leu  Leu  Leu  Ser  Arg
     50                       55                       60

Glu  Leu  Phe  Met  Ser  Tyr  Ser  Tyr  Arg  Asn  Glu  Thr  Glu  Asp  His  Met
65                       70                       75                       80

Lys  Leu  Cys  Val  Lys  Ile  Asn  His  Ile  Leu  Asp  Ser  Val  Ser  Val  Met
                    85                       90                       95

Asn  Arg  Asn  Ser  Asp  Asp  Ile  Val  Glu  Cys  Thr  Leu  Ser  Tyr  Asp  Gly
               100                      105                      110

His  Gly  Ser  Pro  Phe  Val  Leu  Ile  Phe  Glu  Asp  Ser  Phe  Ile  Ser  Glu
          115                      120                      125

Arg  Val  Glu  Tyr  Ser  Thr  Tyr  Leu  Ile  Lys  Asp  Phe  Asp  Thr  Asn  Gly
```

|     |     |     |     |     | 130 |     |     |     |     | 135 |     |     |     |     | 140 |     |     |     |     |
| --- | --- | --- | --- | --- | --- | --- | --- | --- | --- | --- | --- | --- | --- | --- | --- | --- | --- | --- | --- |

Leu Glu Leu Asp Arg Glu Arg Ile Ser Phe Glu Ala Ile Ile Lys Gly
145                 150                 155                 160

Glu Ala Leu His Ser Ala Leu Lys Asp Leu Lys Glu Ile Gly Cys Lys
            165                 170                 175

Glu Cys Tyr Val Tyr Ala Lys Thr Glu Ala Asn Asp Glu Asn Val Phe
        180                 185                 190

Ala Leu Ile Ser Lys Ser Gln Leu Gly Phe Ser Lys Ile Lys Leu Pro
    195                 200                 205

Ser Asn Arg Ser Ile Leu Glu Lys Leu Gln Val Phe Asp Gly Asp Ser
210                 215                 220

Thr Thr Val Ile Asp Gly Phe Ala Val Ile Gly Phe Phe Asp Phe Thr
225                 230                 235                 240

Ser Phe Asp Lys Ile Arg Lys Ser Thr Lys Ile Ala Ser Lys Val Leu
            245                 250                 255

Phe Arg Met Asp Val His Gly Val Leu Ser Val Asn Ile Leu Ser Gln
        260                 265                 270

Thr Asp Asp Val Ile Ile Thr Asp Thr Thr Arg Pro Ser Asn Asn Arg
    275                 280                 285

Pro Gly Ser Ile Arg Gln Leu Gln Leu Pro Lys Asp Tyr Pro Gly Ile
    290                 295                 300

Val Ile Glu Val Cys Met Leu Glu Lys Glu Ser Ile Asp Glu Ala Ala
305                 310                 315                 320

Gln Thr Glu Ile Glu Leu Leu Met Glu Thr Asn Glu Leu Gly Asn Arg
            325                 330                 335

Asn Ser Phe Lys Lys Ser Thr Ile Arg Lys Arg Tyr Gly Thr Asp Lys
        340                 345                 350

Gly Asn Glu Thr Ser Asn Asp Asn Leu Leu Gln Leu Asn Gly Lys Lys
    355                 360                 365

Ile Lys Leu Pro Ser Glu Glu Glu Asn Asn Lys Asn Arg Glu Ser Glu
    370                 375                 380

Asp Glu Glu Asn His Cys Lys Tyr Pro Thr Lys Asp Ile Pro Ile Phe
385                 390                 395                 400

Phe (2) INFORMATION FOR SEQ ID NO:12:

(i) SEQUENCE CHARACTERISTICS:
    (A) LENGTH: 2762 base pairs
    (B) TYPE: nucleic acid
    (C) STRANDEDNESS: single
    (D) TOPOLOGY: linear (ii) MOLECULE TYPE: cDNA to mRNA
    (A) DESCRIPTION: yeast RAD24 cDNA (iii) HYPOTHETICAL: NO (iv) ANTI-SENSE: NO (vi) ORIGINAL SOURCE:
    (A) ORGANISM: Saccharomyces cerevisiae (ix) FEATURE:
    (A) NAME/KEY: CDS
    (B) LOCATION: 3..1982

(xi) SEQUENCE DESCRIPTION: SEQ ID NO:12:

AT ATG GAT AGT ACG AAT TTG AAC AAA CGG CCC TTA TTA CAA TAT AGT  47
  Met Asp Ser Thr Asn Leu Asn Lys Arg Pro Leu Leu Gln Tyr Ser

|  |  |  |  |  |  |  |  |  |  |  |  |  |  |  |  |  |
|---|---|---|---|---|---|---|---|---|---|---|---|---|---|---|---|---|
| 1 | | | | 5 | | | | | 10 | | | | | 15 | | |

| CTC | AGT | TCA | TTG | GGC | TCG | CAA | ATA | ACA | AAA | TGG | AGC | TCA | TCT | AGA | CCG | 95 |
| Leu | Ser | Ser | Leu | Gly | Ser | Gln | Ile | Thr | Lys | Trp | Ser | Ser | Ser | Arg | Pro | |
| | | | | 20 | | | | | 25 | | | | | 30 | | |

| ACT | TCG | CCA | GTT | CGT | AAG | GCG | AGA | AGC | ACT | GAA | AAT | GAC | TTT | CTT | TCC | 143 |
| Thr | Ser | Pro | Val | Arg | Lys | Ala | Arg | Ser | Thr | Glu | Asn | Asp | Phe | Leu | Ser | |
| | | | 35 | | | | | 40 | | | | | 45 | | | |

| AAG | CAA | GAT | ACG | TCT | AGT | ATC | CTC | CCA | AGT | ATC | AAC | GAC | GAC | GGC | GGT | 191 |
| Lys | Gln | Asp | Thr | Ser | Ser | Ile | Leu | Pro | Ser | Ile | Asn | Asp | Asp | Gly | Gly | |
| | | 50 | | | | | 55 | | | | | 60 | | | | |

| GAA | CAG | TGG | TAC | GAA | AAG | TTC | AAG | CCC | AAT | TGT | TTG | GAG | CAA | GTG | GCC | 239 |
| Glu | Gln | Trp | Tyr | Glu | Lys | Phe | Lys | Pro | Asn | Cys | Leu | Glu | Gln | Val | Ala | |
| | 65 | | | | | 70 | | | | | 75 | | | | | |

| ATA | CAT | AAA | AGA | AAA | CTT | AAA | GAT | GTA | CAA | GAA | GCT | TTA | GAT | GCC | ATG | 287 |
| Ile | His | Lys | Arg | Lys | Leu | Lys | Asp | Val | Gln | Glu | Ala | Leu | Asp | Ala | Met | |
| 80 | | | | | 85 | | | | | 90 | | | | | 95 | |

| TTT | TTA | CCT | AAC | GCC | AAG | CAT | AGG | ATC | CTA | CTA | CTG | TCT | GGC | CCC | AGT | 335 |
| Phe | Leu | Pro | Asn | Ala | Lys | His | Arg | Ile | Leu | Leu | Leu | Ser | Gly | Pro | Ser | |
| | | | | 100 | | | | | 105 | | | | | 110 | | |

| GGA | TGC | TCT | AAA | AGT | ACG | GTC | ATA | AAA | GAA | CTC | TCA | AAA | ATC | TTA | GTT | 383 |
| Gly | Cys | Ser | Lys | Ser | Thr | Val | Ile | Lys | Glu | Leu | Ser | Lys | Ile | Leu | Val | |
| | | | | 115 | | | | | 120 | | | | | 125 | | |

| CCT | AAA | TAC | AGA | CAA | AAC | AGC | AAC | GGA | ACG | TCC | TTT | CGA | AGC | ACC | CCG | 431 |
| Pro | Lys | Tyr | Arg | Gln | Asn | Ser | Asn | Gly | Thr | Ser | Phe | Arg | Ser | Thr | Pro | |
| | | | 130 | | | | | 135 | | | | | 140 | | | |

| AAC | GAG | CAT | AAA | GTG | ACC | GAG | TTT | AGA | GGT | GAT | TGT | ATA | GTC | AAC | GAT | 479 |
| Asn | Glu | His | Lys | Val | Thr | Glu | Phe | Arg | Gly | Asp | Cys | Ile | Val | Asn | Asp | |
| | | | 145 | | | | | 150 | | | | | 155 | | | |

| CTT | CCT | CAG | ATG | GAA | AGC | TTT | AGT | GAG | TTC | TTA | AAA | GGC | GCA | CGG | TAT | 527 |
| Leu | Pro | Gln | Met | Glu | Ser | Phe | Ser | Glu | Phe | Leu | Lys | Gly | Ala | Arg | Tyr | |
| 160 | | | | | 165 | | | | | 170 | | | | | 175 | |

| CTT | GTG | ATG | TCC | AAC | CTG | TCA | TTA | ATA | CTT | ATC | GAG | GAC | CTT | CCC | AAC | 575 |
| Leu | Val | Met | Ser | Asn | Leu | Ser | Leu | Ile | Leu | Ile | Glu | Asp | Leu | Pro | Asn | |
| | | | | 180 | | | | | 185 | | | | | 190 | | |

| GTC | TTC | CAT | ATA | GAT | ACC | AGA | CGT | CGA | TTT | CAA | CAA | CTT | ATA | TTA | CAG | 623 |
| Val | Phe | His | Ile | Asp | Thr | Arg | Arg | Arg | Phe | Gln | Gln | Leu | Ile | Leu | Gln | |
| | | | 195 | | | | | 200 | | | | | 205 | | | |

| TGG | CTA | TAT | AGT | TCG | GAG | CCT | CTA | TTA | CCT | CCC | CTT | GTT | ATA | TGT | ATA | 671 |
| Trp | Leu | Tyr | Ser | Ser | Glu | Pro | Leu | Leu | Pro | Pro | Leu | Val | Ile | Cys | Ile | |
| | | 210 | | | | | 215 | | | | | 220 | | | | |

| ACT | GAA | TGT | GAA | ATT | CCA | GAG | AAC | GAT | AAT | AAT | TAT | CGC | AAA | TTT | GGT | 719 |
| Thr | Glu | Cys | Glu | Ile | Pro | Glu | Asn | Asp | Asn | Asn | Tyr | Arg | Lys | Phe | Gly | |
| | 225 | | | | | 230 | | | | | 235 | | | | | |

| ATT | GAT | TAT | ACA | TTT | AGT | GCA | GAA | ACC | ATA | ATG | AAC | AAA | GAA | ATA | TTG | 767 |
| Ile | Asp | Tyr | Thr | Phe | Ser | Ala | Glu | Thr | Ile | Met | Asn | Lys | Glu | Ile | Leu | |
| 240 | | | | | 245 | | | | | 250 | | | | | 255 | |

| ATG | CAT | CCA | AGG | TTG | AAA | AGA | ATT | AAG | TTT | AAT | CCA | ATT | AAC | AGC | ACT | 815 |
| Met | His | Pro | Arg | Leu | Lys | Arg | Ile | Lys | Phe | Asn | Pro | Ile | Asn | Ser | Thr | |
| | | | | 260 | | | | | 265 | | | | | 270 | | |

| TTA | TTA | AAA | AAG | CAC | TTG | AAA | TTT | ATT | TGT | GTA | CAG | AAT | ATG | AAA | ATG | 863 |
| Leu | Leu | Lys | Lys | His | Leu | Lys | Phe | Ile | Cys | Val | Gln | Asn | Met | Lys | Met | |
| | | | | 275 | | | | | 280 | | | | | 285 | | |

| TTG | AAG | GAG | AAA | AAT | AAA | TGG | AAT | AAA | AGA | CAG | GAA | GTC | ATA | GAT | TAT | 911 |
| Leu | Lys | Glu | Lys | Asn | Lys | Trp | Asn | Lys | Arg | Gln | Glu | Val | Ile | Asp | Tyr | |
| | | 290 | | | | | 295 | | | | | 300 | | | | |

| ATT | GCG | CAA | GAG | ACT | GGT | GAT | ATT | AGG | TCG | GCC | ATT | ACG | ACC | CTT | CAA | 959 |
| Ile | Ala | Gln | Glu | Thr | Gly | Asp | Ile | Arg | Ser | Ala | Ile | Thr | Thr | Leu | Gln | |
| | | 305 | | | | | 310 | | | | | 315 | | | | |

| TTT | TGG | GCG | ACA | TCA | AGT | GGA | AGT | TTG | CCG | ATT | TCA | ACC | CGA | GAA | TCC | 1007 |
| Phe | Trp | Ala | Thr | Ser | Ser | Gly | Ser | Leu | Pro | Ile | Ser | Thr | Arg | Glu | Ser | |

|     |     |     |     | 320 |     |     |     |     | 325 |     |     |     |     | 330 |     |     |     |     | 335 |      |
| --- | --- | --- | --- | --- | --- | --- | --- | --- | --- | --- | --- | --- | --- | --- | --- | --- | --- | --- | --- | ---- |
| ACC | ATA | TCA | TAC | TTT | CAT | GCC | ATT | GGG | AAG | GTG | ATA | CAT | GGT | TCC | CAT |     |     |     |     | 1055 |
| Thr | Ile | Ser | Tyr | Phe | His | Ala | Ile | Gly | Lys | Val | Ile | His | Gly | Ser | His |     |     |     |     |      |
|     |     |     |     | 340 |     |     |     |     | 345 |     |     |     |     | 350 |     |     |     |     |     |      |
| AGC | ACG | AAT | AAC | GAT | AAC | GAA | ATG | ATT | AAT | AAC | CTC | TTC | GAA | AAT | TCG |     |     |     |     | 1103 |
| Ser | Thr | Asn | Asn | Asp | Asn | Glu | Met | Ile | Asn | Asn | Leu | Phe | Glu | Asn | Ser |     |     |     |     |      |
|     |     |     |     | 355 |     |     |     |     | 360 |     |     |     |     | 365 |     |     |     |     |     |      |
| AAC | AAT | TTG | TTA | TCG | AAA | GAG | GAT | TTC | AAA | TTA | GGA | ATA | TTA | GAG | AAC |     |     |     |     | 1151 |
| Asn | Asn | Leu | Leu | Ser | Lys | Glu | Asp | Phe | Lys | Leu | Gly | Ile | Leu | Glu | Asn |     |     |     |     |      |
|     |     |     |     | 370 |     |     |     |     | 375 |     |     |     |     | 380 |     |     |     |     |     |      |
| TAT | AAC | ACA | TTT | AAT | AAA | GGC | GAA | TTC | AGC | ATT | TCT | GAT | GCA | TCA | TCA |     |     |     |     | 1199 |
| Tyr | Asn | Thr | Phe | Asn | Lys | Gly | Glu | Phe | Ser | Ile | Ser | Asp | Ala | Ser | Ser |     |     |     |     |      |
|     |     |     |     | 385 |     |     |     |     | 390 |     |     |     |     | 395 |     |     |     |     |     |      |
| ATT | GTG | GAT | TGC | CTG | AGC | GAG | TGT | GAT | AAT | ATG | AAT | GGT | CTA | CCA | GAA |     |     |     |     | 1247 |
| Ile | Val | Asp | Cys | Leu | Ser | Glu | Cys | Asp | Asn | Met | Asn | Gly | Leu | Pro | Glu |     |     |     |     |      |
| 400 |     |     |     |     | 405 |     |     |     |     | 410 |     |     |     |     | 415 |     |     |     |     |      |
| TCC | AAT | GAG | TAT | GGT | TTA | CGA | GAA | GTG | CGC | AAA | ACC | TTT | CGT | AAC | ATC |     |     |     |     | 1295 |
| Ser | Asn | Glu | Tyr | Gly | Leu | Arg | Glu | Val | Arg | Lys | Thr | Phe | Arg | Asn | Ile |     |     |     |     |      |
|     |     |     |     | 420 |     |     |     |     | 425 |     |     |     |     | 430 |     |     |     |     |     |      |
| AGT | AAA | CAA | GGC | CAT | AAT | CAT | GGA | ACG | GTT | TAT | TTT | CCA | AGA | GAA | TGG |     |     |     |     | 1343 |
| Ser | Lys | Gln | Gly | His | Asn | His | Gly | Thr | Val | Tyr | Phe | Pro | Arg | Glu | Trp |     |     |     |     |      |
|     |     |     |     | 435 |     |     |     |     | 440 |     |     |     |     | 445 |     |     |     |     |     |      |
| AAA | GTA | AGA | AAA | TTA | CAA | AAT | TCA | TTT | AAA | GTT | CAA | GCT | GAA | GAT | TGG |     |     |     |     | 1391 |
| Lys | Val | Arg | Lys | Leu | Gln | Asn | Ser | Phe | Lys | Val | Gln | Ala | Glu | Asp | Trp |     |     |     |     |      |
|     |     |     | 450 |     |     |     |     | 455 |     |     |     |     | 460 |     |     |     |     |     |     |      |
| TTA | AAT | GTT | AGT | CTT | TAT | AAG | TAC | AAC | GCG | GTA | CAT | TCT | TTC | AGG | AAT |     |     |     |     | 1439 |
| Leu | Asn | Val | Ser | Leu | Tyr | Lys | Tyr | Asn | Ala | Val | His | Ser | Phe | Arg | Asn |     |     |     |     |      |
|     |     |     | 465 |     |     |     |     | 470 |     |     |     |     | 475 |     |     |     |     |     |     |      |
| ATA | ACT | CTA | GAA | TTT | GGC | TAC | TAC | GCA | CCT | CTA | ATT | AGA | AAG | TGT | CAG |     |     |     |     | 1487 |
| Ile | Thr | Leu | Glu | Phe | Gly | Tyr | Tyr | Ala | Pro | Leu | Ile | Arg | Lys | Cys | Gln |     |     |     |     |      |
| 480 |     |     |     |     | 485 |     |     |     |     | 490 |     |     |     |     | 495 |     |     |     |     |      |
| AGT | TAT | AAA | AAA | AAA | TAC | ATT | CTC | TAT | TAT | TTG | AAG | AAT | CTT | CCG | AGT |     |     |     |     | 1535 |
| Ser | Tyr | Lys | Lys | Lys | Tyr | Ile | Leu | Tyr | Tyr | Leu | Lys | Asn | Leu | Pro | Ser |     |     |     |     |      |
|     |     |     |     | 500 |     |     |     |     | 505 |     |     |     |     | 510 |     |     |     |     |     |      |
| GGC | TCC | TCG | GGG | CCC | AAA | CAA | ACC | ATG | GAC | AAA | TTT | AGT | GAT | ATA | ATG |     |     |     |     | 1583 |
| Gly | Ser | Ser | Gly | Pro | Lys | Gln | Thr | Met | Asp | Lys | Phe | Ser | Asp | Ile | Met |     |     |     |     |      |
|     |     |     | 515 |     |     |     |     | 520 |     |     |     |     | 525 |     |     |     |     |     |     |      |
| AAA | GTT | GAG | AAC | GGA | ATC | GAC | GTT | GTG | GAT | CGG | ATA | GGC | GGG | CCT | ATC |     |     |     |     | 1631 |
| Lys | Val | Glu | Asn | Gly | Ile | Asp | Val | Val | Asp | Arg | Ile | Gly | Gly | Pro | Ile |     |     |     |     |      |
|     |     | 530 |     |     |     |     | 535 |     |     |     |     | 540 |     |     |     |     |     |     |     |      |
| GAA | GCA | CTA | TCT | GTG | GAG | GAT | GGA | CTA | GCA | CCA | TTG | ATG | GAT | AAT | GAT |     |     |     |     | 1679 |
| Glu | Ala | Leu | Ser | Val | Glu | Asp | Gly | Leu | Ala | Pro | Leu | Met | Asp | Asn | Asp |     |     |     |     |      |
|     |     | 545 |     |     |     |     | 550 |     |     |     |     | 555 |     |     |     |     |     |     |     |      |
| AGC | AAT | AAT | TGT | GAC | CAT | TTA | GAG | GAT | CAA | AAA | AAG | GAA | AGG | GAC | AGA |     |     |     |     | 1727 |
| Ser | Asn | Asn | Cys | Asp | His | Leu | Glu | Asp | Gln | Lys | Lys | Glu | Arg | Asp | Arg |     |     |     |     |      |
| 560 |     |     |     |     | 565 |     |     |     |     | 570 |     |     |     |     | 575 |     |     |     |     |      |
| AGG | CTT | CGC | ATG | TTG | ATT | GAC | CAA | TAT | GAA | AGA | AAT | GTG | ATG | ATG | GCT |     |     |     |     | 1775 |
| Arg | Leu | Arg | Met | Leu | Ile | Asp | Gln | Tyr | Glu | Arg | Asn | Val | Met | Met | Ala |     |     |     |     |      |
|     |     |     |     | 580 |     |     |     |     | 585 |     |     |     |     | 590 |     |     |     |     |     |      |
| AAC | GAC | GAT | CTT | GAA | GAC | GAA | GAA | ACT | TCT | TTT | AAT | GAT | GAC | CCT | ATT |     |     |     |     | 1823 |
| Asn | Asp | Asp | Leu | Glu | Asp | Glu | Glu | Thr | Ser | Phe | Asn | Asp | Asp | Pro | Ile |     |     |     |     |      |
|     |     |     |     | 595 |     |     |     |     | 600 |     |     |     |     | 605 |     |     |     |     |     |      |
| GTC | GAT | AGC | GAT | AGC | GAT | AAC | AGC | AAT | AAT | ATT | GGC | AAT | GAA | ACA | TTT |     |     |     |     | 1871 |
| Val | Asp | Ser | Asp | Ser | Asp | Asn | Ser | Asn | Asn | Ile | Gly | Asn | Glu | Thr | Phe |     |     |     |     |      |
|     |     | 610 |     |     |     |     | 615 |     |     |     |     | 620 |     |     |     |     |     |     |     |      |
| GGT | AGA | AGC | GAC | GAA | GAC | GAG | TCT | CTA | TGT | GAA | ATT | CTG | TCC | CAG | AGA |     |     |     |     | 1919 |
| Gly | Arg | Ser | Asp | Glu | Asp | Glu | Ser | Leu | Cys | Glu | Ile | Leu | Ser | Gln | Arg |     |     |     |     |      |
|     |     | 625 |     |     |     |     | 630 |     |     |     |     | 635 |     |     |     |     |     |     |     |      |
| CAG | CCG | CGT | AAA | GCG | CCA | GTT | ATC | AGT | GAG | TCC | CTT | TCA | GAT | TCA | GAT |     |     |     |     | 1967 |
| Gln | Pro | Arg | Lys | Ala | Pro | Val | Ile | Ser | Glu | Ser | Leu | Ser | Asp | Ser | Asp |     |     |     |     |      |

-continued

```
  640                    645                    650                    655
CTG  GAA  ATA  CTC  TAACTTTTTA  CTCTTTAAAT  TTGACGAGAA  AACCCCAGGA                    2019
Leu  Glu  Ile  Leu
                    660

AATATTCCAC  ACAAATCTAT  GCACATTACA  TTCTAGAATA  AATTAATAAA  TAAAATATA                 2079

TACATATATA  TTAATATGTA  TATATGTATG  AATATAGTTT  TCATTACAAA  ATAAGGCTTA                2139

CTGTAGAGCA  TGTTGGAAAT  ATTCAGGATC  TTCTTCTATA  GATTCCTTGA  TAATATCCAA                2199

ACCTCCCTGG  AACTCCCCAT  TGATATATAA  CTGAGGAAAA  GTAGGCCAAT  CAGAAAACTT                2259

CTTCAAGCTT  TGTCTAACGT  TTTCGTCTCT  TAATATATCA  AAAAATCCGA  ACCTTATTTG                2319

GTGTTCTCTG  AGGATACCAA  CTAACTGTCT  AGAAAATCCG  CATTTAGGTT  CTGATGGGCT                2379

TCCTTTCATG  AATAGCATCA  CAGGTGCAGC  TTGTACTAGC  TTCACCAGCC  TAGCATTTAT                2439

TTCTTCTTCA  GTTTCGTCCT  CTTCATCATC  GGAAGACCCG  CTGCTTTCCT  CATCAGACGT                2499

AGATTTAGGA  CCCTTGGCAT  TGTTCGCTAG  TGAGGCAGAA  GCATTCGAAA  GAATTTCTAA                2559

GCTTTTCACA  AACTCCTTAG  GATCTGCGGC  TGATATTTCT  TTTACAATAG  TACCATTTTG                2619

AATGAAGACG  AAGTATGGTA  CGGCTGCAAT  CTCAAAAAGG  TCTGATATTT  CTGGATGTTC                2679

GTCTGCATCT  ATTGATAAAA  ACCGGACATC  CTCTTGCCTA  ACTTTTTCAC  TAACAGCTTC                2739

TAGCACCTGG  CTCATAGTTT  TGC                                                            2762
```

(2) INFORMATION FOR SEQ ID NO:13:

(i) SEQUENCE CHARACTERISTICS:
        (A) LENGTH: 659 amino acids
        (B) TYPE: amino acid
        (D) TOPOLOGY: linear (ii) MOLECULE TYPE: protein
        (A) DESCRIPTION: yeast RAD24 protein (xi) SEQUENCE DESCRIPTION: SEQ ID NO:13:

```
Met  Asp  Ser  Thr  Asn  Leu  Asn  Lys  Arg  Pro  Leu  Leu  Gln  Tyr  Ser  Leu
 1                   5                   10                  15

Ser  Ser  Leu  Gly  Ser  Gln  Ile  Thr  Lys  Trp  Ser  Ser  Ser  Arg  Pro  Thr
               20                  25                  30

Ser  Pro  Val  Arg  Lys  Ala  Arg  Ser  Thr  Glu  Asn  Asp  Phe  Leu  Ser  Lys
               35                  40                  45

Gln  Asp  Thr  Ser  Ser  Ile  Leu  Pro  Ser  Ile  Asn  Asp  Asp  Gly  Gly  Glu
          50                  55                  60

Gln  Trp  Tyr  Glu  Lys  Phe  Lys  Pro  Asn  Cys  Leu  Glu  Gln  Val  Ala  Ile
 65                  70                  75                      80

His  Lys  Arg  Lys  Leu  Lys  Asp  Val  Gln  Glu  Ala  Leu  Asp  Ala  Met  Phe
               85                  90                      95

Leu  Pro  Asn  Ala  Lys  His  Arg  Ile  Leu  Leu  Leu  Ser  Gly  Pro  Ser  Gly
               100                 105                 110

Cys  Ser  Lys  Ser  Thr  Val  Ile  Lys  Glu  Leu  Ser  Lys  Ile  Leu  Val  Pro
          115                 120                 125

Lys  Tyr  Arg  Gln  Asn  Ser  Asn  Gly  Thr  Ser  Phe  Arg  Ser  Thr  Pro  Asn
     130                 135                 140

Glu  His  Lys  Val  Thr  Glu  Phe  Arg  Gly  Asp  Cys  Ile  Val  Asn  Asp  Leu
145                      150                 155                     160

Pro  Gln  Met  Glu  Ser  Phe  Ser  Glu  Phe  Leu  Lys  Gly  Ala  Arg  Tyr  Leu
               165                 170                 175

Val  Met  Ser  Asn  Leu  Ser  Leu  Ile  Leu  Ile  Glu  Asp  Leu  Pro  Asn  Val
               180                 185                 190
```

```
Phe  His  Ile  Asp  Thr  Arg  Arg  Arg  Phe  Gln  Gln  Leu  Ile  Leu  Gln  Trp
          195                 200                      205

Leu  Tyr  Ser  Ser  Glu  Pro  Leu  Leu  Pro  Pro  Leu  Val  Ile  Cys  Ile  Thr
          210                 215                      220

Glu  Cys  Glu  Ile  Pro  Glu  Asn  Asp  Asn  Asn  Tyr  Arg  Lys  Phe  Gly  Ile
225                      230                 235                           240

Asp  Tyr  Thr  Phe  Ser  Ala  Glu  Thr  Ile  Met  Asn  Lys  Glu  Ile  Leu  Met
               245                      250                      255

His  Pro  Arg  Leu  Lys  Arg  Ile  Lys  Phe  Asn  Pro  Ile  Asn  Ser  Thr  Leu
               260                 265                      270

Leu  Lys  Lys  His  Leu  Lys  Phe  Ile  Cys  Val  Gln  Asn  Met  Lys  Met  Leu
               275                 280                      285

Lys  Glu  Lys  Asn  Lys  Trp  Asn  Lys  Arg  Gln  Glu  Val  Ile  Asp  Tyr  Ile
          290                 295                      300

Ala  Gln  Glu  Thr  Gly  Asp  Ile  Arg  Ser  Ala  Ile  Thr  Thr  Leu  Gln  Phe
305                      310                 315                           320

Trp  Ala  Thr  Ser  Ser  Gly  Ser  Leu  Pro  Ile  Ser  Thr  Arg  Glu  Ser  Thr
               325                 330                      335

Ile  Ser  Tyr  Phe  His  Ala  Ile  Gly  Lys  Val  Ile  His  Gly  Ser  His  Ser
               340                 345                      350

Thr  Asn  Asn  Asp  Asn  Glu  Met  Ile  Asn  Asn  Leu  Phe  Glu  Asn  Ser  Asn
          355                 360                      365

Asn  Leu  Leu  Ser  Lys  Glu  Asp  Phe  Lys  Leu  Gly  Ile  Leu  Glu  Asn  Tyr
     370                 375                      380

Asn  Thr  Phe  Asn  Lys  Gly  Glu  Phe  Ser  Ile  Ser  Asp  Ala  Ser  Ser  Ile
385                      390                 395                           400

Val  Asp  Cys  Leu  Ser  Glu  Cys  Asp  Asn  Met  Asn  Gly  Leu  Pro  Glu  Ser
               405                 410                      415

Asn  Glu  Tyr  Gly  Leu  Arg  Glu  Val  Arg  Lys  Thr  Phe  Arg  Asn  Ile  Ser
               420                 425                      430

Lys  Gln  Gly  His  Asn  His  Gly  Thr  Val  Tyr  Phe  Pro  Arg  Glu  Trp  Lys
               435                 440                      445

Val  Arg  Lys  Leu  Gln  Asn  Ser  Phe  Lys  Val  Gln  Ala  Glu  Asp  Trp  Leu
     450                 455                      460

Asn  Val  Ser  Leu  Tyr  Lys  Tyr  Asn  Ala  Val  His  Ser  Phe  Arg  Asn  Ile
465                      470                 475                           480

Thr  Leu  Glu  Phe  Gly  Tyr  Tyr  Ala  Pro  Leu  Ile  Arg  Lys  Cys  Gln  Ser
               485                 490                      495

Tyr  Lys  Lys  Lys  Tyr  Ile  Leu  Tyr  Tyr  Leu  Lys  Asn  Leu  Pro  Ser  Gly
               500                 505                      510

Ser  Ser  Gly  Pro  Lys  Gln  Thr  Met  Asp  Lys  Phe  Ser  Asp  Ile  Met  Lys
               515                 520                      525

Val  Glu  Asn  Gly  Ile  Asp  Val  Val  Asp  Arg  Ile  Gly  Gly  Pro  Ile  Glu
          530                 535                      540

Ala  Leu  Ser  Val  Glu  Asp  Gly  Leu  Ala  Pro  Leu  Met  Asn  Asp  Ser
545                      550                 555                           560

Asn  Asn  Cys  Asp  His  Leu  Glu  Asp  Gln  Lys  Lys  Glu  Arg  Asp  Arg  Arg
               565                 570                      575

Leu  Arg  Met  Leu  Ile  Asp  Gln  Tyr  Glu  Arg  Asn  Val  Met  Met  Ala  Asn
               580                 585                      590

Asp  Asp  Leu  Glu  Asp  Glu  Glu  Thr  Ser  Phe  Asn  Asp  Asp  Pro  Ile  Val
               595                 600                      605

Asp  Ser  Asp  Ser  Asp  Asn  Ser  Asn  Asn  Ile  Gly  Asn  Glu  Thr  Phe  Gly
```

```
                610                              615                          620
Arg  Ser  Asp  Glu  Asp  Glu  Ser  Leu  Cys  Glu  Ile  Leu  Ser  Gln  Arg  Gln
625                      630                      635                          640

Pro  Arg  Lys  Ala  Pro  Val  Ile  Ser  Glu  Ser  Leu  Ser  Asp  Ser  Asp  Leu
               645                      650                      655

Glu  Ile  Leu
```

( 2 ) INFORMATION FOR SEQ ID NO:14:

( i ) SEQUENCE CHARACTERISTICS:
        ( A ) LENGTH: 8351 base pairs
        ( B ) TYPE: nucleic acid
        ( C ) STRANDEDNESS: single
        ( D ) TOPOLOGY: linear ( i i ) MOLECULE TYPE: cDNA to mRNA
        ( A ) DESCRIPTION: yeast MEC1 cDNA ( i i i ) HYPOTHETICAL: NO ( i v ) ANTI-SENSE: NO ( v i ) ORIGINAL SOURCE:
        ( A ) ORGANISM: Saccharomyces cerevisiae ( i x ) FEATURE:
        ( A ) NAME/KEY: CDS
        ( B ) LOCATION: 784..7890

( x i ) SEQUENCE DESCRIPTION: SEQ ID NO:14:

```
ATAAGCTTAC  TGACCAAGAA  AGAGCACGCG  TGTTGGAGTT  TCAAGATTCC  ATTCACTATT      60

CTCCGCGGTA  CTCAGACGAT  AACTATGAGT  ACAGGCATGT  GATGTTACCT  AAGGCCATGC     120

TAAAAGTTAT  CCCATCTGAT  TACTTCAATT  CGGAAGTGGG  GACCCTGCGT  ATATTAACAG     180

AAGACGAATG  GAGAGGCCTC  GGCATCACAC  AGTCTTTGGG  GTGGGAACAT  TATGAATGCC     240

ATGCGCCAGA  ACTACACATT  TTGCTATTCA  AAAGGCCGCT  GAACTACGAG  GCCGAGCTGA     300

GGGCAGCGAC  CGCTGCTGCT  CAACAGCAAC  AGCAACAGCA  GCAACAGCAG  CAACAACAAC     360

AACAGCAACA  TCAAACACAA  TCGATTTCGA  ACGATATGCA  AGTTCCACCC  CAAATCTCCT     420

AGCTTTGATA  TACTCTAATT  ACTGAAATTG  AATTCCTTTT  CAAGGCTCCA  TAACTATATG     480

GAGCATACTA  TGTACTTATC  ATAATAAAGA  ATAAACAAAC  AAGCAAACAA  AAAAAAAAAA     540

AACTATGGAT  CATAGTTTTC  ACCAACAAGC  ATTAGAATAC  AAATAAAATT  TATATAGTGA     600

ATATCCTTCA  AATAAATTTC  TTCTTTCCCT  TATAAATCAA  ATAGATGGAA  CGCACGCTCC     660

AAAACTAGTC  AACTAGAAAA  AAATACCCGC  CGACGGACAA  TTTTGAAGAG  AGATGATTAA     720

TGAAGACAAA  GTGAGGCTGG  ACAACAAGAA  CGACATACAC  CGCGTAAAGG  CCCACAAGAC     780

TGC  ATG  GAA  TCA  CAC  GTC  AAA  TAT  CTT  GAC  GAA  TTG  ATA  TTG  GCA  ATA     828
     Met  Glu  Ser  His  Val  Lys  Tyr  Leu  Asp  Glu  Leu  Ile  Leu  Ala  Ile
      1              5                        10                        15

AAA  GAC  CTG  AAC  TCG  GGG  GTG  GAT  TCA  AAG  GTG  CAG  ATT  AAA  AAA  GTG     876
Lys  Asp  Leu  Asn  Ser  Gly  Val  Asp  Ser  Lys  Val  Gln  Ile  Lys  Lys  Val
                         20                        25                        30

CCC  ACG  GAT  CCA  TCT  TCT  TCT  CAG  GAG  TAC  GCC  AAG  AGT  TTA  AAG  ATC     924
Pro  Thr  Asp  Pro  Ser  Ser  Ser  Gln  Glu  Tyr  Ala  Lys  Ser  Leu  Lys  Ile
                    35                        40                        45

CTG  AAC  ACC  CTC  ATA  AGA  AAC  CTA  AAA  GAT  CAA  AGA  AGG  AAC  AAT  ATC     972
Leu  Asn  Thr  Leu  Ile  Arg  Asn  Leu  Lys  Asp  Gln  Arg  Arg  Asn  Asn  Ile
               50                        55                        60

ATG  AAA  AAT  GAT  ACT  ATA  TTT  TCG  AAA  ACA  GTT  TCC  GCC  CTT  GCC  TTA    1020
Met  Lys  Asn  Asp  Thr  Ile  Phe  Ser  Lys  Thr  Val  Ser  Ala  Leu  Ala  Leu
 65                        70                        75
```

```
TTG TTG GAG TAC AAC CCC TTC TTG CTT GTT ATG AAG GAT TCC AAC GGG     1068
Leu Leu Glu Tyr Asn Pro Phe Leu Leu Val Met Lys Asp Ser Asn Gly
 80              85                  90                  95

AAC TTT GAG ATA CAA AGG CTG ATA GAT GAT TTC CTC AAC ATA TCC GTT     1116
Asn Phe Glu Ile Gln Arg Leu Ile Asp Asp Phe Leu Asn Ile Ser Val
             100                 105                 110

CTG AAC TAT GAT AAT TAC CAC AGA ATA TGG TTT ATG AGG CGA AAA TTA     1164
Leu Asn Tyr Asp Asn Tyr His Arg Ile Trp Phe Met Arg Arg Lys Leu
                 115                 120                 125

GGC AGC TGG TGC AAA GCA TGT GTC GAA TTT TAC GGA AAA CCT GCT AAG     1212
Gly Ser Trp Cys Lys Ala Cys Val Glu Phe Tyr Gly Lys Pro Ala Lys
             130                 135                 140

TTT CAG CTT ACT GCA CAT TTT GAG AAC ACC ATG AAT CTT TAC GAA CAG     1260
Phe Gln Leu Thr Ala His Phe Glu Asn Thr Met Asn Leu Tyr Glu Gln
 145                 150                 155

GCC TTG ACT GAA GTC TTG TTG GGC AAG ACT GAG CTT CTC AAA TTT TAT     1308
Ala Leu Thr Glu Val Leu Leu Gly Lys Thr Glu Leu Leu Lys Phe Tyr
 160             165                 170                 175

GAC ACC TTG AAG GGT CTA TAC ATT CTT TTA TAC TGG TTC ACT TCG GAG     1356
Asp Thr Leu Lys Gly Leu Tyr Ile Leu Leu Tyr Trp Phe Thr Ser Glu
                 180                 185                 190

TAT AGT ACT TTT GGG AAC TCT ATA GCA TTC TTA GAT TCT TCT TTG GGG     1404
Tyr Ser Thr Phe Gly Asn Ser Ile Ala Phe Leu Asp Ser Ser Leu Gly
             195                 200                 205

TTC ACG AAA TTT GAC TTT AAC TTC CAA CGA TTA ATC AGG ATT GTT CTT     1452
Phe Thr Lys Phe Asp Phe Asn Phe Gln Arg Leu Ile Arg Ile Val Leu
         210                 215                 220

TAC GTC TTT GAT TCC TGC GAA CTA GCA GCA CTA GAA TAT GCC GAA ATC     1500
Tyr Val Phe Asp Ser Cys Glu Leu Ala Ala Leu Glu Tyr Ala Glu Ile
 225                 230                 235

CAA CTC AAA TAT ATT TCT CTA GTT GTG GAC TAT GTT TGC AAT AGA ACA     1548
Gln Leu Lys Tyr Ile Ser Leu Val Val Asp Tyr Val Cys Asn Arg Thr
 240                 245                 250                 255

ATT TCC ACA GCC CTG GAT GCC CCA GCG TTA GTT TGT TGT GAA CAA TTA     1596
Ile Ser Thr Ala Leu Asp Ala Pro Ala Leu Val Cys Cys Glu Gln Leu
                 260                 265                 270

AAG TTT GTA TTG ACT ACT ATG CAT CAT TTT TTG GAT AAC AAG TAT GGG     1644
Lys Phe Val Leu Thr Thr Met His His Phe Leu Asp Asn Lys Tyr Gly
             275                 280                 285

CTC TTG GAT AAT GAC CCC ACT ATG GCC AAA GGA ATT CTT CGA CTA TAT     1692
Leu Leu Asp Asn Asp Pro Thr Met Ala Lys Gly Ile Leu Arg Leu Tyr
         290                 295                 300

TCT CTT TGC ATT TCT AAC GAT TTC TCA AAA TGC TTT GTA GAC CAC TTC     1740
Ser Leu Cys Ile Ser Asn Asp Phe Ser Lys Cys Phe Val Asp His Phe
 305                 310                 315

CCA ATT GAC CAG TGG GCA GAT TTT TCA CAA AGT GAA CAT TTT CCG TTC     1788
Pro Ile Asp Gln Trp Ala Asp Phe Ser Gln Ser Glu His Phe Pro Phe
 320                 325                 330                 335

ACG CAG TTG ACT AAT AAA GCT CTC TCG ATT GTA TAT TTT GAT TTG AAA     1836
Thr Gln Leu Thr Asn Lys Ala Leu Ser Ile Val Tyr Phe Asp Leu Lys
                 340                 345                 350

AGA AGG TCC CTA CCT GTT GAA GCT TTA AAG TAC GAT AAT AAG TTC AAC     1884
Arg Arg Ser Leu Pro Val Glu Ala Leu Lys Tyr Asp Asn Lys Phe Asn
             355                 360                 365

ATC TGG GTA TAC CAA TCG GAG CCG GAC TCG AGC TTG AAA AAT GTC ACT     1932
Ile Trp Val Tyr Gln Ser Glu Pro Asp Ser Ser Leu Lys Asn Val Thr
         370                 375                 380

TCT CCC TTT GAT GAT CGA TAT AAG CAG CTG GAA AAG CTA AGG TTG CTA     1980
Ser Pro Phe Asp Asp Arg Tyr Lys Gln Leu Glu Lys Leu Arg Leu Leu
 385                 390                 395
```

| | | | | | | | | | | | | | | | | |
|---|---|---|---|---|---|---|---|---|---|---|---|---|---|---|---|---|
| GTA | CTA | AAG | AAG | TTT | AAC | AAG | ACA | GAA | AGA | GGA | ACT | TTG | CTC | AAA | TAC | 2028 |
| Val | Leu | Lys | Lys | Phe | Asn | Lys | Thr | Glu | Arg | Gly | Thr | Leu | Leu | Lys | Tyr | |
| 400 | | | | | 405 | | | | 410 | | | | | | 415 | |
| CGC | GTG | AAC | CAG | CTA | AGT | CCT | GGA | TTT | TTT | CAA | AGA | GCT | GGA | AAC | GAT | 2076 |
| Arg | Val | Asn | Gln | Leu | Ser | Pro | Gly | Phe | Phe | Gln | Arg | Ala | Gly | Asn | Asp | |
| | | | 420 | | | | | | 425 | | | | | 430 | | |
| TTC | AAG | CTA | ATT | TTA | AAT | GAA | GCA | TCT | GTA | TCC | ATT | CAA | ACT | TGT | TTC | 2124 |
| Phe | Lys | Leu | Ile | Leu | Asn | Glu | Ala | Ser | Val | Ser | Ile | Gln | Thr | Cys | Phe | |
| | | | 435 | | | | | 440 | | | | | 445 | | | |
| AAG | ACA | AAC | AAT | ATA | ACA | AGG | CTA | ACA | TCA | TGG | ACT | GTA | ATT | CTC | GGA | 2172 |
| Lys | Thr | Asn | Asn | Ile | Thr | Arg | Leu | Thr | Ser | Trp | Thr | Val | Ile | Leu | Gly | |
| | | | 450 | | | | 455 | | | | | 460 | | | | |
| CGT | CTA | GCC | TGT | CTA | GAA | TCA | GAG | AAG | TTT | TCC | GGC | ACT | CTG | CCA | AAT | 2220 |
| Arg | Leu | Ala | Cys | Leu | Glu | Ser | Glu | Lys | Phe | Ser | Gly | Thr | Leu | Pro | Asn | |
| | 465 | | | | | 470 | | | | | 475 | | | | | |
| TCC | ACA | AAG | GAT | ATG | GAT | AAT | TGG | TAT | GTT | TGT | CAT | TTA | TGC | GAT | ATT | 2268 |
| Ser | Thr | Lys | Asp | Met | Asp | Asn | Trp | Tyr | Val | Cys | His | Leu | Cys | Asp | Ile | |
| 480 | | | | | 485 | | | | 490 | | | | | | 495 | |
| GAG | AAA | ACT | GGC | AAC | CCT | TTC | GTG | CGA | ATA | AAT | CCA | AAT | AGA | CCA | GAG | 2316 |
| Glu | Lys | Thr | Gly | Asn | Pro | Phe | Val | Arg | Ile | Asn | Pro | Asn | Arg | Pro | Glu | |
| | | | | 500 | | | | | 505 | | | | | 510 | | |
| GCT | GCG | GGT | AAA | TCA | GAA | ATC | TTC | AGG | ATA | CTT | CAT | TCA | AAC | TTT | CTA | 2364 |
| Ala | Ala | Gly | Lys | Ser | Glu | Ile | Phe | Arg | Ile | Leu | His | Ser | Asn | Phe | Leu | |
| | | | 515 | | | | | 520 | | | | | 525 | | | |
| TCT | CAC | CCA | AAT | ATA | GAT | GAA | TTT | AGC | GAA | TCT | TTG | TTA | AGT | GGC | ATC | 2412 |
| Ser | His | Pro | Asn | Ile | Asp | Glu | Phe | Ser | Glu | Ser | Leu | Leu | Ser | Gly | Ile | |
| | | 530 | | | | | 535 | | | | | 540 | | | | |
| TTA | TTT | TCT | CTA | CAT | AGG | ATA | TTT | TCA | CAC | TTT | CAA | CCT | CCA | AAA | CTT | 2460 |
| Leu | Phe | Ser | Leu | His | Arg | Ile | Phe | Ser | His | Phe | Gln | Pro | Pro | Lys | Leu | |
| | 545 | | | | | 550 | | | | | 555 | | | | | |
| ACA | GAT | GGA | AAC | GGT | CAA | ATC | AAT | AAG | AGC | TTT | AAA | CTG | GTA | CAA | AAG | 2508 |
| Thr | Asp | Gly | Asn | Gly | Gln | Ile | Asn | Lys | Ser | Phe | Lys | Leu | Val | Gln | Lys | |
| 560 | | | | | 565 | | | | 570 | | | | | | 575 | |
| TGC | TTT | ATG | AAT | TCT | AAC | AGA | TAC | CTA | CGT | TTA | TTA | AGT | ACT | AGA | ATT | 2556 |
| Cys | Phe | Met | Asn | Ser | Asn | Arg | Tyr | Leu | Arg | Leu | Leu | Ser | Thr | Arg | Ile | |
| | | | | 580 | | | | | 585 | | | | | 590 | | |
| ATA | CCT | TTA | TTC | AAT | ATA | TCA | GAC | TCT | CAT | AAT | TCC | GAA | GAT | GAA | CAC | 2604 |
| Ile | Pro | Leu | Phe | Asn | Ile | Ser | Asp | Ser | His | Asn | Ser | Glu | Asp | Glu | His | |
| | | | 595 | | | | | 600 | | | | | 605 | | | |
| ACT | GCC | ACG | CTG | ATA | AAG | TTT | CTA | CAA | TCT | CAA | AAA | TTG | CCA | GTG | GTG | 2652 |
| Thr | Ala | Thr | Leu | Ile | Lys | Phe | Leu | Gln | Ser | Gln | Lys | Leu | Pro | Val | Val | |
| | | | 610 | | | | 615 | | | | | 620 | | | | |
| AAA | GAA | AAT | TTA | GTC | ATT | GCT | TGG | ACA | CAA | TTA | ACA | TTG | ACG | ACT | TCT | 2700 |
| Lys | Glu | Asn | Leu | Val | Ile | Ala | Trp | Thr | Gln | Leu | Thr | Leu | Thr | Thr | Ser | |
| | | 625 | | | | | 630 | | | | | 635 | | | | |
| AAT | GAT | GTA | TTT | GAT | ACA | CTA | CTT | TTG | AAA | CTG | ATT | GAT | ATT | TTC | AAT | 2748 |
| Asn | Asp | Val | Phe | Asp | Thr | Leu | Leu | Leu | Lys | Leu | Ile | Asp | Ile | Phe | Asn | |
| 640 | | | | | 645 | | | | 650 | | | | | | 655 | |
| TCT | GAT | GAT | TAT | AGT | TTA | CGA | ATA | ATG | ATG | ACT | TTG | CAA | ATT | AAA | AAT | 2796 |
| Ser | Asp | Asp | Tyr | Ser | Leu | Arg | Ile | Met | Met | Thr | Leu | Gln | Ile | Lys | Asn | |
| | | | | 660 | | | | | 665 | | | | | 670 | | |
| ATG | GCC | AAA | ATT | TTA | AAG | AAA | ACA | CCA | TAT | CAA | TTA | CTA | TCG | CCT | ATT | 2844 |
| Met | Ala | Lys | Ile | Leu | Lys | Lys | Thr | Pro | Tyr | Gln | Leu | Leu | Ser | Pro | Ile | |
| | | | 675 | | | | | 680 | | | | | 685 | | | |
| TTA | CCT | GTA | TTA | CTA | AGA | CAG | TTG | GGA | AAA | AAC | CTC | GTG | GAA | AGA | AAA | 2892 |
| Leu | Pro | Val | Leu | Leu | Arg | Gln | Leu | Gly | Lys | Asn | Leu | Val | Glu | Arg | Lys | |
| | | 690 | | | | | 695 | | | | | 700 | | | | |
| GTT | GGC | TTT | CAA | AAT | TTA | ATA | GAA | TTA | TTG | GGA | TAT | CCT | TCA | AAA | ACA | 2940 |
| Val | Gly | Phe | Gln | Asn | Leu | Ile | Glu | Leu | Leu | Gly | Tyr | Pro | Ser | Lys | Thr | |
| 705 | | | | | | 710 | | | | | 715 | | | | | |

| | | | | | | | | | | | | | | | | |
|---|---|---|---|---|---|---|---|---|---|---|---|---|---|---|---|---|
| ATT | CTC | GAT | ATT | TTC | CAG | AGA | TAT | ATC | ATC | CCT | TAT | GCA | ATT | ATT | CAA | 2988 |
| Ile | Leu | Asp | Ile | Phe | Gln | Arg | Tyr | Ile | Ile | Pro | Tyr | Ala | Ile | Ile | Gln | |
| 720 | | | | | 725 | | | | | 730 | | | | | 735 | |
| TAT | AAG | AGC | GAT | GTG | CTA | AGT | GAA | ATT | GCT | AAG | ATT | ATG | TGT | GAT | GGC | 3036 |
| Tyr | Lys | Ser | Asp | Val | Leu | Ser | Glu | Ile | Ala | Lys | Ile | Met | Cys | Asp | Gly | |
| | | | | 740 | | | | | 745 | | | | | 750 | | |
| GAT | ACA | AGT | TTA | ATT | AAC | CAA | ATG | AAG | GTT | AAT | TTA | CTG | AAA | AAA | AAC | 3084 |
| Asp | Thr | Ser | Leu | Ile | Asn | Gln | Met | Lys | Val | Asn | Leu | Leu | Lys | Lys | Asn | |
| | | | | 755 | | | | | 760 | | | | | 765 | | |
| AGT | AGG | CAA | ATA | TTT | GCC | GTA | GCT | TTG | GTA | AAA | CAC | GGA | TTA | TTT | TCT | 3132 |
| Ser | Arg | Gln | Ile | Phe | Ala | Val | Ala | Leu | Val | Lys | His | Gly | Leu | Phe | Ser | |
| | | | 770 | | | | | 775 | | | | | 780 | | | |
| TTG | GAT | ATC | TTG | GAA | ACC | CTT | TTT | TTA | AAT | AGG | GCT | CCA | ACT | TTT | GAC | 3180 |
| Leu | Asp | Ile | Leu | Glu | Thr | Leu | Phe | Leu | Asn | Arg | Ala | Pro | Thr | Phe | Asp | |
| 785 | | | | | 790 | | | | | 795 | | | | | | |
| AAA | GGA | TAT | ATA | ACT | GCA | TAC | CTT | CCC | GAT | TAT | AAA | ACT | TTA | GCT | GAA | 3228 |
| Lys | Gly | Tyr | Ile | Thr | Ala | Tyr | Leu | Pro | Asp | Tyr | Lys | Thr | Leu | Ala | Glu | |
| 800 | | | | | 805 | | | | | 810 | | | | | 815 | |
| ATA | ACG | AAG | CTC | TAC | AAA | AAC | AGC | GTT | ACT | AAA | GAT | GCA | AGT | GAC | AGC | 3276 |
| Ile | Thr | Lys | Leu | Tyr | Lys | Asn | Ser | Val | Thr | Lys | Asp | Ala | Ser | Asp | Ser | |
| | | | | 820 | | | | | 825 | | | | | 830 | | |
| GAG | AAT | GCT | AAT | ATG | ATT | TTA | TGC | TCT | TTG | CGA | TTT | TTA | ATC | ACC | AAT | 3324 |
| Glu | Asn | Ala | Asn | Met | Ile | Leu | Cys | Ser | Leu | Arg | Phe | Leu | Ile | Thr | Asn | |
| | | | 835 | | | | | 840 | | | | | 845 | | | |
| TTT | GAA | AAA | GAC | AAA | AGG | CAT | GGT | TCG | AAG | TAC | AAA | AAT | ATC | AAT | AAC | 3372 |
| Phe | Glu | Lys | Asp | Lys | Arg | His | Gly | Ser | Lys | Tyr | Lys | Asn | Ile | Asn | Asn | |
| 850 | | | | | 855 | | | | | 860 | | | | | | |
| TGG | ACG | GAT | GAT | CAG | GAA | CAA | GCG | TTC | CAA | AAG | AAA | CTA | CAG | GAT | AAT | 3420 |
| Trp | Thr | Asp | Asp | Gln | Glu | Gln | Ala | Phe | Gln | Lys | Lys | Leu | Gln | Asp | Asn | |
| 865 | | | | | 870 | | | | | 875 | | | | | | |
| ATC | TTA | GGT | ATT | TTC | CAA | GTT | TTT | TCG | AGT | GAC | ATA | CAT | GAT | GTT | GAA | 3468 |
| Ile | Leu | Gly | Ile | Phe | Gln | Val | Phe | Ser | Ser | Asp | Ile | His | Asp | Val | Glu | |
| 880 | | | | | 885 | | | | | 890 | | | | | 895 | |
| GGC | CGC | ACC | ACT | TAC | TAC | GAA | AAG | TTA | AGG | GTT | ATC | AAT | GGC | ATT | TCT | 3516 |
| Gly | Arg | Thr | Thr | Tyr | Tyr | Glu | Lys | Leu | Arg | Val | Ile | Asn | Gly | Ile | Ser | |
| | | | | 900 | | | | | 905 | | | | | 910 | | |
| TTT | CTT | ATC | ATA | TAT | GCC | CCC | AAA | AAA | TCA | ATA | ATT | TCC | GCA | TTA | GCC | 3564 |
| Phe | Leu | Ile | Ile | Tyr | Ala | Pro | Lys | Lys | Ser | Ile | Ile | Ser | Ala | Leu | Ala | |
| | | | 915 | | | | | 920 | | | | | 925 | | | |
| CAG | ATT | AGT | ATT | TGT | TTG | CAA | ACA | GGA | CTT | GGG | CTT | AAG | GAA | GTT | CGA | 3612 |
| Gln | Ile | Ser | Ile | Cys | Leu | Gln | Thr | Gly | Leu | Gly | Leu | Lys | Glu | Val | Arg | |
| | | 930 | | | | | 935 | | | | | 940 | | | | |
| TAC | GAG | GCC | TTT | AGA | TGT | TGG | CAT | CTG | TTA | GTT | CGC | CAT | CTA | AAT | GAT | 3660 |
| Tyr | Glu | Ala | Phe | Arg | Cys | Trp | His | Leu | Leu | Val | Arg | His | Leu | Asn | Asp | |
| 945 | | | | | 950 | | | | | 955 | | | | | | |
| GAA | GAA | CTC | TCT | ACT | GTT | ATA | GAT | AGC | TTA | ATT | GCA | TTC | ATA | CTT | CAA | 3708 |
| Glu | Glu | Leu | Ser | Thr | Val | Ile | Asp | Ser | Leu | Ile | Ala | Phe | Ile | Leu | Gln | |
| 960 | | | | | 965 | | | | | 970 | | | | | 975 | |
| AAG | TGG | TCT | GAG | TTC | AAC | GGA | AAA | CTT | CGA | AAT | ATA | GTG | TAC | AGT | ATA | 3756 |
| Lys | Trp | Ser | Glu | Phe | Asn | Gly | Lys | Leu | Arg | Asn | Ile | Val | Tyr | Ser | Ile | |
| | | | | 980 | | | | | 985 | | | | | 990 | | |
| CTG | GAT | ACC | TTA | ATC | AAA | GAG | AAA | TCG | GAC | CTG | ATT | TTG | AAA | TTA | AAA | 3804 |
| Leu | Asp | Thr | Leu | Ile | Lys | Glu | Lys | Ser | Asp | Leu | Ile | Leu | Lys | Leu | Lys | |
| | | | 995 | | | | | 1000 | | | | | 1005 | | | |
| CCT | TAC | ACT | ACT | TTG | GCT | TTA | GTA | GGC | AAG | CCT | GAA | TTA | GGT | ATT | TTA | 3852 |
| Pro | Tyr | Thr | Thr | Leu | Ala | Leu | Val | Gly | Lys | Pro | Glu | Leu | Gly | Ile | Leu | |
| | | 1010 | | | | | 1015 | | | | | 1020 | | | | |
| GCT | CGT | GAT | GGC | CAA | TTT | GCA | AGA | ATG | GTG | AAT | AAA | ATA | AGA | AGT | ACC | 3900 |
| Ala | Arg | Asp | Gly | Gln | Phe | Ala | Arg | Met | Val | Asn | Lys | Ile | Arg | Ser | Thr | |
| 1025 | | | | | 1030 | | | | | 1035 | | | | | | |

```
ACG GAC CTT ATA CCC ATA TTT GCT AAT AAC TTG AAA AGT AGT AAC AAG        3948
Thr Asp Leu Ile Pro Ile Phe Ala Asn Asn Leu Lys Ser Ser Asn Lys
1040            1045                1050                1055

TAT GTC ATA AAC CAA AAT TTA GAC GAT ATA GAG GTA TAT CTT CGG AGA        3996
Tyr Val Ile Asn Gln Asn Leu Asp Asp Ile Glu Val Tyr Leu Arg Arg
                1060                1065                1070

AAG CAG ACA GAA AGA TCG ATT GAT TTT ACA CCA AAG AAG GTT GGG CAA        4044
Lys Gln Thr Glu Arg Ser Ile Asp Phe Thr Pro Lys Lys Val Gly Gln
            1075                1080                1085

ACT TCT GAT ATA ACA TTA GTT TTG GGT GCT TTA TTA GAC ACT TCT CAT        4092
Thr Ser Asp Ile Thr Leu Val Leu Gly Ala Leu Leu Asp Thr Ser His
1090                1095                1100

AAG TTT AGA AAT TTA GAC AAG GAC CTA TGC GAG AAG TGC GCC AAA TGT        4140
Lys Phe Arg Asn Leu Asp Lys Asp Leu Cys Glu Lys Cys Ala Lys Cys
    1105                1110                1115

ATC AGT ATG ATT GGT GTT TTA GAC GTT ACA AAG CAT GAG TTT AAA AGA        4188
Ile Ser Met Ile Gly Val Leu Asp Val Thr Lys His Glu Phe Lys Arg
1120                1125                1130                1135

ACA ACA TAT TCA GAA AAC GAA GTT TAT GAT TTG AAT GAT AGT GTT CAA        4236
Thr Thr Tyr Ser Glu Asn Glu Val Tyr Asp Leu Asn Asp Ser Val Gln
                1140                1145                1150

ACT ATT AAG TTC TTG ATA TGG GTC ATA AAT GAT ATC CTC GTT CCT GCG        4284
Thr Ile Lys Phe Leu Ile Trp Val Ile Asn Asp Ile Leu Val Pro Ala
            1155                1160                1165

TTT TGG CAA AGT GAG AAT CCC AGC AAG CAA TTG TTT GTT GCC CTT GTC        4332
Phe Trp Gln Ser Glu Asn Pro Ser Lys Gln Leu Phe Val Ala Leu Val
        1170                1175                1180

ATA CAG GAA TCA TTA AAA TAT TGC GGG CTA AGT TCA GAG TCA TGG GAT        4380
Ile Gln Glu Ser Leu Lys Tyr Cys Gly Leu Ser Ser Glu Ser Trp Asp
Ile 1185                1190                1195

ATG AAC CAT AAA GAA TTA TAT CCA AAT GAA GCC AAA CTA TGG GAA AAG        4428
Met Asn His Lys Glu Leu Tyr Pro Asn Glu Ala Lys Leu Trp Glu Lys
1200                1205                1210                1215

TTT AAC TCT GTC TCC AAG ACA ACC ATC TAT CCG CTT TTA TCT TCC TTG        4476
Phe Asn Ser Val Ser Lys Thr Thr Ile Tyr Pro Leu Leu Ser Ser Leu
                1220                1225                1230

TAT CTT GCG CAA TCA TGG AAA GAA TAT GTC CCG CTA AAA TAT CCT TCT        4524
Tyr Leu Ala Gln Ser Trp Lys Glu Tyr Val Pro Leu Lys Tyr Pro Ser
            1235                1240                1245

AAT AAC TTC AAG GAA GGA TAC CAA ATT TGG GTG AAA AGG TTT ACA TTG        4572
Asn Asn Phe Lys Glu Gly Tyr Gln Ile Trp Val Lys Arg Phe Thr Leu
        1250                1255                1260

GAT TTA TTG AAA ACA GGT ACA ACA GAA AAT CAT CCA GGA CAC GTG TTT        4620
Asp Leu Leu Lys Thr Gly Thr Thr Glu Asn His Pro Gly His Val Phe
    1265                1270                1275

TCC TCT TTG ATT AGG GAA GAT GAT GGC TCA CTA TCA AAT TTT TTG CTA        4668
Ser Ser Leu Ile Arg Glu Asp Asp Gly Ser Leu Ser Asn Phe Leu Leu
1280                1285                1290                1295

CCT TAT ATT TCT CTG GAC ATT ATT ATC AAG GCA GAA AAA GGA ACT CCA        4716
Pro Tyr Ile Ser Leu Asp Ile Ile Ile Lys Ala Glu Lys Gly Thr Pro
                1300                1305                1310

TAC GCT GAT ATT TTA AAC GGG ATT ATT ATT GAA TTT GAC AGC ATT TTC        4764
Tyr Ala Asp Ile Leu Asn Gly Ile Ile Ile Glu Phe Asp Ser Ile Phe
            1315                1320                1325

ACG TGC AAT CTG GAA GGA ATG AAT AAC TTG CAA GTG GAT TCG TTA AGA        4812
Thr Cys Asn Leu Glu Gly Met Asn Asn Leu Gln Val Asp Ser Leu Arg
        1330                1335                1340

ATG TGC TAT GAA TCC ATC TTC AGA GTT TTC GAA TAT TGC AAA AAA TGG        4860
Met Cys Tyr Glu Ser Ile Phe Arg Val Phe Glu Tyr Cys Lys Lys Trp
    1345                1350                1355
```

| | | | | | | | | | | | | | | | | |
|---|---|---|---|---|---|---|---|---|---|---|---|---|---|---|---|---|
| GCA | ACT | GAG | TTT | AAA | CAA | AAT | TAC | AGT | AAA | CTA | CAC | GGC | ACT | TTT | ATC | 4908 |
| Ala | Thr | Glu | Phe | Lys | Gln | Asn | Tyr | Ser | Lys | Leu | His | Gly | Thr | Phe | Ile | |
| 1360 | | | | | 1365 | | | | | 1370 | | | | | 1375 | |
| ATT | AAA | GAT | ACG | AAA | ACA | ACT | AAC | ATG | CTT | TTG | AGA | ATA | GAT | GAG | TTT | 4956 |
| Ile | Lys | Asp | Thr | Lys | Thr | Thr | Asn | Met | Leu | Leu | Arg | Ile | Asp | Glu | Phe | |
| | | | | 1380 | | | | | 1385 | | | | | 1390 | | |
| TTG | CGA | ACA | ACC | CCT | TCA | GAT | TTG | CTA | GCT | CAA | CGC | TCC | TTA | GAG | ACG | 5004 |
| Leu | Arg | Thr | Thr | Pro | Ser | Asp | Leu | Leu | Ala | Gln | Arg | Ser | Leu | Glu | Thr | |
| | | | | 1395 | | | | | 1400 | | | | | 1405 | | |
| GAT | TCT | TTT | GAA | AGG | TCT | GCT | CTA | TAC | CTT | GAA | CAG | TGC | TAT | CGA | CAG | 5052 |
| Asp | Ser | Phe | Glu | Arg | Ser | Ala | Leu | Tyr | Leu | Glu | Gln | Cys | Tyr | Arg | Gln | |
| | | | 1410 | | | | | 1415 | | | | | 1420 | | | |
| AAT | CCT | CAC | GAT | AAG | AAC | CAA | AAT | GGA | CAA | CTA | CTG | AAA | AAT | TTA | CAA | 5100 |
| Asn | Pro | His | Asp | Lys | Asn | Gln | Asn | Gly | Gln | Leu | Leu | Lys | Asn | Leu | Gln | |
| | | 1425 | | | | | 1430 | | | | | 1435 | | | | |
| ATC | ACA | TAC | GAA | GAA | ATA | GGA | GAC | ATT | GAC | TCA | CTC | GAT | GGT | GTA | CTG | 5148 |
| Ile | Thr | Tyr | Glu | Glu | Ile | Gly | Asp | Ile | Asp | Ser | Leu | Asp | Gly | Val | Leu | |
| 1440 | | | | | 1445 | | | | | 1450 | | | | | 1455 | |
| AGA | ACC | TTT | GCT | ACA | GGA | AAC | TTG | GTT | TCT | AAA | ATT | GAA | GAA | TTG | CAA | 5196 |
| Arg | Thr | Phe | Ala | Thr | Gly | Asn | Leu | Val | Ser | Lys | Ile | Glu | Glu | Leu | Gln | |
| | | | | 1460 | | | | | 1465 | | | | | 1470 | | |
| TAT | TCT | GAA | AAC | TGG | AAA | CTC | GCA | CAA | GAC | TGC | TTT | AAT | GTC | CTC | GGC | 5244 |
| Tyr | Ser | Glu | Asn | Trp | Lys | Leu | Ala | Gln | Asp | Cys | Phe | Asn | Val | Leu | Gly | |
| | | | | 1475 | | | | | 1480 | | | | | 1485 | | |
| AAA | TTT | TCA | GAT | GAC | CCC | AAA | ACT | ACA | ACC | AGG | ATG | CTA | AAG | TCT | ATG | 5292 |
| Lys | Phe | Ser | Asp | Asp | Pro | Lys | Thr | Thr | Thr | Arg | Met | Leu | Lys | Ser | Met | |
| | | | 1490 | | | | | 1495 | | | | | 1500 | | | |
| TAT | GAC | CAC | CAA | TTG | TAT | TCT | CAA | ATA | ATA | TCG | AAC | TCT | TCG | TTC | CAT | 5340 |
| Tyr | Asp | His | Gln | Leu | Tyr | Ser | Gln | Ile | Ile | Ser | Asn | Ser | Ser | Phe | His | |
| | | 1505 | | | | | 1510 | | | | | 1515 | | | | |
| TCT | TCA | GAC | GGA | AAA | ATT | TCT | TTG | TCT | CCA | GAT | GTG | AAG | GAA | TGG | TAC | 5388 |
| Ser | Ser | Asp | Gly | Lys | Ile | Ser | Leu | Ser | Pro | Asp | Val | Lys | Glu | Trp | Tyr | |
| 1520 | | | | | 1525 | | | | | 1530 | | | | | 1535 | |
| AGC | ATA | GGT | CTT | GAA | GCT | GCA | AAT | CTA | GAA | GGC | AAT | GTT | CAA | ACT | TTG | 5436 |
| Ser | Ile | Gly | Leu | Glu | Ala | Ala | Asn | Leu | Glu | Gly | Asn | Val | Gln | Thr | Leu | |
| | | | | 1540 | | | | | 1545 | | | | | 1550 | | |
| AAA | AAT | TGG | GTA | GAA | CAA | ATA | GAG | AGT | TTA | AGA | AAT | ATT | GAC | GAT | AGA | 5484 |
| Lys | Asn | Trp | Val | Glu | Gln | Ile | Glu | Ser | Leu | Arg | Asn | Ile | Asp | Asp | Arg | |
| | | | | 1555 | | | | | 1560 | | | | | 1565 | | |
| GAA | GTA | CTT | TTG | CAG | TAC | AAT | ATT | GCG | AAA | GCT | TTA | ATT | GCC | ATC | TCA | 5532 |
| Glu | Val | Leu | Leu | Gln | Tyr | Asn | Ile | Ala | Lys | Ala | Leu | Ile | Ala | Ile | Ser | |
| | | | | 1570 | | | | | 1575 | | | | | 1580 | | |
| AAC | GAG | GAT | CCA | TTA | AGG | ACT | CAA | AAA | TAC | ATC | CAC | AAT | TCC | TTT | AGG | 5580 |
| Asn | Glu | Asp | Pro | Leu | Arg | Thr | Gln | Lys | Tyr | Ile | His | Asn | Ser | Phe | Arg | |
| | | | | 1585 | | | | | 1590 | | | | | 1595 | | |
| CTT | ATC | GGA | ACA | AAT | TTT | ATA | ACG | TCA | TCT | AAA | GAG | ACG | ACG | CTG | CTA | 5628 |
| Leu | Ile | Gly | Thr | Asn | Phe | Ile | Thr | Ser | Ser | Lys | Glu | Thr | Thr | Leu | Leu | |
| 1600 | | | | | 1605 | | | | | 1610 | | | | | 1615 | |
| AAG | AAA | CAG | AAT | TTA | TTG | ATG | AAA | TTA | CAC | AGT | TTA | TAT | GAC | CTC | AGT | 5676 |
| Lys | Lys | Gln | Asn | Leu | Leu | Met | Lys | Leu | His | Ser | Leu | Tyr | Asp | Leu | Ser | |
| | | | | 1620 | | | | | 1625 | | | | | 1630 | | |
| TTT | TTA | TCT | TCT | GCG | AAA | GAT | AAG | TTT | GAA | TAC | AAA | AGT | AAC | ACT | ACC | 5724 |
| Phe | Leu | Ser | Ser | Ala | Lys | Asp | Lys | Phe | Glu | Tyr | Lys | Ser | Asn | Thr | Thr | |
| | | | | 1635 | | | | | 1640 | | | | | 1645 | | |
| ATA | CTC | GAT | TAT | CGA | ATG | GAA | CGT | ATT | GGG | GCT | GAC | TTC | GTG | CCA | AAT | 5772 |
| Ile | Leu | Asp | Tyr | Arg | Met | Glu | Arg | Ile | Gly | Ala | Asp | Phe | Val | Pro | Asn | |
| | | | | 1650 | | | | | 1655 | | | | | 1660 | | |
| CAT | TAC | ATA | TTG | TCA | ATG | AGA | AAG | TCA | TTT | GAC | CAA | TTG | AAA | ATG | AAT | 5820 |
| His | Tyr | Ile | Leu | Ser | Met | Arg | Lys | Ser | Phe | Asp | Gln | Leu | Lys | Met | Asn | |
| 1665 | | | | | 1670 | | | | | 1675 | | | | | | |

| | | | | | | | | | | | | | | | | |
|---|---|---|---|---|---|---|---|---|---|---|---|---|---|---|---|---|
| GAA | CAA | GCA | GAC | GCT | GAC | TTA | GGA | AAA | ACA | TTC | TTC | ACT | TTA | GCC | CAA | 5868 |
| Glu | Gln | Ala | Asp | Ala | Asp | Leu | Gly | Lys | Thr | Phe | Phe | Thr | Leu | Ala | Gln | |
| 1680 | | | | | 1685 | | | | | 1690 | | | | | 1695 | |
| TTG | GCG | AGA | AAC | AAC | GCT | AGG | CTA | GAT | ATA | GCC | TCC | GAA | TCA | TTA | ATG | 5916 |
| Leu | Ala | Arg | Asn | Asn | Ala | Arg | Leu | Asp | Ile | Ala | Ser | Glu | Ser | Leu | Met | |
| | | | | 1700 | | | | | 1705 | | | | | 1710 | | |
| CAT | TGT | TTG | GAA | AGG | CGG | TTG | CCT | CAG | GCA | GAG | TTG | GAG | TTT | GCT | GAA | 5964 |
| His | Cys | Leu | Glu | Arg | Arg | Leu | Pro | Gln | Ala | Glu | Leu | Glu | Phe | Ala | Glu | |
| | | | 1715 | | | | | 1720 | | | | | 1725 | | | |
| ATA | CTA | TGG | AAG | CAA | GGT | GAG | AAT | GAT | AGA | GCC | TTA | AAG | ATA | GTG | CAA | 6012 |
| Ile | Leu | Trp | Lys | Gln | Gly | Glu | Asn | Asp | Arg | Ala | Leu | Lys | Ile | Val | Gln | |
| | | 1730 | | | | | 1735 | | | | | 1740 | | | | |
| GAA | ATA | CAT | GAA | AAG | TAT | CAA | GAA | AAT | TCC | TCG | GTT | AAT | GCT | CGC | GAT | 6060 |
| Glu | Ile | His | Glu | Lys | Tyr | Gln | Glu | Asn | Ser | Ser | Val | Asn | Ala | Arg | Asp | |
| | | | | 1745 | | | | | 1750 | | | | | 1755 | | |
| CGT | GCC | GCC | GTG | CTA | TTA | AAG | TTT | ACT | GAA | TGG | TTA | GAC | CTT | TCG | AAC | 6108 |
| Arg | Ala | Ala | Val | Leu | Leu | Lys | Phe | Thr | Glu | Trp | Leu | Asp | Leu | Ser | Asn | |
| 1760 | | | | | 1765 | | | | | 1770 | | | | | 1775 | |
| AAT | TCA | GCG | TCC | GAA | CAA | ATT | ATT | AAA | CAA | TAT | CAG | GAT | ATT | TTT | CAG | 6156 |
| Asn | Ser | Ala | Ser | Glu | Gln | Ile | Ile | Lys | Gln | Tyr | Gln | Asp | Ile | Phe | Gln | |
| | | | | 1780 | | | | | 1785 | | | | | 1790 | | |
| ATT | GAT | TCT | AAA | TGG | GAT | AAA | CCA | TAT | TAC | TCT | ATT | GGC | TTA | TAC | TAT | 6204 |
| Ile | Asp | Ser | Lys | Trp | Asp | Lys | Pro | Tyr | Tyr | Ser | Ile | Gly | Leu | Tyr | Tyr | |
| | | | 1795 | | | | | 1800 | | | | | 1805 | | | |
| AGT | AGA | CTA | CTT | GAG | CGC | AAA | AAA | GCA | GAG | GGT | TAT | ATT | ACT | AAT | GGT | 6252 |
| Ser | Arg | Leu | Leu | Glu | Arg | Lys | Lys | Ala | Glu | Gly | Tyr | Ile | Thr | Asn | Gly | |
| | | 1810 | | | | | 1815 | | | | | 1820 | | | | |
| CGT | TTT | GAG | TAC | AGG | GCA | ATA | TCT | TAC | TTT | TTA | TTG | GCA | TTT | GAA | AAG | 6300 |
| Arg | Phe | Glu | Tyr | Arg | Ala | Ile | Ser | Tyr | Phe | Leu | Leu | Ala | Phe | Glu | Lys | |
| | 1825 | | | | | 1830 | | | | | 1835 | | | | | |
| AAC | ACT | GCT | AAA | GTA | AGA | GAA | AAT | TTG | CCC | AAA | GTT | ATC | ACG | TTT | TGG | 6348 |
| Asn | Thr | Ala | Lys | Val | Arg | Glu | Asn | Leu | Pro | Lys | Val | Ile | Thr | Phe | Trp | |
| 1840 | | | | | 1845 | | | | | 1850 | | | | | 1855 | |
| CTA | GAT | ATT | GCG | GCC | GCA | TCA | ATT | TCT | GAA | GCT | CCT | GGA | AAC | AGG | AAG | 6396 |
| Leu | Asp | Ile | Ala | Ala | Ala | Ser | Ile | Ser | Glu | Ala | Pro | Gly | Asn | Arg | Lys | |
| | | | | 1860 | | | | | 1865 | | | | | 1870 | | |
| GAA | ATG | CTG | AGT | AAG | GCT | ACG | GAA | GAT | ATA | TGT | AGT | CAT | GTT | GAA | GAA | 6444 |
| Glu | Met | Leu | Ser | Lys | Ala | Thr | Glu | Asp | Ile | Cys | Ser | His | Val | Glu | Glu | |
| | | | 1875 | | | | | 1880 | | | | | 1885 | | | |
| GCG | CTG | CAG | CAT | TGT | CCC | ACT | TAT | ATT | TGG | TAC | TTT | GTT | TTG | ACT | CAG | 6492 |
| Ala | Leu | Gln | His | Cys | Pro | Thr | Tyr | Ile | Trp | Tyr | Phe | Val | Leu | Thr | Gln | |
| | | 1890 | | | | | 1895 | | | | | 1900 | | | | |
| TTG | TTA | TCT | AGG | TTA | TTA | CAT | TCT | CAT | CAA | TCA | TCG | GCC | CAG | ATA | ATA | 6540 |
| Leu | Leu | Ser | Arg | Leu | Leu | His | Ser | His | Gln | Ser | Ser | Ala | Gln | Ile | Ile | |
| | 1905 | | | | | 1910 | | | | | 1915 | | | | | |
| ATG | CAC | ATA | CTG | CTA | AGT | TTG | GCT | GTT | GAA | TAC | CCC | TCT | CAT | ATT | TTA | 6588 |
| Met | His | Ile | Leu | Leu | Ser | Leu | Ala | Val | Glu | Tyr | Pro | Ser | His | Ile | Leu | |
| 1920 | | | | | 1925 | | | | | 1930 | | | | | 1935 | |
| TGG | TAT | ATC | ACA | GCC | CTT | GTA | AAT | TCC | AAT | TCT | TCA | AAA | AGA | GTT | CTT | 6636 |
| Trp | Tyr | Ile | Thr | Ala | Leu | Val | Asn | Ser | Asn | Ser | Ser | Lys | Arg | Val | Leu | |
| | | | | 1940 | | | | | 1945 | | | | | 1950 | | |
| CGT | GGT | AAG | CAT | ATT | TTA | GAA | AAG | TAT | AGA | CAA | CAT | TCG | CAA | AAT | CCT | 6684 |
| Arg | Gly | Lys | His | Ile | Leu | Glu | Lys | Tyr | Arg | Gln | His | Ser | Gln | Asn | Pro | |
| | | | 1955 | | | | | 1960 | | | | | 1965 | | | |
| CAT | GAT | CTA | GTT | TCT | AGT | GCA | TTG | GAT | TTA | ACG | AAA | GCA | TTA | ACT | CGT | 6732 |
| His | Asp | Leu | Val | Ser | Ser | Ala | Leu | Asp | Leu | Thr | Lys | Ala | Leu | Thr | Arg | |
| | | 1970 | | | | | 1975 | | | | | 1980 | | | | |
| GTC | TGT | TTG | CAA | GAT | GTC | AAA | AGC | ATT | ACA | AGT | AGA | TCA | GGC | AAA | TCT | 6780 |
| Val | Cys | Leu | Gln | Asp | Val | Lys | Ser | Ile | Thr | Ser | Arg | Ser | Gly | Lys | Ser | |
| | 1985 | | | | | 1990 | | | | | 1995 | | | | | |

```
TTA GAA AAA GAC TTC AAA TTT GAC ATG AAC GTG GCC CCA TCT GCA ATG                6828
Leu Glu Lys Asp Phe Lys Phe Asp Met Asn Val Ala Pro Ser Ala Met
2000                2005                2010                2015

GTT GTT CCA GTA AGA AAA AAT TTA GAC ATC ATT TCA CCA CTA GAG TCT                6876
Val Val Pro Val Arg Lys Asn Leu Asp Ile Ile Ser Pro Leu Glu Ser
                2020                2025                2030

AAC TCA ATG AGG GGC TAT CAA CCA TTT AGG CCG GTT GTT TCT ATA ATT                6924
Asn Ser Met Arg Gly Tyr Gln Pro Phe Arg Pro Val Val Ser Ile Ile
            2035                2040                2045

AGA TTC GGA TCA TCT TAT AAA GTG TTT TCT TCA TTA AAG AAG CCA AAA                6972
Arg Phe Gly Ser Ser Tyr Lys Val Phe Ser Ser Leu Lys Lys Pro Lys
        2050                2055                2060

CAA TTG AAC ATA ATA GGT TCA GAT GGC AAC ATT TAT GGG ATC ATG TGT                7020
Gln Leu Asn Ile Ile Gly Ser Asp Gly Asn Ile Tyr Gly Ile Met Cys
    2065                2070                2075

AAG AAG GAA GAT GTC CGA CAA GAT AAC CAA TAT ATG CAG TTC GCC ACA                7068
Lys Lys Glu Asp Val Arg Gln Asp Asn Gln Tyr Met Gln Phe Ala Thr
2080                2085                2090                2095

ACA ATG GAT TTT CTT CTG AGT AAG GAC ATA GCT TCA AGA AAA AGA AGC                7116
Thr Met Asp Phe Leu Leu Ser Lys Asp Ile Ala Ser Arg Lys Arg Ser
                2100                2105                2110

CTG GGC ATA AAT ATT TAC TAC CGT ACT ATC TCT TCG AGA AGA CTG TGG                7164
Leu Gly Ile Asn Ile Tyr Tyr Arg Thr Ile Ser Ser Arg Arg Leu Trp
            2115                2120                2125

GAT ATT GGA AAT GGT ACC GAA TGT TGT AAC TTT AAG ATC TAT TCT TTC                7212
Asp Ile Gly Asn Gly Thr Glu Cys Cys Asn Phe Lys Ile Tyr Ser Phe
        2130                2135                2140

TAC AAG TAC GAA AGT CTG AAA ATT AAG TAT AGC CTG AAA AGT CTA CAT                7260
Tyr Lys Tyr Glu Ser Leu Lys Ile Lys Tyr Ser Leu Lys Ser Leu His
    2145                2150                2155

GAT AGG TGG CAG CAC ACC GCA GTA GAT GGA AAA CTC GAG TTT TAC ATG                7308
Asp Arg Trp Gln His Thr Ala Val Asp Gly Lys Leu Glu Phe Tyr Met
2160                2165                2170                2175

GAA CAG GTA GAT AAA TTT CCT CCA ATC TTG TAC CAA TGG TTT TTA GAA                7356
Glu Gln Val Asp Lys Phe Pro Pro Ile Leu Tyr Gln Trp Phe Leu Glu
                2180                2185                2190

AAC TTT CCT GAT CCA ATC AAT TGG TTC AAC GCC AGG AAT ACG TAT GCC                7404
Asn Phe Pro Asp Pro Ile Asn Trp Phe Asn Ala Arg Asn Thr Tyr Ala
            2195                2200                2205

AGA TCT TAC GCC GTC ATG GCA ATG GTT GGC CAT ATA TTA GGT CTA GGT                7452
Arg Ser Tyr Ala Val Met Ala Met Val Gly His Ile Leu Gly Leu Gly
        2210                2215                2220

GAT AGG CAC TGT GAA AAC ATA TTA CTA GAT ATA CAG ACG GGT AAA GTT                7500
Asp Arg His Cys Glu Asn Ile Leu Leu Asp Ile Gln Thr Gly Lys Val
    2225                2230                2235

CTT CAT GTA GAC TTC GAC TGT TTA TTT GAG AAA GGC AAA AGG TTA CCT                7548
Leu His Val Asp Phe Asp Cys Leu Phe Glu Lys Gly Lys Arg Leu Pro
2240                2245                2250                2255

GTC CCA GAA ATT GTT CCC TTC AGA CTA ACA CCA AAT TTA TTG GAT GCG                7596
Val Pro Glu Ile Val Pro Phe Arg Leu Thr Pro Asn Leu Leu Asp Ala
                2260                2265                2270

TTG GGC ATA ATT GGG ACA GAA GGA ACA TTT AAG AAG TCT AGT GAA GTC                7644
Leu Gly Ile Ile Gly Thr Glu Gly Thr Phe Lys Lys Ser Ser Glu Val
            2275                2280                2285

ACG TTG GCT TTA ATG AGA AAA AAT GAA GTA GCG TTG ATG AAT GTG ATC                7692
Thr Leu Ala Leu Met Arg Lys Asn Glu Val Ala Leu Met Asn Val Ile
        2290                2295                2300

GAA ACA ATT ATG TAC GAT AGA AAC ATG GAC CAC TCA ATT CAA AAA GCG                7740
Glu Thr Ile Met Tyr Asp Arg Asn Met Asp His Ser Ile Gln Lys Ala
    2305                2310                2315
```

```
CTA  AAG  GTC  TTA  AGA  AAC  AAA  ATC  CGC  GGT  ATA  GAT  CCG  CAG  GAT  GGC     7788
Leu  Lys  Val  Leu  Arg  Asn  Lys  Ile  Arg  Gly  Ile  Asp  Pro  Gln  Asp  Gly
2320                      2325                2330                     2335

CTG  GTA  TTG  AGT  GTT  GCT  GGC  CAA  ACA  GAA  ACA  TTG  ATC  CAA  GAA  GCA     7836
Leu  Val  Leu  Ser  Val  Ala  Gly  Gln  Thr  Glu  Thr  Leu  Ile  Gln  Glu  Ala
                    2340                2345                          2350

ACA  TCA  GAA  GAC  AAT  CTA  AGC  AAG  ATG  TAT  ATT  GGT  TGG  CTT  CCA  TTT     7884
Thr  Ser  Glu  Asp  Asn  Leu  Ser  Lys  Met  Tyr  Ile  Gly  Trp  Leu  Pro  Phe
               2355                2360                     2365

TGG  TAACGACTTT  CCACCATTTT  CGGCAACAGA  CGAACTTCCT  CTTGATCTAA                     7937
Trp

CCATCACTGC  AGGTGCTTTT  CTCCGGCGGA  GTTAATAGAT  ACTTATCCCC  GCTTCATGTC              7997

ATACTATCTC  TCTTAACAGG  GATGTTGACA  CCATATAAGT  TAACATAACA  TATACGTACG              8057

TAATAATATT  AAGGACTATC  TCCGATTTCA  AAAGAGAAAC  AACCTAATCA  AGCCTTATTA              8117

TAAGAGCAAA  TTATTCAAAA  AAAGTCTACG  GAGAAAATTA  TTATGGTGGT  TTTAGACAAG              8177

AAGTTATTGG  AAAGATTGAC  TTCTCGTAAG  GTTCCTTAGA  AGAGCTCGAA  GATATGGAAA              8237

ACGATGCTTG  TTGTCTACTT  TACATAACAA  GATGCCTTGA  TTGGACTTA   CATAAGAAAT              8297

GCGTTAAGAA  TTTCCCGAAC  AGTTGCATGT  ATATCTCTTC  CAAATGGCTC  GTGT                    8351
```

( 2 ) INFORMATION FOR SEQ ID NO:15:

( i ) SEQUENCE CHARACTERISTICS:
        ( A ) LENGTH: 2368 amino acids
        ( B ) TYPE: amino acid
        ( D ) TOPOLOGY: linear ( i i ) MOLECULE TYPE: protein
        ( A ) DESCRIPTION: yeast MEC1 protein ( x i ) SEQUENCE DESCRIPTION: SEQ ID NO:15:

```
Met  Glu  Ser  His  Val  Lys  Tyr  Leu  Asp  Glu  Leu  Ile  Leu  Ala  Ile  Lys
 1                  5                    10                       15

Asp  Leu  Asn  Ser  Gly  Val  Asp  Ser  Lys  Val  Gln  Ile  Lys  Lys  Val  Pro
               20                    25                       30

Thr  Asp  Pro  Ser  Ser  Ser  Gln  Glu  Tyr  Ala  Lys  Ser  Leu  Lys  Ile  Leu
          35                    40                       45

Asn  Thr  Leu  Ile  Arg  Asn  Leu  Lys  Asp  Gln  Arg  Arg  Asn  Asn  Ile  Met
     50                    55                       60

Lys  Asn  Asp  Thr  Ile  Phe  Ser  Lys  Thr  Val  Ser  Ala  Leu  Ala  Leu  Leu
65                       70                    75                         80

Leu  Glu  Tyr  Asn  Pro  Phe  Leu  Leu  Val  Met  Lys  Asp  Ser  Asn  Gly  Asn
                    85                    90                       95

Phe  Glu  Ile  Gln  Arg  Leu  Ile  Asp  Asp  Phe  Leu  Asn  Ile  Ser  Val  Leu
               100                   105                      110

Asn  Tyr  Asp  Asn  Tyr  His  Arg  Ile  Trp  Phe  Met  Arg  Arg  Lys  Leu  Gly
          115                   120                      125

Ser  Trp  Cys  Lys  Ala  Cys  Val  Glu  Phe  Tyr  Gly  Lys  Pro  Ala  Lys  Phe
     130                   135                      140

Gln  Leu  Thr  Ala  His  Phe  Glu  Asn  Thr  Met  Asn  Leu  Tyr  Glu  Gln  Ala
145                  150                    155                        160

Leu  Thr  Glu  Val  Leu  Leu  Gly  Lys  Thr  Glu  Leu  Leu  Lys  Phe  Tyr  Asp
                    165                   170                      175

Thr  Leu  Lys  Gly  Leu  Tyr  Ile  Leu  Leu  Tyr  Trp  Phe  Thr  Ser  Glu  Tyr
               180                   185                      190

Ser  Thr  Phe  Gly  Asn  Ser  Ile  Ala  Phe  Leu  Asp  Ser  Ser  Leu  Gly  Phe
```

|     |     |     | 195 |     |     |     | 200 |     |     |     | 205 |     |     |     |
| --- | --- | --- | --- | --- | --- | --- | --- | --- | --- | --- | --- | --- | --- | --- |
| Thr | Lys<br>210 | Phe | Asp | Phe | Asn | Phe<br>215 | Gln | Arg | Leu | Ile | Arg<br>220 | Ile | Val | Leu | Tyr |
| Val<br>225 | Phe | Asp | Ser | Cys | Glu<br>230 | Leu | Ala | Ala | Leu | Glu<br>235 | Tyr | Ala | Glu | Ile | Gln<br>240 |
| Leu | Lys | Tyr | Ile | Ser<br>245 | Leu | Val | Val | Asp | Tyr<br>250 | Val | Cys | Asn | Arg | Thr<br>255 | Ile |
| Ser | Thr | Ala | Leu<br>260 | Asp | Ala | Pro | Ala | Leu<br>265 | Val | Cys | Cys | Glu | Gln<br>270 | Leu | Lys |
| Phe | Val | Leu<br>275 | Thr | Thr | Met | His | His<br>280 | Phe | Leu | Asp | Asn | Lys<br>285 | Tyr | Gly | Leu |
| Leu | Asp<br>290 | Asn | Asp | Pro | Thr | Met<br>295 | Ala | Lys | Gly | Ile | Leu<br>300 | Arg | Leu | Tyr | Ser |
| Leu<br>305 | Cys | Ile | Ser | Asn | Asp<br>310 | Phe | Ser | Lys | Cys | Phe<br>315 | Val | Asp | His | Phe | Pro<br>320 |
| Ile | Asp | Gln | Trp | Ala<br>325 | Asp | Phe | Ser | Gln | Ser<br>330 | Glu | His | Phe | Pro | Phe<br>335 | Thr |
| Gln | Leu | Thr | Asn<br>340 | Lys | Ala | Leu | Ser | Ile<br>345 | Val | Tyr | Phe | Asp | Leu<br>350 | Lys | Arg |
| Arg | Ser | Leu<br>355 | Pro | Val | Glu | Ala | Leu<br>360 | Lys | Tyr | Asp | Asn | Lys<br>365 | Phe | Asn | Ile |
| Trp | Val<br>370 | Tyr | Gln | Ser | Glu | Pro<br>375 | Asp | Ser | Ser | Leu | Lys<br>380 | Asn | Val | Thr | Ser |
| Pro<br>385 | Phe | Asp | Asp | Arg | Tyr<br>390 | Lys | Gln | Leu | Glu | Lys<br>395 | Leu | Arg | Leu | Leu | Val<br>400 |
| Leu | Lys | Lys | Phe | Asn<br>405 | Lys | Thr | Glu | Arg | Gly<br>410 | Thr | Leu | Leu | Lys | Tyr<br>415 | Arg |
| Val | Asn | Gln | Leu<br>420 | Ser | Pro | Gly | Phe | Phe<br>425 | Gln | Arg | Ala | Gly | Asn<br>430 | Asp | Phe |
| Lys | Leu | Ile | Leu<br>435 | Asn | Glu | Ala | Ser | Val<br>440 | Ser | Ile | Gln | Thr<br>445 | Cys | Phe | Lys |
| Thr | Asn<br>450 | Asn | Ile | Thr | Arg | Leu<br>455 | Thr | Ser | Trp | Thr | Val<br>460 | Ile | Leu | Gly | Arg |
| Leu<br>465 | Ala | Cys | Leu | Glu | Ser<br>470 | Glu | Lys | Phe | Ser | Gly<br>475 | Thr | Leu | Pro | Asn | Ser<br>480 |
| Thr | Lys | Asp | Met | Asp<br>485 | Asn | Trp | Tyr | Val | Cys<br>490 | His | Leu | Cys | Asp | Ile<br>495 | Glu |
| Lys | Thr | Gly | Asn<br>500 | Pro | Phe | Val | Arg | Ile<br>505 | Asn | Pro | Asn | Arg | Pro<br>510 | Glu | Ala |
| Ala | Gly | Lys<br>515 | Ser | Glu | Ile | Phe | Arg<br>520 | Ile | Leu | His | Ser | Asn<br>525 | Phe | Leu | Ser |
| His | Pro<br>530 | Asn | Ile | Asp | Glu | Phe<br>535 | Ser | Glu | Ser | Leu | Leu<br>540 | Ser | Gly | Ile | Leu |
| Phe<br>545 | Ser | Leu | His | Arg | Ile<br>550 | Phe | Ser | His | Phe | Gln<br>555 | Pro | Pro | Lys | Leu | Thr<br>560 |
| Asp | Gly | Asn | Gly | Gln<br>565 | Ile | Asn | Lys | Ser | Phe<br>570 | Lys | Leu | Val | Gln | Lys<br>575 | Cys |
| Phe | Met | Asn | Ser<br>580 | Asn | Arg | Tyr | Leu | Arg<br>585 | Leu | Leu | Ser | Thr | Arg<br>590 | Ile | Ile |
| Pro | Leu | Phe<br>595 | Asn | Ile | Ser | Asp | Ser<br>600 | His | Asn | Ser | Glu | Asp<br>605 | Glu | His | Thr |
| Ala | Thr<br>610 | Leu | Ile | Lys | Phe | Leu<br>615 | Gln | Ser | Gln | Lys | Leu<br>620 | Pro | Val | Val | Lys |

```
Glu  Asn  Leu  Val  Ile  Ala  Trp  Thr  Gln  Leu  Thr  Leu  Thr  Thr  Ser  Asn
625                 630                      635                           640

Asp  Val  Phe  Asp  Thr  Leu  Leu  Leu  Lys  Leu  Ile  Asp  Ile  Phe  Asn  Ser
                    645                 650                           655

Asp  Asp  Tyr  Ser  Leu  Arg  Ile  Met  Met  Thr  Leu  Gln  Ile  Lys  Asn  Met
               660                      665                      670

Ala  Lys  Ile  Leu  Lys  Lys  Thr  Pro  Tyr  Gln  Leu  Leu  Ser  Pro  Ile  Leu
          675                      680                     685

Pro  Val  Leu  Leu  Arg  Gln  Leu  Gly  Lys  Asn  Leu  Val  Glu  Arg  Lys  Val
     690                      695                700

Gly  Phe  Gln  Asn  Leu  Ile  Glu  Leu  Leu  Gly  Tyr  Pro  Ser  Lys  Thr  Ile
705                      710                     715                           720

Leu  Asp  Ile  Phe  Gln  Arg  Tyr  Ile  Ile  Pro  Tyr  Ala  Ile  Ile  Gln  Tyr
                    725                      730                           735

Lys  Ser  Asp  Val  Leu  Ser  Glu  Ile  Ala  Lys  Ile  Met  Cys  Asp  Gly  Asp
               740                      745                     750

Thr  Ser  Leu  Ile  Asn  Gln  Met  Lys  Val  Asn  Leu  Leu  Lys  Lys  Asn  Ser
          755                      760                          765

Arg  Gln  Ile  Phe  Ala  Val  Ala  Leu  Val  Lys  His  Gly  Leu  Phe  Ser  Leu
     770                      775                     780

Asp  Ile  Leu  Glu  Thr  Leu  Phe  Leu  Asn  Arg  Ala  Pro  Thr  Phe  Asp  Lys
785                      790                      795                           800

Gly  Tyr  Ile  Thr  Ala  Tyr  Leu  Pro  Asp  Tyr  Lys  Thr  Leu  Ala  Glu  Ile
                    805                      810                           815

Thr  Lys  Leu  Tyr  Lys  Asn  Ser  Val  Thr  Lys  Asp  Ala  Ser  Asp  Ser  Glu
               820                      825                     830

Asn  Ala  Asn  Met  Ile  Leu  Cys  Ser  Leu  Arg  Phe  Leu  Ile  Thr  Asn  Phe
          835                      840                          845

Glu  Lys  Asp  Lys  Arg  His  Gly  Ser  Lys  Tyr  Lys  Asn  Ile  Asn  Asn  Trp
     850                      855                     860

Thr  Asp  Asp  Gln  Glu  Gln  Ala  Phe  Gln  Lys  Lys  Leu  Gln  Asp  Asn  Ile
865                      870                      875                           880

Leu  Gly  Ile  Phe  Gln  Val  Phe  Ser  Ser  Asp  Ile  His  Asp  Val  Glu  Gly
                    885                      890                           895

Arg  Thr  Thr  Tyr  Tyr  Glu  Lys  Leu  Arg  Val  Ile  Asn  Gly  Ile  Ser  Phe
               900                      905                     910

Leu  Ile  Ile  Tyr  Ala  Pro  Lys  Lys  Ser  Ile  Ile  Ser  Ala  Leu  Ala  Gln
          915                      920                          925

Ile  Ser  Ile  Cys  Leu  Gln  Thr  Gly  Leu  Gly  Leu  Lys  Glu  Val  Arg  Tyr
     930                      935                     940

Glu  Ala  Phe  Arg  Cys  Trp  His  Leu  Leu  Val  Arg  His  Leu  Asn  Asp  Glu
945                      950                      955                           960

Glu  Leu  Ser  Thr  Val  Ile  Asp  Ser  Leu  Ile  Ala  Phe  Ile  Leu  Gln  Lys
                    965                      970                           975

Trp  Ser  Glu  Phe  Asn  Gly  Lys  Leu  Arg  Asn  Ile  Val  Tyr  Ser  Ile  Leu
               980                      985                     990

Asp  Thr  Leu  Ile  Lys  Glu  Lys  Ser  Asp  Leu  Ile  Leu  Lys  Leu  Lys  Pro
          995                      1000                         1005

Tyr  Thr  Thr  Leu  Ala  Leu  Val  Gly  Lys  Pro  Glu  Leu  Gly  Ile  Leu  Ala
     1010                      1015                    1020

Arg  Asp  Gly  Gln  Phe  Ala  Arg  Met  Val  Asn  Lys  Ile  Arg  Ser  Thr  Thr
1025                     1030                     1035                          1040

Asp  Leu  Ile  Pro  Ile  Phe  Ala  Asn  Asn  Leu  Lys  Ser  Ser  Asn  Lys  Tyr
                    1045                     1050                          1055
```

```
Val Ile Asn Gln Asn Leu Asp Asp Ile Glu Val Tyr Leu Arg Arg Lys
             1060                1065                1070

Gln Thr Glu Arg Ser Ile Asp Phe Thr Pro Lys Lys Val Gly Gln Thr
         1075                1080                1085

Ser Asp Ile Thr Leu Val Leu Gly Ala Leu Leu Asp Thr Ser His Lys
         1090                1095                1100

Phe Arg Asn Leu Asp Lys Asp Leu Cys Glu Lys Cys Ala Lys Cys Ile
1105                1110                1115                1120

Ser Met Ile Gly Val Leu Asp Val Thr Lys His Glu Phe Lys Arg Thr
                 1125                1130                1135

Thr Tyr Ser Glu Asn Glu Val Tyr Asp Leu Asn Asp Ser Val Gln Thr
             1140                1145                1150

Ile Lys Phe Leu Ile Trp Val Ile Asn Asp Ile Leu Val Pro Ala Phe
         1155                1160                1165

Trp Gln Ser Glu Asn Pro Ser Lys Gln Leu Phe Val Ala Leu Val Ile
         1170                1175                1180

Gln Glu Ser Leu Lys Tyr Cys Gly Leu Ser Ser Glu Ser Trp Asp Met
1185                1190                1195                1200

Asn His Lys Glu Leu Tyr Pro Asn Glu Ala Lys Leu Trp Glu Lys Phe
                 1205                1210                1215

Asn Ser Val Ser Lys Thr Thr Ile Tyr Pro Leu Leu Ser Ser Leu Tyr
             1220                1225                1230

Leu Ala Gln Ser Trp Lys Glu Tyr Val Pro Leu Lys Tyr Pro Ser Asn
         1235                1240                1245

Asn Phe Lys Glu Gly Tyr Gln Ile Trp Val Lys Arg Phe Thr Leu Asp
         1250                1255                1260

Leu Leu Lys Thr Gly Thr Thr Glu Asn His Pro Gly His Val Phe Ser
1265                1270                1275                1280

Ser Leu Ile Arg Glu Asp Asp Gly Ser Leu Ser Asn Phe Leu Leu Pro
                 1285                1290                1295

Tyr Ile Ser Leu Asp Ile Ile Ile Lys Ala Glu Lys Gly Thr Pro Tyr
             1300                1305                1310

Ala Asp Ile Leu Asn Gly Ile Ile Ile Glu Phe Asp Ser Ile Phe Thr
         1315                1320                1325

Cys Asn Leu Glu Gly Met Asn Asn Leu Gln Val Asp Ser Leu Arg Met
         1330                1335                1340

Cys Tyr Glu Ser Ile Phe Arg Val Phe Glu Tyr Cys Lys Lys Trp Ala
1345                1350                1355                1360

Thr Glu Phe Lys Gln Asn Tyr Ser Lys Leu His Gly Thr Phe Ile Ile
                 1365                1370                1375

Lys Asp Thr Lys Thr Thr Asn Met Leu Leu Arg Ile Asp Glu Phe Leu
             1380                1385                1390

Arg Thr Thr Pro Ser Asp Leu Leu Ala Gln Arg Ser Leu Glu Thr Asp
         1395                1400                1405

Ser Phe Glu Arg Ser Ala Leu Tyr Leu Glu Gln Cys Tyr Arg Gln Asn
         1410                1415                1420

Pro His Asp Lys Asn Gln Asn Gly Gln Leu Leu Lys Asn Leu Gln Ile
1425                1430                1435                1440

Thr Tyr Glu Glu Ile Gly Asp Ile Asp Ser Leu Asp Gly Val Leu Arg
                 1445                1450                1455

Thr Phe Ala Thr Gly Asn Leu Val Ser Lys Ile Glu Glu Leu Gln Tyr
         1460                1465                1470

Ser Glu Asn Trp Lys Leu Ala Gln Asp Cys Phe Asn Val Leu Gly Lys
```

1475                         1480                          1485

Phe Ser Asp Asp Pro Lys Thr Thr Thr Arg Met Leu Lys Ser Met Tyr
    1490                        1495                       1500

Asp His Gln Leu Tyr Ser Gln Ile Ile Ser Asn Ser Ser Phe His Ser
1505                        1510                       1515                       1520

Ser Asp Gly Lys Ile Ser Leu Ser Pro Asp Val Lys Glu Trp Tyr Ser
                1525                        1530                       1535

Ile Gly Leu Glu Ala Ala Asn Leu Glu Gly Asn Val Gln Thr Leu Lys
                        1540                        1545                       1550

Asn Trp Val Glu Gln Ile Glu Ser Leu Arg Asn Ile Asp Asp Arg Glu
            1555                        1560                       1565

Val Leu Leu Gln Tyr Asn Ile Ala Lys Ala Leu Ile Ala Ile Ser Asn
1570                        1575                       1580

Glu Asp Pro Leu Arg Thr Gln Lys Tyr Ile His Asn Ser Phe Arg Leu
1585                        1590                       1595                       1600

Ile Gly Thr Asn Phe Ile Thr Ser Ser Lys Glu Thr Thr Leu Leu Lys
                        1605                       1610                       1615

Lys Gln Asn Leu Leu Met Lys Leu His Ser Leu Tyr Asp Leu Ser Phe
                    1620                       1625                       1630

Leu Ser Ser Ala Lys Asp Lys Phe Glu Tyr Lys Ser Asn Thr Thr Ile
                1635                        1640                       1645

Leu Asp Tyr Arg Met Glu Arg Ile Gly Ala Asp Phe Val Pro Asn His
    1650                       1655                        1660

Tyr Ile Leu Ser Met Arg Lys Ser Phe Asp Gln Leu Lys Met Asn Glu
1665                       1670                        1675                       1680

Gln Ala Asp Ala Asp Leu Gly Lys Thr Phe Phe Thr Leu Ala Gln Leu
                    1685                        1690                       1695

Ala Arg Asn Asn Ala Arg Leu Asp Ile Ala Ser Glu Ser Leu Met His
                1700                        1705                       1710

Cys Leu Glu Arg Arg Leu Pro Gln Ala Glu Leu Glu Phe Ala Glu Ile
            1715                        1720                       1725

Leu Trp Lys Gln Gly Glu Asn Asp Arg Ala Leu Lys Ile Val Gln Glu
        1730                        1735                       1740

Ile His Glu Lys Tyr Gln Glu Asn Ser Ser Val Asn Ala Arg Asp Arg
1745                        1750                       1755                       1760

Ala Ala Val Leu Leu Lys Phe Thr Glu Trp Leu Asp Leu Ser Asn Asn
                    1765                        1770                       1775

Ser Ala Ser Glu Gln Ile Ile Lys Gln Tyr Gln Asp Ile Phe Gln Ile
                    1780                        1785                       1790

Asp Ser Lys Trp Asp Lys Pro Tyr Tyr Ser Ile Gly Leu Tyr Tyr Ser
            1795                        1800                       1805

Arg Leu Leu Glu Arg Lys Lys Ala Glu Gly Tyr Ile Thr Asn Gly Arg
    1810                        1815                       1820

Phe Glu Tyr Arg Ala Ile Ser Tyr Phe Leu Leu Ala Phe Glu Lys Asn
1825                        1830                       1835                       1840

Thr Ala Lys Val Arg Glu Asn Leu Pro Lys Val Ile Thr Phe Trp Leu
                    1845                        1850                       1855

Asp Ile Ala Ala Ala Ser Ile Ser Glu Ala Pro Gly Asn Arg Lys Glu
                    1860                        1865                       1870

Met Leu Ser Lys Ala Thr Glu Asp Ile Cys Ser His Val Glu Glu Ala
                1875                        1880                       1885

Leu Gln His Cys Pro Thr Tyr Ile Trp Tyr Phe Val Leu Thr Gln Leu
                    1890                        1895                       1900

```
Leu Ser Arg Leu Leu His Ser His Gln Ser Ser Ala Gln Ile Ile Met
1905                1910                1915                1920

His Ile Leu Leu Ser Leu Ala Val Glu Tyr Pro Ser His Ile Leu Trp
           1925                1930                1935

Tyr Ile Thr Ala Leu Val Asn Ser Ser Ser Lys Arg Val Leu Arg
                1940                1945                1950

Gly Lys His Ile Leu Glu Lys Tyr Arg Gln His Ser Gln Asn Pro His
       1955                1960                1965

Asp Leu Val Ser Ser Ala Leu Asp Leu Thr Lys Ala Leu Thr Arg Val
           1970                1975                1980

Cys Leu Gln Asp Val Lys Ser Ile Thr Ser Arg Ser Gly Lys Ser Leu
1985                1990                1995                2000

Glu Lys Asp Phe Lys Phe Asp Met Asn Val Ala Pro Ser Ala Met Val
           2005                2010                2015

Val Pro Val Arg Lys Asn Leu Asp Ile Ile Ser Pro Leu Glu Ser Asn
           2020                2025                2030

Ser Met Arg Gly Tyr Gln Pro Phe Arg Pro Val Val Ser Ile Ile Arg
           2035                2040                2045

Phe Gly Ser Ser Tyr Lys Val Phe Ser Ser Leu Lys Pro Lys Gln
   2050                2055                2060

Leu Asn Ile Ile Gly Ser Asp Gly Asn Ile Tyr Gly Ile Met Cys Lys
2065                2070                2075                2080

Lys Glu Asp Val Arg Gln Asp Asn Gln Tyr Met Gln Phe Ala Thr Thr
               2085                2090                2095

Met Asp Phe Leu Leu Ser Lys Asp Ile Ala Ser Arg Lys Arg Ser Leu
               2100                2105                2110

Gly Ile Asn Ile Tyr Tyr Arg Thr Ile Ser Ser Arg Arg Leu Trp Asp
           2115                2120                2125

Ile Gly Asn Gly Thr Glu Cys Cys Asn Phe Lys Ile Tyr Ser Phe Tyr
           2130                2135                2140

Lys Tyr Glu Ser Leu Lys Ile Lys Tyr Ser Leu Lys Ser Leu His Asp
2145                2150                2155                2160

Arg Trp Gln His Thr Ala Val Asp Gly Lys Leu Glu Phe Tyr Met Glu
               2165                2170                2175

Gln Val Asp Lys Phe Pro Pro Ile Leu Tyr Gln Trp Phe Leu Glu Asn
           2180                2185                2190

Phe Pro Asp Pro Ile Asn Trp Phe Asn Ala Arg Asn Thr Tyr Ala Arg
           2195                2200                2205

Ser Tyr Ala Val Met Ala Met Val Gly His Ile Leu Gly Leu Gly Asp
2210                2215                2220

Arg His Cys Glu Asn Ile Leu Leu Asp Ile Gln Thr Gly Lys Val Leu
2225                2230                2235                2240

His Val Asp Phe Asp Cys Leu Phe Glu Lys Gly Lys Arg Leu Pro Val
               2245                2250                2255

Pro Glu Ile Val Pro Phe Arg Leu Thr Pro Asn Leu Leu Asp Ala Leu
           2260                2265                2270

Gly Ile Ile Gly Thr Glu Gly Thr Phe Lys Lys Ser Ser Glu Val Thr
           2275                2280                2285

Leu Ala Leu Met Arg Lys Asn Glu Val Ala Leu Met Asn Val Ile Glu
   2290                2295                2300

Thr Ile Met Tyr Asp Arg Asn Met Asp His Ser Ile Gln Lys Ala Leu
2305                2310                2315                2320

Lys Val Leu Arg Asn Lys Ile Arg Gly Ile Asp Pro Gln Asp Gly Leu
           2325                2330                2335
```

```
Val  Leu  Ser  Val  Ala  Gly  Gln  Thr  Glu  Thr  Leu  Ile  Gln  Glu  Ala  Thr
               2340                2345                     2350

Ser  Glu  Asp  Asn  Leu  Ser  Lys  Met  Tyr  Ile  Gly  Trp  Leu  Pro  Phe  Trp
          2355                     2360                2365
```

( 2 ) INFORMATION FOR SEQ ID NO:16:

( i ) SEQUENCE CHARACTERISTICS:
        ( A ) LENGTH: 2934 base pairs
        ( B ) TYPE: nucleic acid
        ( C ) STRANDEDNESS: single
        ( D ) TOPOLOGY: linear ( i i ) MOLECULE TYPE: cDNA to mRNA
        ( A ) DESCRIPTION: yeast MEC2 cDNA ( i i i ) HYPOTHETICAL: NO ( i v ) ANTI-SENSE: NO ( v i ) ORIGINAL SOURCE:
        ( A ) ORGANISM: Saccharomyces cerevisiae ( i x ) FEATURE:
        ( A ) NAME/KEY: CDS
        ( B ) LOCATION: 395..2724

( x i ) SEQUENCE DESCRIPTION: SEQ ID NO:16:

```
ATTAATAGCC  TGCTTCCTTT  TAATTAAGCC  GGAAAGTGTT  TGTCACAGAT  GTCAATGAAA      60

CGTGCATCTA  TTAACATATT  TATTTTCATT  TCGAGGGTGA  GGTGGTGTGG  ACGCGTTGAT     120

ACGGCAACGG  GAGTGACGCG  TAAAATTGGC  AGAAAAATCA  TCACCGTGGG  TAGACTTGGA     180

AATGAAAACA  TTTATAGAAT  AAAGGTACAG  GTTGAGAAGA  TAAAGGGTAC  CAAAGTTACC     240

ATTTTGAAAT  CTCTGATCAA  GAAAAGGTAA  GAAAGCAGAA  AAGGACGGTA  GAGATTATTG     300

GAAGACAAAC  TAATTTTGTA  TATGCATTCG  ATTTTCTTAA  GCTTTAAAAG  AGAGAATAGT     360

GAGAAAAGAT  AGTGTTACAC  AACATCAACT  AAAA ATG GAA AAT ATT ACA CAA           412
                                        Met Glu Asn Ile Thr Gln
                                        1               5

CCC ACA CAG CAA TCC ACG CAG GCT ACT CAA AGG TTT TTG ATT GAG AAG            460
Pro Thr Gln Gln Ser Thr Gln Ala Thr Gln Arg Phe Leu Ile Glu Lys
            10                  15                  20

TTT TCT CAA GAA CAG ATC GGC GAA AAC ATT GTG TGC AGG GTC ATT TGT            508
Phe Ser Gln Glu Gln Ile Gly Glu Asn Ile Val Cys Arg Val Ile Cys
        25                  30                  35

ACC ACG GGT CAA ATT CCC ATC CGA GAT TTG TCA GCT GAT ATT TCA CAA            556
Thr Thr Gly Gln Ile Pro Ile Arg Asp Leu Ser Ala Asp Ile Ser Gln
        40                  45                  50

GTG CTT AAG GAA AAA CGA TCC ATA AAG AAA GTT TGG ACA TTT GGT AGA            604
Val Leu Lys Glu Lys Arg Ser Ile Lys Lys Val Trp Thr Phe Gly Arg
55                  60                  65                  70

AAC CCA GCC TGT GAC TAT CAT TTA GGA AAC ATT TCA AGA CTG TCA AAT            652
Asn Pro Ala Cys Asp Tyr His Leu Gly Asn Ile Ser Arg Leu Ser Asn
                75                  80                  85

AAG CAT TTC CAA ATA CTA CTA GGA GAA GAC GGT AAC CTT TTA TTG AAT            700
Lys His Phe Gln Ile Leu Leu Gly Glu Asp Gly Asn Leu Leu Leu Asn
            90                  95                  100

GAC ATT TCC ACT AAT GGG ACC TGG TTA AAT GGG CAA AAA GTC GAG AAG            748
Asp Ile Ser Thr Asn Gly Thr Trp Leu Asn Gly Gln Lys Val Glu Lys
            105                 110                 115

AAC AGC AAT CAG TTA CTG TCT CAA GGT GAT GAA ATA ACC GTT GGT GTA            796
Asn Ser Asn Gln Leu Leu Ser Gln Gly Asp Glu Ile Thr Val Gly Val
            120                 125                 130
```

| | | | | | | | | | | | | | | | | |
|---|---|---|---|---|---|---|---|---|---|---|---|---|---|---|---|---|
| GGC | GTG | GAA | TCA | GAT | ATT | TTA | TCT | CTG | GTC | ATT | TTC | ATA | AAC | GAC | AAA | 844 |
| Gly | Val | Glu | Ser | Asp | Ile | Leu | Ser | Leu | Val | Ile | Phe | Ile | Asn | Asp | Lys | |
| 135 | | | | 140 | | | | | 145 | | | | | | 150 | |
| TTT | AAG | CAG | TGC | CTC | GAG | CAG | AAC | AAA | GTT | GAT | CGC | ATA | AGA | TCT | AAC | 892 |
| Phe | Lys | Gln | Cys | Leu | Glu | Gln | Asn | Lys | Val | Asp | Arg | Ile | Arg | Ser | Asn | |
| | | | | 155 | | | | | 160 | | | | | 165 | | |
| CTG | AAA | AAT | ACC | TCT | AAA | ATA | GCT | TCT | CCT | GGT | CTT | ACA | TCA | TCT | ACT | 940 |
| Leu | Lys | Asn | Thr | Ser | Lys | Ile | Ala | Ser | Pro | Gly | Leu | Thr | Ser | Ser | Thr | |
| | | | 170 | | | | 175 | | | | | 180 | | | | |
| GCA | TCA | TCA | ATG | GTG | GCC | AAC | AAG | ACT | GGT | ATT | TTT | AAG | GAT | TTT | TCG | 988 |
| Ala | Ser | Ser | Met | Val | Ala | Asn | Lys | Thr | Gly | Ile | Phe | Lys | Asp | Phe | Ser | |
| | | 185 | | | | | 190 | | | | | 195 | | | | |
| ATT | ATT | GAC | GAA | GTG | GTG | GGC | CAG | GGT | GCA | TTT | GCC | ACA | GTA | AAG | AAA | 1036 |
| Ile | Ile | Asp | Glu | Val | Val | Gly | Gln | Gly | Ala | Phe | Ala | Thr | Val | Lys | Lys | |
| | | 200 | | | | | 205 | | | | | 210 | | | | |
| GCC | ATT | GAA | AGA | ACT | ACT | GGG | AAA | ACA | TTC | GCG | GTG | AAG | ATT | ATA | AGT | 1084 |
| Ala | Ile | Glu | Arg | Thr | Thr | Gly | Lys | Thr | Phe | Ala | Val | Lys | Ile | Ile | Ser | |
| 215 | | | | | 220 | | | | | 225 | | | | | 230 | |
| AAA | CGC | AAA | GTA | ATA | GGC | AAT | ATG | GAT | GGT | GTG | ACA | AGA | GAG | TTA | GAA | 1132 |
| Lys | Arg | Lys | Val | Ile | Gly | Asn | Met | Asp | Gly | Val | Thr | Arg | Glu | Leu | Glu | |
| | | | | 235 | | | | 240 | | | | | 245 | | | |
| GTA | TTG | CAA | AAG | CTC | AAT | CAT | CCA | AGG | ATA | GTA | CGA | TTG | AAA | GGA | TTT | 1180 |
| Val | Leu | Gln | Lys | Leu | Asn | His | Pro | Arg | Ile | Val | Arg | Leu | Lys | Gly | Phe | |
| | | | 250 | | | | | 255 | | | | | 260 | | | |
| TAT | GAA | GAT | ACT | GAG | AGT | TAT | TAT | ATG | GTG | ATG | GAG | TTC | GTT | TCT | GGT | 1228 |
| Tyr | Glu | Asp | Thr | Glu | Ser | Tyr | Tyr | Met | Val | Met | Glu | Phe | Val | Ser | Gly | |
| | | | 265 | | | | 270 | | | | | 275 | | | | |
| GGT | GAC | TTA | ATG | GAT | TTT | GTT | GCT | GCT | CAT | GGT | GCG | GTT | GGA | GAA | GAT | 1276 |
| Gly | Asp | Leu | Met | Asp | Phe | Val | Ala | Ala | His | Gly | Ala | Val | Gly | Glu | Asp | |
| | 280 | | | | 285 | | | | | 290 | | | | | | |
| GCT | GGG | AGG | GAG | ATA | TCC | AGG | CAG | ATA | CTC | ACA | GCA | ATA | AAA | TAC | ATT | 1324 |
| Ala | Gly | Arg | Glu | Ile | Ser | Arg | Gln | Ile | Leu | Thr | Ala | Ile | Lys | Tyr | Ile | |
| 295 | | | | | 300 | | | | | 305 | | | | | 310 | |
| CAC | TCT | ATG | GGC | ATC | AGC | CAT | CGT | GAC | CTA | AAG | CCC | GAT | AAT | ATT | CTT | 1372 |
| His | Ser | Met | Gly | Ile | Ser | His | Arg | Asp | Leu | Lys | Pro | Asp | Asn | Ile | Leu | |
| | | | | 315 | | | | 320 | | | | | 325 | | | |
| ATT | GAA | CAA | GAC | GAT | CCT | GTA | TTG | GTA | AAG | ATA | ACC | GAC | TTT | GGT | CTG | 1420 |
| Ile | Glu | Gln | Asp | Asp | Pro | Val | Leu | Val | Lys | Ile | Thr | Asp | Phe | Gly | Leu | |
| | | | 330 | | | | | 335 | | | | | 340 | | | |
| GCA | AAA | GTA | CAA | GGA | AAT | GGG | TCT | TTT | ATG | AAA | ACC | TTC | TGT | GGC | ACT | 1468 |
| Ala | Lys | Val | Gln | Gly | Asn | Gly | Ser | Phe | Met | Lys | Thr | Phe | Cys | Gly | Thr | |
| | | 345 | | | | | 350 | | | | | 355 | | | | |
| TTG | GCA | TAT | GTG | GCA | CCT | GAA | GTC | ATC | AGA | GGT | AAA | GAT | ACA | TCC | GTA | 1516 |
| Leu | Ala | Tyr | Val | Ala | Pro | Glu | Val | Ile | Arg | Gly | Lys | Asp | Thr | Ser | Val | |
| | 360 | | | | | 365 | | | | | 370 | | | | | |
| TCT | CCT | GAT | GAA | TAC | GAA | GAA | AGG | AAT | GAG | TAC | TCT | TCG | TTA | GTG | GAT | 1564 |
| Ser | Pro | Asp | Glu | Tyr | Glu | Glu | Arg | Asn | Glu | Tyr | Ser | Ser | Leu | Val | Asp | |
| 375 | | | | | 380 | | | | | 385 | | | | | 390 | |
| ATG | TGG | TCA | ATG | GGA | TGT | CTT | GTG | TAT | GTT | ATC | CTA | ACG | GGC | CAC | TTA | 1612 |
| Met | Trp | Ser | Met | Gly | Cys | Leu | Val | Tyr | Val | Ile | Leu | Thr | Gly | His | Leu | |
| | | | | 395 | | | | | 400 | | | | | 405 | | |
| CCT | TTT | AGT | GGT | AGC | ACA | CAG | GAC | CAA | TTA | TAT | AAA | CAG | ATT | GGA | AGA | 1660 |
| Pro | Phe | Ser | Gly | Ser | Thr | Gln | Asp | Gln | Leu | Tyr | Lys | Gln | Ile | Gly | Arg | |
| | | | 410 | | | | | 415 | | | | | 420 | | | |
| GGC | TCA | TAT | CAT | GAA | GGG | CCC | CTC | AAA | GAT | TTC | CGG | ATA | TCT | GAA | GAA | 1708 |
| Gly | Ser | Tyr | His | Glu | Gly | Pro | Leu | Lys | Asp | Phe | Arg | Ile | Ser | Glu | Glu | |
| | | 425 | | | | | 430 | | | | | 435 | | | | |
| GCA | AGA | GAT | TTC | ATA | GAT | TCA | TTG | TTA | CAG | GTG | GAT | CCA | AAT | AAT | AGG | 1756 |
| Ala | Arg | Asp | Phe | Ile | Asp | Ser | Leu | Leu | Gln | Val | Asp | Pro | Asn | Asn | Arg | |
| | 440 | | | | | 445 | | | | | 450 | | | | | |

| | | | | | | | | | | | | | | | | |
|---|---|---|---|---|---|---|---|---|---|---|---|---|---|---|---|---|
| TCG | ACA | GCT | GCA | AAA | GCC | TTG | AAT | CAT | CCC | TGG | ATC | AAG | ATG | AGT | CCA | 1804 |
| Ser | Thr | Ala | Ala | Lys | Ala | Leu | Asn | His | Pro | Trp | Ile | Lys | Met | Ser | Pro | |
| 455 | | | | 460 | | | | | 465 | | | | | | 470 | |
| TTG | GGC | TCA | CAA | TCA | TAT | GGT | GAT | TTT | TCA | CAA | ATA | TCC | TTA | TCA | CAA | 1852 |
| Leu | Gly | Ser | Gln | Ser | Tyr | Gly | Asp | Phe | Ser | Gln | Ile | Ser | Leu | Ser | Gln | |
| | | | | 475 | | | | | 480 | | | | | 485 | | |
| TCG | TTG | TCG | CAG | CAG | AAA | TTA | TTA | GAA | AAT | ATG | GAC | GAT | GCT | CAA | TAC | 1900 |
| Ser | Leu | Ser | Gln | Gln | Lys | Leu | Leu | Glu | Asn | Met | Asp | Asp | Ala | Gln | Tyr | |
| | | | 490 | | | | | 495 | | | | | 500 | | | |
| GAA | TTT | GTC | AAA | GCG | CAA | AGG | AAA | TTA | CAA | ATG | GAG | CAA | CAA | CTT | CAA | 1948 |
| Glu | Phe | Val | Lys | Ala | Gln | Arg | Lys | Leu | Gln | Met | Glu | Gln | Gln | Leu | Gln | |
| | | 505 | | | | | 510 | | | | | 515 | | | | |
| GAA | CAG | GAT | CAG | GAA | GAC | CAA | GAT | GGA | AAA | ATT | CAA | GGA | TTT | AAA | ATA | 1996 |
| Glu | Gln | Asp | Gln | Glu | Asp | Gln | Asp | Gly | Lys | Ile | Gln | Gly | Phe | Lys | Ile | |
| | 520 | | | | | 525 | | | | | 530 | | | | | |
| CCC | GCA | CAC | GCC | CCT | ATT | CGA | TAT | ACA | CAG | CCC | AAA | AGC | ATT | GAA | GCA | 2044 |
| Pro | Ala | His | Ala | Pro | Ile | Arg | Tyr | Thr | Gln | Pro | Lys | Ser | Ile | Glu | Ala | |
| 535 | | | | | 540 | | | | | 545 | | | | | 550 | |
| GAA | ACT | AGA | GAA | CAA | AAA | CTT | TTA | CAT | TCC | AAT | AAT | ACT | GAG | AAT | GTC | 2092 |
| Glu | Thr | Arg | Glu | Gln | Lys | Leu | Leu | His | Ser | Asn | Asn | Thr | Glu | Asn | Val | |
| | | | | 555 | | | | | 560 | | | | | 565 | | |
| AAG | AGC | TCA | AAG | AAA | AAG | GGT | AAT | GGT | AGG | TTT | TTA | ACT | TTA | AAA | CCA | 2140 |
| Lys | Ser | Ser | Lys | Lys | Lys | Gly | Asn | Gly | Arg | Phe | Leu | Thr | Leu | Lys | Pro | |
| | | | 570 | | | | | 575 | | | | | 580 | | | |
| TTG | CCT | GAC | AGC | ATT | ATT | CAA | GAA | AGC | CTG | GAG | ATT | CAG | CAA | GGT | GTG | 2188 |
| Leu | Pro | Asp | Ser | Ile | Ile | Gln | Glu | Ser | Leu | Glu | Ile | Gln | Gln | Gly | Val | |
| | | 585 | | | | | 590 | | | | | 595 | | | | |
| AAT | CCA | TTT | TTC | ATT | GGT | AGA | TCC | GAG | GAT | TGC | AAT | TGT | AAA | ATT | GAA | 2236 |
| Asn | Pro | Phe | Phe | Ile | Gly | Arg | Ser | Glu | Asp | Cys | Asn | Cys | Lys | Ile | Glu | |
| | 600 | | | | | 605 | | | | | 610 | | | | | |
| GAC | AAT | AGG | TTG | TCT | CGA | GTT | CAT | TGC | TTC | ATT | TTC | AAA | AAG | AGG | CAT | 2284 |
| Asp | Asn | Arg | Leu | Ser | Arg | Val | His | Cys | Phe | Ile | Phe | Lys | Lys | Arg | His | |
| 615 | | | | | 620 | | | | | 625 | | | | | 630 | |
| GCT | GTA | GGC | AAA | AGC | ATG | TAT | GAA | TCT | CCG | GCA | CAA | GGT | TTA | GAT | GAT | 2332 |
| Ala | Val | Gly | Lys | Ser | Met | Tyr | Glu | Ser | Pro | Ala | Gln | Gly | Leu | Asp | Asp | |
| | | | | 635 | | | | | 640 | | | | | 645 | | |
| ATT | TGG | TAT | TGC | CAC | ACC | GGA | ACT | AAC | GTG | AGC | TAT | TTA | AAT | AAT | AAC | 2380 |
| Ile | Trp | Tyr | Cys | His | Thr | Gly | Thr | Asn | Val | Ser | Tyr | Leu | Asn | Asn | Asn | |
| | | | 650 | | | | | 655 | | | | | 660 | | | |
| CGC | ATG | ATA | CAG | GGT | ACG | AAA | TTC | CTT | TTA | CAA | GAC | GGA | GAT | GAA | ATC | 2428 |
| Arg | Met | Ile | Gln | Gly | Thr | Lys | Phe | Leu | Leu | Gln | Asp | Gly | Asp | Glu | Ile | |
| | | 665 | | | | | 670 | | | | | 675 | | | | |
| AAG | ATC | ATT | TGG | GAT | AAA | AAC | AAT | AAA | TTT | GTC | ATT | GGC | TTT | AAA | GTG | 2476 |
| Lys | Ile | Ile | Trp | Asp | Lys | Asn | Asn | Lys | Phe | Val | Ile | Gly | Phe | Lys | Val | |
| | 680 | | | | | 685 | | | | | 690 | | | | | |
| GAA | ATT | AAC | GAT | ACT | ACA | GGT | CTG | TTT | AAC | GAG | GGA | TTA | GGT | ATG | TTA | 2524 |
| Glu | Ile | Asn | Asp | Thr | Thr | Gly | Leu | Phe | Asn | Glu | Gly | Leu | Gly | Met | Leu | |
| 695 | | | | | 700 | | | | | 705 | | | | | 710 | |
| CAA | GAA | CAA | AGA | GTA | GTA | CTT | AAG | CAA | ACA | GCC | GAA | GAA | AAA | GAT | TTG | 2572 |
| Gln | Glu | Gln | Arg | Val | Val | Leu | Lys | Gln | Thr | Ala | Glu | Glu | Lys | Asp | Leu | |
| | | | | 715 | | | | | 720 | | | | | 725 | | |
| GTG | AAA | AAG | TTA | ACC | CAG | ATG | ATG | GCA | GCT | CAA | CGT | GCA | AAT | CAA | CCC | 2620 |
| Val | Lys | Lys | Leu | Thr | Gln | Met | Met | Ala | Ala | Gln | Arg | Ala | Asn | Gln | Pro | |
| | | | 730 | | | | | 735 | | | | | 740 | | | |
| TCG | GCT | TCT | TCT | TCA | TCA | ATG | TCG | GCT | AAG | AAG | CCG | CCA | GTT | AGC | GAT | 2668 |
| Ser | Ala | Ser | Ser | Ser | Ser | Met | Ser | Ala | Lys | Lys | Pro | Pro | Val | Ser | Asp | |
| | | 745 | | | | | 750 | | | | | 755 | | | | |
| ACA | AAT | AAT | AAC | GGC | AAT | AAT | TCG | GTA | CTA | AAC | GAC | TTG | GTA | GAG | TCA | 2716 |
| Thr | Asn | Asn | Asn | Gly | Asn | Asn | Ser | Val | Leu | Asn | Asp | Leu | Val | Glu | Ser | |
| 760 | | | | | 765 | | | | | 770 | | | | | | |

| | | | | | |
|---|---|---|---|---|---|
| CCG ATT AA TGCGAATACG GGGAACATTT TGAAGAGAAT ACATTCGGTA AGTTTATCGC | | | | | 2774 |
| Pro Ile | | | | | |
| 775 | | | | | |
| AATCACAAAT TGATCCTAGT AAGAAGGTTA AAAGGGCAAA ATTGGACCAA ACCTCAAAAG | | | | | 2834 |
| GCCCCGAGAA TTTGCAATTT TCGTAACCAA GGACAAATAC CCATAGAAAA TGCTGCCCCT | | | | | 2894 |
| TTTTAAGAGA GAAGATGGTA GATACCAATA CTCAGAATTC | | | | | 2934 |

( 2 ) INFORMATION FOR SEQ ID NO:17:

( i ) SEQUENCE CHARACTERISTICS:
( A ) LENGTH: 776 amino acids
( B ) TYPE: amino acid
( D ) TOPOLOGY: linear ( i i ) MOLECULE TYPE: protein
( A ) DESCRIPTION: yeast MEC2 protein ( x i ) SEQUENCE DESCRIPTION: SEQ ID NO:17:

```
Met  Glu  Asn  Ile  Thr  Gln  Pro  Thr  Gln  Gln  Ser  Thr  Gln  Ala  Thr  Gln
  1              5                   10                       15
Arg  Phe  Leu  Ile  Glu  Lys  Phe  Ser  Gln  Gln  Ile  Gly  Glu  Asn  Ile
         20                       25                       30
Val  Cys  Arg  Val  Ile  Cys  Thr  Thr  Gly  Gln  Ile  Pro  Ile  Arg  Asp  Leu
              35                  40                       45
Ser  Ala  Asp  Ile  Ser  Gln  Val  Leu  Lys  Glu  Lys  Arg  Ser  Ile  Lys  Lys
     50                       55                       60
Val  Trp  Thr  Phe  Gly  Arg  Asn  Pro  Ala  Cys  Asp  Tyr  His  Leu  Gly  Asn
 65                       70                       75                       80
Ile  Ser  Arg  Leu  Ser  Asn  Lys  His  Phe  Gln  Ile  Leu  Leu  Gly  Glu  Asp
                   85                       90                       95
Gly  Asn  Leu  Leu  Leu  Asn  Asp  Ile  Ser  Thr  Asn  Gly  Thr  Trp  Leu  Asn
              100                      105                      110
Gly  Gln  Lys  Val  Glu  Lys  Asn  Ser  Asn  Gln  Leu  Leu  Ser  Gln  Gly  Asp
              115                      120                      125
Glu  Ile  Thr  Val  Gly  Val  Gly  Val  Glu  Ser  Asp  Ile  Leu  Ser  Leu  Val
         130                      135                      140
Ile  Phe  Ile  Asn  Asp  Lys  Phe  Lys  Gln  Cys  Leu  Glu  Gln  Asn  Lys  Val
145                      150                      155                      160
Asp  Arg  Ile  Arg  Ser  Asn  Leu  Lys  Asn  Thr  Ser  Lys  Ile  Ala  Ser  Pro
                   165                      170                      175
Gly  Leu  Thr  Ser  Ser  Thr  Ala  Ser  Ser  Met  Val  Ala  Asn  Lys  Thr  Gly
              180                      185                      190
Ile  Phe  Lys  Asp  Phe  Ser  Ile  Ile  Asp  Glu  Val  Val  Gly  Gln  Gly  Ala
         195                      200                      205
Phe  Ala  Thr  Val  Lys  Lys  Ala  Ile  Glu  Arg  Thr  Thr  Gly  Lys  Thr  Phe
     210                      215                      220
Ala  Val  Lys  Ile  Ile  Ser  Lys  Arg  Lys  Val  Ile  Gly  Asn  Met  Asp  Gly
225                      230                      235                      240
Val  Thr  Arg  Glu  Leu  Glu  Val  Leu  Gln  Lys  Leu  Asn  His  Pro  Arg  Ile
                   245                      250                      255
Val  Arg  Leu  Lys  Gly  Phe  Tyr  Glu  Asp  Thr  Glu  Ser  Tyr  Tyr  Met  Val
              260                      265                      270
Met  Glu  Phe  Val  Ser  Gly  Gly  Asp  Leu  Met  Asp  Phe  Val  Ala  Ala  His
         275                      280                      285
Gly  Ala  Val  Gly  Glu  Asp  Ala  Gly  Arg  Glu  Ile  Ser  Arg  Gln  Ile  Leu
     290                      295                      300
```

| | | | | | | | | | | | | | | |
|---|---|---|---|---|---|---|---|---|---|---|---|---|---|---|
| Thr | Ala | Ile | Lys | Tyr | Ile | His | Ser | Met | Gly | Ile | Ser | His | Arg | Asp | Leu |
| 305 | | | | 310 | | | | | 315 | | | | | | 320 |
| Lys | Pro | Asp | Asn | Ile | Leu | Ile | Glu | Gln | Asp | Pro | Val | Leu | Val | Lys |
| | | | | 325 | | | | | 330 | | | | 335 | |
| Ile | Thr | Asp | Phe | Gly | Leu | Ala | Lys | Val | Gln | Gly | Asn | Gly | Ser | Phe | Met |
| | | | 340 | | | | | 345 | | | | | 350 | | |
| Lys | Thr | Phe | Cys | Gly | Thr | Leu | Ala | Tyr | Val | Ala | Pro | Glu | Val | Ile | Arg |
| | | 355 | | | | | 360 | | | | | 365 | | | |
| Gly | Lys | Asp | Thr | Ser | Val | Ser | Pro | Asp | Glu | Tyr | Glu | Arg | Asn | Glu |
| | 370 | | | | | 375 | | | | 380 | | | | |
| Tyr | Ser | Ser | Leu | Val | Asp | Met | Trp | Ser | Met | Gly | Cys | Leu | Val | Tyr | Val |
| 385 | | | | | 390 | | | | 395 | | | | | | 400 |
| Ile | Leu | Thr | Gly | His | Leu | Pro | Phe | Ser | Gly | Ser | Thr | Gln | Asp | Gln | Leu |
| | | | | 405 | | | | | 410 | | | | | 415 | |
| Tyr | Lys | Gln | Ile | Gly | Arg | Gly | Ser | Tyr | His | Glu | Gly | Pro | Leu | Lys | Asp |
| | | | 420 | | | | | 425 | | | | | 430 | | |
| Phe | Arg | Ile | Ser | Glu | Glu | Ala | Arg | Asp | Phe | Ile | Asp | Ser | Leu | Leu | Gln |
| | | 435 | | | | | 440 | | | | | 445 | | | |
| Val | Asp | Pro | Asn | Asn | Arg | Ser | Thr | Ala | Ala | Lys | Ala | Leu | Asn | His | Pro |
| 450 | | | | | 455 | | | | | 460 | | | | | |
| Trp | Ile | Lys | Met | Ser | Pro | Leu | Gly | Ser | Gln | Ser | Tyr | Gly | Asp | Phe | Ser |
| 465 | | | | | 470 | | | | | 475 | | | | | 480 |
| Gln | Ile | Ser | Leu | Ser | Gln | Ser | Leu | Ser | Gln | Lys | Leu | Leu | Glu | Asn |
| | | | | 485 | | | | | 490 | | | | | 495 |
| Met | Asp | Asp | Ala | Gln | Tyr | Glu | Phe | Val | Lys | Ala | Gln | Arg | Lys | Leu | Gln |
| | | | 500 | | | | | 505 | | | | | 510 | | |
| Met | Glu | Gln | Gln | Leu | Gln | Glu | Gln | Asp | Gln | Glu | Asp | Gln | Asp | Gly | Lys |
| | | 515 | | | | | 520 | | | | | 525 | | | |
| Ile | Gln | Gly | Phe | Lys | Ile | Pro | Ala | His | Ala | Pro | Ile | Arg | Tyr | Thr | Gln |
| 530 | | | | | 535 | | | | | 540 | | | | | |
| Pro | Lys | Ser | Ile | Glu | Ala | Glu | Thr | Arg | Glu | Gln | Lys | Leu | Leu | His | Ser |
| 545 | | | | | 550 | | | | | 555 | | | | | 560 |
| Asn | Asn | Thr | Glu | Asn | Val | Lys | Ser | Ser | Lys | Lys | Gly | Asn | Gly | Arg |
| | | | | 565 | | | | | 570 | | | | | 575 |
| Phe | Leu | Thr | Leu | Lys | Pro | Leu | Pro | Asp | Ser | Ile | Ile | Gln | Glu | Ser | Leu |
| | | | 580 | | | | | 585 | | | | | 590 | | |
| Glu | Ile | Gln | Gln | Gly | Val | Asn | Pro | Phe | Phe | Ile | Gly | Arg | Ser | Glu | Asp |
| | | 595 | | | | | 600 | | | | | 605 | | | |
| Cys | Asn | Cys | Lys | Ile | Glu | Asp | Asn | Arg | Leu | Ser | Arg | Val | His | Cys | Phe |
| 610 | | | | | 615 | | | | | 620 | | | | | |
| Ile | Phe | Lys | Lys | Arg | His | Ala | Val | Gly | Lys | Ser | Met | Tyr | Glu | Ser | Pro |
| 625 | | | | | 630 | | | | | 635 | | | | | 640 |
| Ala | Gln | Gly | Leu | Asp | Asp | Ile | Trp | Tyr | Cys | His | Thr | Gly | Thr | Asn | Val |
| | | | | 645 | | | | | 650 | | | | | 655 | |
| Ser | Tyr | Leu | Asn | Asn | Asn | Arg | Met | Ile | Gln | Gly | Thr | Lys | Phe | Leu | Leu |
| | | | 660 | | | | | 665 | | | | | 670 | | |
| Gln | Asp | Gly | Asp | Glu | Ile | Lys | Ile | Ile | Trp | Asp | Lys | Asn | Asn | Lys | Phe |
| | | 675 | | | | | 680 | | | | | 685 | | | |
| Val | Ile | Gly | Phe | Lys | Val | Glu | Ile | Asn | Asp | Thr | Thr | Gly | Leu | Phe | Asn |
| | 690 | | | | | 695 | | | | | 700 | | | | |
| Glu | Gly | Leu | Gly | Met | Leu | Gln | Glu | Gln | Arg | Val | Val | Leu | Lys | Gln | Thr |
| 705 | | | | | 710 | | | | | 715 | | | | | 720 |
| Ala | Glu | Glu | Lys | Asp | Leu | Val | Lys | Lys | Leu | Thr | Gln | Met | Met | Ala | Ala |
| | | | | 725 | | | | | 730 | | | | | 735 | |

```
Gln  Arg  Ala  Asn  Gln  Pro  Ser  Ala  Ser  Ser  Ser  Ser  Met  Ser  Ala  Lys
               740                      745                      750

Lys  Pro  Pro  Val  Ser  Asp  Thr  Asn  Asn  Asn  Gly  Asn  Asn  Ser  Val  Leu
          755                      760                      765

Asn  Asp  Leu  Val  Glu  Ser  Pro  Ile
     770                      775
```

( 2 ) INFORMATION FOR SEQ ID NO:18:

( i ) SEQUENCE CHARACTERISTICS:
        ( A ) LENGTH: 3551 base pairs
        ( B ) TYPE: nucleic acid
        ( C ) STRANDEDNESS: single
        ( D ) TOPOLOGY: linear ( i i ) MOLECULE TYPE: cDNA to mRNA
        ( A ) DESCRIPTION: yeast MEC3 cDNA ( v i ) ORIGINAL SOURCE:
        ( A ) ORGANISM: Saccharomyces cerevisiae ( i x ) FEATURE:
        ( A ) NAME/KEY: CDS
        ( B ) LOCATION: 1467..3227

( x i ) SEQUENCE DESCRIPTION: SEQ ID NO:18:

```
AACTTCTTCA  AATGCAGCGA  TAGCTTGGAA  CACACCTTCC  AAGTCTTTGC  AAGGGATGAC        60
CACTTCATGT  GTCGACGAAC  TTTCCTGTTC  AGCCTTTTCC  ACCATAACGG  ATATGTCATT       120
AAATTCAGTA  TCACCGCTAG  TATCAGCTGT  GTAAATGTTT  CCCCGCGTAT  CTGCGATCGA       180
GCTATCCTCA  ATTCTTAATA  AATCTTCATC  GTAGCGGATA  TTCTCTTCCA  TCTCTCGATC       240
TCTAGTATTG  GTATATAGTG  AAGACATCGG  TTTATCCGCT  TCGATAATCG  GAAGAGATCC       300
TTCCTCCTGC  CGGCCGTCTG  TGTCGATGTG  CTGGTTTTGG  GAAGGATTGT  CAGTGAGCCC       360
TTCTTGGCGT  TGTATCACAG  AATCTAAGGG  TCCATTCCAA  CATATTTCCA  AATGCCAATC       420
TAATTCATTC  ACAATTATCT  TGAGTTCTAC  ATCATCACCT  TCATTTCCAT  GCTCCTTTTT       480
TTTGACTCCC  ATTAAATGAA  TGTGGTTGAC  ATTGCTGTAC  CGTTCAACAC  GTCTAATGAA       540
CCCGTGGAAG  CGGAGCCAAA  CTCACCCGAT  ATTGGTGGTA  GCTTGTACAT  CATCAGTTGA       600
ATATAGTTAA  TCATTGGCTC  TTGTATTCGC  GTATGCTTGT  GCTCGGAATA  ATAGTTTGAC       660
AGGTACTTTG  AACGAATGAT  ATAACCTTAT  TGCTTGCTAG  TAGATTTCCT  GTGCCTACTG       720
TGGTTGGTAA  ACCATTGTGC  TCATCCACTC  CCCCATCCAT  AACTATAGCG  TCATTTGGGC       780
CGCTGGTATG  TACAATTTCT  TCGAATGTTA  TACCTAAAGC  ACAAATGGGG  TTCGGTTTTG       840
AGGTTGTATC  TACGCCTCCT  GCTGTTCCTC  CTGAAAGTGT  TCCGTTATTT  GTATTCCATT       900
CTGGCATTGA  CTGTAGTTTT  ATAATCATAT  TAGAGAAGAT  CCTTGGTTCA  TTACTCGATC       960
ATATCTTTTA  AACACACTCA  ATAAACAATC  ACAATTGACA  CTCCATTGTT  ATTGTATTAA      1020
GCTCGCGAGC  TGATATAACT  GTTATATAAT  CTGAATACAT  CATGAGGAAT  GGTACACCAA      1080
AGCTGACCAG  TATCCCCTCG  TAATATTGTA  CCGTTGTTAC  TGCTGTTGAG  TGATGATTTT      1140
GGAGTGGATA  TTATTGTCAA  TCTTTCACTA  TTAAATCTTA  AGATAGCCGT  CTTTCGTAGC      1200
GAACGAACTG  TATTGATAGT  AGTTCTTAGC  AATTTATAAT  CATCAGGTGC  TTCACAACCA      1260
TTTACTATCA  ATTTTAATTT  CATTTAACTG  AATTAAGACA  CACCTTTTGT  CTTCTTTTTT      1320
CTCTCATCAT  CTCCGTATGT  TTATCTTGCT  ATTTTGATGT  AAATAAAAAA  GTTGAATAAT      1380
AGACGAGGGC  AAGTATAACT  CGCCTATATT  GTAGCCGCAA  CCATTGAAAA  AAAGCCATGA      1440
ATATGAGAAA  ATAGTTGCAC  ATAAAA ATG CTG AAA TTT AGA ATT AGG CCA AAT          1493
```

|  |  |  |  |  |  |  |  |  | Met | Leu | Lys | Phe | Arg | Ile | Arg | Pro | Asn |  |
|---|---|---|---|---|---|---|---|---|---|---|---|---|---|---|---|---|---|---|
|  |  |  |  |  |  |  |  |  | 1 |  |  |  | 5 |  |  |  |  |  |

```
AGA  CAT  ATA  CGG  TGT  TAT  AAA  CGA  CAC  GCA  TAT  TTC  TTA  CGA  TAT  AAC                1541
Arg  His  Ile  Arg  Cys  Tyr  Lys  Arg  His  Ala  Tyr  Phe  Leu  Arg  Tyr  Asn
10             15                  20                  25

CAT  ACG  ACT  ACC  CCT  GCA  CAG  AAG  TTA  CAA  GCA  CAG  ATC  GAG  CAA  ATA                1589
His  Thr  Thr  Thr  Pro  Ala  Gln  Lys  Leu  Gln  Ala  Gln  Ile  Glu  Gln  Ile
                    30                  35                  40

CCT  CTC  GAA  AAT  TAC  AGA  AAT  TTT  TCT  ATA  GTT  GCC  CAT  GTT  GAC  CAT                1637
Pro  Leu  Glu  Asn  Tyr  Arg  Asn  Phe  Ser  Ile  Val  Ala  His  Val  Asp  His
               45                  50                  55

GGG  AAG  TCA  ACC  TTA  AGT  GAC  AGA  CTG  CTG  GAA  ATA  ACG  CAT  GTC  ATC                1685
Gly  Lys  Ser  Thr  Leu  Ser  Asp  Arg  Leu  Leu  Glu  Ile  Thr  His  Val  Ile
          60                  65                  70

GAT  CCC  AAT  GCG  AGA  AAT  AAA  CAA  GTT  TTG  GAT  AAA  TTG  GAA  GTC  GAA                1733
Asp  Pro  Asn  Ala  Arg  Asn  Lys  Gln  Val  Leu  Asp  Lys  Leu  Glu  Val  Glu
     75                  80                  85

AGA  GAA  AGA  GGT  ATT  ACT  ATA  AAG  GCG  CAA  ACA  TGT  TCG  ATG  TTT  TAT                1781
Arg  Glu  Arg  Gly  Ile  Thr  Ile  Lys  Ala  Gln  Thr  Cys  Ser  Met  Phe  Tyr
90                  95                  100                 105

AAA  GAT  AAG  AGG  ACC  GGA  AAA  AAC  TAT  CTT  TTA  CAT  TTA  ATT  GAC  ACG                1829
Lys  Asp  Lys  Arg  Thr  Gly  Lys  Asn  Tyr  Leu  Leu  His  Leu  Ile  Asp  Thr
                    110                 115                 120

CCA  GGA  CAT  GTG  GAC  TTC  AGA  GGT  GAA  GTT  TCA  CGG  TCA  TAT  GCG  TCT                1877
Pro  Gly  His  Val  Asp  Phe  Arg  Gly  Glu  Val  Ser  Arg  Ser  Tyr  Ala  Ser
               125                 130                 135

TGT  GGG  GGA  GCA  ATT  CTT  TTG  GTT  GAT  GCA  TCA  CAA  GGC  ATA  CAA  GCA                1925
Cys  Gly  Gly  Ala  Ile  Leu  Leu  Val  Asp  Ala  Ser  Gln  Gly  Ile  Gln  Ala
          140                 145                 150

CAG  ACG  GTT  GCT  AAT  TTT  TAT  TTA  GCC  TTC  AGT  TTA  GGA  TTG  AAA  TTG                1973
Gln  Thr  Val  Ala  Asn  Phe  Tyr  Leu  Ala  Phe  Ser  Leu  Gly  Leu  Lys  Leu
     155                 160                 165

ATT  CCA  GTA  ATA  AAC  AAA  ATT  GAT  CTC  AAT  TTT  ACA  GAT  GTT  AAA  CAG                2021
Ile  Pro  Val  Ile  Asn  Lys  Ile  Asp  Leu  Asn  Phe  Thr  Asp  Val  Lys  Gln
170                 175                 180                 185

GTA  AAG  GAT  CAG  ATA  GTG  AAT  AAC  TTT  GAG  CTC  CCC  GAG  GAA  GAT  ATA                2069
Val  Lys  Asp  Gln  Ile  Val  Asn  Asn  Phe  Glu  Leu  Pro  Glu  Glu  Asp  Ile
                    190                 195                 200

ATC  GGA  GTA  AGT  CGT  AAA  ACA  GCA  TTA  AAT  GTA  GAG  GAA  CTG  TTA  CTA                2117
Ile  Gly  Val  Ser  Arg  Lys  Thr  Ala  Leu  Asn  Val  Glu  Glu  Leu  Leu  Leu
               205                 210                 215

CCG  GCT  ATA  ATT  GAT  CGT  ATA  CCA  CCA  CCA  ACT  GGG  AGG  CCT  GAT  AAA                2165
Pro  Ala  Ile  Ile  Asp  Arg  Ile  Pro  Pro  Pro  Thr  Gly  Arg  Pro  Asp  Lys
          220                 225                 230

CCC  TTC  AGA  GCA  TTA  TTA  GTG  GAT  TCT  TGG  TAC  GAC  GCA  TAC  TTA  GGA                2213
Pro  Phe  Arg  Ala  Leu  Leu  Val  Asp  Ser  Trp  Tyr  Asp  Ala  Tyr  Leu  Gly
     235                 240                 245

GCG  GTT  CTT  CTA  GTG  AAT  ATT  GTT  GAT  GGT  TTT  GTA  CGT  AAA  AAT  GAC                2261
Ala  Val  Leu  Leu  Val  Asn  Ile  Val  Asp  Gly  Phe  Val  Arg  Lys  Asn  Asp
250                 255                 260                 265

AAA  GTT  ATT  TGT  GCT  CAG  ACA  AAA  GAA  AAA  TAC  GAA  GTC  AAA  GAT  ATT                2309
Lys  Val  Ile  Cys  Ala  Gln  Thr  Lys  Glu  Lys  Tyr  Glu  Val  Lys  Asp  Ile
                    270                 275                 280

GGA  ATC  ATG  TAT  CCT  GAC  AGA  ACT  TCT  ACA  GGT  ACG  CTA  AAG  ACA  GGA                2357
Gly  Ile  Met  Tyr  Pro  Asp  Arg  Thr  Ser  Thr  Gly  Thr  Leu  Lys  Thr  Gly
               285                 290                 295

CAA  GTT  GGC  TAT  CTA  GTG  CTG  GGA  ATG  AAG  GAT  TCT  AAA  GAA  GCA  AAA                2405
Gln  Val  Gly  Tyr  Leu  Val  Leu  Gly  Met  Lys  Asp  Ser  Lys  Glu  Ala  Lys
          300                 305                 310

ATT  GGA  GAT  ACT  ATA  ATG  CAT  TTA  AGT  AAA  GTA  AAT  GAA  ACG  GAA  GTA                2453
```

| | | | | | | | | | | | | | | | |
|---|---|---|---|---|---|---|---|---|---|---|---|---|---|---|---|
| Ile | Gly | Asp | Thr | Ile | Met | His | Leu | Ser | Lys | Val | Asn | Glu | Thr | Glu | Val |
| | | 315 | | | | 320 | | | | 325 | | | | | |

| CTT | CCC | GGA | TTT | GAA | GAA | CAA | AAA | CCC | ATG | GTA | TTT | GTG | GGT | GCT | TTC | 2501 |
|---|---|---|---|---|---|---|---|---|---|---|---|---|---|---|---|---|
| Leu | Pro | Gly | Phe | Glu | Glu | Gln | Lys | Pro | Met | Val | Phe | Val | Gly | Ala | Phe | |
| 330 | | | | | 335 | | | | 340 | | | | | 345 | | |

| CCG | GCT | GAT | GGG | ATT | GAA | TTC | AAA | CCC | ATG | GAT | GAT | GAT | ATG | AGT | AGA | 2549 |
|---|---|---|---|---|---|---|---|---|---|---|---|---|---|---|---|---|
| Pro | Ala | Asp | Gly | Ile | Glu | Phe | Lys | Pro | Met | Asp | Asp | Asp | Met | Ser | Arg | |
| | | | | 350 | | | | | 355 | | | | | 360 | | |

| CTT | GTT | CTC | AAC | GAT | AGG | TCA | GTT | ACT | TTG | GAA | CGT | CAG | ACC | TCC | AAT | 2597 |
|---|---|---|---|---|---|---|---|---|---|---|---|---|---|---|---|---|
| Leu | Val | Leu | Asn | Asp | Arg | Ser | Val | Thr | Leu | Glu | Arg | Gln | Thr | Ser | Asn | |
| | | | | 365 | | | | | 370 | | | | | 375 | | |

| GCT | TTG | GGT | CAA | GGT | TGG | AGA | TTG | GGC | TTT | TTA | GGA | TCT | TTA | CAT | GCA | 2645 |
|---|---|---|---|---|---|---|---|---|---|---|---|---|---|---|---|---|
| Ala | Leu | Gly | Gln | Gly | Trp | Arg | Leu | Gly | Phe | Leu | Gly | Ser | Leu | His | Ala | |
| | | 380 | | | | | 385 | | | | | 390 | | | | |

| TCT | GTT | TTT | CGT | GAA | CGA | CTA | GAA | AAA | GAG | TAT | GGT | TCG | AAA | TTG | ATC | 2693 |
|---|---|---|---|---|---|---|---|---|---|---|---|---|---|---|---|---|
| Ser | Val | Phe | Arg | Glu | Arg | Leu | Glu | Lys | Glu | Tyr | Gly | Ser | Lys | Leu | Ile | |
| | 395 | | | | | 400 | | | | | 405 | | | | | |

| ATT | ACT | CAA | CCC | ACA | GTT | CCT | TAT | TTG | GTG | GAG | TTT | ACC | GAT | GGT | AAG | 2741 |
|---|---|---|---|---|---|---|---|---|---|---|---|---|---|---|---|---|
| Ile | Thr | Gln | Pro | Thr | Val | Pro | Tyr | Leu | Val | Glu | Phe | Thr | Asp | Gly | Lys | |
| 410 | | | | | 415 | | | | | 420 | | | | | 425 | |

| AAA | AAA | CTT | ATA | ACA | AAT | CCG | GAT | GAG | TTT | CCA | GAC | GGA | GCA | ACA | AAG | 2789 |
|---|---|---|---|---|---|---|---|---|---|---|---|---|---|---|---|---|
| Lys | Lys | Leu | Ile | Thr | Asn | Pro | Asp | Glu | Phe | Pro | Asp | Gly | Ala | Thr | Lys | |
| | | | | 430 | | | | | 435 | | | | | 440 | | |

| AGG | GTG | AAC | GTT | GCT | GCT | TTC | CAT | GAA | CCG | TTT | ATA | GAG | GCA | GTT | ATG | 2837 |
|---|---|---|---|---|---|---|---|---|---|---|---|---|---|---|---|---|
| Arg | Val | Asn | Val | Ala | Ala | Phe | His | Glu | Pro | Phe | Ile | Glu | Ala | Val | Met | |
| | | | 445 | | | | | 450 | | | | | 455 | | | |

| ACA | TTG | CCC | CAG | GAA | TAT | TTA | GGT | AGT | GTC | ATA | CGC | TTA | TGC | GAT | AGT | 2885 |
|---|---|---|---|---|---|---|---|---|---|---|---|---|---|---|---|---|
| Thr | Leu | Pro | Gln | Glu | Tyr | Leu | Gly | Ser | Val | Ile | Arg | Leu | Cys | Asp | Ser | |
| | | 460 | | | | | 465 | | | | | 470 | | | | |

| AAT | AGA | GGA | GAA | CAA | ATT | GAT | ATA | ACA | TAC | CTA | AAC | ACC | AAT | GGA | CAA | 2933 |
|---|---|---|---|---|---|---|---|---|---|---|---|---|---|---|---|---|
| Asn | Arg | Gly | Glu | Gln | Ile | Asp | Ile | Thr | Tyr | Leu | Asn | Thr | Asn | Gly | Gln | |
| | 475 | | | | | 480 | | | | | 485 | | | | | |

| GTG | ATG | TTA | AAA | TAT | TAC | CTT | CCG | CTA | TCG | CAT | CTA | GTC | GAT | GAC | TTT | 2981 |
|---|---|---|---|---|---|---|---|---|---|---|---|---|---|---|---|---|
| Val | Met | Leu | Lys | Tyr | Tyr | Leu | Pro | Leu | Ser | His | Leu | Val | Asp | Asp | Phe | |
| 490 | | | | | 495 | | | | | 500 | | | | | 505 | |

| TTT | GGT | AAA | TTA | AAA | TCG | GTG | TCC | AGA | GGA | TTT | GCC | TCT | TTA | GAT | TAT | 3029 |
|---|---|---|---|---|---|---|---|---|---|---|---|---|---|---|---|---|
| Phe | Gly | Lys | Leu | Lys | Ser | Val | Ser | Arg | Gly | Phe | Ala | Ser | Leu | Asp | Tyr | |
| | | | | 510 | | | | | 515 | | | | | 520 | | |

| GAG | GAT | GCT | GGC | TAT | AGA | ATT | TCT | GAT | GTT | GTA | AAA | CTG | CAA | CTC | TTG | 3077 |
|---|---|---|---|---|---|---|---|---|---|---|---|---|---|---|---|---|
| Glu | Asp | Ala | Gly | Tyr | Arg | Ile | Ser | Asp | Val | Val | Lys | Leu | Gln | Leu | Leu | |
| | | | 525 | | | | | 530 | | | | | 535 | | | |

| GTT | AAT | GGA | AAT | GCG | ATT | GAT | GCC | TTG | TCA | AGA | GTA | CTT | CAT | AAA | TCG | 3125 |
|---|---|---|---|---|---|---|---|---|---|---|---|---|---|---|---|---|
| Val | Asn | Gly | Asn | Ala | Ile | Asp | Ala | Leu | Ser | Arg | Val | Leu | His | Lys | Ser | |
| | | 540 | | | | | 545 | | | | | 550 | | | | |

| GAA | GTA | GAG | AGA | GTG | CGT | AGA | GAA | TGG | GTA | AAG | AAG | TTT | AAA | GAG | TAT | 3173 |
|---|---|---|---|---|---|---|---|---|---|---|---|---|---|---|---|---|
| Glu | Val | Glu | Arg | Val | Arg | Arg | Glu | Trp | Val | Lys | Lys | Phe | Lys | Glu | Tyr | |
| | 555 | | | | | 560 | | | | | 565 | | | | | |

| GTT | AAA | TCA | CAA | TTA | TAT | GAG | GTC | TTA | TAC | AGG | CCC | GAG | CTA | ATA | ACA | 3221 |
|---|---|---|---|---|---|---|---|---|---|---|---|---|---|---|---|---|
| Val | Lys | Ser | Gln | Leu | Tyr | Glu | Val | Leu | Tyr | Arg | Pro | Glu | Leu | Ile | Thr | |
| 570 | | | | | 575 | | | | | 580 | | | | | 585 | |

| AGA | TAATCGCTAG | AGAAACAATT | AAGGCAAGAA | GAAAAGATGT | TCTCCAAAAG | 3274 |
|---|---|---|---|---|---|---|
| Arg | | | | | | |

CTGCATGCTT CTGATGTCTC ACGAAGGAAA AAACTTTTGG CGAAACAGAA AGAGGGAAAA　　3334

AGCATATGAA AACTGTAGGT AATATTCAAA TCAACCAAGA GGCATATCAG GCTTTTTTGC　　3394

GCCGTTAGCA TTGCATATTA TTGTTATTAC CATTTTAAAA TTATACCAAG CTGTACATAG　　3454

TTAAGTACTT TCATTTGTA AATAAAGAG AAAAATAGAT TAATAAATAT TATAATGACA　　3514

TAACATTATG CTTTAAGTAT TTCTCAAGTG TAACTAC　　3551

( 2 ) INFORMATION FOR SEQ ID NO:19:

( i ) SEQUENCE CHARACTERISTICS:
        ( A ) LENGTH: 586 amino acids
        ( B ) TYPE: amino acid
        ( D ) TOPOLOGY: linear ( i i ) MOLECULE TYPE: protein
        ( A ) DESCRIPTION: yeast MEC3 protein ( x i ) SEQUENCE DESCRIPTION: SEQ ID NO:19:

```
Met Leu Lys Phe Arg Ile Arg Pro Asn Arg His Ile Arg Cys Tyr Lys
 1               5                  10                  15

Arg His Ala Tyr Phe Leu Arg Tyr Asn His Thr Thr Thr Pro Ala Gln
                20                  25                  30

Lys Leu Gln Ala Gln Ile Glu Gln Ile Pro Leu Glu Asn Tyr Arg Asn
            35                  40                  45

Phe Ser Ile Val Ala His Val Asp His Gly Lys Ser Thr Leu Ser Asp
        50                  55                  60

Arg Leu Leu Glu Ile Thr His Val Ile Asp Pro Asn Ala Arg Asn Lys
65                  70                  75                  80

Gln Val Leu Asp Lys Leu Glu Val Glu Arg Glu Arg Gly Ile Thr Ile
                85                  90                  95

Lys Ala Gln Thr Cys Ser Met Phe Tyr Lys Asp Lys Arg Thr Gly Lys
               100                 105                 110

Asn Tyr Leu Leu His Leu Ile Asp Thr Pro Gly His Val Asp Phe Arg
            115                 120                 125

Gly Glu Val Ser Arg Ser Tyr Ala Ser Cys Gly Gly Ala Ile Leu Leu
        130                 135                 140

Val Asp Ala Ser Gln Gly Ile Gln Ala Gln Thr Val Ala Asn Phe Tyr
145                 150                 155                 160

Leu Ala Phe Ser Leu Gly Leu Lys Leu Ile Pro Val Ile Asn Lys Ile
                165                 170                 175

Asp Leu Asn Phe Thr Asp Val Lys Gln Val Lys Asp Gln Ile Val Asn
            180                 185                 190

Asn Phe Glu Leu Pro Glu Glu Asp Ile Ile Gly Val Ser Arg Lys Thr
        195                 200                 205

Ala Leu Asn Val Glu Glu Leu Leu Pro Ala Ile Ile Asp Arg Ile
210                 215                 220

Pro Pro Pro Thr Gly Arg Pro Asp Lys Pro Phe Arg Ala Leu Leu Val
225                 230                 235                 240

Asp Ser Trp Tyr Asp Ala Tyr Leu Gly Ala Val Leu Leu Val Asn Ile
                245                 250                 255

Val Asp Gly Phe Val Arg Lys Asn Asp Lys Val Ile Cys Ala Gln Thr
            260                 265                 270

Lys Glu Lys Tyr Glu Val Lys Asp Ile Gly Ile Met Tyr Pro Asp Arg
        275                 280                 285

Thr Ser Thr Gly Thr Leu Lys Thr Gly Gln Val Gly Tyr Leu Val Leu
290                 295                 300

Gly Met Lys Asp Ser Lys Glu Ala Lys Ile Gly Asp Thr Ile Met His
305                 310                 315                 320

Leu Ser Lys Val Asn Glu Thr Glu Val Leu Pro Gly Phe Glu Glu Gln
                325                 330                 335

Lys Pro Met Val Phe Val Gly Ala Phe Pro Ala Asp Gly Ile Glu Phe
            340                 345                 350

Lys Pro Met Asp Asp Asp Met Ser Arg Leu Val Leu Asn Asp Arg Ser
```

```
                    3 5 5                              3 6 0                              3 6 5
Val  Thr  Leu  Glu  Arg  Gln  Thr  Ser  Asn  Ala  Leu  Gly  Gln  Gly  Trp  Arg
     3 7 0                   3 7 5                    3 8 0
Leu  Gly  Phe  Leu  Gly  Ser  Leu  His  Ala  Ser  Val  Phe  Arg  Glu  Arg  Leu
3 8 5                    3 9 0                    3 9 5                        4 0 0
Glu  Lys  Glu  Tyr  Gly  Ser  Lys  Leu  Ile  Ile  Thr  Gln  Pro  Thr  Val  Pro
               4 0 5                   4 1 0                        4 1 5
Tyr  Leu  Val  Glu  Phe  Thr  Asp  Gly  Lys  Lys  Lys  Leu  Ile  Thr  Asn  Pro
               4 2 0                   4 2 5                        4 3 0
Asp  Glu  Phe  Pro  Asp  Gly  Ala  Thr  Lys  Arg  Val  Asn  Val  Ala  Ala  Phe
          4 3 5                        4 4 0                   4 4 5
His  Glu  Pro  Phe  Ile  Glu  Ala  Val  Met  Thr  Leu  Pro  Gln  Glu  Tyr  Leu
     4 5 0                        4 5 5                    4 6 0
Gly  Ser  Val  Ile  Arg  Leu  Cys  Asp  Ser  Asn  Arg  Gly  Glu  Gln  Ile  Asp
4 6 5                         4 7 0                    4 7 5                   4 8 0
Ile  Thr  Tyr  Leu  Asn  Thr  Asn  Gly  Gln  Val  Met  Leu  Lys  Tyr  Tyr  Leu
               4 8 5                             4 9 0                    4 9 5
Pro  Leu  Ser  His  Leu  Val  Asp  Asp  Phe  Phe  Gly  Lys  Leu  Lys  Ser  Val
               5 0 0                        5 0 5                    5 1 0
Ser  Arg  Gly  Phe  Ala  Ser  Leu  Asp  Tyr  Glu  Asp  Ala  Gly  Tyr  Arg  Ile
          5 1 5                        5 2 0                    5 2 5
Ser  Asp  Val  Val  Lys  Leu  Gln  Leu  Leu  Val  Asn  Gly  Asn  Ala  Ile  Asp
     5 3 0                         5 3 5                   5 4 0
Ala  Leu  Ser  Arg  Val  Leu  His  Lys  Ser  Glu  Val  Glu  Arg  Val  Arg  Arg
5 4 5                         5 5 0                    5 5 5                   5 6 0
Glu  Trp  Val  Lys  Lys  Phe  Lys  Glu  Tyr  Val  Lys  Ser  Gln  Leu  Tyr  Glu
               5 6 5                        5 7 0                    5 7 5
Val  Leu  Tyr  Arg  Pro  Glu  Leu  Ile  Thr  Arg
               5 8 0                        5 8 5
```

CELL CYCLE CHECKPOINT GENES

This application is a continuation of Ser. No. 08/198,446 filed Feb. 18, 1994, now U.S. Pat. No. 5,674,996 which is a continuation-in-part of International application Ser. No. PCT/US93/04458 filed May 12, 1993, which is a continuation-in-part of Ser. No. 07/884,426 filed May 14, 1992, now abandoned, and Ser. No. 07/882,051 filed May 12, 1992, now abandoned.

This invention was made with government support under grant GM17709 awarded by the National Institutes of Health and grant CA57156 awarded by the National Cancer Institute. The government has certain rights in the invention.

FIELD OF THE INVENTION

The invention relates generally to molecular biology, genetic engineering, and recombinant techniques, and specifically to checkpoint genes and proteins and surveillance mechanisms for controlling timing of the cell cycle prior to mitosis so that DNA damage by radiation, chemicals, or drugs can be repaired.

BACKGROUND OF THE INVENTION

Cellular resistance to DNA damage and replication errors is critical to survival of cells, tissues, and organisms. Radiation induces DNA strand breaks. Failure to repair even one DNA strand break can be lethal in yeasts. Cellular resistance to DNA damage consists of separate processes for recognition of damage and repair Control mechanisms exist for arresting the cell division cycle (cdc) until DNA repair is completed. Delay can occur in different phases of the cell cycle depending on the type of DNA damage and the stage in the cell cycle at which the damage occurs. In particular, damage resulting from DNA strand breaks caused by ionizing radiation or topoisomerase inhibitors causes delay of the cell cycle in the G2 phase before entry into mitosis. The delay may be observed as a decline in the mitotic index of human or yeast cells approximately one hour post irradiation.

Several classes of mutations in yeasts have been defined that result in deregulation of the cell cycle. Temperature-sensitive (ts) mutations in yeast cdc genes can result in death at defined points in the cell cycle when strains are shifted to the non-permissive temperature, and lethality may increase in a temperature-sensitive manner (1). More than thirty-two different cdc genes have been identified in S. cerevisiae (2). One such mutant, cdc9-8$^{ts}$, is a DNA ligase mutant in which the temperature-dependent increase in lethality presumably occurs because of a general failure in ligating chromosomal DNA Okazaki fragments following chromosomal DNA replication. The molecular activities of most cdc genes is largely unknown.

Recently a new class of cell cycle regulatory mutations has been identified and labeled checkpoint mutations (3). Checkpoints exist to ensure that DNA synthesis is completed before mitosis begins; that anaphase is delayed until all the chromosomes arrive on the metaphase plate; that centrosome duplication does not occur until DNA has been synthesized; and, that initiation of DNA synthesis is coordinated between different regions in a chromosome. In yeast, RAD9 is one such checkpoint gene of S. cerevisiae that mediates G2 delay after DNA damage. rad9 mutants have greatly increased radiation sensitivity (less than 0.1% survival at 8000 rads for rad9 yeasts vs. 30% for RAD+ yeasts) (4). Direct visualization of budding yeasts after irradiation shows that rad9 cells continue into mitosis despite potentially lethal DNA damage and die in subsequent generations. RAD9 protein is not required for DNA repair, and RAD9 is not an essential gene in the cell cycle. In the absence of DNA damage, rad9 cells display normal cell cycle kinetics but accumulate spontaneous chromosome loss at a higher rate than wild-type strains. Northern blot analyses of RNA from yeast in different parts of the cell cycle and from pre- and post-irradiated cells show a constant level of RAD9 MRNA. The yeast RAD9 gene has been cloned, and the translated open reading frame encodes 1309 amino acids that exhibit no significant homology to any other known proteins in the database (4). No human genes have been identified that mediate the G2 delay induced by DNA damage.

The simultaneous presence of both a rad9 checkpoint mutation and a cdc9-8 mutation (i.e., in a double mutant strain) substantially increases the rate of cell death when cells are shifted to the nonpermissive temperature (4). This increase in lethality is presumably due to DNA strand breaks resulting from incomplete DNA synthesis (cdc9-8) and failure to properly delay the cycle to repair the damage (rad9).

CDC34 (not to be confused with p34$^{cdc2}$) is an essential gene in yeast required for the transition from late G1 to the initiation of DNA synthesis (5). Sequence analysis and enzymatic assays support the notion that CDC34 is an E2 ubiquitin ligase. The target protein ubiquitinated by CDC34 is unknown.

While it has been possible to study checkpoint genes in yeast, few of their human counterparts have been identified and it is not presently known whether events observed in yeast will be generally applicable to cell cycles of higher eukaryotes.

SUMMARY OF THE INVENTION

A genetic protocol is disclosed to identify human checkpoint cDNAs based on increased lethality of yeast mutants having a temperature-sensitive mutation that produces damaged DNA and a checkpoint gene mutation that hinders DNA repair. The strategy utilizes the cdc9-8 yeast strain with a DNA ligase mutation (temperature sensitive for DNA damage), and the mec1 or rad9 checkpoint mutations (impaired in G2 arrest and thereby in DNA repair).

The subject screening assay uses the double mutants mec-1,cdc9-8 (ATCC No. 74155) and rad9,cdc9-8 (ATCC No. 74154 ) as yeast test cells to select and isolate human checkpoint cDNA clones that are capable of complementing or suppressing a defective yeast G2 checkpoint function. Feasibility of the assay was established in experiments that identified three novel human genes involved in human cell cycle control: huCDC34, huRAD9$_{compA}$, and huRAD9$_{compB}$.

The huCDC34 cDNA clone (clone #1; alias 171tx61) was identified as suppressing the mec-1 checkpoint mutation that renders mec1,cdc9 cells temperature sensitive for growth at 30° C. Clone #1 did not suppress the checkpoint defect in rad9,cdc9-8. The nucleotide sequence of clone #1 is shown in FIG. 1. Sequence analysis revealed a surprising homology between the isolated human cDNA and the previously cloned CDC34 gene of S. cerevisiae. (Yeast CDC34 is a member of the E2 ubiquitin ligase family and has no significant homology with MEC1.) Human clone #1 cDNA complemented a cdc34$^{ts}$ yeast mutation, confirming its identity as a human homolog of yeast CDC34. The huCDC34 gene is expressed in multiple cell lines, and Southern blot analysis reveals evidence for a single gene that is highly conserved in higher eukaryotes. The huCDC34 gene was mapped to a telomeric region of chromosome 19p13.3, and the mouse CDC34 gene mapped to chromosome 11. The position of the huCDC34 gene in the genome has not been preserved during evolution, designating a novel region of synteny in chromosome 19.

The huRAD9$_{compA}$ cDNA clone (clone #2; alias 83tx42) was identified as suppressing the rad9 checkpoint mutation that renders rad9,cdc9 cells temperature sensitive for growth at 30° C. Clone #2 suppressed the checkpoint defect in rad9,cdc9-8 as well as mec1,cdc9-8 cells, but failed to complement the defect in the cdc9-8 cells. The nucleotide sequence of clone #2 is shown in FIG. 2. The long open reading frame (ORF) in clone #2 had no significant homology to any previously described protein. The phenotype of huRAD9$_{compA}$ appears to be a slowing of the cell cycle during S phase to allow more time for DNA repair.

The huRAD9$_{compB}$ cDNA clone (clone #3; alias 171tx23) was identified as suppressing the mec-1 checkpoint mutation that renders mec-1,cdc9 cells temperature sensitive for growth at 30° C. Clone #3 suppressed the checkpoint defect in rad9,cdc9-8 or mec1,cdc9-8 cells, but not in cdc9-8 cells. Clone #3 was capable of conferring radiation resistance upon a single mutant mec1 or rad9 cell. The nucleotide sequence of clone #3 is shown in FIG. 3. The ORF in clone #3 had no significant homology to any previously described protein. The phenotype of clone #3 suggests that it may act in a G2 arrest pathway that is either downstream of, or independent from, both RAD9 and MEC 1.

These results demonstrate the success of the subject protocol for selecting and isolating novel human cDNAs that are active in regulating the human cell division cycle.

BRIEF DESCRIPTION OF THE DRAWINGS

FIGS. 1, 2, and 3 depict the disclosed huCDC34, huRAD9$_{compA}$, and huRAD9$_{compB}$ cDNAS, respectively.

FIGS. 4A–4B, 5A–5B, 6A–6E, 7A–7B and 8A–8C depict the disclosed RAD17, RAD24, MEC1, MEC2, and MEC3 cDNAs, respectively.

DETAILED DESCRIPTION OF THE PREFERRED EMBODIMENT

Methods are disclosed for selecting and isolating human cDNAs responsible for radiation sensitivity and resistance. The methods are based on selecting human cDNAs that complement or suppress checkpoint mutations in yeast cells. The strategy involves using yeast double mutants that are: 1) conditional for DNA damage (e.g., as the result of a DNA ligase mutation); and, 2) mutant for a cell cycle checkpoint function that is necessary to repair damaged DNA (e.g., a G2 checkpoint where arrest allows DNA repair).

Prior to conducting the experiments described below, it was not known whether human checkpoint genes could exert their actions in yeast. While certain other cdc genes had been shown to be capable of crossing over between yeast and man, it was reasoned that critical checkpoint functions could be species specific and highly evolved to fit the functions of a yeast or human cell. Expression of a human checkpoint cDNA in a double mutant yeast cell might either go unnoticed, because the human protein could be incapable of rescuing the double lethal mutation, or it might even prove lethal when in a yeast background. Considering the improbable nature of any effect, a screen assay was developed for screening hundreds of thousands of transformants. Remarkably, in the first series of experiments, a single active clone (clone #1) was identified out of a total of 200,000 transformants. Sequence analysis revealed significant homology of the human cDNA to the CDC34 gene of S. cerevisiae. Clone #1 human cDNA efficiently complements a yeast cdc34 mutation, identifying it as a human homolog of yeast CDC34. The result of this assay was particularly unexpected since all previous reports linked the function of yeast CDC34 to events in the late G1 phase of the cell cycle prior to entry into S phase. Interestingly, the limited sequence homology between yeast and man was not sufficient for yeast cDNA to identify human CDC34. (S. Plon, unpublished.)

As used herein, "checkpoint" is intended to mean a timepoint in the cell cycle of a eukaryotic cell at which progression to mitosis may be arrested if the cell contains chromosomal DNA with one or more strand breaks. Illustrative methods by which DNA strand breaks may be introduced into chromosomal DNA include DNA ligase mutations, topoisomerase mutations, X-irradiation, gamma-irradiation, and treatment with drugs (e.g., hydroxyurea), or treatment with chemotherapeutic agents, e.g., 5-fluorouracil, ectopside, and the like.

"Checkpoint gene" is intended to mean a gene whose expression (i.e., as RNA or protein) is capable of arresting a cell cycle at a checkpoint in a eukaryotic cell having chromosomal DNA with one or more strand breaks, but not in a eukaryotic cell having native chromosomal DNA, i.e., without DNA strand breaks. The checkpoint gene is capable of conferring upon a eukaryotic cell increased capacity to protect against potentially lethal damage, meaning that the subject eukaryotic cell has an increased capacity for arresting cell mitosis when chromosomal DNA is damaged, e.g., by drugs or radiation. Illustrative examples of eukaryotic checkpoint genes include RAD-9, MEC-1, RAD17, RAD24, MEC-2, and MEC-3. The mec1, mec2, and mec3 genes were identified in S. cerevisiae as mutations that are also deficient for G2 arrest after DNA strand breaks. See Example 4 and FIGS. 4A–4B, 5A–5B, 6A–6E, 7A–7B and 8A–8C.

By convention, and as followed herein, terms in capitalized italics refer to the wild-type gene; lowercase italics refer to mutants of the gene; and capitalized nonitalics refer to proteins encoded by the wild-type gene.

"Complementation" is used herein as a genetic term intended to mean that the subject genetic element is homologous to a mutant genetic element such that when introduced into a cell it rescues the cell from the effects of the mutation. For example, MEC-1 DNA rescues the mec-1 defect in a mec-1,cdc9-8 cell (and RAD9 rescues the rad9 defect in a rad9,cdc9-8 cell) through a process herein referred to as complementation, and the MEC-1 (or RAD9) DNA so capable is referred to as a "complementing cDNA." Similarly, huCDC34 is homologous with yeast CDC34 and able to complement the mutation in single (or double mutant) cells, e.g., single mutant cells of yeast strain cdc34.

"Suppression," "suppress," "suppressing," and "suppressed" are used herein as genetic terms intended to mean rescue of a mutant phenotype by a non-homologous genetic element that circumvents the effects of mutation. For example, human CDC34 is not homologous with mec-1, (i.e., no significant homology detectable by computer-assisted alignment and sequence comparison), and yet huCDC34 is capable of rescuing the mec-1 defect in a mec-1,cdc9-8 cell. Similarly, human RAD9$_{compA}$ is not homologous with RAD9 and yet it is capable of rescuing the rad9 defect in a rad9, cdc9-8 cell by suppressing the mutant checkpoint rad9 function.

"G2 arrest" is intended to mean arrest in the interval of the cell cycle following DNA replication and before mitosis.

Illustrative examples of ways in which a cell cycle may be arrested in G2 include X-irradiation, gamma-irradiation, ectopside, and other physical and chemical agents.

A highly sensitive and selective yeast temperature-sensitive selection assay system has now been developed for identifying and isolating mammalian checkpoint genes operative in compensating for a defective G2 checkpoint function. The checkpoint genes so identified are operative in G1 arrest and/or G2 arrest. Using this assay human cDNA clones have been identified and isolated that encode human checkpoint proteins that are functionally active in correcting defects resulting from mutations in yeast checkpoint genes. Three representative human checkpoint cDNA clones which suppress for a defective G2 checkpoint function in a yeast mutant have been identified by this process.

An exemplary method for isolating and selecting human checkpoint cDNA clones that suppress a checkpoint mutation in a double mutant yeast test cell is conveniently conducted using the following steps. First, a double mutant test cell is constructed with a mutation in gene #1 that is "conditionally" responsible for DNA damage, and a mutation in gene #2 that causes a growing cell to fail to arrest the cell cycle at a checkpoint where a native (wild-type) cell would arrest if DNA damage was present. The mutation in gene #1 is thus made potentially lethal by the additional mutation in gene #2. "Conditionally," as used herein, is intended to mean that if the mutation in gene #1 is silent the cells grow normally, but when the mutation is induced to become active at a restrictive condition the cells undergo DNA damage. "Restrictive conditions" include, for example, shifting the temperature from a permissive to a restrictive temperature, or adding an inducer or activator that promotes expression of the DNA damage phenotype of the mutant of gene #1. Yeast double mutant test cells are constructed by mating the respective single mutants of gene #1 and gene #2 and by then selecting recombinants, e.g., using selectable markers. The yeast double mutant test cell has the following desirable phenotypic properties: under permissive conditions the cell grows, but when shifted to restrictive conditions DNA damage results; the mutation in gene #2 prevents cell cycle arresting to repair the damage, and chromosomal aberrations result. Preferably, the double mutant yeast test cells fail to grow under the restrictive conditions, and most preferably the double mutant test cells die when the restrictive conditions are imposed. Illustrative examples of double mutant test cells are provided by mec-1,cdc9-8 and rad9,cdc9-8. In both of the latter test cells the mutation in gene #1 is provided by cdc9, which is conditionally lethal at a restrictive temperature; and the mutation in gene #2 is a mec-1 or rad9 mutation capable of preventing G2 arrest in response to DNA damage. There are multiple cdc9 alleles; one preferred allele is provided by the cdc9-8ts strain. rad9 yeast mutants lack a functional RAD9 protein that is essential in yeast at a G2 checkpoint. The mec1, cdc9-8 or rad9,cdc9-8 double mutant test cells die more rapidly at 36° C. than RAD9,cdc9-8 or MEC1,cdc9-8, respectively. The latter two different illustrative double mutant yeast strains have been deposited: rad9,cdc9-8 cells as ATCC No. 74154; and mec-1,cdc8-9 cells as ATCC No. 74155.

Second, pooled human cDNA is inserted into a plasmid vector having a selectable marker under the control of a yeast promoter, and the vector is introduced into cultures of the yeast double mutant test cells, e.g., using lithium acetate transfection. Transformants are selected as individual colonies (based on marker expression and temperature), but en masse on microbiological culture plates. Next, tests are conducted to determine the plasmid dependence of the phenotypic expression (e.g., plasmid-dependent growth). In this case the yeast cells are "cured" of the plasmid and then tested for phenotype (e.g., viability or growth). The latter test results are used to ensure that the phenotype selected (e.g., growth or viability) in the transformant is dependent upon the presence of the human cDNA in a plasmid DNA, and not on some other random genetic event. In the illustrative examples it was necessary to isolate about 200,000 transformants so that sufficient transformants would be available for selection of the rare suppressor human cDNA clones.

Third, transformants from step 2 are tested to isolate the few colonies whose phenotype (e.g., viability or cell growth) is not conditioned by the activity of gene #1 (made lethal by the effects of gene #2). In this case the few transformants that are capable of growth have been rescued through the action of a human cDNA that either complements or suppresses gene #1 or gene #2. For example, with cdc9-8$^{ts}$ the conditional nature of the double mutant test cells is conveniently determined by assaying cell viability as a function of temperature. The rad9,cdc9-8 cells have a phenotype of rapid death at the restrictive temperature and less than 1 in 1000 of the human cDNA transformants survived the shift from the permissive temperature (23° C.) to the restrictive temperature (30° C.). "Suppression" of the double mutant yeast test cell phenotype (e.g., lack of growth and particularly lethality in this example) is intended to mean that the subject human checkpoint DNA increases expression of the phenotype (e.g., viability) of the rad9,cdc9-8ts double mutant without complementing either the rad9 gene or the cdc9-8 gene, with "complementation" requiring genotypic homology in order to rescue the phenotype.

Fourth, clones isolated under restrictive conditions are considered to be candidate clones for human checkpoint DNAs. Candidate clones are subjected to further phenotypic and nucleotide sequencing analysis to confirm their identity as human checkpoint clones. Three common methods (illustrated in the Examples, below) can be used to distinguish complementing cDNA clones from clones that exert their effects in the double mutant test cells via suppression:

First, cell viability of transformants may be compared with that of double mutant test cells, vector-transformed control cells, and double mutant test cells transformed by the native (wild-type) gene. The comparisons are conducted under different restrictive conditions (e.g., at different temperatures, such as 37° C., 34° C., or 30° C. for rad9, cdc9-8 cells). In the illustrative examples presented below, when complementing huCDC34 DNA (or the yeast MEC-1 gene) was introduced into a cdc34 cell (or mec-1 cell) the mutant acquired the growth characteristics of the native wild-type CDC34 or MEC-1 transformed cells. In contrast, human cDNAs exerting their effects on the double mutant test cells through suppression, rather than complementation, can exhibit distinctive differences in these comparative tests.

Second, growth rates of human transformants may be compared at different restrictive conditions with growth rates of vector-transformed control cells, and double mutant test cells transformed by the native gene. In this case the homolog should theoretically provide greater phenotypic expression than the suppressor cDNA; however, those skilled in the art will recognize that phenotypic expression of genes can be undependable.

Third, confirmation that a human cDNA acts by suppression, rather than complementation, is provided by sequencing the cDNA in the screened transformant (i.e., in the plasmid DNA from the transformant) and determining that the cDNA does not have a nucleotide sequence homologous with either gene #1 or gene #2. In all cases, complementing human cDNA clones are those that have a nucleotide sequence more than 35% and preferably more than 50% homologous with gene #1 (e.g., cdc9-8) or gene #2 (e.g., rad9 or mec-1). The three human checkpoint genes isolated are capable of correcting the deleterious effects of a mutant yeast checkpoint gene. While all three clones could correct the defect either by supplying the missing gene product (e.g., complementing with a homologous human gene product), or by substituting the missing yeast mutant checkpoint function with a different phenotypically compensating function (e.g., suppression), only the latter suppression has been observed. All three of the human cDNA clones isolated acted by suppression, and not complementation: i.e., clone #1, huCDC34 (FIG. 1), suppressed the defect in mec1,cdc9-8; clone #2, huRAD9$_{compA}$ (FIG. 2), suppressed the defect in rad9,cdc9-8 and mec1,cdc9-8 (and is not homologous to RAD9); and clone #3, huRAD9$_{compB}$ (FIG. 3), suppressed the defect in mec1,cdc9-8 (and is not homologous to MEC-1).

Pursuant to the present disclosure, novel checkpoints for DNA repair may be identified through a variety of methods commonly known and used in the art. Similarly, methods are available for selecting novel checkpoint mutants.

DNA repair can result from DNA strand breaks induced by a variety of treatments, e.g., irradiation treatment with chemical agents or errors during DNA replication. Thus, DNA replication mutants are also useful (in place of DNA repair mutants) as sources of cells for constructing the subject double mutant test cells. Representative examples of DNA replication mutants include cdc2, cdc17, and cdc13. Other examples are described in Weinert et al., *Genetics* 134: 63–80, 1993.

The rad9,cdc9 and mec-1,cdc8-9 cells are also useful for identifying and isolating other novel human checkpoint genes, e.g., "huX", "huY", and "huZ", that suppress mutant checkpoint functions. These novel human checkpoint genes are, in turn, used to clone mouse genes "moX", "moY", and "moZ" from which mutant genes "mo$^x$", "mo$^y$", and "mo$^z$" may be constructed (e.g., by site-directed mutagenesis and screening for a defective "mo$^x$", "mo$^y$", and "mo$^z$" checkpoint function in the assay with the rad9,cdc9 or mec-1,cdc 9 cells). The mutant DNAs are in turn useful for constructing mutant murine cell lines (i.e., defective in a checkpoint function) in which DNA strand breakage can be induced, e.g., by radiation or drugs. The latter murine cells with DNA damage and a mutant checkpoint gene are useful for screening to identify novel human compensatory genes, e.g., "huA", "huB", and "huC". These genes may include human homologs of the native moX, moY, or moZ genes, and/or nonhomologous human genes that suppress moX, moY, or moZ without supplying the missing gene product per se. Those skilled in the art will recognize that this process of the invention is useful for identifying natural inhibitors, cofactors, accessory proteins, and dominant negative and positive regulatory genes affecting expression (e.g., genes that encode enzyme inhibitors of X, Y, or Z, dominant negative or positive transcriptional regulators, and accessory proteins, such as cyclins, that modify the function of a checkpoint gene product in the cell cycle). It is considered highly likely that novel tumor suppressor genes (e.g., similar to Rb, the retinoblastoma gene) will be included in the latter group of genes.

The subject human checkpoint DNAs that are isolated through the practice of the methods of the invention are useful in constructing stable test cell lines of yeast, *E. coli*, and mammalian cells that have the subject checkpoint DNAs stably integrated in their genomes. The latter test cells may be used for screening chemicals, candidate drugs, radiation, etc., for their effects on checkpoint gene expression. The subject human checkpoint genes are also useful for altering sensitivity of a cell to radiation- or drug-induced DNA damage. Increasing sensitivity of tumor cells to chemotherapeutic drugs and radiation may be desirable, i.e., to increase the lethality of low-dose radiation or a therapeutic drug. Conversely, decreasing sensitivity of patient bone marrow cells to the drugs or radiation may be highly advantageous, and the effect may be obtained by modifying the activity of a checkpoint gene product. For example, overexpression of a native (i.e., genetic wild-type; nonmutant) checkpoint gene in a cell may increase cellular resistance to DNA damage. In this case, the increased resistance may be achieved by introducing additional copies of the subject genes into a cell. While not wishing to be limited by any particular mechanism, overexpression of the subject checkpoint may confer increased resistance to DNA strand-breaking drugs, by enhancing cellular functions for: surveillance to determine if DNA is broken (i.e., a noncheckpoint gene); stopping or delaying mitosis so that DNA can be repaired (i.e., a checkpoint gene); and promoting DNA repair mechanisms (i.e., a noncheckpoint gene). Methods are provided herein for experimentally discriminating among these three alternatives.

In another illustrative example, decreasing expression of a human checkpoint gene in a cell (e.g., by introducing antisense embodiments of a checkpoint gene into the cell, or by introducing dominant negative modulators) may increase radiation sensitivity of the cell.

In another illustrative example, overexpression of a checkpoint gene in a malignant cell may be used to uncouple the downstream uncontrolled growth induced by an oncogene- or growth factor-mediated signal transduction pathway. Over-expression of a human checkpoint gene in a cell may be accomplished using drugs that activate the promoter of the checkpoint gene, or by using gene therapy viral vectors to introduce and alter expression of the human checkpoint gene in the target cell.

The invention also provides for diagnostic screening of cells, such as in tumor biopsy samples, to determine the level of checkpoint gene expression and rearrangement as an indicator of sensitivity of the (tumor) cells to DNA damage by radiation or chemotherapeutic drugs. Other uses of the subject checkpoint genes include gene therapy to increase radiation resistance of bone marrow cells (i.e., prior to transplantation into recipients who may need additional radiation or drug therapy; e.g., AIDS patients with malignant lymphoma). Assays are also contemplated for identifying chromosomal rearrangement of human checkpoint genes, e.g., in tumor cells and genetic deficiency diseases. Examples are provided of how FISH (fluorescence in situ hybridization) was used to map the far telomeric region of human chromosome 19p13.3. Since telomeric regions in chromosomes (teleosomes) are subject to frequent rearrangement from incomplete DNA replication and telomerase terminal extension, it is thought highly likely that mapping rearrangements of human checkpoint genes may be useful diagnostically for identifying the underlying cause of gene rearrangements in cancer predisposition syndromes and for identifying targets for gene therapy.

EXAMPLE 1

Cloning of a MEC$_{comp}$ and Identification as CDC34

In order for the cloning scheme to be successful, a cDNA source containing an intact checkpoint mechanism was required. The U118 glioblastoma cell line fulfilled this requirement, as shown by the results of experiments in which the cells were exposed to graded doses of cesium-137 gamma irradiation. Twenty-four hours after exposure of a logarithmically growing culture to 900 cGy, there was a clear accumulation of cells in G2 when compared to unirradiated controls.

A cdc9-8,rad9::HIS3,leu2 strain (9085-8-3) was constructed in order to select for RAD9 genes. rad9::HIS3 signifies a deletion mutant of the RAD9 gene by insertion of the HIS3 gene. This type of mutation has a very low reversion frequency. Phenotypic growth characteristics of double mutant yeast test cells and the single mutant cdc9-8 cells are shown in Tables 1 and 2, below.

TABLE 1

Temperature dependence of growth of mutant strains of S. cerevisiae.

| STRAIN | TEMPERATURE[a] | | |
|---|---|---|---|
| | 23° C. | 30° C. | 34° C. |
| cdc9-8,RAD+ | +++ | ++ | − |
| cdc9-8,rad9 | +++ | − | − |
| CDC+,rad9 | +++ | +++ | +++ |

[a]Log phase liquid cultures grown at 23° C. were diluted and spread onto plates containing rich media, after which the plates were incubated at the indicated temperatures for three days. Growth is scored as +++, large colonies, ++, small colonies, −, no colonies/no growth.

TABLE 2

Temperature dependence of viability of mutant strains of S. cerevisiae.

| STRAIN | TEMPERATURE[a] | | | |
|---|---|---|---|---|
| | 23° C. | 30° C. | 34° C. | 36° C. |
| mec1,cdc9-8 | 100% | <0.01% | ND | ND |
| rad9,cdc9-8 | 100% | <0.1% | ND | ND |
| cdc9-8 | 100% | 100% | 10% | <0.10% |

[a]Percent viable cells after 3–5 days. ND, not determined.

We also obtained a cdc9-8,mec1-A401,leu2 strain (171-10-2) for selection of MEC1 function. No deletion mutant of mec1 was available. The mec1-A401 allele is a radiation-sensitive mec1 allele that has effects similar to the rad9 mutation on the growth of cdc9-8.

The experimental design was as follows. Log phase cultures of the yeast test strains grown at 23° C. were made competent for transformation by the lithium acetate method. Transformation of the strains was performed with the ADANS vector (control) or DNA from the pooled cDNA library. The transformed yeast was spread on plates with leucine-deficient media at 23° C. for 20–24 hours to select for those yeast which had taken up the DNA and allow expression of the cDNA insert. The plates were then transferred to a 30° C. incubator and allowed to grow for five to seven days.

Control experiments in which the cdc9-8,rad9::HIS3,leu2 strain was transformed with the ADANS vector alone showed that only one in ten thousand LEU+ cells would grow at 30° C. under these conditions. The background rate (number of cells growing at 30° C. after transformation with the vector alone) for the cdc9-8,mec1-A401,leu2 strain was one in five to ten thousand and somewhat more variable.

A series of transformations of the cDNA library into the two test strains were performed. Any colonies that grew within five to seven days at 30° C. were streaked out for single colonies, and plasmid dependence for growth at 30° C. was determined. This was accomplished by growing the transformants nonselectively in liquid culture (rich media at 23° C.) and then plating on rich media to allow spontaneous loss of the plasmid. Replica plating to minus leucine or rich plates at 30° C. demonstrated whether growth at 30° C. required the presence of the plasmid. Plasmid dependence was confirmed by isolating the plasmid from the yeast transformant, amplifying the DNA in E. coli, and retransforming the original yeast strains and selecting for growth at 30° C.

After screening approximately two hundred thousand cDNAs for complementation of the mec1,cdc9-8 strain, there were 15 primary transformants, only one of which (named 171tx6) showed plasmid dependence for growth at 30° C. Transformation of the cdc9-8,mec1 strain with 171tx6 DNA revealed that approximately 20–30% of the LEU+ colonies grew at 30° C. compared to a control of less than 0.1%. Transformation with a plasmid containing the authentic yeast MEC1 gene under its own promoter resulted in nearly 100% viability at 30° C. However, the selection scheme could potentially select for human DNA ligase cDNAs, which can complement the mutant yeast DNA ligase. Transformation of a cdc9-8,MEC+ strain did not show any evidence that 171tx6 was complementing the ligase mutation directly (e.g., the maximum permissive temperature was still 30° C.). The growth phenotype of transformants having the 171tx6 DNA, or subclone 171tx61 DNA, are shown in Table 3 below.

TABLE 3

Suppression of a lethal growth phenotype in S. cerevisiae mutants by transformation with huCDC34 (171tx61).

| CELLS | VECTOR | TEMPERATURE[a] | |
|---|---|---|---|
| | | 23° C. | 30° C. |
| mec1,cdc9-8 | control ADANS | + | − |
| | 171tx6 | + | + |
| | 171tx61 | + | + |
| rad9,cdc9-8 | control ADANS | + | − |
| | 171tx61 | + | + |

[a]Growth, determined by colony assays similar to those presented in Table 1; +, growth; −, no growth.

Due to the manner in which the library was constructed, there were three unique cDNA inserts in the 171tx6 clone. Each was subcloned into the ADANS vector, and only one of these cDNAs was active (171tx61) in the complementation assay. Sequence analysis of the 171tx61 cDNA insert revealed a striking homology between 171tx61 and the yeast cell cycle gene CDC34, with a 50% perfect conservation of amino acids in the 110 amino acid conserved core. A lesser homology to other members of this family of proteins was also observed. This family of proteins encodes the ubiquitin ligase E2 enzymes that are an integral part of the complex that targets ubiquitin to cellular proteins. Other members of the E2 family include RAD6, UBC4, and UBC5. 171tx61 did not show any homology to the yeast mec1 gene. Southern blot analysis with this cDNA as probe revealed substantial cross-species hybridization between human, mouse, chicken and Drosophila DNA, and a pattern suggesting only a single gene (data not shown). In addition, a single 1.8 kb transcript has been detected in several cell lines by Northern blot analysis (data not shown).

Interestingly, the human 171tx61 nucleotide sequence terminates prior to the carboxy-terminal region of the yeast CDC34 gene and prior to an Asp rich region that was thought essential for CDC34 protein and in particular ubiquitin conjugating activity. Since huCDC34 protein appears functional in yeast, the results suggest that the COOH terminus is not requisite for enzymatic activity.

In order to determine if 171tx61 was the human homologue of CDC34, we obtained a cdc34 temperature-sensitive yeast strain from Breck Byers. Transformation of this strain with 171tx61 revealed almost 100% complementation of the cdc34 mutation, allowing rapid growth of the temperature-sensitive strain at 37° C. See Table 4.

TABLE 4

Complementation of growth of an of S. cerevisiae cdc34 mutant by transformation with huCDC34

| VECTOR | TEMPERATURE[a] | |
|---|---|---|
| | 30° C. | 37° C. |
| control ADANS | + | − |
| 171tx61 | + | + |

[a]Growth, determined by colony assays similar to those presented in Table 1; +, growth; −, no growth.

Complementation of the cdc34 mutation by the 171tx61 cDNA appeared specific for the CDC34 member of the E2 family, as it did not complement the radiation sensitivity of a rad6 mutant strain. Thus, we consider 171tx61 the human homolog of cdc34 and renamed it huCDC34. Complementation of the mec1-A401 mutation was unique to the human CDC34. Expression of the S. cerevisiae CDC34 gene from the ADANS expression vector showed no complementation or suppression of the lethal phenotype in mec1,cdc9-8 (e.g., growth at 30° C.) (data not shown). Ubiquitin conjugating enzymes were not previously thought to function at checkpoints in the G2 phase of the cell cycle.

The mechanisms by which overexpression of the huCDC34 protein results in the complementation of the mec1-A401,cdc9 strain are presently under investigation. A current hypothesis is that overexpression of CDC34 results in a slowing of the normal cell cycle, in particular a lengthening of late S or G2 phase(s) allowing the mutant cdc9 more time to function. Consistent with this hypothesis, the doubling time of the mec1 strain containing the ADANS control vector was 120 minutes, while that strain containing the huCDC34 had a doubling time of 160 minutes. (Comparing doubling times is a method by which certain complementing and suppressing human cDNA clones may be distinguished from one another.)

The sequence of the 1374 basepair tx61 cDNA encoded one long open reading frame of 298 amino acids, which was in frame with the first 14 amino acids of the ADH gene resulting in a fusion protein. Surprisingly, analysis of the translated sequence with the PATMAT homology program revealed a high degree of homology to the S. cerevisiae cell cycle gene CDC34 and several other members of the ubiquitin ligase (UBC) family. There is 50% perfect homology between tx6l and CDC34 in the 108 amino acids flanking the active site cysteine. Multiple alignment analysis of tx61 with CDC34 (UBC3), RAD6 (UBC2), and UBCS revealed that the human tx61 is most closely related to yeast CDC34, and yeast CDC34 is more related to tx61, than the other yeast members of the family. For example, there is an insertion in the CDC34 (12 amino acids) and tx6l (13 amino acids) proteins between the two highly conserved regions surrounding the active site, which is not found in most other members of the family. In addition, they share a highly acidic carboxy terminal end that distinguishes a subgroup of the UBC genes (CDC34 and RAD6) from the other UBC genes. The wheat germ UBC7 gene is also very homologous to tx61 but does not have the acidic carboxy terminal end. Interestingly, the human 171tx61 nucleotide sequence terminates prior to the carboxy-terminal region of the yeast CDC34 gene, and prior to an Asp rich region that was thought essential for CDC34 protein and in particular ubiquitin conjugase activity. Since huCDC34 protein appears functional in yeast the results suggest that the COOH terminus of huCDC34 protein is not requisite for ubiquitin conjugase enzymatic activity.

Southern blot analysis using the human CDC34 cDNA as a probe revealed specific hybridization to one or a few bands in human, mouse, and hamster genomic DNA. A polymorphic pattern was observed with this probe in different normal human genomic samples confirming utility as an RFLP chromosomal marker. Hybridization to chicken genomic DNA was also detected, as was weak hybridization to Drosophila melanogaster DNA, but not to any lower species including S. cerevisiae.

Northern blot analysis of several human cancer cell lines reveals hybridization to a unique band of approximately 1.4 kb in length, suggesting that the tx61 cDNA was nearly full length. Poly A+ RNA from two human neuroblastoma cell lines (SK-M-KCNR and SK-N-AS) and multiple hematopoeitic tumor cell lines was assayed. Human CDC34 was expressed in all of these lines as expected for a cell cycle regulatory gene, and quantitation revealed only two to fourfold differences among these lines. In addition, RNA from SMS-KCNR cells, which have differentiated and exited the cell cycle after treatment with retinoic acid, showed no decrease in the expression level of huCDC34 mRNA. SK-N-AS cells that are resistant to retinoic acid also show no decrease in huCDC34 mRNA expression after treatment with retinoic acid. Thus, no evidence for decreased transcription of human CDC34 was found when cells were not cycling.

To further characterize the human CDC34 gene, two overlapping genomic cosmid DNA clones (34cos2 and 34cos4) were isolated that are homologous to the human CDC34 CDNA. The cosmid clones were identified by screening a human placental cosmid library. That these cosmids represented the human CDC34 gene, and not some other gene, was confirmed by comparison of the restriction map of the cosmids and genomic DNA when probed with the CDC34 cDNA.

Hybridization by fluorescence in situ hybridization (FISH) with cosmid 34cos2 showed positive results in 41 of 42 metaphase human lymphocyte cells examined. The FISH signals were localized to chromosomes 19 at band p13.3 and in the telomeric end of band 19p13.3. One metaphase cell had signals on only one chromosome 19. Hybridization with cosmid 34cos4 demonstrated signals on both chromosome 19 homologs in 38 of 40 metaphase cells examined, and on only one chromosome 19 homolog in the other 2 cells. The signals from 34cos4 were also located at the very telomeric end of band 19p13.3 and were indistinguishable from the signals generated from hybridization with 34cos2. There was no significant hybridization to any other human chromosomes.

An independent confirmation of this chromosomal localization was obtained by Southern blot analysis of human hamster somatic cell hybrids containing a single normal human chromosome 19. Hybridization with the human CDC34 cDNA revealed hybridization to the same bands in total human genomic DNA and the chromosome 19 hybrid.

Human CDC34 cDNA has also been used to map the location of the homologous gene in the mouse genome: the location is at chromosome 11D by RFLP analysis of interspecific crosses using four different polymorphisms. This region of mouse 11 is highly syntenic to human chromosome 17q. Given these results, the genomic DNA from a human chromosome 17 mouse somatic cell hybrid was also probed with the human CDC34 cDNA, but no hybridization signal was detected (other than that expected for the mouse genome).

The finding that the human homolog of the yeast protein CDC34 complements a mec1 mutation was surprising. The cdc34 mutation causes cells to arrest at the G1/S boundary after the activity of START. The arrested cells accumulate multiple buds but do not initiate DNA synthesis. There has been no reason to suspect that CDC34 plays a role in any phase of the cell cycle other than G1, and, given the essential nature of CDC34 at G1/S, there was no reason to look for an effect of a cdc34 mutation on a G2 checkpoint.

One question from the above results was whether the yeast CDC34 protein (rather than human) might have a compensating effect on the mec1,cdc9-8 strain similar to that of huCDC34. Initial attempts at compensation used a plasmid containing the *S. cerevisiae* CDC34 gene under its own promoter showed no compensatory effect on the double mutant cells. To overexpress the yeast CDC34 gene in a manner similar to the experiment with the huCDC34, a fragment of the yeast CDC34 gene was subcloned that contained the entire open reading frame downstream from an ADH promoter in an ADANS vector. This construct, scCDC34, efficiently complemented the cdc34$^{ts}$ mutation but very surprisingly had no effect on the mec1,cdc9 strain for growth at 30° C. in numerous experiments.

Further studies were conducted to characterize the interaction of the huCDC34 DNA with the phenotype expressed by the mec1 mutant. One model considered that the effect of overexpressing huCDC34 in the mec1,cdc9 strain might be nonspecific, e.g., a slowing of the cell cycle by huCDC34 that allows enough time for the mutant DNA ligase to work. To address this hypothesis, the doubling times of logarithmically growing cultures of mec1 strains were measured at 30° C. in the presence of plasmids. The doubling time was prolonged approximately 30%, i.e., from 2 hours with the control vector to 2 hours and 20 minutes with the huCDC34, but FACS analysis of propidium iodide stained yeast cells did not show significant differences in DNA content between the control vector transformed and huCDC34 transformed cells. Thus, it was reasoned that if slowing the cell cycle by only 20 minutes was sufficient to suppress for the mec1, cdc9-8 defects, then one might expect that an even less noticeable effect would be seen if cells were arrested for a longer period of time. As a test model, it was found that raising the temperature of a mec1,cdc9-8 strain to 37° C. resulted in rapid lethality with less than 0.1% viability after 6 hours, while a MEC+,cdc9-8 strain showed much slower loss of viability, i.e., 5% loss in viability after 6 hours. When huCDC34 transformants were tested in this assay system, it was found, unexpectedly, that huCDC34 partially restored viability to the mutant mec-1,cdc9-8 background, even after 6 hours at elevated temperature. Thus, a nonspecific slowing did not appear responsible for the compensatory effects of huCDC34.

Interestingly, expression of the huCDC34 gene does not suppress for the other two phenotypes of a mec1 strain, namely, radiation sensitivity and hydroxyurea sensitivity. Comparison of transformants, double mutants, and DNA-repair mutants for effects of drugs or irradiation on the cell cycle is another method by which complementing human cDNA clones may be distinguished from compensating cDNA clones by virtue of phenotypic similarities and differences, respectively. The survival curves are superimposable for a mec1 strain transformed with a control vector or the huCDC34 DNA and then exposed to graded doses of radiation. In contrast, a mec1 strain carrying a MEC1 plasmid or a wild type strain with the control vector are radiation resistant. Similarly, transformation with huCDC34 DNA had no effect on hydroxyurea sensitivity (mec1 strains are unique among the known G2 checkpoint mutations in their exquisite hydroxyurea sensitivity).

The following results support the concept that the effect of the huCDC34 gene on the mec1 phenotype is specific: huCDC34 DNA does not suppress for a rad9,cdc9-8 strain at 30° C. or a MEC+,cdc9-8 strain at 34° C.; and, transformation with the huCDC34 DNA decreases the lethality of a mec1,cdc9-8 strain even after 6 hours at the nonpermissive temperature. Surprisingly, the yeast CDC34 gene does not have the effects that huCDC34 has on the mec1 strain. Even when overexpressed there is no effect of yeast CDC34 on the mec1,cdc9 8 strain at 30° C. By way of explanation, perhaps the huCDC34 protein is less specific than its yeast counterpart and it is able to ubiquitinate a cyclin during the G2 phase of the cell cycle. In this manner the huCDC34 protein may delay the cell cycle and suppress the lethal phenotype in the mec1,cdc9-8 cells.

It was also found that although the huCDC34 gene had a significant effect on the cdc9 mutant (defective in DNA ligase), it had no effect on radiation sensitivity or hydroxyurea sensitivity of a mec1 strain. Two additional human checkpoint cDNAs were isolated (RAD9$_{compA}$ and RAD9$_{compB}$); see Example 2 below. It is proposed that yeast possesses separate mechanisms for creating the cdc9 checkpoint and the radiation checkpoint, although both pathways must utilize MEC1 and RAD9.

The G1 target(s) of yeast CDC34 is unknown. A possible S or G2 target of human CDC34 is one of the B-type cyclins, CLB1-6, of *S. cerevisiae* that contains a ubiquitin targeting signal. Several of these cyclins have been found to be expressed at a high level in both the S and G2 phases of the cell cycle.

The data maps the location of CDC34 to the far telomeric region of the short arm of human chromosome 19. The telomeric location of this cell cycle gene in humans is intriguing given the role of telomeric shortening in cellular senescence. A recent model of senescence proposes that repression of essential genes found near the telomere occurs by a change in chromatin structure as telomeres shorten. It is instructive to determine how close to the 19p telomere the human CDC34 is located, as well as the expression of this gene in cells that are nearing senescence.

In contrast to the human mapping data, mapping of this gene in the mouse places it in a nontelomeric position on chromosome 11D. This region maps to a long region of synteny on human chromosome 17q, but we do not find any evidence for a CDC34 homolog on human chromosome 17; thus CDC34 defines a new region of homology between mouse chromosome 11 and human chromosome 19.

This is the first human homolog identified of the group of genes (CDC34, CDC4, and CDC53) required for the late G1 to S transition in budding yeast. Absence of any one of these functions results in cell cycle arrest before DNA synthesis is initiated and the formation of multiple pseudobuds. Identification of the components of the G1 to S transition in human cells will be essential for defining how the initiation of DNA synthesis is regulated and the mechanisms that control the G1/S transition after DNA damage.

EXAMPLE 2

Isolation of Human Genes huRAD9$_{compA}$ and huRAD9$_{compB}$

A fundamental aspect of radiation resistance is the capacity of cells to detect DNA damage and delay entry into mitosis for a time sufficient to repair the damage. Failure of this mechanism results in unrepaired DNA damage and cell death during mitosis. Both the RAD9 and MEC-1 genes play an integral role in the DNA repair surveillance mechanism, and isolation of human CDC34 as a compensatory cDNA clone for the MEC1 yeast gene is described above. The experiments described below were designed to identify and investigate human cDNA clones complementing or compensating for the function of the yeast RAD9 gene in mediating radiation resistance.

Human RAD9$_{compA}$:

In an attempt to clone compensating and complementing RAD9 cDNAs, approximately 300,000 LEU+ human cDNA transformants of the rad9,cdc9-8 strain were screened. Forty-five transformants were identified that grew at 30° C. These forty-five transformants were evaluated to determine the plasmid dependence of their growth, as described in the materials and methods below. One transformant (named 83tx42) was identified that showed plasmid dependence for growth at 30° C. When the plasmid was isolated and retransformed into the rad9,cdc9-8,leu2 strain, approximately 10% of the colonies grew at 30° C. compared to less than 0.1% of the control transfectants. Interestingly, when 83tx42 was transformed into the mec1,cdc9-8 strain, the cells showed similar levels of growth at 30° C. as 83tx42 in a rad9,cdc9-8 strain. Conversely, 83tx42 had no effect on the cdc9-8,RAD+,MEC+ strain, suggesting that it did not directly complement the ligase mutation. 83tx42 contains an approximately 2 kb cDNA insert. Since the cDNA suppressed for the defects of rad9 in the cdc9-8,rad9 strain it was termed huRAD9$_{compA}$. The nucleotide sequence of huRAD9$_{compA}$ is shown in FIG. 2.

Human RAD9$_{compB}$:

In an attempt to identify additional clones compensating and complementing cDNAs, approximately 100,000 LEU+ human cDNA transformants of the mec, cdc9-8 strain were screened. Twenty transformants were identified that grew at 30° C. These transformants were evaluated to determine the plasmid dependence of their growth (as described in the materials and methods below). One transformant (named 171tx23) was identified that showed plasmid dependence for growth at 30° C. When the plasmid was isolated and retransformed into the mec1,cdc9-8,leu2 strain, approximately 20% of the colonies grew at 30° C. compared to less than 0.1% of the control transfectants. Interestingly, when 171tx23 was transformed into the cdc9-8 strain, the cells showed similar levels of growth at 30° C. as in a mec1, cdc9-8 strain (Table 5, below). Conversely, 171tx23 had no effect on the cdc9 strain, suggesting that it did not directly complement the ligase mutation. 117tx23 contains an approximately 1.6 kb cDNA insert.

TABLE 5

Suppression of a lethal growth phenotype in *S. cerevisiae* mutants by transformation with huCDC$_{compB}$ (171tx23).

| CELLS | VECTOR | TEMPERATURE[a] 23° C. | 30° C. |
|---|---|---|---|
| mec1,cdc9-8 | control ADANS | + | − |
| | tx23 | + | + |
| | MEC-1 | + | + |
| rad9,cdc9-8 | control ADANS | + | − |
| | tx23 | + | + |
| | RAD9 | + | + |

[a]Growth, determined by colony assays similar to those presented in Table 1; +, growth; −, no growth.

The nucleotide sequence of 117tx23 is shown in FIG. 3. Clone #3 cDNA confers radiation resistance upon both the mec-1 and rad9 transformants. For this experiment, the mec1 or rad9,117tx23 transformants were exposed to 20 Grey or 60 Grey of X-irradiation; ADANS vector transformed mec1 or rad9 cells were used as controls. The clone #3 117tx23 transformed mec-1 or rad9 cells showed 20-fold greater survival after three days of culture.

EXAMPLE 3

Regulation of Human Cell Cycle Genes

Antibodies to the huCDC34 fusion protein were prepared, and antibodies to RAD9$_{compA}$ may be prepared by a similar method. To produce antibodies, the respective cDNAs were subcloned into prokaryotic GST expression vectors designed to produce large quantities of the protein in *E. coli*. The recombinant fusion proteins were used for immunization of rabbits for production of polyclonal antisera. Rabbits showing a positive ELISA response to the fusion protein were boosted with thrombin-treated fusion protein. (The GST region of the fusion protein is thrombin sensitive.) Anti-huCDC34 had an endpoint ELISA titer of $10^4$. Antibodies are useful in assays evaluating the level of expression of the R4D9 and MEC-1 genes at the protein level. For instance, antisera to huCDC34 and huRAD9$_{compA}$ is useful in Western blot and immunoprecipitation analyses with protein extracts of mammalian cell lines. Such experiments provide information regarding expression of these genes and how post-translational modification, e.g., phosphorylation and glycosylation, may alter expression. In particular, expression assays may be performed in cells before and after irradiation to monitor for changes in the levels of proteins and how changes in checkpoint gene expression correlate with radiation sensitivity or resistance of cells.

To address whether increased expression (overexpression) of a checkpoint gene in a mammalian cell may increase the radiation resistance of the cell, huRAD9$_{compB}$ cDNA was inserted into the pLXSN retroviral vector. The huRAD9$_{compB}$ DNA is under the control of the MuLV LTR promoter. The vector is useful for monitoring changes in G2 arrest and radiation sensitivity of retroviral vector transduced mammalian cells, as compared to that of control pLXN vector transduced control cells.

To show that huRAD9$_{compB}$ plays an important role in radiation sensitivity, hurad9$_{compB}$ mutant mammalian cells are constructed and the mutation is correlated with increased sensitivity of the cells to graded doses of radiation.

Negative selection, i.e., for down-regulation or negative-regulators of RAD9, huCDC34, huRAD9$_{compA}$, or huRAD9$_{compB}$ function, is accomplished in a yeast screening assay. For example, cdc13-1 is a temperature-sensitive *S. cerevisiae* cell cycle mutant that causes arrest late in G2 if cells with the mutant genotype are shifted to the restrictive temperature. The maximum permissive temperature for cdc13, i.e., the temperature that still allows colonies to form in a yeast with normal RAD9 function, is 25° C. However, in cdc13 strains in which RAD9 is also deleted the maximum restrictive temperature increases to 28° C. (Presumably, at 28° C. RAD9 acts on problems due to the cdc13 mutation and arrests the cells in G2.) In the absence of RAD9, the cells continue to cycle and the cdc13 damage does not make the cells nonviable. Above 28° C., the cdc13 RAD+ or rad9 strains do not grow. The result of this effect is that one can select against RAD9 function by growing a cdc13,RAD+strain at 28° C. and isolating colonies that can grow at 28° C. Although the difference between the restrictive and permissive temperatures is only three degrees, it has been found that less than one per thousand cdc13,RAD+ cells will grow at 28° C., as contrasted with growth of almost 100% of cdc13,rad9 cells. Using such negative selection, two methods are possible for isolating dominant cDNAs that negatively regulate RAD9. The first is to randomly mutate the plasmid containing the yeast RAD9 cDNA. The pool of mutagenized plasmids is transformed into the cdc13, leu2, RAD+ strain and selected for growth at 28° C. The plasmid from any colony that grows at 28° C. is isolated and retested in the same assay. Sequence analysis of active clones is performed to determine what mutation has occurred. The mutant RAD9 gene is then transfected into wild-type yeast and the changes in radiation sensitivity and G2 arrest determined. The goal is to find a mutant RAD9 that can interfere with the function of a normal RAD9 and increase radiation sensitivity. Dominant negative mutants can act by binding the normal protein and forming nonfunctional heterodimers if the protein is normally a homodimer, or by directly interacting with the normal target of the RAD9 gene.

An alternative approach is to directly mutate a huCDC34, huRAD9$_{compA}$, huRAD9$_{compB}$, or huRAD9 gene and then to transform the cdc13,leu2,RAD+ strain with pooled cDNAs from a library and select for growth at 28° C. This method allows selection of unique clones which, when overexpressed, may interfere with the function of one or more of the four human cDNAs. Similarly, clones isolated in this manner can be sequenced and tested for their effect on radiation resistance and G2 arrest in wild-type yeast.

Any RAD9 or cDNA clone that has a dominant negative effect on radiation sensitivity in yeast may be subcloned into a mammalian expression vector and transfected into cell lines with moderate to high radioresistance, such as HeLa S3 and U118. Stable lines in which the transfected genes are highly expressed may be isolated along with cell lines containing vector controls, and the radiation sensitivity of the cell lines may be determined and compared. Given that deletion of the RAD9 gene in yeasts does not affect viability, it is expected that transfectants will be viable. Changes in cell survival after irradiation and G2 arrest are determined. The goal is to create molecules that actively decrease radiation resistance of tumor cells by interfering with the normal checkpoint function. These molecules represent unique reagents that can decrease radiation resistance in vivo and may have therapeutic efficacy.

Materials and Methods

Assay Strategy: A simple genetic assay was developed for selecting human checkpoint genes by complementation of defined yeast mutations. In addition to radiation sensitivity, the presence of a checkpoint mutation increases the lethality of several temperature-sensitive cell cycle mutations. The presence of either a rad9 or mec1 mutation decreases the maximum permissive temperature (from 30° C. to 25° C.) of a strain with a DNA ligase mutation (cdc9-8). Presumably, the increased lethality of the checkpoint mutation is a consequence of cells with multiple DNA strand breaks entering mitosis. Thus, after transformation with a human cDNA library, selection for growth at 30° C. of a mec1, cdc9-8, or rad9,cdc9-8 strain will allow selection for cDNAs that suppress for or complement the MEC1, RAD9, or CDC9 function.

Human cDNA Library: A human cDNA library was obtained in which the yeast expression vector ADANS contained an ADH promoter and first 14 amino acids of the ADH gene flanking the human cDNA insert and the promoter was followed by a LEU2 selectable marker gene. The source of cDNA was the human glioblastoma U118 cell line, which maintains an intact G2 arrest mechanism after irradiation.

Transformation of cdc9-8,mec-1: Logarithmically growing cultures of a mec, cdc9-8, leu2 strain were transformed with DNA from the cDNA library using the lithium acetate method. The cultures were plated and selected for growth on leucine-deficient media at 30° C. Five days after transformation of the mec1,cdc9-8 strain with the control ADANS vector less than 0.1% of LEU+ transformants formed a colony at 30° C. Transformation with the human tx6 cDNA or its subclone, tx61, resulted in 10–20% viability of LEU+ transformants at 30° C.; for comparison, transformation with the authentic MEC1 gene results in near 100% viability at 30° C.

Yeast and Bacterial Strains: The *S. cerevisiae* strains described in these experiments were congenic with A364a. Sources of the strains are indicated: 171-10-2 (MATα, cdc9-8, mec1-A401, leu2, ura3, ade2 ade3, trp1—T. Weinert), 9085-1-8-3 (MATα, cdc9-8, rad9::HIS3, leu2, ura3, trp1), 9085-1-10-4 (MATα, cdc9-8, leu2, his3), SJ1098-3d (MATα, cdc34-2, leu2-3, ura3, trp1—B. Byers). All bacterial transformations were performed in the SURE strain (Stratagene, La Jolla, Calif.).

DNAs: A human placental cosmid library in pWE15 was obtained. The S. c. CDC34 plasmid was constructed by subcloning a PCR amplified 1.0 kb piece of the CDC34 gene downstream of the HindIII site in the ADANS plasmid. The MEC1 and RAD9 plasmids were provided by T. Weinert. Somatic cell hybrid DNAs were obtained from the Coriell Cell Repository (Camden, N.J.). Both the human chromosome 19 hybrid (GM1Q449, #5HL9-4) and the human chromosome 17 hybrid (GM10498, #MN-22.6) contain greater than 90% of cells with a single human chromosome, and the chromosome 19 hybrid was negative by Southern blot analysis for a known chromosome 17 marker. The sequence of both strands of the cDNA insert was determined by dideoxy sequencing using Sequenase 2.0 (US Biochemical, Cleveland, Ohio).

Yeast Transformation: Logarithmic cultures of the indicated strain were transformed according to a modification of the method of Schiestl and Gietz (6), in which the DNA and 50% PEG solution are added directly to the yeast in lithium acetate without any preincubation. Plasmid DNA from yeast was extracted by glass bead disruption and transformed into *E. coli* by electroporation (Bio Rad, Hercules, Calif.). Plasmid DNA from a single colony was retransformed into the parent yeast strain to check for plasmid dependence.

Northern and Southern Analysis: Total genomic DNA was restricted according to the manufacturer's recommendations and separated on 0.7% agarose gels with TBE buffer. Transfer to GeneScreen Plus and hybridization was performed according to manufacturer's recommendations (NEN, Boston, Mass.). The most stringent wash was 0.2xSSC plus 1% SDS at 65° C. The human CDC34 probe was a 784 bp PCR product labeled by random oligonucleotide-primed synthesis (Boehringer Mannheim, Indianapolis, Ind.). The oligonucleotides used to generate the PCR product are 5'-AACACCTACTACGAGGGCGGC-3' and 5'-GCCCGTCCACCGAGCCCCGAG-3'. Poly A+ RNA, a gift of Carol Thiele, was separated on 1% agarose, formaldehyde gels, and also transferred to GeneScreen Plus membrane. The filter was sequentially hybridized with the human CDC34 PCR probe and a rat GADPH cDNA. Quantitation of the hybridization signal on the Northern blot was performed by direct phosphorimaging of the hybridized filter (Molecular Dynamics, Sunnyvale, Calif.).

Fluorescent In Situ Hybridization: As described previously (7), posthybridization washes were performed at 42° C. and 50° C. for 34cos2 and 34cos4, respectively.

EXAMPLE 4

Description for Yeast Checkpoint Control Genes

We have cloned and sequenced five new genes that are necessary for the G2/M checkpoint control. See Tables 6–9 and FIGS. 4A–4B, 5A–5B, 6A–6E, 7A–7B and 8A–8C. These genes, RAD17, RAD24, MEC1, MEC2, and MEC3 are responsible for recognizing if the cell has suffered DNA damage in the form of radiation or chemical damage or if the cell has failed to complete DNA replication because of chemical inhibition or intrinsic error. Upon recognizing damage or failure these genes are responsible for inhibiting mitosis. The purpose of this checkpoint control is that it preserves the viability of the cell and the integrity of the genome by providing the cell time to repair these insults prior to undertaking mitosis. These genes are potentially useful in developing cancer chemotherapeutic agents, cancer chemoprevention agents, and environmental toxicology tests. The genes can be used to produce proteins that can then be screened for chemical agents that would interfere with checkpoint controls. Such tests could be carried out in vitro or in vivo. Also the cloned genes can be used to develop yeast strains in which these genes are deleted and such yeast strains can then be used to find the homologous human genes (according to the procedures described above). The deleted yeast strains can also be used as hosts for the homologous human genes in which agents that inhibit the human gene products are being sought.

The ultimate goal of detecting agents that interfere with these checkpoint genes is as follows. In cancer chemotherapy such inhibitors would be expected to enormously enhance the efficacy of the commonly used chemotherapeutic agents and permit their use at much lower and less toxic doses. In cancer chemoprevention, agents that enhance a checkpoint control function could be given to patients in order to slow or prevent the evolution of tumor cells to more malignant forms. In environmental toxicology, one would screen for agents that inhibit checkpoint controls because such agents would be potentially carcinogenic.

Those skilled in the art will recognize that this process of the invention is useful for identifying natural inhibitors, cofactors, accessory proteins, and dominant negative and positive regulatory genes affecting expression (e.g. genes that encode protein inhibitors of checkpoint genes, dominant negative or positive transcriptional regulators, and accessory proteins such as cyclins that modify the function of a checkpoint gene product).

TABLE 6

RAD17

The nucleic acid sequence of rad17 SEQ ID NO:1:

AGCAGGAATTGGTAACGCCAGGTTTTCCCGATCAGACGTTGTAAAACAGGCCA
GTGAATTGTAATACGACTCACTATAGGGCGAATTGGGTACCGGGCCCCCCCTC
GAGGTCGACGGTATCGATAAGCTTGATATCGAATTCCTGCAGCCCCTAAAATGC
CATTTGTTCAAATGGATCAAATTTCCCAATTTTATCATTTTCGAGAAAATATGGT
GTGCCTGAAGATGAACTGTTTCAGACAATTGATCTTTTTGAGAAAAAGGATCCT
GCCATTGTTTTCCAAACGTTGAAGTCACTATCTCGTTACGCCAACAAAAAACATA
CAGATAGATTTCCAGTTCTAGGACCACAACTGTCAACAAAGAAGCCAAGACCCC
CGGTTAAGTCTAAACCAAAACATCTACAAGATGGTACTGGATGGAGCACTTTTG
AATACGGTTATATGAAAGGTGCATCTCAGGCTACTGAAGGAGTGGTGTTAGGA
CAACGGAGAGATATAGTTTAGAGAATTATTATTAACACTTTCTCTGGCAGAAATT
GATAAATAAACATTTAAGAACCCTATATACGCAACCAAAGTTCCTTTGATATATT
TTAGTTTTCCATCAAAGTTTTCCTACATAAACACTAAGGTGGCTAGAGACGCGT
AACAAAAGTTAACGTTACCGGTAAAAATGTGATTATACAAATCAATCTCACAGA
ACGGTGTGGAAACAAAGTAGTTGAAGGATTTCAACTATGCGAATCAACAGTGA
GCTAGCGAACAAGTTTTCTGCCTCAACGGTGCACTTAGAACATATCACAACTGC
TTTAAGTTGTTTAACACCTTTTGGTTCTAAAGACGATGTGCTTATATTCATTGAT
GCTGATGGGCTGTCATTTGTCAGGGAGAATAATCATGTGATAAAAATCCAACTA
CTGTTATCTCGGGAGCTATTTATGTCTTATTCGTATAGAAATGAAACTGAGGATC
ACATGAAACTTTGTGTAAAAATAAATCATATCTTAGATAGCGTTAGCG

The protein sequence of rad17 SEQ ID NO:11:

MRINSELANKFSASTVHLEHITTALSCLTPFGSKDDVLIFIDADGLSFVRENNHVIKI
QLLLSRELFMSYSYRNETEDHMKLCVKINHILDSVSVMNRNSDDIVECTLSYDGHG
SPFVLIFEDSFISERVEYSTYLIKDFDTNGLELDRERISFEAIIKGEALHSALKDLKEIG
CKECYVYAKTEANDENVFALISKSQLGFSKIKLPSNRSILEKLQVFDGDSTTVIDGF
AVIGFFDFTSFDKIRKSTKIASKVLFRMDVHGVLSVNILSQTDDVIITDTTRPSNNRP
GSIRQLQLPKDYPGIVIEVCMLEKESIDEAAQTEIELLMETNELGNRNSFKKSTIRKR
YGTDKGNETSNDNLLQLNGKKIKLPSEEENNKNRESEDEENHCKYPTKDIPIFF

TABLE 7

RAD24

The nucleic acid sequence of rad24 SEQ ID NO:2:

GATCTTTTCCTTTCGCTCTTCAATATTACCATCCTCATTTTCCTCATTTTCTTTCAA
TTGTCTGATGAATATATCAGCAGTTCCAATAATAAGATCATGGGGTATATCATTG
CCTAAAACTTCTGTAACCCACTGCAAAATCTGCTCGTAAGTTTCGACATTTGAG
GGATCCTTTGGATAATAATGTAACCTGAAATCGGAGGAAGAATTCAAAATGGTG
TTATGCTGCTGAATTTTTTTCAATGATGCGCTCTTTCCAGTTTTTTCAACGGCTAC
ATCATTTTCTTTTAGTCCTTTATTAATGTTATTGCACAGGCCCTGTCCCATATCCT
TAGCACTAATTCTACCACTCATGGATTTTGGTTGTGATATTTCCGCATCCCTTTG
AGGATTTTGGCTGGTATTCATAAAGCGTTTATCAACTTTCAACACCTTATTGGAC
ATCTCATCATAACGATAAATTTCTCTAATTTTTTTGGCCTTATCCTTCGTTTCATG
CTCAGTCATTTTTAATAACGAAGGCTCACGGTAAATCTTCCAAAGCAATTACTTA
TATTTACCTTCACCTTATTTTACTCAAGATTATCTCTATTAGTGTATTATTCCTTTA
TAGTAGACATAGCTTTAGTAGCATAAATTTTTAATATTCTCGTAAAGAGCGACAA
TATTCAATATTAGATCGTCAAAGAAGCAAACACGCATTGATATCTGAGAGATCA
TCACAATGCGTTAATAGTACTTGATTCAACACCACTAATTATCAAGTTTGTTCCT
GTCTGAATGATATGGATAGTACGAATTTGAACAAACGGCCCTTATTACAATATA
GTCTCAGTTCATTGGGCTCGCAAATAACAAAATGGAGCTCATCTAGACCGACTT
CGCCAGTTCGTAAGGCGAGAAGCACTGAAAATGACTTTCTTTCCAAGCAAGATA
CGTCTAGTATCCTCCCAAGTATCAACGACGACGGCGGTGAACAGTGGTACGAA
AAGTTCAAGCCCAATTGTTTGGAGCAAGTGGCCA

The protein sequence of rad24 SEQ ID NO:13:

MDSTNLNKRPLLQYSLSSLGSQITKWSSSRPTSPVRKARSTENDFLSKQDTSSILPS
INDDGGEQWYEKFKPNCLEQVAIHKRKLKDVQEALDAMFLPNAKHRILLLSGPSG
CSKSTVIKELSKILVPKYRQNSNGTSFRSTPNEHKVTEFRGDCIVNDLPQMESFSEF
LKGARYLVMSNLSLILIEDLPNVFHIDTRRRFQQLILQWLYSSEPLLPPLVICITECEI
PENDNNYRKFGIDYTFSAETIMNKEILMHPRLKRIKFNPINSTLLKKHLKFICVQN
MKMLKEKNKWNKRQEVIDYIAQETGDIRSAITTLQFWATSSGSLPISTRESTISYFH
AIGKVIHGSHSTNNDNEMINNLFENSNNLLSKEDFKLGILENYNTFNKGEFSISDA
SSIVDCLSECDNMNGLPESNEYGLREVRKTFRNISKQGHNHGTVYFPREWKVRKL
QNSFKVQAEDWLNVSLYKYNAVHSFRNITLEFGYYAPLIRKCQSYKKKYILYYLK
NLPSGSSGPKQTMDKFSDIMKVENGIDVVDRIGGPIEALSVEDGLAPLMDNDSNN
CDHLEDQKKERDRRLRMLIDQYERNVMMANDDLEDEETSFNDDPIVDSDSDNSNN
IGNETFGRSDEDESLCEILSQRQPRKAPVISESLSDSDLEIL

TABLE 8

MEC1

The nucleic acid sequence of mec1 SEQ ID NO:3:

ATAAGCTTACTGACCAAGAAAGAGCACGCGTGTTGGAGTTTCAAGATTCCATTC
ACTATTCTCCGCGGTACTCAGACGATAACTATGAGTACAGGCATGTGATGTTAC
CTAAGGCCATGCTAAAAGTTATCCCATCTGATTACTTCAATTCGGAAGTGGGGA
CCCTGCGTATATTAACAGAAGACGAATGGAGAGGCCTCGGCATCACACAGTCT
TTGGGGTGGGAACATTATGAATGCCATGCGCCAGAACTACACATTTTGCTATTC
AAAAGGCCGCTGAACTACGAGGCCGAGCTGAGGGCAGCGACCGCTGCTGCTC
AACAGCAACAGCAACAGCAGCAACAGCAGCAACAACAACAACAGCAACATCAA
ACACAATCGATTTCGAACGATATGCAAGTTCCACCCCAAATCTCCTAGCTTTGAT
ATACTCTAATTACTGAAATTGAATTCCTTTTCAAGGCTCCATAACTATATGGAGC
ATACTATGTACTTATCATAATAAAGAATAAACAAACAAGCAACAAAAAAAAAAA
AAAACTATGGATCATAGTTTTCACCAACAAGCATTAGAATACAAATAAAATTTAT
ATAGTGAATATCCTTCAAATAAATTTCTTCTTTCCCTTATAAATCAAATAGATGGA
ACGCACGCTCCAAAACTAGTCAACTAGAAAAAAAATACCCGCCGACGGACAATTT
TGAAGAGAGATGATTAATGAAGACAAAGTGAGGCTGGACAACAAGAACGACAT
ACACCGCGTAAAGGCCCACAAGACTGCATGGAATCACACGTCAAATATCTTGA
CGAATTGATATTGGCAATAAAAGACCTGAACTCGGGGGTGGATTCAAAGGTGC
AGATTAAAAAAGTGCCCACGGATCCATCTTCTTCTCAGGAGTACGCCAAGAGTT
TAAAGATCCTGAACACCCTCATAAGAAACCTAAAAGATCAAAGAAGGAACAATA
TCATGAAAAATGATACTATATTTTCGAAAACAGTTTCCGCCCTTGCCTTATTG

The protein sequence for mec1 SEQ ID NO:4:

MESHVKYLDELILAIKDLNSGVDSKVQIKKVPTDPSSSQEYAKSLKILNTLIRNLKD
QRRNNIMKNDTIFSKTVSALALLLEYNPFLLVMKDSNGNFEIQRLIDDFLNISVLNY
DNYHRIWFMRRKLGSWCKACVEFYGKPAKFQLTAHFENTMNLYEQALTEVLLGK
TELLKFYDTLKGLYILLYWFTSEYSTFGNSIAFLDSSLGFTKFDFNFQRLIRIVLYVF
DSCELAALEYAEIQLKYISLVVDYVCNRTISTALDAPALVCCEQLKFVLTTMHHFLD
NKYGLLDNDPTMAKGILRLYSLCISNDFSKCFVDHFPIDQWADFSQSEHFPFTQLT
NKALSIVYFDLKRRSLPVEALKYDNKFNIWVYQSEPDSSLKNVTSPFDDRYKQLEK
LRLLVLKKFNKTERGTLLKYRVNQLSPGFFQRAGNDFKLILNEASVSIQTCFKTNN
ITRLTSWTVILGRLACLESEKFSGTLPNSTKDMDNWYVCHLCDIEKTGNPFVRINP
NRPEAAGKSEIFRILHSNFLSHPNIDEFSESLLSGILFSLHRIFSHFQPPKLTDGNGQI
NKSFKLVQKCFMNSNRYLRLLSTRIIPLFNISDSHNSEDEHTATLIKFLQSQKLPVV

TABLE 8-continued

MEC1

KENLVIAWTQLTLTTSNDVFDTLLLKLIDIFNSDDYSLRIMMTLQIKNMAKILKKTP
YQLLSPILPVLLRQLGKNLVERKVGFQNLIELLGYPSKTILDIFQRYIIPYAIIQYKSD
VLSEIAKIMCDGDTSLINQMKVNLLKKNSRQIFAVALVKHGLFSLDILETLFLNRAP
TFDKGYITAYLPDYKTLAEITKLYKNSVTKDASDSENANMILCSLRFLITNFEKDKR
HGSKYKNINNWTDDQEQAFQKKLQDNILGIFQVFSSDIHDVEGRITYYEKLRVING
ISFLIIYAPKKSIISALAQISICLQTGLGLKEVRYEAFRCWHLLVRHLNDEELSTVIDS
LIAFILQKWSEFNGKLRNIVYSILDTLIKEKSDLILKLKPYTTLALVGKPELGIL

TABLE 9

MEC2

Nucleic acid sequence of mec2 SEQ ID NO:5:

AGAAAAGATAGTGTTACACAACATCAACTAAAAATGGAAAATATTACACAACCC
ACACAGCAATCCACGCAGGCTACTCAAAGGTTTTTGATTGAGAAGTTTTCTCAA
GAACAGATCGGCGAAAACATTGTGTGCAGGGTCATTTGTACCACGGGTCAAAT
TCCCATCCGAGATTTGTCAGCTGATATTTCACAAGTGCTTAAGGAAAAACGATC
CATAAAGAAAGTTTGGACATTTGGTAGAAACCCAGCCTGTGACTATCATTTAGG
AAACATTTCAAGACTGTCAAATAAGCATTTCCAAATACTACTAGGAGAAGACGG
TAACCTTTTATTGAATGACATTTCCACTAATGGGACCTGGTTAAATGGGCAAAA
AGTCGAGAAGAACAGCAATCAGTTACTGTCTCAAGGTGATGAAATAACCGTTG
GTGTAGGCGTGGAATCAGATATTTTATCTCTGGTCATTTTCATAAACGACAAATT
TAAGCAGTGCCTCGAGCAGAACAAAGTTGATCGCATAAGATCTAACCTGAAAA
ATACCTCTAAAATAGCTTCTCCTGGTCTTACATCATCTACTGCATCATCAATGGT
GGCCAACAAGACTGGTATTTTTAAGGATTTTTCGATTATTGACGAAGTGGTGGG
CCAGGGTGCATTTGCCACAGTAAAGAAAGCCATTGAAAGAACTACTGGGAAAA
CATTCGCGGTGAAGATTATAAGTAAACGCAAAGTAATAGGCAATATGGATGGT
GTGACAAGAGAGTTAGAAGTATTGCAAAAGCTCAATCATCCAAGGATAGTACG
ATTGAAAGGATTTTATGAAGATACTGAGAGTTATTATATGGTGATGGAGTTCGT
TTCTGGTGGTGACTTAATGGATTTTGTTGCTGCTCATGGTGCGGTTGGAGAAGA
TGCTGGGAGGGAGATATCCAGGCAGATACTCACAGCAATAAAATACATTCACT
CTATGGGCATCAGCCATCGTGACCTAAAGCCCGATAATATTCTTATTGAACA

The protein sequence of mec2 SEQ ID NO:6:

MENITQPTQQSTQATQRFLIEKFSQEQIGENIVCRVICTTGQIPIRDLSADISQVLKEK
RSIKKVWTFGRNPACDYHLGNISRLSNKHFQILLGEDGNLLLNDISTNGTWLNGQ
KVEKNSNQLLSQGDEITVGVGVESDILSLVIFINDKFKQCLEQNKVDRIRSNLKNTS
KIASPGLTSSTASSMVANKTGIFKDFSIIDEVVGQGAFATVKKAIERTTGKTFAVKII
SKRKVIGNMDGVTRELEVLQKLNHPRIVRLKGFYEDTESYYMVMEFVSGGDLMD
FVAAHGAVGEDAGREISRQILTAIKYIHSMGISHRDLKPDNILIEQDDPVLVKITDFG
LAKVQGNGSFMKTFCGTLAYVAPEVIRGKDTSVSPDEYEERNEYSSLVDMWSMG
CLVYVILTGHLPFSGSTQDQLYKQIGRGSYHEGPLKDFRISEEARDFIDSLLQVDPN
NRSTAAKALNHPWIKMSPLGSQSYGDFSQISLSQSLSQQKLLENMDDAQYEFVKA
QRKLQMEQQLQEQDQEDQDGKIQGFKIPAHAPIRYTQPKSIEAETREQKLLHSNNT
ENVKSSKKKGNGRFLTLKPLPDSIIQESLEIQQGVNPFFIGRSEDCNCKIEDNRLSR
VHCFIFKKRHAVGKSMYESPAQGLDDIWYCHTGTNVSYLNNNRMIQGTKFLLQD
GDEIKIIWDKNNKFVIGFKVEINDTTGLFNEGLGMLQEQRVVLKQTAEEKDLVKKL
TQMMAAQRANQPSASSSSMSAKKPPVSDTNNNGNNSVLNDLVESPINANTGNIL
KRIHSVSLSQSQIDPSKKVKRAKLDQTSKGPENLQFS

Citations

1. Pringle, J. R. and Hartwell, L. H. 1981. The *Saccharomyces cerevisiae* cell cycle. In: *The Molecular Biology of the Yeast Saccharomyces: Life cycle and inheritance* (ed. J. N. Strathen et al.) Cold Spring Harbor Laboratory, Cold Spring Harbor, N.Y., p. 97.

2. Hartwell, L. H., 1973. *J. Bacteriology* 115:966–974.

3. Hartwell, L. H. and T. A. Weinert. 1989. Checkpoints: Controls that ensure the order of cell cycle events. *Science* 246:629–634.

4. Weinert, T. A. and L. H. Hartwell. 1988. The RAD9 gene controls the cell cycle response to DNA damage in *Saccharomyces cerevisiae*. *Science* 241:317–322.

5. Goebl, M. G., Yochem, J., Jentsch, S., McGrath, J. P. Varsharsky, A. and Byers, B. 1988. The yeast cell cycle gene CDC34 encodes a ubiquitin-conjugating enzyme. *Science* 241:1331–1335.

6. Schiestl, R. H. and Giets, R. H. 1989. High efficiency transformation of intact yeast cells using single stranded nucleic acids as a carrier. *Curr. Genet.* 16:339–346.

7. Chance, P. F., Alderson, M. K., Leppig, K. A., Lensch, M. W., Matsunami, N., Smith, B. et al. 1993. DNA deletion associated with hereditary neuropathy with liability to pressure palsies. *Cell* 72:143–152.

The embodiments of the invention in which an exclusive property or privilege is claimed are defined as follows:

1. A nucleotide sequence capable of hybridizing under stringent conditions with the huRAD$_{compA}$ nucleotide sequence of SEQ ID NO:8, or constants thereof.

2. A nucleotide sequence capable of hybridizing under stringent conditions with the huRAD$_{compB}$ nucleotide sequence of SEQ ID NO:9, or constants thereof.

3. The nucleotide sequence of claim 2, capable of arresting a cell cycle in an S phase or a G2 phase in a cdc9,rad9 cell or a mec1,cdc9 cell.

4. The nucleotide sequence of claim 3, capable of arresting a cell cycle in a G2 phase in a rad9 cell.

5. The nucleotide sequence of claim 3, capable of conferring radiation resistance to a cell.

6. A method for isolating a human checkpoint cDNA that is capable of restoring growth at a restrictive temperature in a yeast test cell, wherein the yeast test cell comprises a genome having a first gene that forms a DNA strand break at a restrictive temperature and a second gene that fails to induce a cell cycle arrest in response to the DNA strand break, whereby the growth of the yeast test cell is inhibited at the restrictive temperature, the method comprising the steps of:

obtaining a human cDNA library comprising a plurality of human cDNA clones;

inserting the human cDNA clones individually into plasmid vectors comprising a selectable marker gene;

transforming a culture of the yeast test cells with the plasmid vectors from the preceding step;

selecting for yeast test cells transformed with the selectable marker gene;

growing the selected transformants at the restrictive temperature and isolating a candidate transformant capable of growing at the restrictive temperature; and identifying the human cDNA carried by the candidate transformant as a human checkpoint cDNA by sequencing the human cDNA carried by the candidate transformant and determining that the human cDNA is less than 50% homologous with both the first gene and the second gene.

7. An antibody against the human CDC 34 protein.

* * * * *

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

On the title page:

| | | |
|---|---|---|
| [75] | Inventors | "Tucson, Ark.;" should read --Tucson, Ariz.;-- |
| [63] | Related U.S. App. Data, line 3 | "04458 May 12, 1997," should read --04458, May 12, 1993,-- |
| [56] | Refs. Cited (Publs., #5, line 3) | Delete space between "E$_{232}$K," and """ |
| [56] | Refs. Cited (Publs., #18, line 2) | After "cycle" insert --control-- |
| [56] | Refs. Cited (Publs., #26, line 2) | "cDNAS,"" should read --cDNAs,"-- |
| [56] | Refs. Cited (Publs., #28, line 2) | "CCCI,"" should read --CCC1,"-- |

UNITED STATES PATENT AND TRADEMARK OFFICE
CERTIFICATE OF CORRECTION

PATENT NO. : 5,866,338  
DATED : February 2, 1999  
INVENTOR(S) : L.H. Hartwell et al.

Page 2 of 34

It is certified that error appears in the above-identified patent and that said Letters Patent is hereby corrected as shown below:

| COLUMN | LINE | ERROR |
|---|---|---|
| [57] | Abstract lines 1 & 2 of text | "huCDC34, huRAD9$_{compA}$, and huRAD9$_{compB}$" should read --*huCDC34, huRAD9$_{compA}$, and huRAD9$_{compB}$*-- |
| [57] | Abstract line 25 of text | "RAD17, RAD24, MEC1, MEC2, and MEC3" should read --*RAD17, RAD24, MEC1, MEC2, and MEC3*-- |
| 1 | 30 | After "repair" insert --.-- |
| 1 | 48 | "cdc9-8$^{ts}$," should read --*cdc9-8$^{ts}$*,-- |
| 1 | 62 | "RAD9" should appear in character italics |
| 1 | 63 | "rad9" should appear in character italics |
| 1 | 65 | "rad9" should appear in character italics |
| 1 | 65 | "RAD+" should read --*RAD+*-- |
| 1 | 67 | "rad9" should appear in character italics |
| 2 | 2 | "RAD9" should appear in character italics |
| 2 | 4 | "rad9" should appear in character italics |

UNITED STATES PATENT AND TRADEMARK OFFICE
CERTIFICATE OF CORRECTION

PATENT NO. : 5,866,338  
DATED : February 2, 1999  
INVENTOR(S) : L.H. Hartwell et al.

Page 3 of 34

It is certified that error appears in the above-identified patent and that said Letters Patent is hereby corrected as shown below:

| COLUMN | LINE | ERROR |
|---|---|---|
| 2 | 8 | "RAD9" should appear in character italics |
| 2 | 8 | "MRNA." should read --mRNA.-- |
| 2 | 9 | "RAD9" should appear in character italics |
| 2 | 14 | "rad9" should appear in character italics |
| 2 | 15 | "cdc9-8" should appear in character italics |
| 2 | 19 | "(cdc9-8)" should read --(*cdc9-8*)-- |
| 2 | 21 | "(rad9)." should read --(*rad9*).-- |
| 2 | 22 | "CDC34" should appear in character italics |
| 2 | 40 | "cdc9-8" should appear in character italics |
| 2 | 42 | "mec1 or rad9" should read --*mec1* or *rad9*-- |
| 2 | 45 | "mec-1,cdc9-8" should appear in character italics |
| 2 | 45 | "rad9,cdc9-8" should appear in character italics |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
|---|---|---|
| 2 | 51-52 | "huCDC34, huRAD9$_{compA}$, and huRAD9$_{compB}$." should read --*huCDC34, huRAD9$_{compA}$, and huRAD9$_{compB}$*.-- |
| 2 | 53 | "huCDC34" should appear in character italics |
| 2 | 53 | "171tx61)" should read --*171tx61)*-- |
| 2 | 54 | "mec-1" should appear in character italics |
| 2 | 55 | "mec1,cdc9" should appear in character italics |
| 2 | 57 | "rad9,cdc9-8." should appear in character italics |
| 2 | 60 | "CDC34" should appear in character italics |
| 2 | 62 | "MEC1.)" should read --*MEC1.)*-- |
| 2 | 63 | "cdc34$^{ts}$" should read --*cdc34$^{ts}$*-- |
| 2 | 64 | "CDC34." should appear in character italics |
| 2 | 65 | "huCDC34" should appear in character italics |
| 2 | 67 | "huCDC34" should appear in character italics |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
|---|---|---|
| 3 | 2 | "CDC34" should appear in character italics |
| 3 | 3 | "huCDC34" should appear in character italics |
| 3 | 6 | "huRAD9$_{compA}$" should read --$huRAD9_{compA}$-- |
| 3 | 6 | "83tx42)" should read --$83tx42$)-- |
| 3 | 7 | "rad9" should appear in character italics |
| 3 | 8 | "rad9,cdc9" should appear in character italics |
| 3 | 10 | "rad9,cdc9-8" should appear in character italics |
| 3 | 10 | "mec1,cdc9-8" should appear in character italics |
| 3 | 11 | "cdc9-8" should appear in character italics |
| 3 | 15 | "huRAD9$_{compA}$" should read --$huRAD9_{compA}$-- |
| 3 | 17 | "huRAD9$_{compB}$" should read --$huRAD9_{compB}$-- |
| 3 | 17 | "171tx23)" should read --$171tx23$)-- |
| 3 | 18 | "mec-1" should appear in character italics |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
| --- | --- | --- |
| 3 | 19 | "mec-1,cdc9" should appear in character italics |
| 3 | 21 | "rad9,cdc9-8 or mec1,cdc9-8" should read --*rad9,cdc9-8* or *mec1,cdc9-8*-- |
| 3 | 21 | "cdc9-8" should appear in character italics |
| 3 | 23 | "mec1 or rad9" should read --*mec1* or *rad9*-- |
| 3 | 35-36 | "huCDC34, huRAD9$_{compA}$, and huRAD9$_{compB}$" should read --*huCDC34, huRAD9$_{compA}$,* and *huRAD9$_{compB}$*-- |
| 3 | 38 | "RAD17, RAD24, MEC1, MEC2, and MEC3" should read --*RAD17, RAD24, MEC1, MEC2,* and *MEC3*-- |
| 3 | 55 | "cdc" should appear in character italics |
| 4 | 2 | "CDC34" should appear in character italics |
| 4 | 4 | "cdc34" should appear in character italics |
| 4 | 5 | "CDC34." should appear in character italics |
| 4 | 7 | "CDC34" should appear in character italics |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
|---|---|---|
| 4 | 33-34 | "RAD-9, MEC-1, RAD17, RAD24, MEC-2, and MEC-3." should read --*RAD-9, MEC-1, RAD17, RAD24, MEC-2,* and *MEC-3*.-- |
| 4 | 34 | "mec1, mec2, and mec3" should read --*mec1, mec2,* and *mec3*-- |
| 4 | 46 | "MEC-1" should appear in character italics |
| 4 | 46 | "mec-1" should appear in character italics |
| 4 | 47 | "mec-1,cdc9-8" should appear in character italics |
| 4 | 47 | "RAD9" should appear in character italics |
| 4 | 47 | "rad9" should appear in character italics |
| 4 | 48 | "rad9,cdc9-8" should appear in character italics |
| 4 | 49 | "MEC-1 (or RAD9)" should read --*MEC-1* (or *RAD9*)-- |
| 4 | 51 | "huCDC34" should appear in character italics |
| 4 | 51 | "CDC34" should appear in character italics |
| 4 | 53 | "cdc34." should appear in character italics |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
|---|---|---|
| 4 | 58 | "CDC34" should appear in character italics |
| 4 | 58 | "mec-1," should appear in character italics |
| 4 | 61 | "huCDC34" should appear in character italics |
| 4 | 61 | "mec-1" should appear in character italics |
| 4 | 62 | "mec-1,cdc9-8" should appear in character italics |
| 4 | 62 | "$RAD9_{compA}$" should read --$RAD9_{compA}$-- |
| 4 | 63 | "RAD9" should appear in character italics |
| 4 | 64 | "rad9" should appear in character italics |
| 4 | 64 | "rad9, cdc9-8" should read --$rad9,cdc9-8$-- |
| 4 | 65 | "rad9" should appear in character italics |
| 5 | 46-47 | "mec-1,cdc9-8" should appear in character italics |
| 5 | 47 | "rad9,cdc9-8." should appear in character italics |
| 5 | 48 | "cdc9," should appear in character italics |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
| --- | --- | --- |
| 5 | 50 | "mec-1 or rad9" should read --*mec-1* or *rad9*-- |
| 5 | 52 | "cdc9" should appear in character italics |
| 5 | 52 | "cdc9-8ts" should read --*cdc9-8$^{ts}$*-- |
| 5 | 53 | "rad9" should appear in character italics |
| 5 | 54-55 | "mec1,cdc9-8" should appear in character italics and should not break between lines |
| 5 | 55 | "rad9,cdc9-8" should appear in character italics |
| 5 | 56 | "RAD9,cdc9-8 or MEC1,cdc9-8," should read --*RAD9,cdc9-8* or *MEC1,cdc9-8*,-- |
| 5 | 58 | "rad9,cdc9-8" should appear in character italics |
| 5 | 66-67 | "en masse" should appear in character italics |
| 6 | 19 | "cdc9-8$^{ts}$" should read --*cdc9-8$^{ts}$*-- |
| 6 | 22 | "rad9,cdc9-8" should appear in character italics |
| 6 | 30 | "rad9,cdc9-8ts" should read --*rad9,cdc9-8$^{ts}$*-- |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
|---|---|---|
| 6 | 31 | "rad9" should appear in character italics |
| 6 | 32 | "cdc9-8" should appear in character italics |
| 6 | 48-49 | "rad9,cdc9-8" should appear in character italics and should not break between lines |
| 6 | 50 | "huCDC34" should appear in character italics |
| 6 | 50 | "MEC-1" should appear in character italics |
| 6 | 51 | "cdc34" should appear in character italics |
| 6 | 51 | "mec-1" should appear in character italics |
| 6 | 53 | "CDC34 or MEC-1" should read --$CDC34$ or $MEC$-$1$-- |
| 7 | 6 | "cdc9-8)" should read --$cdc9$-$8$)-- |
| 7 | 7 | "rad9 or mec-1)." should read --$rad9$ or $mec$-$1$).-- |
| 7 | 17 | "huCDC34" should appear in character italics |
| 7 | 18 | "mec1,cdc9-8;" should appear in character italics |
| 7 | 18 | "huRAD9$_{compA}$" should read --$huRAD9_{compA}$-- |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
|---|---|---|
| 7 | 19 | "rad9,cdc9-8 and mec1,cdc9-8" should read --*rad9,cdc9-8* and *mec1,cdc9-8*-- |
| 7 | 20 | "RAD9);" should read --*RAD9*);-- |
| 7 | 20 | "huRAD9$_{compB}$" should read --*huRAD9$_{compB}$*-- |
| 7 | 21 | "mec1,cdc9-8" should appear in character italics |
| 7 | 22 | "MEC-1)." should read --*MEC-1)*.-- |
| 7 | 33 | "cdc2, cdc17, and cdc13." should read --*cdc2, cdc17,* and *cdc13.*-- |
| 7 | 36 | "rad9,cdc9" should appear in character italics |
| 7 | 40-41 | ""moX", "moY", and "moZ"" should read --"*moX*", "*moY*", and "*moZ*"-- |
| 7 | 41 | ""mo$^x$", "mo$^y$", and "mo$^z$"" should read --"*mo$^x$*", "*mo$^y$*", and "*mo$^z$*"-- |
| 7 | 43 | ""mo$^x$", "mo$^y$", and "mo$^z$"" should read --"*mo$^x$*", "*mo$^y$*", and "*mo$^z$*"-- |
| 7 | 44 | "rad9,cdc9" should appear in character italics |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
|---|---|---|
| 7 | 44-45 | "mec-1,cdc 9" should read --*mec-1,cdc9*-- and should not break between lines |
| 7 | 51 | ""huA", "huB", and "huC"." should read --"*huA*", "*huB*", and "*huC*".-- |
| 7 | 52 | "moX, moY, or moZ" should read --*moX, moY,* or *moZ*-- |
| 7 | 53-54 | "moX, moY, or moZ" should read --*moX, moY,* or *moZ*-- |
| 8 | 53 | "in situ" should appear in character italics |
| 8 | 64 | "MEC$_{comp}$" should read --MEC$_{comp}$-- |
| 9 | 8 | "cdc9-8,rad9::HIS3,leu2" should appear in character italics |
| 9 | 9 | "RAD9" should appear in character italics |
| 9 | 9 | "rad9::HIS3" should appear in character italics |
| 9 | 10 | "RAD9" should appear in character italics |
| 9 | 11 | "HIS3" should appear in character italics |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
|---|---|---|
| 9 (Table 1, first column) | 22-24 | All text in Column 1 under "STRAIN" should appear in character italics |
| 9 (Table 2, first column) | 37-39 | All text in Column 1 under "STRAIN" should appear in character italics |
| 9 (Table 2, third column) | 38 | After "<0.1%" insert ----- |
| 9 | 42 | "cdc9-8,mec1-A401,leu2" should appear in character italics |
| 9 | 44 | "mec1" should appear in character italics |
| 9 | 44 | "mec1-A401" should appear in character italics |
| 9 | 45 | "mec1" should appear in character italics |
| 9 | 45 | "rad9" should appear in character italics |
| 9 | 46 | "cdc9-8." should appear in character italics |
| 9 | 58 | "cdc9-8,rad9::HIS3,leu2" should appear in character italics |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
|---|---|---|
| 9 | 63 | "cdc9-8,mec1-A401,leu2" should appear in character italics |
| 10 | 13 | "mec1,cdc9-8" should appear in character italics |
| 10 | 15 | "171tx6)" should read --*171tx6*)-- |
| 10 | 16 | "cdc9-8,mec1" should appear in character italics |
| 10 | 17 | "171tx6" should appear in character italics |
| 10 | 20 | "MEC1" should appear in character italics |
| 10 | 24 | "cdc9-8,MEC+" should read --*cdc9-8,MEC+*-- |
| 10 | 25 | "171tx6" should appear in character italics |
| 10 | 28 | "171tx6" should appear in character italics |
| 10 | 28 | "171tx61" should appear in character italics |
| 10 (Table 3, title) | 33 | "huCDC34 (171tx61)." should appear in character italics |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
| --- | --- | --- |
| 10 (Table 3, column 1) | 37 & 40 | All text in Column 1 under "CELLS" should appear in character italics |
| 10 (Table 3, column 2) | 37-41 | All text in Column 2 under "VECTOR" should appear in character italics |
| 10 | 46 | "171tx6" should appear in character italics |
| 10 | 48 | "(171tx61)" should read --(*171tx61*)-- |
| 10 | 49 | "171tx61" should appear in character italics |
| 10 | 50 | "171tx61" should appear in character italics |
| 10 | 51 | "CDC34," should appear in character italics |
| 10 | 57 | "171tx61" should appear in character italics |
| 10 | 58 | "mec1" should appear in character italics |
| 10 | 61 | "Drosophila" should appear in character italics |
| 10 | 65 | "171tx61" should appear in character italics |
| 10 | 67 | "CDC34" should appear in character italics |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
|---|---|---|
| 11 | 5 | "171tx61" should appear in character italics |
| 11 | 6 | "CDC34," should appear in character italics |
| 11 | 6 | "cdc34" should appear in character italics |
| 11 | 8 | "171tx61" should appear in character italics |
| 11 | 9 | "cdc34" should appear in character italics |
| 11 (Table 4, title) | 13 | "cdc34" should appear in character italics |
| 11 (Table 4, title) | 14 | "huCDC34" should appear in character italics |
| 11 (Table 4, column 1) | 19-20 | All text in Column 1 under "VECTOR" should appear in character italics |
| 11 | 24 | "cdc34" should appear in character italics |
| 11 | 24 | "171tx61" should appear in character italics |
| 11 | 27 | "rad6" should appear in character italics |
| 11 | 27 | "171tx61" should appear in character italics |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
|---|---|---|
| 11 | 28 | "cdc34" should appear in character italics |
| 11 | 28 | "huCDC34." should appear in character italics |
| 11 | 29 | "mec1-A401" should appear in character italics |
| 11 | 30 | "CDC34." should appear in character italics |
| 11 | 30 | "CDC34" should appear in character italics |
| 11 | 32 | "mec1,cdc9-8" should appear in character italics |
| 11 | 37 | "huCDC34" should appear in character italics |
| 11 | 38 | "mec1-A401,cdc9" should appear in character italics |
| 11 | 39 | "CDC34" should appear in character italics |
| 11 | 42 | "cdc9" should appear in character italics |
| 11 | 43 | "mec1" should appear in character italics |
| 11 | 45 | "huCDC34" should appear in character italics |
| 11 | 49 | "tx61" should appear in character italics |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
|---|---|---|
| 11 | 55 | "CDC34" should appear in character italics |
| 11 | 58 | "tx61" should appear in character italics |
| 11 | 59 | "CDC34 (UBC3), RAD6 (UBC2)," should read --*CDC34 (UBC3), RAD6 (UBC2)*,-- |
| 11 | 59 | "UBCS" should read --*UBC5*-- |
| 11 | 60 | "tx61" should appear in character italics |
| 11 | 60 | "CDC34," should appear in character italics |
| 11 | 61 | "CDC34" should appear in character italics |
| 11 | 61 | "tx61," should appear in character italics |
| 12 | 1 | "UBC" should appear in character italics |
| 12 | 1 | "(CDC34 and RAD6)" should read --(*CDC34* and *RAD6*)-- |
| 12 | 2 | "UBC7" should appear in character italics |
| 12 | 3 | "tx61" should appear in character italics |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
|---|---|---|
| 12 | 4 | "171tx61" should appear in character italics |
| 12 | 6 | "CDC34" should appear in character italics |
| 12 | 12 | "CDC34" should appear in character italics |
| 12 | 22 | "tx61" should appear in character italics |
| 12 | 25 | "CDC34" should appear in character italics |
| 12 | 31 | "huCDC34" should appear in character italics |
| 12 | 33 | "huCDC34" should appear in character italics |
| 12 | 35 | "CDC34" should appear in character italics |
| 12 | 37 | "CDC34" should appear in character italics |
| 12 | 38-39 | "(34cos2 and 34cos4)" should read --(*34cos2* and *34cos4*)-- |
| 12 | 40 | "CDC34 CDNA." should read --*CDC34* cDNA-- |
| 12 | 42 | "CDC34" should appear in character italics |
| 12 | 45 | "CDC34" should appear in character italics |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
|--------|------|-------|
| 12 | 46 | "in situ" should appear in character italics |
| 12 | 47 | "34cos2" should appear in character italics |
| 12 | 52 | "34cos4" should appear in character italics |
| 12 | 55 | "34cos4" should appear in character italics |
| 12 | 57 | "34cos2." should appear in character italics |
| 12 | 64 | "CDC34" should appear in character italics |
| 12 | 66 | "CDC34" should appear in character italics |
| 13 | 6 | "CDC34" should appear in character italics |
| 13 | 10 | "mec1" should appear in character italics |
| 13 | 11 | "cdc34" should appear in character italics |
| 13 | 17 | "cdc34" should appear in character italics |
| 13 | 20 | "mec1,cdc9-8" should appear in character italics |
| 13 | 21 | "huCDC34." should appear in character italics |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
|---|---|---|
| 13 | 22 | "CDC34" should appear in character italics |
| 13 | 24 | "CDC34" should appear in character italics |
| 13 | 25 | "huCDC34," should appear in character italics |
| 13 | 26 | "CDC34" should appear in character italics |
| 13 | 29 | "scCDC34," should appear in character italics |
| 13 | 29 | "cdc34$^{ts}$" should read --$cdc34^{ts}$-- |
| 13 | 30 | "mec1,cdc9" should appear in character italics |
| 13 | 33 | "huCDC34" should appear in character italics |
| 13 | 34 | "mec1" should appear in character italics |
| 13 | 35 | "huCDC34" should appear in character italics |
| 13 | 35 | "mec1,cdc9" should appear in character italics |
| 13 | 36 | "huCDC34" should appear in character italics |
| 13 | 39 | "mec1" should appear in character italics |

UNITED STATES PATENT AND TRADEMARK OFFICE
CERTIFICATE OF CORRECTION

PATENT NO.  : 5,866,338
DATED       : February 2, 1999
INVENTOR(S) : L.H. Hartwell et al.

It is certified that error appears in the above-identified patent and that said Letters Patent is hereby corrected as shown below:

| COLUMN | LINE | ERROR |
|---|---|---|
| 13 | 42 | "huCDC34," should appear in character italics |
| 13 | 45 | "huCDC34" should appear in character italics |
| 13 | 47-48 | "mec1,cdc9-8" should appear in character italics and should not break between lines |
| 13 | 51 | "mec1,cdc9-8" should appear in character italics |
| 13 | 53 | "MEC+,cdc9-8" should read --*MEC+,cdc9-8*-- |
| 13 | 55 | "huCDC34" should appear in character italics |
| 13 | 56 | "huCDC34" should appear in character italics |
| 13 | 57 | "mec-1,cdc9-8" should appear in character italics |
| 13 | 60 | "huCDC34." should appear in character italics |
| 13 | 61 | "huCDC34" should appear in character italics |
| 13 | 62 | "mec1" should appear in character italics |
| 14 | 3 | "mec1" should appear in character italics |
| 14 | 4 | "huCDC34" should appear in character italics |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
|---|---|---|
| 14 | 5 | "mec1" should appear in character italics |
| 14 | 5 | "MEC1" should appear in character italics |
| 14 | 7 | "huCDC34" should appear in character italics |
| 14 | 8 | "(mec1" should read --(*mec1*-- |
| 14 | 12 | "huCDC34" should appear in character italics |
| 14 | 12 | "mec1" should appear in character italics |
| 14 | 13 | "huCDC34" should appear in character italics |
| 14 | 13 | "rad9,cdc9-8" should appear in character italics |
| 14 | 14 | "MEC+,cdc9-8" should read --*MEC+,cdc9-8*-- |
| 14 | 15 | "huCDC34" should appear in character italics |
| 14 | 16 | "mec1,cdc9-8" should appear in character italics |
| 14 | 17 | "CDC34" should appear in character italics |
| 14 | 18 | "huCDC34" should appear in character italics |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
|---|---|---|
| 14 | 18 | "mec1" should appear in character italics |
| 14 | 19 | "CDC34" should appear in character italics |
| 14 | 25 | "mec1,cdc9-8" should appear in character italics |
| 14 | 26 | "huCDC34" should appear in character italics |
| 14 | 27 | "cdc9" should appear in character italics |
| 14 | 29 | "mec1" should appear in character italics |
| 14 | 30-31 | "($RAD9_{compA}$ and $RAD9_{compB}$);" should read --($RAD9_{compA}$ and $RAD9_{compB}$);-- |
| 14 | 32 | "cdc9" should appear in character italics |
| 14 | 42 | "CDC34" should appear in character italics |
| 14 | 50 | "CDC34" should appear in character italics |
| 14 | 56 | "CDC34" should appear in character italics |
| 14 | 57 | "CDC34" should appear in character italics |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
| --- | --- | --- |
| 14 | 60 | "(CDC34, CDC4, and CDC53)" should read --(*CDC34*, *CDC4*, and *CDC53*)-- |
| 15 | 4-5 | "huRAD9$_{compA}$ and huRAD9$_{compB}$" should read --*huRAD9$_{compA}$* and *huRAD9$_{compB}$*-- |
| 15 | 13 | "RAD9 and MEC-1" should read --*RAD9* and *MEC-1*-- |
| 15 | 15 | "CDC34" should appear in character italics |
| 15 | 16 | "MEC1" should appear in character italics |
| 15 | 19 | "RAD9" should appear in character italics |
| 15 | 23 | "Human RAD9$_{compA}$:" should read --Human RAD9$_{compA}$:-- |
| 15 | 26 | "RAD9" should appear in character italics |
| 15 | 27 | "rad9,cdc9-8" should appear in character italics |
| 15 | 32 | "83tx42)" should read --*83tx42)*-- |
| 15 | 34 | "rad9,cdc9-8,leu2" should appear in character italics |
| 15 | 37 | "83tx42" should appear in character italics |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
|---|---|---|
| 15 | 37 | "mec1,cdc9-8" should appear in character italics |
| 15 | 38 | "83tx42" should appear in character italics |
| 15 | 39 | "rad9,cdc9-8" should appear in character italics |
| 15 | 39 | "83tx42" should appear in character italics |
| 15 | 40 | "cdc9-8,RAD+,MEC+" should read --*cdc9-8,RAD+,MEC+*-- |
| 15 | 41 | "83tx42" should appear in character italics |
| 15 | 43 | "rad 9 in the cdc9-8,rad9" should read --*rad 9* in the *cdc9-8,rad9*-- |
| 15 | 44 | "huRAD9$_{compA}$." should read --*huRAD9$_{compA}$*.-- |
| 15 | 45 | "huRAD9$_{compA}$" should read --*huRAD9$_{compA}$*-- |
| 15 | 47 | "Human RAD9$_{compB}$:" should read --Human RAD9$_{compB}$:-- |
| 15 | 51 | mec, cdc9-8" should read --*mec1,cdc9-8*-- |
| 15 | 56 | "171tx23)" should read --*171tx23*)-- |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
| --- | --- | --- |
| 15 | 59 | "mec1,cdc9-8,leu2" should appear in character italics |
| 15 | 62 | "171tx23" should appear in character italics |
| 15 | 62 | "cdc9-8" should appear in character italics |
| 15 | 63-64 | "mec1,cdc9-8" should appear in character italics and should not break between lines |
| 15 | 64 | "171tx23" should appear in character italics |
| 15 | 65 | "cdc9" should appear in character italics |
| 15 | 66 | "117tx23" should appear in character italics |
| 16 (Table5, title) | 5 | "huCDC$_{compB}$ (171tx23)." should appear in character italics |
| 16 (Table5, column 1) | 9 & 12 | All text in Column 1 under "CELLS" should appear in character italics |
| 16 (Table5, column 2) | 9-14 | All text in Column 2 under "VECTOR" should appear in character italics |
| 16 | 17 | "117tx23" should appear in character italics |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
|---|---|---|
| 16 | 19 | "mec-1 and rad9" should read --*mec-1* and *rad9*-- |
| 16 | 20 | "mec1 or rad9,117tx23" should read --*mec1* or *rad9,117tx23*-- |
| 16 | 21 | "ADANS" should appear in character italics |
| 16 | 22 | "mec1 or rad9" should read --*mec1* or *rad9*-- |
| 16 | 23 | "117tx23" should appear in character italics |
| 16 | 23 | "mec-1 or rad9" should read --*mec-1* or *rad9*-- |
| 16 | 30 | "RAD9$_{compA}$" should read --RAD9$_{compA}$-- |
| 16 | 41 | "R4D9 and MEC-1" should read --*RAD9* and *MEC-1*-- |
| 16 | 42 | "huRAD9$_{compA}$" should read --huRAD9$_{compA}$-- |
| 16 | 56 | "huRAD9$_{compB}$" should read --*huRAD9$_{compB}$*-- |
| 16 | 57 | "huRAD9$_{compB}$" should read --huRAD9$_{compB}$-- |
| 16 | 62 | "huRAD9$_{compB}$" should read --*huRAD9$_{compB}$*-- |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
|---|---|---|
| 16 | 63 | "hurad9$_{compB}$" should read --*hurad9$_{compB}$*-- |
| 16<br>17 | 67 through<br>1 | "RAD9, huCDC34, huRAD9$_{compA}$, or huRAD9$_{compB}$" should read --*RAD9, huCDC34, huRAD9$_{compA}$,* or *huRAD9$_{compB}$*-- |
| 17 | 2 | "cdc13-1" should appear in character italics |
| 17 | 6 | "cdc13," should appear in character italics |
| 17 | 8 | "cdc13" should appear in character italics |
| 17 | 8 | "RAD9" should appear in character italics |
| 17 | 10 | "RAD9" should appear in character italics |
| 17 | 11 | "cdc13" should appear in character italics |
| 17 | 12 | "RAD9," should appear in character italics |
| 17 | 12 | "cdc13" should appear in character italics |
| 17 | 13-14 | "cdc13 RAD+ or rad9" should read --*cdc13 RAD+* or *rad9*-- |
| 17 | 15 | "RAD9" should appear in character italics |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
|---|---|---|
| 17 | 16 | "cdc13,RAD+" should read --*cdc13,RAD+*-- |
| 17 | 19 | "cdc13,RAD+" should read --*cdc13,RAD+*-- |
| 17 | 21 | "cdc13,rad9" should appear in character italics |
| 17 | 23 | "RAD9." should appear in character italics |
| 17 | 24 | "RAD9" should appear in character italics |
| 17 | 25-26 | "cdc13, leu2, RAD+" should read --*cdc13, leu2, RAD+*-- |
| 17 | 30 | "RAD9" should appear in character italics |
| 17 | 32 | "RAD9" should appear in character italics |
| 17 | 33 | "RAD9" should appear in character italics |
| 17 | 37 | "RAD9" should appear in character italics |
| 17 | 39-40 | "huCDC34, huRAD9$_{compA}$, huRAD9$_{compB}$, or huRAD9" should read --*huCDC34, huRAD9$_{compA}$, huRAD9$_{compB}$,* or *huRAD9*-- |
| 17 | 41 | "cdc13,leu2,RAD+" should read --*cdc13,leu2,RAD+*-- |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
|---|---|---|
| 17 | 56 | "RAD9" should appear in character italics |
| 17 | 62-63 | "in vivo" should appear in character italics |
| 18 | 4 | "rad9 or mec1" should read --*rad9* or *mec1*-- |
| 18 | 6 | "(cdc9-8)." should read --(*cdc9-8*).-- |
| 18 | 10-11 | "mec1,cdc9-8," should appear in character italics and should not break between lines |
| 18 | 11 | "rad9,cdc9-8" should appear in character italics |
| 18 | 12-13 | "MEC1, RAD9, or CDC9" should read --*MEC1, RAD9,* or *CDC9*-- |
| 18 | 22 | "cdc9-8,mec-1:" should appear in character italics |
| 18 | 23 | "mec, cdc9-8, leu2" should read --*mec1,cdc9-8,leu2*-- |
| 18 | 27 | "mec1,cdc9-8" should appear in character italics |
| 18 | 29 | "tx6" should appear in character italics |
| 18 | 30 | "tx61," should appear in character italics |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
|---|---|---|
| 18 | 36-37 | "(MATα, cdc9-8, mec1-A401, leu2, ura3, ade2 ade3, trp1" should read --*(MATa, cdc9-8, mec1-A401, leu2, ura3, ade2 ade3, trp1*-- |
| 18 | 38-39 | "9085-1-8-3 (MATα, cdc9-8, rad9::HIS3, leu2, ura3, trp1), 9085-1-10-4 (MATα, cdc9-8, leu2, his3)," should appear in character italics |
| 18 | 40 | "(MATα, cdc34-2, leu2-3, ura3, trp1" should read --*(MATa, cdc34-2, leu2-3, ura3, trp1*-- |
| 18 | 45 | "S. c. CDC34" should appear in character italics |
| 18 | 46 | "CDC34" should appear in character italics |
| 18 | 48 | "MEC1 and RAD9" should read --*MEC1* and *RAD9*-- |
| 18 | 51 | "(GM1Q449," should read --(GM10449,-- |
| 19 | 4 | "Plus" should appear in character italics |
| 19 | 7 | "CDC34" should appear in character italics |
| 19 | 14 | "Plus" should appear in character italics |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
|---|---|---|
| 19 | 16 | "CDC34" should appear in character italics |
| 19 | 16 | "GADPH" should appear in character italics |
| 19 | 20 | "In Situ" should appear in character italics |
| 24 | 51 | "CDC34" should appear in character italics |
| 107 (Claim 1, | 42 line 2) | "huRAD$_{compA}$" should read --$huRAD_{compA}$-- |
| 107 (Claim 1, | 43 line 3) | "constants" should read --complements-- |
| 107 (Claim 2, | 45 line 2) | "huRAD$_{compB}$" should read --$huRAD_{compB}$-- |
| 107 (Claim 2, | 46 line 3) | "constants" should read --complements-- |
| 107 (Claim 3, | 47 line 1) | "of claim 2," should read --of claim 1,-- |
| 107 (Claim 3, | 48 line 2) | "cdc9,rad9" should appear in character italics |

UNITED STATES PATENT AND TRADEMARK OFFICE
CERTIFICATE OF CORRECTION

PATENT NO. : 5,866,338
DATED : February 2, 1999
INVENTOR(S) : L.H. Hartwell et al.

It is certified that error appears in the above-identified patent and that said Letters Patent is hereby corrected as shown below:

| COLUMN | LINE | ERROR |
|---|---|---|
| 107 (Claim 3, | 49 line 3) | "mec1,cdc9" should appear in character italics |
| 107 (Claim 4, | 50 line 1) | "of claim 3," should read --of claim 2,-- |
| 107 (Claim 4, | 51 line 2) | "rad9" should appear in character italics |
| 107 (Claim 5, | 52 line 1) | "of claim 3," should read --of claim 2,-- |

Signed and Sealed this

Twenty-eighth Day of September, 1999

Attest:

Q. TODD DICKINSON

*Attesting Officer*   *Acting Commissioner of Patents and Trademarks*